US011147249B2

(12) United States Patent
Rosenthal et al.

(10) Patent No.: US 11,147,249 B2
(45) Date of Patent: Oct. 19, 2021

(54) SIGLEC TRANSGENIC MICE AND METHODS OF USE THEREOF

(71) Applicant: ALECTOR LLC, South San Francisco, CA (US)

(72) Inventors: Arnon Rosenthal, Woodside, CA (US); Seung-Joo Lee, San Francisco, CA (US)

(73) Assignee: ALECTOR LLC, South San Francisco, CA (US)

( * ) Notice: Subject to any disclaimer, the term of this patent is extended or adjusted under 35 U.S.C. 154(b) by 828 days.

(21) Appl. No.: 15/836,089

(22) Filed: Dec. 8, 2017

(65) Prior Publication Data

US 2018/0160661 A1 Jun. 14, 2018

Related U.S. Application Data

(60) Provisional application No. 62/431,661, filed on Dec. 8, 2016.

(51) Int. Cl.
*A01K 67/027* (2006.01)
*C12N 15/85* (2006.01)
*C07K 14/705* (2006.01)

(52) U.S. Cl.
CPC ...... *A01K 67/0276* (2013.01); *A01K 67/0275* (2013.01); *C07K 14/7056* (2013.01); *C07K 14/70596* (2013.01); *C12N 15/8509* (2013.01); *A01K 2207/15* (2013.01); *A01K 2217/05* (2013.01); *A01K 2217/052* (2013.01); *A01K 2217/07* (2013.01); *A01K 2217/15* (2013.01); *A01K 2227/105* (2013.01); *A01K 2267/01* (2013.01); *A01K 2267/03* (2013.01)

(58) Field of Classification Search
None
See application file for complete search history.

(56) References Cited

U.S. PATENT DOCUMENTS

| | | |
|---|---|---|
| 4,469,863 A | 9/1984 | Ts'o et al. |
| 4,873,191 A | 10/1989 | Wagner et al. |
| 5,175,384 A | 12/1992 | Krimpenfort et al. |
| 5,536,821 A | 7/1996 | Agrawal et al. |
| 5,541,306 A | 7/1996 | Agrawal et al. |
| 5,602,229 A | 2/1997 | Malabarba et al. |
| 5,614,622 A | 3/1997 | Iyer et al. |
| 5,637,683 A | 6/1997 | Usher et al. |
| 5,637,684 A | 6/1997 | Cook et al. |
| 5,700,922 A | 12/1997 | Cook |
| 5,717,083 A | 2/1998 | Cook et al. |
| 5,719,262 A | 2/1998 | Buchardt et al. |
| 5,739,308 A | 4/1998 | Kandimalla et al. |
| 5,739,314 A | 4/1998 | Roy et al. |
| 5,773,601 A | 6/1998 | Agrawal |
| 5,886,165 A | 3/1999 | Kandimalla et al. |
| 5,929,226 A | 7/1999 | Padmapriya et al. |
| 5,955,599 A | 9/1999 | Iyer et al. |
| 5,962,674 A | 10/1999 | Iyer et al. |
| 5,977,296 A | 11/1999 | Nielsen et al. |
| 6,037,521 A | 3/2000 | Sato et al. |
| 6,066,778 A | 5/2000 | Ginsburg et al. |
| 6,117,992 A | 9/2000 | Iyer |
| 6,140,482 A | 10/2000 | Iyer et al. |
| 6,455,308 B1 | 9/2002 | Freier |

FOREIGN PATENT DOCUMENTS

| | | |
|---|---|---|
| WO | 1995/02697 A1 | 1/1995 |
| WO | 1999/032619 A1 | 7/1999 |
| WO | 2000/044895 A1 | 8/2000 |
| WO | 2000/056746 A2 | 9/2000 |
| WO | 2000/075372 A1 | 12/2000 |
| WO | 2001/014398 A1 | 3/2001 |
| WO | 2001/029058 A1 | 4/2001 |
| WO | 2001/036646 A1 | 5/2001 |

OTHER PUBLICATIONS

Green et al, 1999, J Immunol. Meth.,vol. 231: pp. 11-23.*
Macdonald, L. et al., PNAS 2014, vol. 111: pp. 5147-5152.*
Alphey et al., "High Resolution Crystal Structures of Siglec-7—Insights into Ligand Specificity in the Siglec Family", The Journal of Biological Chemistry, vol. 278, No. 5, Jan. 31, 2003, pp. 3372-3377.
Ariga et al., "Role of Ganglioside Metabolism in the Pathogenesis of Alzheimer's Disease—A Review", Journal of Lipid Research; vol. 49, 2008, pp. 1157-1175.
Attrill et al., "Siglec-7 Undergoes a Major Conformational Change When Complexed with the =(2,8)-Disialylganglioside GT1b", The Journal of Biological Chemistry, vol. 281, No. 43, Oct. 27, 2006, pp. 32774-32783.
Beattie et al., "ProNGF Induces p75-Mediated Death of Oligodendrocytes following Spinal Cord Injury", Neuron, vol. 36, No. 3, Oct. 24, 2002, pp. 375-386.
Bennett et al., "New Tools for Studying Microglia in the Mouse and Human CNS", PNAS, vol. 113, No. 12, Feb. 16, 2016, pp. E1738-E1746.

(Continued)

*Primary Examiner* — Michael D Burkhart
(74) *Attorney, Agent, or Firm* — Morrison & Foerster LLP

(57) ABSTRACT

Provided herein are transgenic non-human animals whose genomes comprise two or more human genes selected from CD33, Siglec-5, Siglec-7, Siglec-9, Siglec-11, Siglec-14, and Siglec-16, to methods of screening candidate agents that bind to and/or modulate the function and/or activity of at least one of the human genes in the transgenic non-human animals, and to methods of screening candidate agents to determine their effect on one or more activities and/or functions associated with expression of at least one of the human genes in the transgenic non-human animals. Further provided herein are methods of recapitulating a human Siglec immune system in a non-human animal, and methods of generating a non-human animal disease model comprising a human Siglec repertoire.

18 Claims, 40 Drawing Sheets
(32 of 40 Drawing Sheet(s) Filed in Color)
Specification includes a Sequence Listing.

(56) References Cited

OTHER PUBLICATIONS

Blesa et al., "Parkinson's Disease: Animal Models and Dopaminergic Cell Vulnerability", Frontiers in Neuroanatomy, vol. 8, No. 155, Dec. 2014, pp. 1-12.
Bradley et al., "Formation of Germ-Line Chimaeras from Embryo-Derived Teratocarcinoma Cell Lines", Nature, vol. 309, May 17, 1984, pp. 255-256.
Cowan et al., "Antibody-Based Therapy of Acute Myeloid Leukemia with Gemtuzumab Ozogamicin", Frontiers in Bioscience, vol. 18, Jun. 2013, pp. 1311-1334.
Crocker et al., "Molecular Analysis of Sialoside Binding to Sialoadhesin by NMR and Site-Directed Mutagenesis", Biochemical Journal, vol. 341, 1999, pp. 355-361.
Crocker et al., "Siglecs and Their Roles in the Immune System", Nature Reviews, Immunology, vol. 7, Apr. 2007, pp. 255-266.
Crocker et al., "Siglecs, Sialic Acids and Innate Immunity", Trends in Immunology, vol. 22, No. 6, Jun. 2001, pp. 337-342.
Cruts et al., "Loss of Progranulin Function in Frontotemporal Lobar Degeneration", Trends Genetics, vol. 24, No. 4, 2008, pp. 186-194.
Evans et al., "Establishment in Culture of Pluripotential Cells from Mouse Embryos", Nature, vol. 292, Jul. 9, 1981, pp. 154-156.
Gordon et al., "Genetic Transformation of Mouse Embryos by Microinjection of Purified DNA", Proceedings of the National Academy of Sciences, vol. 77, No. 12, Dec. 1980, pp. 7380-7384.
Gossler et al., "Transgenesis by Means of Blastocyst-Derived Embryonic Stem Cell Lines", Proceedings of the National Academy of Sciences, vol. 83, Dec. 1986, pp. 9065-9069.
Götz et al., "Animal Models for Alzheimer's Disease and Frontotemporal Dementia: A Perspective", ASN Neuro, vol. 1, No. 4, 2009, pp. 251-264.
Götz et al., "Animal Models of Alzheimer's Disease and Frontotemporal Dementia", Nature Reviews Neuroscience, vol. 9, Jul. 2008, pp. 532-544.
Gunten et al., "Basic and Clinical Immunology of Siglecs", Annals of the New York Academy of Sciences, vol. 1143, Nov. 2008, pp. 61-82.
Harrington et al., "Secreted proNGF is a Pathophysiological Death-Inducing Ligand after Adult CNS Injury", PNAS, vol. 101, No. 16, Apr. 20, 2004, pp. 6226-6230.
Hutton et al., "Association of Missense and 5'-Splice-Site Mutations in Tau with the Inherited Dementia FTDP-17", Nature, vol. 393, Jun. 18, 1998, pp. 702-705.
Koson et al., "Truncated Tau Expression Levels Determine Life Span of a Rat Model of Tauopathy without Causing Neuronal Loss or Correlating with Terminal Neurofibrillary Tangle Load", European Journal of Neuroscience, vol. 28, 2008, pp. 239-246.
Laird et al., "Progranulin is Neurotrophic in Vivo and Protects against a Mutant TDP-43 Induced Axonopathy", PLoS One, vol. 5, No. 10, Oct. 2010, pp. 1-7.
Lo, Cecilia W., "Transformation by Iontophoretic Microinjection of DNA: Multiple Integrations without Tandem Insertions", Molecular and Cellular Biology, vol. 3, 1983, pp. 1803-1814.
Luk et al., "Pathological α-Synuclein Transmission Initiates Parkinson-like Neurodegeneration in Non-transgenic Mice", Science, vol. 338, Nov. 16, 2012, pp. 949-953.
Macauley et al., "Siglec-Mediated Regulation of Immune Cell Function in Disease", Nature Reviews Immunology, vol. 14, No. 10, Oct. 2014, pp. 653-666.
May et al., "Crystal Structure of the N-Terminal Domain of Sialoadhesin in Complex with 3' Sialyllactose at 1.85 Å Resolution", Molecular Cell, vol. 1, Apr. 1998, pp. 719-728.
McMillan et al., "CD33-Related Sialic-Acid-Binding Immunoglobulin-Like Lectins in Health and Disease", Carbohydrate Research, vol. 343, 2008, pp. 2050-2056.
Neary et al., "Frontotemporal Lobar Degeneration: A Consensus on Clinical Diagnostic Criteria", Neurology, vol. 51, Dec. 1998, pp. 1546-1554.
Neumann et al., "TDP-43 Proteinopathy in Frontotemporal Lobar Degeneration and Amyotrophic Lateral Sclerosis", Arch Neurol., vol. 64, No. 10, Oct. 2007, pp. 1388-1394.
O'Reilly et al., "Siglecs as Targets for Therapy in Immune Cell Mediated Disease", Trends Pharmacol Sci., vol. 30, No. 5, May 2009, pp. 240-248.
Philips et al., "Rodent Models of Amyotrophic Lateral Sclerosis", Current Protocols in Pharmacology, vol. 69, 2016, pp. 1-26.
Putten et al., "Efficient Insertion of Genes into the Mouse Germ Line via Retroviral Vectors", Proceedings of the National Academy of Sciences USA, vol. 82, 1985, pp. 6148-6152.
Ramaswamy et al., "Animal Models of Huntington's Disease", ILAR Journal, vol. 48, No. 4, 2007, pp. 356-373.
Ratnavalli et al., "The Prevalence of Frontotemporal Dementia", Neurology, vol. 58, 2002, pp. 1615-1621.
Robertson et al., "Germ-Line Transmission of Genes Introduced into Cultured Pluripotential Cells by Retroviral Vector", Nature, vol. 323, Oct. 2, 1986, pp. 445-448.
Schymick et al., "Progranulin Mutations and Amyotrophic Lateral Sclerosis or Amyotrophic Lateral Sclerosis—Frontotemporal Dementia Phenotypes", Journal of Neurology, Neurosurgery and Psychiatry, vol. 78, 2007, pp. 754-756.
Svennerholm, Lars, "The Gangliosides", Journal of Lipid Research, vol. 5, 1964, pp. 144-155.
Thompson et al., "Germ Line Transmission and Expression of a Corrected HPRT Gene Produced by Gene Targeting in Embryonic Stem Cells", Cell, vol. 56, Jan. 27, 1989, pp. 313-321.
Varki et al., "Siglecs—The Major Subfamily of I-Type Lectins", Glycobiology, vol. 16, No. 1, 2006, pp. 1R-27R.

\* cited by examiner

FIG. 2

| Receptor | Fluorophore | Cell Type |
|---|---|---|
| Live Cells | Aqua Dye | Exclude Dead Cells |
| mCD3 | PerCp-Cy5.5 | T-cells |
| mCD11b | Pacific Blue | Myeloid |
| mNK1.1 | APC-Cy7 | Natural Killer Cells |
| mLy6G | PE-Cy7 | Neutrophils/G-MDSC |
| mLy6C | Alexa 488 | Mono/Macrophage/Neutrophil/Mo-MDSC |
| hCD33 | APC | Alector BAC-Tg Target Myeloid/MDSC |
| hSiglec-7 or 9 | PE | Alector BAC-Tg Target Myeloid/MDSC |

FIG. 8

| Receptor | Fluorophore | Cell Type |
|---|---|---|
| Live Cells | Aqua Dye | Exclude Dead Cells |
| mCD11b | PerCpCy5.5 | Microglia High |
| mCD45 | PE-Cy7 | Microglia Mid |
| mF4/80 | Pacific Blue | Microglia+ |
| hCD33 | APC | Alector BAC-Tg Target |

FIG. 22

SIGLEC TRANSGENIC MICE AND METHODS OF USE THEREOF

CROSS-REFERENCE TO RELATED APPLICATIONS

This application claims the benefit of U.S. Provisional Application No. 62/431,661, filed Dec. 8, 2016, the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022001300SEQLIST.txt, date recorded: Nov. 28, 2017, size: 133 KB).

FIELD OF THE INVENTION

The present disclosure relates to transgenic non-human animals whose genomes comprise two or more human genes selected from CD33, Siglec-5, Siglec-7, Siglec-9, Siglec-11, Siglec-14, and Siglec-16, and to uses of such transgenic non-human animals.

BACKGROUND

Sialic acid-binding Ig-like lectinproteins (Siglecs) are type 1, immunoglobulin-like, transmembrane proteins expressed on immune and hematopoietic cells, including immature and mature myeloid cells, such as monocytes, macrophages, dendritic cells, neutrophils, and microglial cells, as well as lymphoid cells, such as natural killer cells, and subsets of T cells (Crocker et al. (2007) Nat Rev Immunol. 7:255-266; O'Reilly and Paulson (2009) Trends in Pharm. Sci. 30:5:240-248; and Macauley et al. (2014) Nat. Rev. Imm 14: 653-666). The Siglec family of lectins binds sialic acid residues of glycoproteins and glycolipids. One potential glycolipid binding target for Siglec proteins is gangliosides; that is, glycolipids that consist of a ceramide linked to a sialylated glycan. Most gangliosides share a common lacto-ceramide core and one or more sialic acid residues. Diversity in the Siglec ligands is generated by the addition of other neutral sugars and sialic acid in different linkages, either branched or terminal, and modification of sialic acid itself.

Fourteen Siglec proteins have been identified in humans and nine in mice that are comprised of 2-17 extracellular Ig domains including an amino-terminal V-set domain that contains the sialic acid-binding site. These include CD33 (also known as Siglec-3), Siglec-5, Siglec-7, Siglec-9, and Siglec-11. These proteins have been implicated in immune system function in health and disease. The sialic acid-binding region is located on the V-set Ig-like domain, which contains a two aromatic residues and one arginine motif highly conserved in all Siglecs (Crocker et al. (2007) Nat Rev Immunol. 7:255-266; McMillan and Crocker (2008) Carbohydr Res. 343:2050-2056; Von Gunten and Bochner (2008) Ann NY Acad Sci. 1143:61-82; May et al. (1998) Mol Cell. 1:719-728; Crocker et al. (1999) Biochem J. 341:355-361; and Crocker and Varki (2001) Trends Immunol. 2:337-342). The binding sites to sialylated ligands have been mapped by crystal structures with and without ligand bound (Attrill et al., (2006) J. Biol. Chem. 281 32774-32783; Alphey et al. (2003) J. Biol. Chem. 278:5 3372-3377; Varki et al., Glycobiology, 16 pp. 1R-27R; and May et al. (1998) Mol. Cell 1:5:719-728). Since cell membranes are rich in sialic acids, ligand binding by Siglecs can occur in cis and in trans, both affecting their functional properties. Each Siglec has a distinct preference for binding the diverse types of sialylated glycans that are found on the surface of mammalian cells (Crocker et al. (2007) Nat Rev Immunol. 7:255-266; and Crocker et al. (2007) Nat Rev Immunol. 7:255-266). Most Siglec proteins, including CD33, Siglec-7 and Siglec-9, contain one or more immunoreceptor tyrosine-based inhibitory motif (ITIM) sequences in their cytoplasmic tails, which enable them as inhibitory receptors and negative regulators of immune functions through recruitment of the tyrosine phosphatases SHP1 and SHP2 (Crocker et al. (2007) Nat Rev Immunol. 7:255-266; McMillan and Crocker (2008) Carbohydr Res. 343:2050-2056; and Von Gunten and Bochner (2008) Ann NY Acad Sci. 1143:61-82). Certain Siglecs contain immunoreceptor tyrosine-based activating motif (ITAM) sequences in their cytoplasmic tails, which enable them to act as activating receptors and positive regulators of immune function through predicted recruitment of spleen tyrosine kinase (Syk) (Macauley S M. et al., (2014) *Nature Reviews Immunology* 14, 653-666). The Siglec protein family is associated with multiple human diseases including, autoimmunity, susceptibility to infection, multiple types of cancer including lymphoma, leukemia and acute myeloid leukemia, systemic lupus erythematosus, rheumatoid arthritis, neurodegenerative disorders, asthma, allergy, sepsis, chronic obstructive pulmonary disease, graft-versus-host disease, eosinophilia, and osteoporosis (Macauley S M. et al., (2014) *Nature Reviews Immunology* 14, 653-666).

Genome-wide association studies (GWAS) performed on extended cohorts (e.g., thousands of individuals) identified two single nucleotide polymorphism (SNP) variants, rs3865444$^C$ (also known as rs3826656) and rs3865444$^A$, in CD33 as genetic modulators of risk for late onset Alzheimer's disease (AD). The minor allele rs3865444$^A$ SNP has been associated with significantly reduced CD33 protein levels and was reported to confer protection against AD. In contrast, the rs3865444$^C$ risk allele has been associated with a 7-fold increase in cell surface expression of CD33 in the monocytes of young and older individuals homozygous for this allele, while the heterozygous carriers of the rs3865444$^{AC}$ variant displayed a 3-4 fold increase in CD33 cell surface expression. CD33 is also expressed at all three stages of activation in microglia and macrophages in the human brain, but there is no effect of age on CD33 surface expression. rs3865444$^C$ homozygosity and heterozygosity were also associated with reduced phagocytic ability of monocyte internalization of amyloid beta 42 (Abeta 42) peptide, accumulation of neuritic amyloid pathology and fibrillar amyloid on in vivo imaging, and increased numbers of activated human microglia that may be less functional and fail to clear amyloid beta plaques, indicating that the rs3865444 allele may be dominant for functional traits and have a role in amyloid accumulation in the presymptomatic phase of Alzheimer's disease (AD). CD33 mRNA and protein levels as well as the number of CD33-positive microglia were shown to increase in AD brains relative to age-matched controls. However, AD brains from carriers of the rs3865444$^{AA}$ allele of the CD33 SNP rs3865444, were still associated with lower levels of both CD33 microglial expression and the levels of insoluble Abeta 42 peptide compared to AD brains from carrier of the rs3865444$^C$ non-protective allele. Increased number of CD33-immunoreactive microglia was shown to be positively correlated with insoluble Abeta 42 levels and the amyloid plaque burden in AD cases.

While Siglec proteins, including CD33, are known to be associated with multiple human diseases, in vivo study of these proteins, and their potential roles in human disease, remains challenging as no suitable animal model for studying human Siglecs has been developed. A major limitation in developing animal models useful for the study of in vivo Siglec protein functions is that mammalian Siglecs, such as CD33, are highly divergent evolutionarily. This high evolutionary divergence observed between mammalian Siglecs indicates that key features of the human Siglecs, such as ITIM and ligand binding domains, may not be structurally conserved. Moreover, expression patterns and protein-protein interactions of the human Siglecs, including physical associations among Siglec proteins, may not be conserved in other mammalian species. Due to the high likelihood of both structural and functional differences in mammalian Siglec proteins, indicated by low evolutionary conservation of these proteins across mammalian species, current animal models are unsuitable proxies for the in vivo study of the functions and interactions of human Siglec proteins, as well as their role in human diseases.

All references cited herein, including patent applications, patent publications, and non-patent literature are herein incorporated by reference in their entirety, as if each individual reference were specifically and individually indicated to be incorporated by reference.

BRIEF SUMMARY

There is a need for suitable animal models useful for the in vivo study of human Siglec protein functions, including animal models coordinately expressing multiple human Siglec proteins in relevant cell types. Additionally, there is a need for animal models suitable for testing candidate agents targeting human Siglec proteins in vivo, and for animal disease models which express some or all of the human Siglec genes to study the association of various human Siglec proteins and disease (e.g., Alzheimer's disease and cancer). Accordingly, the present disclosure relates, in part, to transgenic non-human animals (e.g., mice) harboring multiple human Siglec genes which effectively express human Siglec proteins in myeloid and/or natural killer (NK) cell lineages. These transgenic animals are useful for the investigation and establishment of functional and pathological properties of human Siglec genes in vivo, and to the development of therapeutics that target human Siglec genes and their products. The present disclosure is based, in part, on the surprising finding that transgenic animals were generated that coordinately expressed multiple human Siglec proteins (See e.g., Examples 1 and 2), and further, that expression of these Siglec proteins in the transgenic animals at least partially recapitulated the highly coordinated expression pattern of these proteins observed with the relevant corresponding human cells (See e.g., Examples 2 and 3).

Accordingly, certain aspects of the present disclosure relate to a transgenic non-human animal whose genome comprises two or more human genes, wherein the two or more human genes are selected from the group consisting of CD33, Siglec-5, Siglec-7, Siglec-9, Siglec-11, Siglec-14, and Siglec-16, wherein the two or more human genes are expressed in one or more cells of the transgenic non-human animal, and wherein the one of more cells selected from the group consisting of myeloid cells, natural killer (NK) cells, T cells, microglia, and any combination thereof.

In some embodiments that may be combined with any of the preceding embodiments, the transgenic non-human animal is a rodent. In some embodiments that may be combined with any of the preceding embodiments, the transgenic non-human animal is a mouse. In some embodiments that may be combined with any of the preceding embodiments, the genome comprises the human genes Siglec-5 and Siglec-14. In some embodiments that may be combined with any of the preceding embodiments, the genome comprises the human genes Siglec-11 and Siglec-16. In some embodiments that may be combined with any of the preceding embodiments, the genome comprises at least three human genes. In some embodiments that may be combined with any of the preceding embodiments, the genome comprises the human genes CD33, Siglec-7, and Siglec-9. In some embodiments that may be combined with any of the preceding embodiments, the genome comprises the human genes CD33, Siglec-5, Siglec-7, Siglec-9, Siglec-11, Siglec-14, and Siglec-16. In some embodiments that may be combined with any of the preceding embodiments, one or more of the human genes comprise all intronic and exonic sequences of the one or more genes. In some embodiments that may be combined with any of the preceding embodiments, one or more of the human genes comprise at least one flanking sequence at the 5' and/or 3' end of the one or more genes. In some embodiments that may be combined with any of the preceding embodiments, the flanking sequence is at least 10,000 base pairs in length. In some embodiments that may be combined with any of the preceding embodiments, the flanking sequence comprises one or more human transcriptional regulatory elements. In some embodiments that may be combined with any of the preceding embodiments, the one or more human transcriptional regulatory elements directs expression of one or more of the human CD33, Siglec-5, Siglec-7, Siglec-9, Siglec-11, Siglec-14, and/or Siglec-16 genes. In some embodiments that may be combined with any of the preceding embodiments, the one or more human transcriptional regulatory elements directs coordinate expression of at least two of the human CD33, Siglec-5, Siglec-7, Siglec-9, Siglec-11, Siglec-14, and/or Siglec-16 genes. In some embodiments that may be combined with any of the preceding embodiments, the human CD33 gene encodes a polypeptide at least 95% identical to a polypeptide encoded by the nucleic acid sequence of SEQ ID NO: 15. In some embodiments that may be combined with any of the preceding embodiments, the human CD33 gene encodes a polypeptide at least 95% identical to a sequence selected from the group consisting of SEQ ID NOS: 1-3. In some embodiments that may be combined with any of the preceding embodiments, the human CD33 gene comprises one or more single nucleotide polymorphisms (SNPs) selected from the group consisting of: (a) SNP rs3865444$^{AC}$; (b) SNP rs3865444$^{CC}$; (c) SNP rs3865444$^{AA}$; (d) SNP rs35112940$^{GG,\ AA,\ AG}$; (e) SNP rs12459419$^{CC,\ CT\ or\ TT}$; and (f) any combination thereof. In some embodiments that may be combined with any of the preceding embodiments, the human Siglec-5 gene encodes a polypeptide at least 95% identical to a polypeptide encoded by the nucleic acid sequence of SEQ ID NO: 16. In some embodiments that may be combined with any of the preceding embodiments, the human Siglec-5 gene encodes a polypeptide at least 95% identical to SEQ ID NO: 4. In some embodiments that may be combined with any of the preceding embodiments, the human Siglec-7 gene encodes a polypeptide at least 95% identical to a polypeptide encoded by the nucleic acid sequence of SEQ ID NO: 17. In some embodiments that may be combined with any of the preceding embodiments, the human Siglec-7 gene encodes a polypeptide at least 95% identical to a sequence selected from the group consisting of SEQ ID NOS: 5-8. In some embodiments that may be combined with any of the preceding embodiments, the human Siglec-9 gene encodes a polypeptide at least 95% identical to a polypeptide encoded by the nucleic acid sequence of SEQ ID NO: 18. In some embodiments that may be combined with any of the preceding embodiments, the human Siglec-9 gene encodes a polypeptide at least 95% identical to SEQ ID NO: 9 or SEQ ID NO: 10. In some embodiments that may be combined with any of the preceding embodiments, the human Siglec-11 encodes a polypeptide at least 95% identical to a polypeptide encoded by the nucleic acid sequence of SEQ ID NO: 19. In some embodiments that may be combined with any of the preceding embodiments, the human Siglec-11 gene encodes a polypeptide at least 95% identical to SEQ ID NO: 11 or SEQ ID NO: 12. In some embodiments that may be combined with any of the preceding embodiments, the human Siglec-14 gene encodes a polypeptide at least 95% identical to a polypeptide encoded by the nucleic acid sequence of SEQ ID NO: 20. In some embodiments that may be combined with any of the preceding embodiments, the human Siglec-14 gene encodes a polypeptide at least 95% identical to SEQ ID NO: 13. In some embodiments that may be combined with any of the preceding embodiments, the human Siglec-16 gene encodes a polypeptide at least 95% identical to a polypeptide encoded by the nucleic acid sequence of SEQ ID NO: 21. In some embodiments that may be combined with any of the preceding embodiments, the human Siglec-16 gene encodes a polypeptide at least 95% identical to SEQ ID NO: 14. In some embodiments that may be combined with any of the preceding embodiments, the myeloid cells are selected from the group consisting of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments that may be combined with any of the preceding embodiments, the NK cells are selected from the group consisting of M1 NK cells, activated M1 NK cells, M2 NK cells, and any combination thereof. In some embodiments that may be combined with any of the preceding embodiments, the T cells are selected from the group consisting of T helper cells, cytotoxic T cells, regulatory T cells (Tregs), and any combination thereof. In some embodiments that may be combined with any of the preceding embodiments, the microglia are selected from the group consisting of brain microglial, M1 microglia, activated M1 microglia, M2 microglia, and any combination thereof. In some embodiments that may be combined with any of the preceding embodiments, expression of the two or more human genes in the one or more cells of the transgenic non-human animal recapitulates the expression pattern of the two or more human genes in a corresponding human cell. In some embodiments that may be combined with any of the preceding embodiments, the one or more cells of the transgenic non-human animal are one or more cells selected from the group consisting of monocytes, macrophages, dendritic cells, and microglia. In some embodiments that may be combined with any of the preceding embodiments, the corresponding human cell is a human cell selected from the group consisting of a monocyte, a macrophage, a dendritic cell, and a microglial cell. In some embodiments that may be combined with any of the preceding embodiments, the two or more human genes are co-expressed. In some embodiments that may be combined with any of the preceding embodiments, co-expression of the two or more human genes suppresses one or more myeloid immune cell functions. In some embodiments that may be combined with any of the preceding embodiments, the one or more myeloid immune cell functions are selected from the group consisting of: (a) phagocytosis; (b) antigen presentation; (c) immune cell recruitment; (d) immune cell maturation, migration, proliferation, differentiation, and/or survival; (e) modulation of adaptive immune cells such as B cells and T cells; (f) expression and/or secretion of one or more cytokines and/or chemokines; (g) tumor infiltration, tumor cell recognition, and/or tumor cell killing; (h) releasing granules (degranulation) or neutrophil extracellular traps (NETs); (i) anti-parasitic activities; (j) bactericidal activities; (k) clearance of cellular debris and/or protein aggregates; and (l) any combination thereof. In some embodiments that may be combined with any of the preceding embodiments, expression of the two or more human genes humanizes the Siglec repertoire on the one or more cells of the transgenic non-human animal. In some embodiments that may be combined with any of the preceding embodiments, the mouse comprises a genome comprising one or more non-functional murine genes, wherein the one or more non-functional murine genes are selected from the group consisting of murine CD33, murine Siglec-5, murine Siglec-7, murine Siglec-9, murine Siglec-11, and any combination thereof. In some embodiments that may be combined with any of the preceding embodiments, the mouse comprises a genome comprising a non-functional murine CD33 gene, a non-functional murine Siglec-5 gene, a non-functional murine Siglec-7 gene, a non-functional murine Siglec-9 gene, and a non-functional murine Siglec-11 gene. In some embodiments that may be combined with any of the preceding embodiments, the transgenic non-human animal is predisposed to develop one or more diseases. In some embodiments that may be combined with any of the preceding embodiments, the transgenic non-human animal is treated or interbred to generate one or more animal disease models. In some embodiments that may be combined with any of the preceding embodiments, the one or more diseases are selected from the group consisting of neurodegenerative diseases, immune-related diseases, infectious diseases, and proliferative disorders. In some embodiments that may be combined with any of the preceding embodiments, the neurodegenerative diseases are one or more diseases selected from the group consisting of dementia, frontotemporal dementia (FTD), Alzheimer's disease, Parkinson's disease, amyotrophic lateral sclerosis (ALS), Huntington's disease, taupathy disease, and multiple sclerosis. In some embodiments that may be combined with any of the preceding embodiments, the disease is Alzheimer's disease.

Other aspects of the present disclosure relate to a method of screening candidate agents, the method comprising i) administering one or more candidate agents to a transgenic non-human animal, wherein the genome of the transgenic non-human animal comprises two or more human genes, wherein the two or more human genes are selected from the group consisting of CD33, Siglec-5, Siglec-7, Siglec-9, Siglec-11, Siglec-14, and Siglec-16, wherein the two or more human genes are expressed in one or more cells of the transgenic non-human animal, and wherein the one or more cells selected from the group consisting of myeloid cells, natural killer (NK) cells, T cells, microglia, and any combination thereof; and ii) determining whether the one or more candidate agents bind to and/or modulates the function and/or activity of at least one of the two or more human genes in the transgenic non-human animal.

Other aspects of the present disclosure relate to a method of screening candidate agents, the method comprising i) administering one or more candidate agents to a transgenic non-human animal, wherein the genome of the transgenic non-human animal comprises two or more human genes, wherein the two or more human genes are selected from the group consisting of CD33, Siglec-5, Siglec-7, Siglec-9, Siglec-11, Siglec-14, and Siglec-16, wherein the two or more human genes are expressed in one or more cells of the transgenic non-human animal, and wherein the one of more cells selected from the group consisting of myeloid cells, natural killer (NK) cells, T cells, microglia, and any combination thereof; and ii) determining the effect of the one or more candidate agents on one or more activities and/or functions associated with the expression of at least one of the two or more human genes in the transgenic non-human animal.

In some embodiments that may be combined with any of the preceding embodiments, the candidate agent inhibits one or more activities and/or functions associated with the expression of human CD33, human Siglec-5, human Siglec-7, human Siglec-9, human Siglec-11, human Siglec-14, and/or human Siglec-16 genes in the transgenic non-human animal. In some embodiments that may be combined with any of the preceding embodiments, the one or more candidate agents are two or more candidate agents. In some embodiments that may be combined with any of the preceding embodiments, the two or more candidate agents target two or more of the human genes. In some embodiments that may be combined with any of the preceding embodiments, each of the two or more candidate agents targets a human gene selected from the group consisting of CD33, Siglec-5, Siglec-7, Siglec-9, Siglec-11, Siglec-14, and Siglec-16, and wherein each of the two or more candidate agents targets a different human gene. In some embodiments that may be combined with any of the preceding embodiments, the one or more activities and/or functions associated with expression of the two or more human genes are selected from the group consisting of: (a) immune cell suppression; (b) decreased expression of one or more pro-inflammatory cytokines, optionally wherein the one or more pro-inflammatory cytokines are selected from a group consisting IFN-a4, IFN-beta, IL-1β, IL-1alpha, TNF-α, IL-6, IL-8, CRP, IL-20 family members, LIF, IFN-gamma, OSM, CNTF, GM-CSF, IL-11, IL-12, IL-17, IL-18, CRP, MCP-1, and MIP-1-beta; (c) decreased expression of one or more pro-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; (d) increased expression of one or more anti-inflammatory cytokines, optionally wherein the one or more anti-inflammatory cytokines are selected from the group consisting of IL4, IL10, IL13, IL35, IL16, TGF-beta, IL1ra, G-CSF, and soluble receptors for TNF, IFN-beta1a, IFN-beta1b, and IL6; (e) increased expression of one or more anti-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; (f) inhibition of extracellular signal-regulated kinase (ERK) phosphorylation; (g) decreasing tyrosine phosphorylation on one or more cellular proteins, optionally, wherein the one or more cellular proteins comprise ZAP-70 and the tyrosine phosphorylation occurs on Tyr-319 of ZAP-70; (h) decreased expression of C—C chemokine receptor 7 (CCR7); (i) inhibition of microglial cell chemotaxis toward CCL19-expressing and CCL21-expressing cells; (j) decreasing T cell proliferation induced by one or more cells selected from the group consisting of dendritic cells, bone marrow-derived dendritic cells, monocytes, microglia, M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells; (k) inhibition of osteoclast production, decreased rate of osteoclastogenesis, or both; (l) decreasing survival of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (m) decreasing proliferation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (n) inhibiting migration of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (o) inhibiting one or more functions of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (p) inhibiting maturation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (q) inhibition of one or more types of clearance selected from the group consisting of apoptotic neuron clearance, nerve tissue debris clearance, non-nerve tissue debris clearance, bacteria clearance, other foreign body clearance, disease-causing protein clearance, disease-causing peptide clearance, and tumor cell clearance; optionally wherein the disease-causing protein is selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; (r) inhibition of phagocytosis of one or more of apoptotic neurons, nerve tissue debris, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; (s) inhibition of tumor cell killing by one or more of microglia, macrophages, neutrophils, NK cells, dendritic cells, bone marrow-derived dendritic cells, neutrophils, T cells, T helper cells, or cytotoxic T cells; (t) inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; (u) inhibition of anti-tumor cell metastasis activity of one or more of microglia, macrophages, neutrophils, NK cells, dendritic cells, bone marrow-derived dendritic cells, neutrophils, T cells, T helper cells, or cytotoxic T cells; (v) inhibition of one or more ITAM motif containing receptors, optionally wherein the one or more ITAM motif containing receptors are selected from the group consisting of TREM1, TREM2, Sirp beta, FcgR, DAP10, and DAP12; (w) inhibition of signaling by one or more pattern recognition receptors (PRRs), optionally wherein the one or more PRRs are selected from the group consisting of receptors that identify pathogen-associated molecular patterns (PAMPs), receptors that identify damage-associated molecular patterns (DAMPs), and any combination thereof; (x) inhibition of one or more receptors comprising the motif D/Ex$_{0\ 2}$YxxL/IX$_{6\ 8}$YxxL/I (SEQ ID NO: 22); (y) inhibition of signaling by one or more Toll-like receptors; (z) inhibition of the JAK-STAT signaling pathway; (aa) inhibition of nuclear factor kappa-light-chain-enhancer of activated B cells (NFκB); (bb) de-phosphorylation of an ITAM motif containing receptor; (cc) decreased expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; (dd) decreasing expression of one or more ITAM-dependent genes, optionally wherein the one or more ITAM-dependent genes are activated by nuclear factor of activated T cells (NFAT) transcription factors; (ee) promoting differentiation of one or more of immunosuppressor dendritic cells, immunosuppressor macrophages, immunosuppressor neutrophils, immunosuppressor NK cells, myeloid derived suppressor cells, tumor-associated macrophages, tumor-associated neutrophils, tumor-associated NK cells, and regulatory T cells; (ff) rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; (gg) increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; (hh) increasing the number of tumor-promoting myeloid/granulocytic immune-suppressive cells in a tumor, in peripheral blood, or other lymphoid organ; (ii) enhancing tumor-promoting activity of myeloid-derived suppressor cells; (jj) increasing expression of tumor-promoting cytokines in a tumor or in peripheral blood, optionally wherein the tumor-promoting cytokines are TGF-beta or IL-10; (kk) increasing tumor infiltration of tumor-promoting FoxP3+ regulatory T lymphocytes; (ll) enhancing tumor-promoting activity of myeloid-derived suppressor cells (MDSC); (mm) decreasing activation of tumor-specific T lymphocytes with tumor killing potential; (nn) decreasing infiltration of tumor-specific NK cells with tumor killing potential; (oo) decreasing the tumor killing potential of NK cells; (pp) decreasing infiltration of tumor-specific B lymphocytes with potential to enhance immune response; (qq) decreasing infiltration of tumor-specific T lymphocytes with tumor killing potential; (rr) increasing tumor volume; (ss) increasing tumor growth rate; (tt) increasing metastasis; (uu) increasing rate of tumor recurrence; (vv) decreasing efficacy of one or more immune-therapies that modulate anti-tumor T cell responses, optionally wherein the one or more immune-therapies are immune-therapies that target one or more target proteins selected from the group consisting of PD1/PDL1, CTLA4, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, and any combination thereof, or cancer vaccines; (ww) inhibition of PLCγ/PKC/calcium mobilization; (xx) inhibition of PI3K/Akt, Ras/MAPK signaling; and (yy) any combination thereof. In some embodiments that may be combined with any of the preceding embodiments, the transgenic non-human animal suffers from a disease, disorder, and/or injury. In some embodiments that may be combined with any of the preceding embodiments, administering the one or more candidate agents reduces or eliminates one or more signs and/or symptoms of the disease, disorder, and/or injury. In some embodiments that may be combined with any of the preceding embodiments, the disease, disorder, and/or injury is one or more of autoimmunity, susceptibility to infection, cancer, proliferative disorders, and neurodegenerative disorders. In some embodiments that may be combined with any of the preceding embodiments, the disease, disorder, and/or injury is one or more of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV infection, and Haemophilus influenza infection. In some embodiments that may be combined with any of the preceding embodiments, the effect of the one or more candidate agents is selected from the group consisting of: (a) reducing cell surface levels of one or more polypeptides encoded by the human CD33, Siglec-5, Siglec-7, Siglec-9, Siglec-11, Siglec-14, or Siglec-16 genes; (b) competing for binding with a natural ligand of one or more polypeptides encoded by the human CD33, Siglec-5, Siglec-7, Siglec-9, Siglec-11, Siglec-14, or Siglec-16 genes; (c) reducing T cell proliferation and/or phagocytosis; (d) increasing the survival of macrophages, neutrophils, NK cells, and/or dendritic cells; (e) inducing CCR7 and/or F-actin in microglia, macrophages, neutrophils, NK cells, and/or dendritic cells; (f) increasing expression of one or more inflammatory cell surface markers on macrophages, neutrophils, and/or NK cells; (g) suppressing myeloid-derived suppressor cell (MDSC) proliferation, activation, and/ or function; (h) reducing IL-10 secretion from one or more myeloid cells; (i) inducing SYK and/or ERK activation and/or phosphorylation; and (j) any combination thereof. In some embodiments that may be combined with any of the preceding embodiments, the transgenic non-human animal is a rodent. In some embodiments that may be combined with any of the preceding embodiments, the transgenic non-human animal is a mouse. In some embodiments that may be combined with any of the preceding embodiments, the genome comprises the human genes Siglec-5 and Siglec-14. In some embodiments that may be combined with any of the preceding embodiments, the genome comprises the human genes Siglec-11 and Siglec-16. In some embodiments that may be combined with any of the preceding embodiments, the genome comprises three or more human genes. In some embodiments that may be combined with any of the preceding embodiments, the genome comprises the human genes CD33, Siglec-7, and Siglec-9. In some embodiments that may be combined with any of the preceding embodiments, the genome comprises the human genes CD33, Siglec-5, Siglec-7, Siglec-9, Siglec-11, Siglec-14, and Siglec-16. In some embodiments that may be combined with any of the preceding embodiments, one or more of the human genes comprise all intronic and exonic sequences of the one or more genes. In some embodiments that may be combined with any of the preceding embodiments, one or more of the human genes comprise at least one flanking sequence at the 5' and/or 3' end of the one or more genes. In some embodiments that may be combined with any of the preceding embodiments, the flanking sequence is at least 10,000 base pairs in length. In some embodiments that may be combined with any of the preceding embodiments, the flanking sequence comprises one or more human transcriptional regulatory elements. In some embodiments that may be combined with any of the preceding embodiments, the one or more human transcriptional regulatory elements direct expression of one or more of human CD33, Siglec-5, Siglec-7, Siglec-9, Siglec-11, Siglec-14, and/or Siglec-16 genes. In some embodiments that may be combined with any of the preceding embodiments, the one or more human transcriptional regulatory elements direct coordinate expression of two or more of human CD33, Siglec-5, Siglec-7, Siglec-9, Siglec-11, Siglec-14, and/or Siglec-16 genes. In some embodiments that may be combined with any of the preceding embodiments, the human CD33 encodes a polypeptide at least 95% identical to a polypeptide encoded by the nucleic acid sequence of SEQ ID NO: 15. In some embodiments that may be combined with any of the preceding embodiments, the human CD33 gene encodes a polypeptide at least 95% identical to a sequence selected from the group consisting of SEQ ID NOS: 1-3. In some embodiments that may be combined with any of the preceding embodiments, the human CD33 gene comprises one or more single nucleotide polymorphisms (SNPs) selected from the group consisting of: (a) SNP rs3865444$^{AC}$; (b) SNP rs3865444$^{CC}$; (c) SNP rs3865444$^{AA}$; (d) SNP rs35112940$^{GG, AA, AG}$; (e) SNP rs12459419$^{CC, CT\ or\ TT}$; and (f) any combination thereof. In some embodiments that may be combined with any of the preceding embodiments, the human Siglec-5 gene encodes a polypeptide at least 95% identical to a polypeptide encoded by the nucleic acid sequence of SEQ ID NO: 16. In some embodiments that may be combined with any of the preceding embodiments, the human Siglec-5 gene encodes a polypeptide at least 95% identical to SEQ ID NO: 4. In some embodiments that may be combined with any of the preceding embodiments, the human Siglec-7 gene encodes a polypeptide at least 95% identical to a polypeptide encoded by the nucleic acid sequence of SEQ ID NO: 17. In some embodiments that may be combined with any of the preceding embodiments, the human Siglec-7 gene encodes a polypeptide at least 95% identical to a sequence selected from the group consisting of SEQ ID NOS: 5-8. In some embodiments that may be combined with any of the preceding embodiments, the human Siglec-9 gene encodes a polypeptide at least 95% identical to a polypeptide encoded by the nucleic acid sequence of SEQ ID NO: 18. In some embodiments that may be combined with any of the preceding embodiments, the human Siglec-9 gene encodes a polypeptide at least 95% identical to SEQ ID NO: 9 or SEQ ID NO: 10. In some embodiments that may be combined with any of the preceding embodiments, the human Siglec-11 encodes a polypeptide at least 95% identical to a polypeptide encoded by the nucleic acid sequence of SEQ ID NO: 19. In some embodiments that may be combined with any of the preceding embodiments, the human Siglec-11 gene encodes a polypeptide at least 95% identical to SEQ ID NO: 11 or SEQ ID NO: 12. In some embodiments that may be combined with any of the preceding embodiments, the human Siglec-14 gene encodes a polypeptide at least 95% identical to a polypeptide encoded by the nucleic acid sequence of SEQ ID NO: 20. In some embodiments that may be combined with any of the preceding embodiments, the human Siglec-14 gene encodes a polypeptide at least 95% identical to SEQ ID NO: 13. In some embodiments that may be combined with any of the preceding embodiments, the human Siglec-16 gene encodes a polypeptide at least 95% identical to a polypeptide encoded by the nucleic acid sequence of SEQ ID NO: 21. In some embodiments that may be combined with any of the preceding embodiments, the human Siglec-16 gene encodes a polypeptide at least 95% identical to SEQ ID NO: 14. In some embodiments that may be combined with any of the preceding embodiments, the myeloid cells are selected from the group consisting of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments that may be combined with any of the preceding embodiments, the NK cells are selected from the group consisting of M1 NK cells, activated M1 NK cells, M2 NK cells, and any combination thereof. In some embodiments that may be combined with any of the preceding embodiments, the T cells are selected from the group consisting of T helper cells, cytotoxic T cells, regulatory T cells (Tregs), and any combination thereof. In some embodiments that may be combined with any of the preceding embodiments, the microglia are selected from the group consisting of brain microglial, M1 microglia, activated M1 microglia, M2 microglia, and any combination thereof. In some embodiments that may be combined with any of the preceding embodiments, expression of the two or more human genes in the one or more cells of the transgenic non-human animal recapitulates the expression pattern of the two or more human genes in a corresponding human cell. In some embodiments that may be combined with any of the preceding embodiments, the one or more cells of the transgenic non-human animal are one or more cells selected from the group consisting of monocytes, macrophages, dendritic cells, and microglia. In some embodiments that may be combined with any of the preceding embodiments, the corresponding human cell is a human cell selected from the group consisting of a monocyte, a macrophage, a dendritic cell, and a microglial cell. In some embodiments that may be combined with any of the preceding embodiments, the two or more human genes are co-expressed. In some embodiments that may be combined with any of the preceding embodiments, co-expression of the two or more human genes suppresses one or more myeloid immune cell functions. In some embodiments that may be combined with any of the preceding embodiments, the one or more myeloid immune cell functions are selected from the group consisting of: (a) phagocytosis; (b) antigen presentation; (c) immune cell recruitment; (d) immune cell maturation, migration, proliferation, differentiation, and/or survival; (e) modulation of adaptive immune cells such as B cells and T cells; (f) expression and/or secretion of one or more cytokines and/or chemokines; (g) tumor infiltration, tumor cell recognition, and/or tumor cell killing; (h) releasing granules (degranulation) or neutrophil extracellular traps (NETs); (i) anti-parasitic activities; (j) bactericidal activities; (k) clearance of cellular debris and/or protein aggregates; and (l) any combination thereof. In some embodiments that may be combined with any of the preceding embodiments, expression of the two or more human genes humanizes the Siglec repertoire on the one or more cells of the transgenic non-human animal. In some embodiments that may be combined with any of the preceding embodiments, the mouse comprises a genome comprising one or more non-functional murine genes, wherein the one or more non-functional murine genes are selected from the group consisting of murine CD33, murine Siglec-5, murine Siglec-7, murine Siglec-9, murine Siglec-11, and any combination thereof. In some embodiments that may be combined with any of the preceding embodiments, the mouse comprises a genome comprising a non-functional murine CD33 gene, a non-functional murine Siglec-5 gene, a non-functional murine Siglec-7 gene, a non-functional murine Siglec-9 gene, and a non-functional murine Siglec-11 gene.

Other aspects of the present disclosure relate to a method for recapitulating a human Siglec immune system in a non-human animal, the method comprising generating a transgenic non-human animal whose genome comprises two or more human genes, wherein the two or more human genes are selected from the group consisting of CD33, Siglec-5, Siglec-7, Siglec-9, Siglec-11, Siglec-14, and Siglec-16, wherein the two or more human genes are coordinately expressed in one or more cells of the transgenic non-human animal, and wherein the one of more cells selected from the group consisting of myeloid cells, natural killer (NK) cells, T cells, microglia, and any combination thereof.

In some embodiments that may be combined with any of the preceding embodiments, the transgenic non-human animal is a rodent. In some embodiments that may be combined with any of the preceding embodiments, the transgenic non-human animal is a mouse. In some embodiments that may be combined with any of the preceding embodiments, the genome comprises the human genes Siglec-5 and Siglec-14. In some embodiments that may be combined with any of the preceding embodiments, the genome comprises the human genes Siglec-11 and Siglec-16. In some embodiments that may be combined with any of the preceding embodiments, the genome comprises three or more human genes. In some embodiments that may be combined with any of the preceding embodiments, the genome comprises the human genes CD33, Siglec-7, and Siglec-9. In some embodiments that may be combined with any of the preceding embodiments, the genome comprises seven human genes. In some embodiments that may be combined with any of the preceding embodiments, the genome comprises the human genes CD33, Siglec-5, Siglec-7, Siglec-9, Siglec-11, Siglec-14, and Siglec-16. In some embodiments that may be combined with any of the preceding embodiments, one or more of the human genes comprise all intronic and exonic sequences of the one or more genes. In some embodiments that may be combined with any of the preceding embodiments, one or more of the human genes comprise at least one flanking sequence at the 5' and/or 3' end of the one or more genes. In some embodiments that may be combined with any of the preceding embodiments, the flanking sequence is at least 10,000 base pairs in length. In some embodiments that may be combined with any of the preceding embodiments, the flanking sequence comprises one or more human transcriptional regulatory elements. In some embodiments that may be combined with any of the preceding embodiments, the one or more human transcriptional regulatory elements directs expression of one or more of human CD33, Siglec-5, Siglec-7, Siglec-9, Siglec-11, Siglec-14, and/or Siglec-16 genes. In some embodiments that may be combined with any of the preceding embodiments, the one or more human transcriptional regulatory elements directs coordinate expression of at least two of human CD33, Siglec-5, Siglec-7, Siglec-9, Siglec-11, Siglec-14, and/or Siglec-16 genes. In some embodiments that may be combined with any of the preceding embodiments, the human CD33 gene encodes a polypeptide at least 95% identical to a polypeptide encoded by the nucleic acid sequence of SEQ ID NO: 15. In some embodiments that may be combined with any of the preceding embodiments, the human CD33 gene encodes a polypeptide at least 95% identical to a sequence selected from the group consisting of SEQ ID NOS: 1-3. In some embodiments that may be combined with any of the preceding embodiments, the human CD33 gene comprises one or more single nucleotide polymorphisms (SNPs) selected from the group consisting of: (a) SNP rs3865444$^{AC}$; (b) SNP rs3865444$^{CC}$; (c) SNP rs3865444$^{AA}$; (d) SNP rs35112940$^{GG,\ AA,\ AG}$; (e) SNP rs12459419$^{CC,\ CT\ or\ TT}$; and (f) any combination thereof. In some embodiments that may be combined with any of the preceding embodiments, the human Siglec-5 gene encodes a polypeptide at least 95% identical to a polypeptide encoded by the nucleic acid sequence of SEQ ID NO: 16. In some embodiments that may be combined with any of the preceding embodiments, the human Siglec-5 gene encodes a polypeptide at least 95% identical to SEQ ID NO: 4. In some embodiments that may be combined with any of the preceding embodiments, the human Siglec-7 gene encodes a polypeptide at least 95% identical to a polypeptide encoded by the nucleic acid sequence of SEQ ID NO: 17. In some embodiments that may be combined with any of the preceding embodiments, the human Siglec-7 gene encodes a polypeptide at least 95% identical to a sequence selected from the group consisting of SEQ ID NOS: 5-8. In some embodiments that may be combined with any of the preceding embodiments, the human Siglec-9 gene encodes a polypeptide at least 95% identical to a polypeptide encoded by the nucleic acid sequence of SEQ ID NO: 18. In some embodiments that may be combined with any of the preceding embodiments, the human Siglec-9 gene encodes a polypeptide at least 95% identical to SEQ ID NO: 9 or SEQ ID NO: 10. In some embodiments that may be combined with any of the preceding embodiments, the human Siglec-11 encodes a polypeptide at least 95% identical to a polypeptide encoded by the nucleic acid sequence of SEQ ID NO: 19. In some embodiments that may be combined with any of the preceding embodiments, the human Siglec-11 gene encodes a polypeptide at least 95% identical to SEQ ID NO: 11 or SEQ ID NO: 12. In some embodiments that may be combined with any of the preceding embodiments, the human Siglec-14 gene encodes a polypeptide at least 95% identical to a polypeptide encoded by the nucleic acid sequence of SEQ ID NO: 20. In some embodiments that may be combined with any of the preceding embodiments, the human Siglec-14 gene encodes a polypeptide at least 95% identical to SEQ ID NO: 13. In some embodiments that may be combined with any of the preceding embodiments, the human Siglec-16 gene encodes a polypeptide at least 95% identical to a polypeptide encoded by the nucleic acid sequence of SEQ ID NO: 21. In some embodiments that may be combined with any of the preceding embodiments, the human Siglec-16 gene encodes a polypeptide at least 95% identical to SEQ ID NO: 14. In some embodiments that may be combined with any of the preceding embodiments, the two or more human genes are expressed in a myeloid cell, a natural killer (NK) cell, or both a myeloid cell and an NK cell of the transgenic non-human animal. In some embodiments that may be combined with any of the preceding embodiments, the myeloid cells are selected from the group consisting of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments that may be combined with any of the preceding embodiments, the NK cells are selected from the group consisting of M1 NK cells, activated M1 NK cells, M2 NK cells, and any combination thereof. In some embodiments that may be combined with any of the preceding embodiments, the T cells are selected from the group consisting of T helper cells, cytotoxic T cells, regulatory T cells (Tregs), and any combination thereof. In some embodiments that may be combined with any of the preceding embodiments, the microglia are selected from the group consisting of brain microglial, M1 microglia, activated M1 microglia, M2 microglia, and any combination thereof. In some embodiments that may be combined with any of the preceding embodiments, coordinate expression of the two or more human genes suppresses one or more myeloid immune cell functions. In some embodiments that may be combined with any of the preceding embodiments, the one or more myeloid immune cell functions are selected from the group consisting of: (a) phagocytosis; (b) antigen presentation; (c) immune cell recruitment; (d) immune cell maturation, migration, proliferation, differentiation, and/or survival; (e) modulation of adaptive immune cells such as B cells and T cells; (f) expression and/or secretion of one or more cytokines and/or chemokines; (g) tumor infiltration, tumor cell recognition, and/or tumor cell killing; (h) releasing granules (degranulation) or neutrophil extracellular traps (NETs); (i) anti-parasitic activities; (j) bactericidal activities; (k) clearance of cellular debris and/or protein aggregates; and (l) any combination thereof. In some embodiments that may be combined with any of the preceding embodiments, coordinate expression of the two or more human genes humanizes the Siglec repertoire on the one or more cells of the transgenic non-human animal. In some embodiments that may be combined with any of the preceding embodiments, the mouse comprises a genome that does not encode at least one murine gene, wherein the murine gene is selected from the group consisting of murine CD33, murine Siglec-5, murine Siglec-7, murine Siglec-9 and murine Siglec-11. In some embodiments that may be combined with any of the preceding embodiments, the mouse comprises a genome comprising one or more non-functional murine genes, wherein the one or more non-functional murine genes are selected from the group consisting of murine CD33, Siglec-5, murine Siglec-7, murine Siglec-9, murine Siglec-11, and any combination thereof.

Other aspects of the present disclosure relate to a method of generating a non-human animal disease model with a human Siglec repertoire, the method comprising introducing one or more genetic determinants of a disease into the genome of the non-human animal of any of the preceding embodiments. In some embodiments, the one or more genetic determinants are introduced into the genome of the non-human animal by mating. In some embodiments, the one or more genetic determinants are introduced into the genome of the non-human animal by mating with a disease model non-human animal. In some embodiments, the one or more genetic determinants are introduced into the genome of the non-human animal by genetic manipulation. In some embodiments, the disease is selected from the group consisting of cancer, proliferative disorders, infectious diseases, and neurodegenerative disorders such as Alzheimer's disease. In some embodiments, the genetic determinant is a polynucleotide encoding a polypeptide comprising one or more mutations, wherein the polypeptide is selected from the group consisting of amyloid precursor protein (APP), presenilin 1 (PS1), presenilin 2 (PS2), alpha-synuclein, serine/threonine-protein kinase PINK1, parkin, leucine-rich repeat serine/threonine protein kinase 2 (LRRK2), protein deglycase (DJ-1), probable cation-transporting ATPase 13A2 (ATP13A2), superoxide dismutase (SOD1), TAR DNA-binding protein 43 (TDP-43), RNA-binding protein FUS, huntingtin (HTT), translation endoplasmic reticulum ATPase (VCP), microtubule-associated protein tau (MAPT), progranulin, protein C9orf72, charged multivesicular body protein 2b (CHMP2B), and any combinations thereof.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 2 shows glycan-binding specificities of human Siglec proteins. This figure shows a summary of the most commonly reported specificities for the most commonly studied sialylated glycans. Relative binding within studies of each Siglec is indicated as ++, strong binding; +, detectable binding; and –, very weak or undetectable binding. Not shown is the recently reported strong-binding preference of hSiglec-8 and mSiglec-F for 6'-sulfated-sialyl-Lewis x (sLex) and of hSiglec-9 for 6-sulfated-sLex. With a few exceptions (CD22 and MAG), results of binding specificity studies of human Siglecs by different investigators using different assays have varied significantly. In addition to assay formats and glycan linker issues, the density and arrangement of the ligands studied could be responsible for this variation (Varki et al., (2006) Glycobiol. 16:1R-27R).

FIG. 7A shows results of FACS analysis demonstrating human CD33 and human Siglec-9 expression on CD11b-positive and CD11b-negative primary cells from non-transgenic and BACRP11-891J20 transgenic mice. Numbers indicate the percentage of cells with staining with an antibody to CD33 or Siglec-9 as indicated (black line) above isotype control background levels (represented by grey area). Arrows indicate animals with transgene expression above background levels in CD11b+ peripheral blood cells. FIG. 7B shows results of FACS analysis demonstrating human CD33 and human Siglec-9 co-expression on CD11b-positive cells in sera from non-transgenic and BACRP11-891J20 transgenic mice. Arrows indicate transgenic animals with transgene expression significantly above background seen with naïve sera.

FIG. 8 shows the antibody panel for FACS expression analysis of human CD33, human Siglec-7, and human Siglec-9 on peripheral blood or spleen cells from non-transgenic and BACRP11-891J20 transgenic mice.

FIG. 22 shows the antibody panel for FACS expression analysis of human CD33 on brain microglia from BACRP11-891J20 transgenic mice.

FIG. 35A shows results of FACS analysis demonstrating the expression pattern of human Siglec-5 and human Siglec-7 on primary dendritic cells (hDC) from peripheral blood of a human patient stained with an isotype control antibody (blue line) or an anti-human Siglec-5 antibody or anti-human Siglec-7 antibody (red lines). FIG. 35B shows results of FACS analysis demonstrating the expression pattern of human Siglec-5 and human Siglec-Ion primary bone marrow-derived dendritic cells from control non-transgenic mice (#25 and #42) and BACCTD-2026P14 transgenic mice (#26, #27, #30, #40, and #41) stained with an isotype control antibody (blue line) or an anti-human Siglec-5 antibody or anti-human Siglec-7 antibody (red lines).

DETAILED DESCRIPTION

Figure 1:
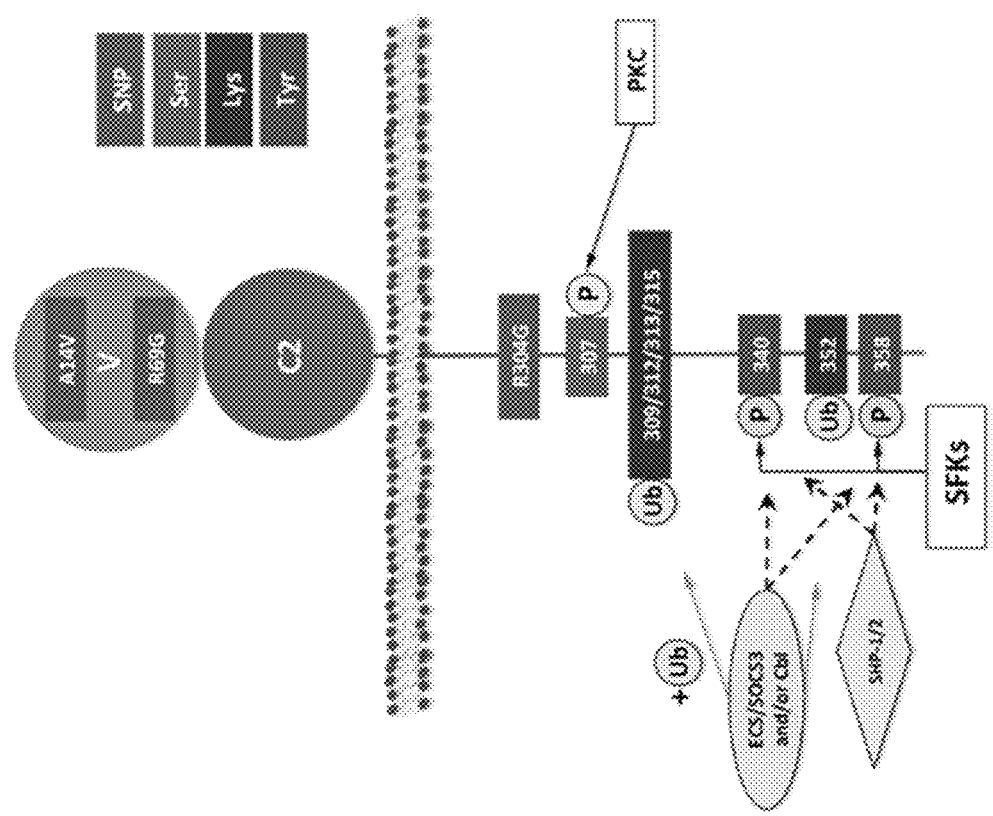
FIG. 1 shows the structure of CD33, and a scheme depicting the domain structure of CD33 as well as individual amino acids that have been implicated in phosphorylation or ubiquitination events or that have been identified as residues of relatively frequent non-synonymous single nucleotide polymorphisms (SNPs). Abbreviations: CBL: casitas B-lineage lymphoma E3 ubiquitin ligase; C2: C2-set Ig-like domain; ECS: Elongin B/C-Cullin-5 SPRY domain ubiquitin ligase; P: phospho-; PKC: protein kinase C; SFKs: Src-family kinases; SHP-½: Src homology region 2 domain-containing phosphatase-1 and –2; SOCS3: suppressor of cytokine signaling 3; Ub: ubiquitin; V: V-set Ig-like domain. (Cowan et al., (2013) Frontiers in Bioscience 18:1311-1334).

The present disclosure relates to transgenic non-human animals whose genomes comprise two or more human genes selected from the group consisting of CD33, Siglec-5, Siglec-7, Siglec-9, Siglec-11, Siglec-14, and Siglec-16; to methods of screening candidate agents that bind to and/or modulate the function and/or activity of at least one of the human genes in the transgenic non-human animals; to methods of screening candidate agents to determine their effect on one or more activities and/or functions associated with expression of at least one of the human genes in the transgenic non-human animals; to methods of recapitulating a human Siglec immune system in a non-human animal; and to methods of generating a non-human animal disease model comprising a human Siglec repertoire.

The following description sets forth exemplary methods, parameters, and the like. It should be recognized, however, that such description is not intended as a limitation on the scope of the present disclosure but is instead provided as a description of exemplary embodiments.

General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): PCR 2: *A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); Gene Transfer Vectors for Mammalian Cells (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions

As used herein, a "subject" or an "individual" refers to any animal, including non-human primates, domestic and farm animals, and zoo, sports, or pet animals, such as dogs, horses, cats, cows, as well as animals used in research, such as mice and rats.

As used herein, the term "animal" or "non-human animal" includes all vertebrate and invertebrate animals, except humans. Examples of animals include, but are not limited to, domesticated animals (e.g., cows, sheep, cats, dogs, and horses), primates (e.g., non-human primates such as monkeys), rabbits, and rodents (e.g., mice and rats). In some embodiments, the animal is a mouse. Additionally, the term refers to an individual animal in all stages of developments, including embryonic and fetal stages. As used herein, the term "transgenic animal" or "transgenic non-human animal" refers to an animal containing one or more cells bearing genetic information (e.g., DNA) received, directly or indirectly, by deliberate genetic manipulation at a subcellular level, such as by microinjection or infection with recombinant virus. This introduced DNA molecule mar be integrated within a chromosome, or it may be extra-chromosomally replicating DNA.

As used herein, the term "germ cell-line transgenic animal" refers to a transgenic animal in which the genetic information was introduced into a germ line cell, thereby conferring the ability to transfer the information to offspring. If such offspring in fact possess some or all of that information, then they too are transgenic animals.

As used herein, the term "wild-type" refers to a nucleic acid, polypeptide, and/or animal (e.g., a mouse or rat) when isolated from a naturally occurring source. A wild-type nucleic acid, polypeptide, and/or animal (e.g., a mouse or rat) is that which is most frequently observed in a population and is thus arbitrarily designated the "normal" or "wild-type" form of that nucleic acid, polypeptide, and/or animal. In contrast, the term "modified" or "mutant" refers to a nucleic acid, polypeptide, and/or animal (e.g., a mouse or rat) that displays modifications in sequence and/or functional properties (e.g., altered characteristics) when compared to the wild-type nucleic acid, polypeptide, and/or animal (e.g., a mouse or rat).

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability to elicit a desired response in the individual. A therapeutically effective amount is also one in which any toxic or detrimental effects are outweighed by the therapeutically beneficial effects.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, the terms "coordinately expressed" and "coordinate expression" refers to the co-regulated expression of two or more polynucleotides.

As used herein, the terms "polypeptide," "protein," and "peptide" are used interchangeably and may refer to a polymer of two or more amino acids.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; saltforming counterions such as sodium; and/or nonionic surfactants such as TWEEN™, polyethylene glycol (PEG), and PLURONICS™.

As used herein, the term "candidate agent" refers to a molecule that reduces (including significantly), decreases, blocks, inhibits, or interferes with a Siglec (mammalian, such as a human Siglec) biological activity in vitro, in situ, and/or in vivo. The term "agent" implies no specific mechanism of biological action whatsoever, and expressly includes and encompasses all possible pharmacological, physiological, and biochemical interactions with a Siglec whether direct or indirect, and whether interacting with a Siglec, one or more of its ligands, or through another mechanism, and its consequences which can be achieved by a variety of different, and chemically divergent, compositions. Exemplary agents include, without limitation, an antibody that specifically binds to a Siglec, a soluble Siglec receptor protein, a soluble Siglec-Fc fusion protein (e.g., Siglec immunoadhesins), a soluble Siglec receptor that binds to a Siglec ligand, a Siglec-Fc fusion protein (e.g., Siglec immunoadhesin) that binds to a Siglec ligand, an anti-sense molecule directed to a nucleic acid encoding a Siglec, a short interfering RNA ("siRNA") molecule directed to a nucleic acid encoding a Siglec, a Siglec inhibitory compound, an RNA or DNA aptamer that binds to a Siglec, and a Siglec structural analog. In some embodiments, a Siglec inhibitor (e.g., an antibody) binds (physically interacts with) an agent that decreases cellular levels of a Siglec, inhibits interaction between a Siglec and one or more Siglec ligands, or both, binds to a Siglec ligand, and/or inhibits (reduces) Siglec synthesis or production. In other embodiments, an agent of the present disclosure binds a Siglec and prevents its binding to one or more of its ligands. In still other embodiments, an agent of the present disclosure reduces or eliminates expression (i.e., transcription or translation) of a Siglec.

As used herein, the term "agent that binds or interacts with a Siglec" refers to a molecule that either directly or indirectly interacts with a Siglec protein. The term "agent" implies no specific mechanism of biological action whatsoever, and expressly includes and encompasses all possible pharmacological, physiological, and biochemical interactions with a Siglec whether direct or indirect, and whether interacting with a Siglec or through another mechanism, and its consequences which can be achieved by a variety of different, and chemically divergent, compositions.

As used herein, the term "RNA interference" or "RNAi" refers generally to a process in which a double-stranded RNA molecule or a short hairpin RNA molecule reducing or inhibiting the expression of a nucleic acid sequence with which the double-stranded or short hairpin RNA molecule shares substantial or total homology. The term "short interfering RNA" or "siRNA" or "RNAi agent" refers to an RNA sequence that elicits RNA interference. See Kreutzer et al., WO 00/44895; Zernicka-Goetz et al., WO 01/36646; Fire, WO 99/32619; Mello and Fire, WO 01/29058. As used herein, siRNA molecules include RNA molecules encompassing chemically modified nucleotides and non-nucleotides. The term "ddRNAi agent" refers to a DNA-directed RNAi agent that is transcribed from an exogenous vector. The terms "short hairpin RNA" or "shRNA" refer to an RNA structure having a duplex region and a loop region. In certain embodiments, ddRNAi agents are expressed initially as shRNAs.

As used herein, the term "aptamer" refers to a heterologous oligonucleotide capable of binding tightly and specifically to a desired molecular target, such as, for example, common metabolic cofactors (e.g., Coenzyme A, S-adenosyl methionine, and the like), proteins (e.g., complement protein C5, antibodies, and the like), or conserved structural elements in nucleic acid molecules (e.g., structures important for binding of transcription factors and the like). Aptamers typically comprise DNA or RNA nucleotide sequences ranging from about 10 to about 100 nucleotides in length, from about 10 to about 75 nucleotides in length, from about 10 to about 50 nucleotides in length, from about 10 to about 35 nucleotides in length, and from about 10 to about 25 nucleotides in length. Synthetic DNA or RNA oligonucleotides can be made using standard solid phase phosphoramidite methods and equipment, such as by using a 3900 High Throughput DNA Synthesizer™, available from Applied Biosystems (Foster City, Calif.). Aptamers frequently incorporate derivatives or analogs of the commonly occurring nucleotides found in DNA and RNA (e.g., A, G, C, and T/U), including backbone or linkage modifications (e.g., peptide nucleic acid (PNA) or phosphothioate linkages) to increase resistance to nucleases, binding avidity, or to otherwise alter their pharmacokinetic properties. Exemplary modifications are set forth in U.S. Pat. Nos. 6,455,308; 4,469,863; 5,536,821; 5,541,306; 5,637,683; 5,637,684; 5,700,922; 5,717,083; 5,719,262; 5,739,308; 5,773,601; 5,886,165; 5,929,226; 5,977,296; 6,140,482; and in WIPO publications WO 00/56746 and WO 01/14398. Methods for synthesizing oligonucleotides comprising such analogs or derivatives are disclosed, for example, in the patent publications cited above, and in U.S. Pat. Nos. 6,455,308; 5,614,622; 5,739,314; 5,955,599; 5,962,674; 6,117,992; and in WO 00/75372.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to a "gene" is a reference to from one to many genes.

It is understood that aspect and embodiments of the present disclosure described herein include "comprising," "consisting," and "consisting essentially of" aspects and embodiments.

Transgenic Non-Human Animals

Certain aspects of the present disclosure relate to transgenic non-human animals whose genomes comprise two or more human genes selected from the group consisting of CD33, Siglec-5, Siglec-7, Siglec-9, Siglec-11, Siglec-14, and Siglec-16. In some embodiments, the two or more human genes are expressed (e.g., co-expressed) in one or more cells of the transgenic non-human animal. In some embodiments, the two or more human genes are coordinately expressed in one or more cells of the transgenic animal. In some embodiments, expression (e.g., co-expression, coordinate expression) of the two or more human genes in the transgenic non-human animal recapitulates the expression pattern of the two or more human genes in a corresponding human cell. In some embodiments, expression (e.g., co-expression, coordinate expression) of the two or more human genes humanizes the Siglec repertoire on the one or more cells of the transgenic non-human animal. In some embodiments, the one or more cells of the transgenic non-human animal are one or more of myeloid cells, natural killer (NK) cells, T cells, microglia, and any combinations thereof.

In some embodiments, the two or more human genes are expressed (e.g., co-expressed) in one or more myeloid cells of the transgenic non-human animal. In some embodiments, the two or more human genes are coordinately expressed in one or more myeloid cells of the transgenic non-human animal. In some embodiments, expression (e.g., co-expression, coordinate expression) of the two or more human genes in one or more myeloid cells of the transgenic non-human animal recapitulates the expression pattern of the two or more human genes in a corresponding human myeloid cell. In some embodiments, the one or more myeloid cells are one or more of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments, expression (e.g., co-expression, coordinate expression) of the two or more human genes on one or more myeloid cells humanizes the Siglec repertoire on the one or more myeloid cells.

In some embodiments, the two or more human genes are expressed (e.g., co-expressed) in one or more natural killer (NK) cells of the transgenic non-human animal. In some embodiments, the two or more human genes are coordinately expressed in one or more NK cells of the transgenic non-human animal. In some embodiments, expression (e.g., co-expression, coordinate expression) of the two or more human genes in one or more NK cells of the transgenic non-human animal recapitulates the expression pattern of the two or more human genes in a corresponding human NK cell. In some embodiments, the one or more NK cells are one or more of M1 NK cells, activated M1 NK cells, M2 NK cells, and any combination thereof. In some embodiments, expression (e.g., co-expression, coordinate expression) of the two or more human genes on one or NK cells humanizes the Siglec repertoire on the one or more NK cells.

In some embodiments, the two or more human genes are expressed (e.g., co-expressed) in one or more T cells of the transgenic non-human animal. In some embodiments, the two or more human genes are coordinately expressed in one or more T cells of the transgenic non-human animal. In some embodiments, expression (e.g., co-expression, coordinate expression) of the two or more human genes in one or more T cells of the transgenic non-human animal recapitulates the expression pattern of the two or more human genes in a corresponding human T cell. In some embodiments, the one or more T cells are one or more of T helper cells, cytotoxic T cells, regulatory T cells (Tregs), and any combination thereof. In some embodiments, expression (e.g., co-expression, coordinate expression) of the two or more human genes on one or more T cells humanizes the Siglec repertoire on the one or more T cells.

In some embodiments, the two or more human genes are expressed (e.g., co-expressed) in one or more microglial cells of the transgenic non-human animal. In some embodiments, the two or more human genes are coordinately expressed in one or more microglial cells of the transgenic non-human animal. In some embodiments, expression (e.g., co-expression, coordinate expression) of the two or more human genes in one or more microglial cells of the transgenic non-human animal recapitulates the expression pattern of the two or more human genes in a corresponding human microglial cell. In some embodiments, the one or more microglial cells are one or more of brain microglial cells, M1 microglial cells, activated M1 microglial cells, M2 microglial cells, and any combination thereof. In some embodiments, expression (e.g., co-expression, coordinate expression) of the two or more human genes on one or more microglial cells humanizes the Siglec repertoire on the one or more microglial cells.

In some embodiments, expression (e.g., co-expression, coordinate expression) of the two or more human genes in the transgenic non-human animals suppresses one or more myeloid immune cell functions in the transgenic non-human animal. In some embodiments, the one or more myeloid immune cell functions are one or more of phagocytosis; antigen presentation; immune cell recruitment, maturation, migration, proliferation, differentiation, and/or immune cell survival; modulation of adaptive immune cells (e.g., B cells and/or T cells); expression and/or secretion of one or more cytokines and/or chemokines (e.g., IL-1 alpha, IL-1beta, IL-1Ra, IL-4, IL-6, IL-8, IL-10, IL-11, IL-12, IL-13, IL-16, IL-17, IL-18, IL-20, IL-33, IL-35, CRP, LIF, MCP-1, MIP-1 beta, TNFalpha, IFN alpha, IFN, beta, IFN gamma, OSM, CNTF, G-CSF, GM-CSF, TGF beta, Osteopontin, CXCL9, CXCL10, etc.); tumor infiltration, tumor cell recognition, and/or tumor cell killing; releasing granules (degranulation) and/or neutrophil extracellular traps (NETs); anti-parasitic activities; bactericidal activities; clearance of cellular debris and/or protein aggregates; and any combinations thereof.

In some embodiments, expression (e.g., co-expression, coordinate expression) of the two or more human genes in the transgenic non-human animals suppresses one or more myeloid immune cell functions by about 5%, about 10%, about 15%, about 20%, about 25%, about 30%, about 35%, about 40%, about 45%, about 50%, about 55%, about 60%, about 70%, about 75%, about 80%, about 85%, about 90%, about 95%, or about 99% relative to a control non-human animal (e.g., an animal not expressing the two or more human genes). In some embodiments, expression (e.g., co-expression, coordinate expression) of the two or more human genes in the transgenic non-human animals suppresses one or more myeloid immune cell functions by about 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 10 fold, about 100 fold or about 1000 fold relative to a control non-human animal (e.g., an animal not expressing the two or more human genes).

Transgenic non-human animals of the present disclosure may be any non-human animal known in the art. Examples of non-human animals may include, without limitation, laboratory animals (e.g., mice, rats, hamsters, gerbils, guinea pigs, etc.), livestock (e.g., horses, cattle, pigs, sheep, goats, ducks, geese, chickens, etc.), non-human primates (e.g., apes, chimpanzees, orangutans, monkeys, etc.), fish, amphibians (e.g., frogs, salamanders, etc.), reptiles (e.g., snakes, lizards, etc.), and other animals (e.g., foxes, weasels, rabbits, mink, beavers, ermines, otters, sable, seals, coyotes, chinchillas, deer, muskrats, possums, etc.).

In some embodiments, the transgenic non-human animal is a rodent (e.g., a mouse, a rat, a hamster, a gerbil, or a guinea pig). Hamster strains useful for generating transgenic hamsters may include, but are not limited to, Syrian hamsters, Chinese hamsters, European hamsters, and Djungarian hamsters. Rat strains useful for generating transgenic rats may include, but are not limited to, Sprague Dawley® rats, Lewis rats, Fischer 344 rats, Long Evans rats, CD-IGS rats, and Wistar rats. In some embodiments, the transgenic non-human animal is a mouse. Mouse strains useful for generating transgenic mice may include, but are not limited to, CD-1® Nude mice, CD-1 mice, NU/NU mice, BALB/C Nude mice, NIH-III mice, SCID™ mice, outbred SCID™ mice, SCID Beige mice, C3H mice, C57BL/6 mice, DBA/2 mice, FVB mice, CB17 mice, 129 mice, SJL mice, B6C3F1 mice, BDF1 mice, CDF1 mice, CB6F1 mice, CF-1 mice, Swiss Webster mice, SKH1 mice, PGP mice, and B6SJL mice, and congenic mice. In some embodiments, mice useful for generating transgenic mice may further include, but are not limited to, hybrids of any of the aforementioned mouse strains, $F_1$ hybrids of any of the aforementioned mouse strains, $F_2$ hybrids of any of the aforementioned mouse strains, and outbred mice of any of the aforementioned mouse strains.

In some embodiments, the transgenic non-human animals of the present disclosure are chimeric transgenic non-human animals. In some embodiments, the transgenic non-human animals of the present disclosure are transgenic non-human animals with germ cells and somatic cells containing one or more (e.g., one or more, two or more, three or more, four or more, five or more, six or more, etc.) nucleotide sequences encoding two or more human genes selected from the group consisting of CD33, Siglec-5, Siglec-7, Siglec-9, Siglec-11, Siglec-14, and Siglec-16. In some embodiments, the one or more nucleotides sequences are stably integrated into the genome of the transgenic non-human animals. In some embodiments, the one or more nucleotides are bacterial artificial chromosomes stably integrated in to the genome of the transgenic non-human animal. In some embodiments, the one or more nucleotide sequences are extrachromosomal. In some embodiments, the extrachromosomal nucleotide sequence is provided as a minichromosome, a yeast artificial chromosome, or a bacterial artificial chromosome.

In some embodiments, the genomes of the transgenic non-human animals of the present disclosure comprise any of 1, 2, 3, 4, 5, 6, 7, 8, 9, 10, 11, 12, 13, 14, 15 or more copies of the two or more human genes selected from the group consisting of CD33, Siglec-5, Siglec-7, Siglec-9, Siglec-11, Siglec-14, and Siglec-16. In some embodiments, the copy number of the two or more human genes is the same in the genome of the transgenic non-human animal (e.g., the same number of copies of a first and second human gene, the same number of copies of a first, second, and third human gene, etc.). In some embodiments, the copy number of the two or more human genes is different in the genome of the transgenic non-human animal (e.g., a different number of copies of a first and second human gene, a different number of copies of a first, second, and third human gene, etc.). In some embodiments, the genome of the transgenic non-human animal comprises three or more human genes, and the copy number of at least two of the human genes is the same (e.g., the same number of copies of the first and second human gene, and a different number of copies of the third human gene; the same number of copies of the first and third human gene, and a different number of copies of the second human gene, etc.).

In some embodiments, a transgenic non-human animal of the present disclosure is pre-disposed to develop one or more diseases, disorders, and/or injuries. In some embodiments, the one or more diseases, disorders, and/or injuries is one or more of autoimmunity, susceptibility to infection, cancer, proliferative disorders, and/or neurodegenerative disorders. In some embodiments, the one or more diseases, disorders, and/or injuries is one or more of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV infection, and Haemophilus influenza infection.

In some embodiments, the transgenic non-human animal is treated to generate one or more animal disease models (e.g., a transgenic non-human animal being implanted with a syngeneic tumor such as melanoma). In some embodiments, the transgenic non-human animal is interbred to generate one or more animal diseases models. In some embodiments, the transgenic non-human animal is bred with a disease model non-human animal. In some embodiments, the disease model non-human animal is a model of cancer (e.g., melanoma, acute myeloid leukemia, etc.), proliferative disorders, immune-related disease, infectious diseases (e.g., bacterial infections), and/or neurodegenerative diseases/disorders (e.g., Alzheimer's disease). In some embodiments, the neurodegenerative diseases/disorders are one or more of dementia, frontotemporal dementia (FTD), Alzheimer's disease, Parkinson's disease, amyotrophic lateral sclerosis (ALS), Huntington's disease, taupathy disease, and multiple sclerosis. In some embodiments, the disease model non-human animal is an Alzheimer's disease model non-human animal. In some embodiments, the genome of the disease model non-human animal comprises a polynucleotide comprising one or more mutations. In some embodiments, the one or more mutations are one or more inactivating mutations. Examples of inactivating mutations may include, but are not limited to, deletions, insertions, point mutations, and rearrangements. In some embodiments, the genome of the disease model non-human animal comprises a polynucleotide encoding a polypeptide comprising one or more mutations. In some embodiments, the polypeptide comprising one or more mutations is one or more of the polypeptides amyloid precursor protein (APP), presenilin 1 (PS1), presenilin 2 (PS2), alpha-synuclein, serine/threonine-protein kinase PINK1, parkin, leucine-rich repeat serine/threonine protein kinase 2 (LRRK2), protein deglycase (DJ-1), probable cation-transporting ATPase 13A2 (ATP13A2), superoxide dismutase (SOD1), TAR DNA-binding protein 43

(TARDBP), RNA-binding protein FUS, huntingtin (HTT), translation endoplasmic reticulum ATPase (VCP), microtubule-associated protein tau (MAPT), progranulin, protein C9orf72, charged multivesicular body protein 2b (CHMP2B), and clinical mutant forms thereof.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the Progranulin gene.

Alzheimer's Disease

Alzheimer's disease (AD), is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

Taupathy Disease

Taupathy diseases, or Tauopathies, are a class of neurodegenerative disease caused by aggregation of the microtubule-associated protein tau within the brain. Alzheimer's disease (AD) is the most well-known taupathy disease, and involves an accumulation of tau protein within neurons in the form of insoluble neurofibrillary tangles (NFTs). Other taupathy diseases and disorders include progressive supranuclear palsy, dementia pugilistica (chromic traumatic encephalopathy), frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, and frontotemporal lobar degeneration.

Animal models have been developed to model various aspects of dementia, FTD, AD, and Taupathy diseases, including, for example, the accumulation of protein aggregation (e.g., plaques and neurofibrillary tangles) leading to lesions in the brain, the spreading of key histopathological markers (e.g., amyloid β plaques and neurofibrillary tangles) that lead to the definition of the Braak stages, and the formation of distinct clinical features (e.g., neuronal/synapse loss at specific predilection sites, early memory deficits, parkinsonism, memory loss in advanced stages) of FTD, AD, and Taupathy diseases. Examples of animal models useful for modeling one or more signs or symptoms of AD and/or FTD and/or Taupathy diseases may include, without limitation, the mouse strains PDAPP, J20, APP23, Tg2576, JNPL3, pR5, and 5XFAD, and the rat strains SHR72 and SHR318) (See e.g., Götz, J. and Ittner, L. M. (2008) *Nat. Rev. Nerurosci.* 9:352-44; Koson, P. et al. (2008) *Eur. J. Neurosci.* 28(2): 239-46; and Götz, J. and Götz, N. N. (2009) *ASN Neuro.* 1(4)).

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

Animal models have been developed to model various aspects of Parkinson's disease, including, for example, fragmented and dysfunctional mitochondria, altered mitophagy, ubiquitin proteasome dysfunction, altered reactive oxygen species production and calcium handling, alterations in motor function and behavior, and sensitivities to complex I toxins. Examples of animal models useful for modeling one or more signs or symptoms of Parkinson's disease may include, without limitation, toxin-based models (e.g., MPTP mice, MPTP monkeys, 6-OHDA rats, Rotenone, paraquat/maneb, MET/MDMA, etc.), genetic mutation models (e.g., mutations in a-synuclein, LRKK2, PINK1, PARKIN, DJ-1, ATP13A2, etc.), a-synuclein AAV virus injection model, a-synuclein preformed fibril injection model (See e.g., Luk, K C et al., *Science* 2012 Nov. 16; 338(6109): 949-953), and other models (SHH, Nurr 1, Engrailedl, Pitx3, C-rel-NFKB, MitoPark, Atg7, VMAT2, etc.) (See e.g., Blesa, J. and Przedborski, J. (2014) *Front. Neuroanat.* 8: 155).

Amyotrophic Lateral Sclerosis (ALS)

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that Progranulin plays a role in ALS (Schymick, J C et al., (2007) J Neurol Neurosurg Psychiatry; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al, Proc. Natl. Acad. Sci USA (2004), 101, pp 6226-30).

Animal models have been developed to model various aspects of ALS, including, for example, axonal and mitochondrial dysfunction, progressive neuromuscular dysfunction, gliosis, and motor neuron loss. Examples of animal models useful for modeling one or more signs or symptoms of ALS may include, without limitation, genetic mutation models (e.g., mutations in SOD1, TDP-43, FUS, VCP, etc.), and the mouse models SOD1$^{G37R}$, SOD1$^{H46R}$, SOD1$^{G93A}$, TDP-43$^{WT}$, TDP-43 G348C, and FUS$^{R521C}$ (See e.g., Philips, T. and Rothstein, J. (2016) *Curr. Protoc. Pharmacol.* 69: 1-21).

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

Animal models have been developed to model various aspects of Huntington's disease, including, for example, production and aggregation of huningtin protein in striatal neurons as well as neurons in other regions (such as the cortex, thalamus, hypothalamus, and substantia nigra pars compacta), involuntary hyperkinetic (choreaform) movements of the arms, legs, and/or face, and severe cognitive changes. Examples of animal models useful for modeling one or more signs or symptoms of ALS may include, without limitation, toxin-based models (e.g., quinolinic acid, 3-nitroproprionic acid, etc.), genetic mutation models (e.g., mutations in mouse, rat, or primate HTT, etc.), and the mouse models R6/2, R6/1, N171-82Q, and YAC (See e.g., Ramaswamy, S. et al. (2007) ILAR J. 48(4): 356-73).

Human Genes

Certain aspects of the present disclosure relate to transgenic non-human animals whose genomes comprise two or more of the human CD33, Siglec-5, Siglec-7, Siglec-9, Siglec-11, Siglec-14, and/or Siglec-16 genes.

Human CD33 Gene

In some embodiments, the genome of a transgenic non-human animal of the present disclosure comprises a human CD33 gene. In some embodiments, the genome of the transgenic non-human animal comprises an inactivating mutation in the endogenous CD33 gene. In some embodiments, the transgenic non-human animal comprises a non-functional endogenous CD33 gene. In some embodiments, the genome of the transgenic non-human animal comprises a human CD33 gene and lacks an endogenous CD33 gene. In some embodiments, the genome of the transgenic non-human animal comprises a human CD33 gene and a non-functional endogenous CD33 gene. In some embodiments, the transgenic non-human animal is a mouse. In some embodiments, the genome of the mouse comprises an inactivating mutation in the endogenous murine CD33 gene. In some embodiments, the genome of the mouse comprises a non-functional murine CD33 gene. In some embodiments, the genome of the mouse comprises a human CD33 gene and lacks an endogenous murine CD33 gene. In some embodiments, the genome of the mouse comprises a human CD33 gene and a non-functional murine CD33 gene.

In some embodiments, the human CD33 gene comprises all intronic and exonic sequences of the CD33 gene encoded on chromosome 19 in the human genome. An exemplary polynucleotide comprising all intronic and exonic sequences of the CD33 gene encoded on chromosome 19 in the human genome is shown in SEQ ID NO: 15. In some embodiments, the human CD33 gene comprises the coding sequence for the human CD33 protein/polypeptide. In some embodiments, the human CD33 protein/polypeptide is encoded by a nucleic acid comprising the sequence of SEQ ID NO: 15. In some embodiments, the human CD33 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 15.

In some embodiments, the human CD33 gene comprises a flanking sequence at the 5' end of the coding sequence for the human CD33 polypeptide. In some embodiments, the human CD33 gene comprises a flanking sequence at the 3' end of the coding sequence for the human CD33 polypeptide. In some embodiments, the human CD33 gene comprises a flanking sequence at the 5' end and 3' end of the coding sequence for the human CD33 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human CD33 gene in one or more cells of the transgenic non-human animal. In some embodiments, the one or more human transcriptional regulatory elements direct expression of the human CD33 gene and one or more additional genes in one or more cells of the transgenic non-human animal. In some embodiments, the one or more additional genes are one or more (e.g., one or more, two or more, three or more, four or more, five or more, or all six) of the human Siglec-5, Siglec-7, Siglec-9, Siglec-11, Siglec-14, and/or Siglec-16 genes. In some embodiments, the one or more human transcriptional regulatory elements direct coordinate expression of the human CD33 gene and the one or more additional genes in one or more cells of the transgenic non-human animal. In some embodiments, the one or more cells of the transgenic non-human animal are one or more of myeloid cells, natural killer (NK) cells, T cells, and/or microglia.

CD33 is variously referred to as a CD33 molecule, Siglec-3, Siglec-3, CD33 antigen (Gp67), P67, Gp67, sialic acid-binding-Ig-like lectin 3, myeloid cell surface antigen CD33, or FLJ00391.

CD33 is an immunoglobulin-like receptor primarily expressed on myeloid lineage cells, including without limitation, macrophages, dendritic cells, osteoclasts, monocytes, and microglia. In some embodiments, CD33 forms a receptor-signaling complex with CD64. In some embodiments, CD33 signaling results in the downstream inhibition of PI3K or other intracellular signals.

An exemplary amino acid sequence of human CD33 is set forth below as SEQ ID NO: 1:

```
        10         20         30         40         50
MPLLLLLPLL WAGALAMDPN FWLQVQESVT VQEGLCVLVP CTFFHPIPYY 60         70         80         90        100
DKNSPVHGYW FREGAIISRD SPVATNKLDQ EVQEETQGRF RLLGDPSRNN 110        120        130        140        150
CSLSIVDARR RDNGSYFFRM ERGSTKYSYK SPQLSVHVTD LTHRPKILIP 160        170        180        190        200
GTLEPGHSKN LTCSVSWACE QGTPPIFSWL SAAPTSLGPR TTHSSVLIIT 210        220        230        240        250
PRPQDHGTNL TCQVKFAGAG VTTERTIQLN VTYVPQNPTT GIFPGDGSGK 260        270        280        290        300
QETRAGVVHG AIGGAGVTAL LALCLCLIFF IVKTHRRKAA RTAVGRNDTH 310        320        330        340        350
PTTGSASPKH QKKSKLHGPT ETSSCSGAAP TVEMDEELHY ASLNFHGMNP

360
SKDTSTEYSE VRTQ
```

In some embodiments, the CD33 is a preprotein that includes a signal sequence. In some embodiments, the CD33 is a mature protein. In some embodiments, the mature CD33 protein does not include a signal sequence. In some embodiments, the mature CD33 protein is expressed on a cell. In some embodiments, the mature CD33 protein is expressed on a cell, such as the surface of a cell.

Human CD33 proteins contain several domains, including without limitation, a signal sequence located at amino acid residues 1-17 of SEQ ID NO: 1, an extracellular immunoglobulin-like variable-type (IgV) domain located at amino acid residues 19-135 of SEQ ID NO: 1, an Ig-like C2-type domain located at amino acid residues 145-228 of SEQ ID NO: 1, a transmembrane domain located at amino acid residues 260-282 of SEQ ID NO: 1, an ITIM motif 1 located at amino acid residues 338-343 of SEQ ID NO: 1, and an ITIM motif 2 located at amino acid residues 356-361 of SEQ ID NO: 1. As one of skill in the art will appreciate, the beginning and ending residues of the domains of the present disclosure may vary depending upon the computer modeling program used or the method used for determining the domain In some embodiments, a human CD33 gene of the present disclosure encodes a polypeptide comprising the sequence of SEQ ID NO: 1. In some embodiments, a human CD33 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 1.

In some embodiments, a human CD33 gene of the present disclosure encodes an N-terminal truncation, a C-terminal truncation, or a fragment of a polypeptide comprising the sequence of SEQ ID NO: 1. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, but fewer than 364, consecutive amino acids ofSEQ ID NO: 1.

In some embodiments, a human CD33 gene of the present disclosure encodes a polypeptide comprising the sequence of SEQ ID NO: 2. In some embodiments, a human CD33 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 2.

In some embodiments, a human CD33 gene of the present disclosure encodes an N-terminal truncation, a C-terminal truncation, or a fragment of a polypeptide comprising the sequence of SEQ ID NO: 2. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, but fewer than 310, consecutive amino acids of SEQ ID NO: 2.

In some embodiments, a human CD33 gene of the present disclosure encodes a polypeptide comprising the sequence of SEQ ID NO: 3. In some embodiments, a human CD33 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 3.

In some embodiments, a human CD33 gene of the present disclosure encodes an N-terminal truncation, a C-terminal truncation, or a fragment of a polypeptide comprising the sequence of SEQ ID NO: 3. N-terminal truncations, C-terminal truncations, or fragments may comprise least 10, at least 25, at least 50, at least 75, at least 100, at least 125, at least 150, at least 175, at least 200, at least 225, but fewer than 237, consecutive amino acids of SEQ ID NO: 3.

In some embodiments, a human CD33 gene of the present disclosure comprises one or more (e.g., one or more, two or more, three or more, four or more, five or more, etc.) single nucleotide polymorphisms (SNPs). In some embodiments, the one or more SNPs are one or more of SNP rs3865444$^{AC}$, SNP rs3865444$^{CC}$, SNP rs3865444$^{AA}$, SNP rs35112940$^{GG, AA, AG}$, SNP rs12459419$^{CC, CT\ or\ TT}$, and any combinations thereof.

In some embodiments, the human CD33 gene encodes a polypeptide comprising one or more (e.g., one or more, two or more, three or more, four or more, five or more, six or more, seven or more, eight or more, nine or more, 10 or more, or 11) mutations selected from: an alanine to valine mutation at a position corresponding to position 14 of SEQ ID NO: 1; a tryptophan to arginine mutation at a position corresponding to position 22 of SEQ ID NO: 1; an arginine to glycine mutation at a position corresponding to position 69 of SEQ ID NO: 1; a serine to asparagine mutation at a position corresponding to position 128 of SEQ ID NO: 1; an arginine to tryptophan mutation at a position corresponding to position 202 of SEQ ID NO: 1; an isoleucine to leucine mutation at a position corresponding to position 242 of SEQ ID NO: 1; a phenylalanine to leucine mutation at a position corresponding to position 243 of SEQ ID NO: 1; a valine to isoleucine mutation at a position corresponding to position 267 of SEQ ID NO: 1; a valine to leucine mutation at a position corresponding to position 294 of SEQ ID NO: 1; a glycine to arginine mutation at a position corresponding to position 304 of SEQ ID NO: 1; and a threonine to alanine mutation at a position corresponding to position 331 of SEQ ID NO: 1. In some embodiments, the human CD33 gene encodes a polypeptide comprising a glycine to arginine mutation at a position corresponding to position 304 of SEQ ID NO: 1. In some embodiments, the human CD33 gene encodes a polypeptide comprising an alanine to valine mutation at a position corresponding to position 14 of SEQ ID NO: 1. In some embodiments, the human CD33 gene encodes a polypeptide comprising a glycine to arginine mutation at a position corresponding to position 304 of SEQ ID NO: 1 and an alanine to valine mutation at a position corresponding to position 14 of SEQ ID NO: 1.

Human Siglec-5 gene

In some embodiments, the genome of a transgenic non-human animal of the present disclosure comprises a human Siglec-5 gene. In some embodiments, the genome of the transgenic non-human animal comprises an inactivating mutation in the endogenous Siglec-5 gene. In some embodiments, the genome of the transgenic non-human animal comprises a non-functional endogenous Siglec-5 gene. In some embodiments, the genome of the transgenic non-human animal comprises a human Siglec-5 gene and lacks an endogenous Siglec-5 gene. In some embodiments, the genome of the transgenic non-human animal comprises a human Siglec-5 gene and a non-functional endogenous Siglec-5 gene. In some embodiments, the transgenic non-human animal is a mouse. In some embodiments, the genome of the mouse comprises an inactivating mutation in the endogenous murine Siglec-5 gene. In some embodiments, the genome of the mouse comprises a non-functional murine Siglec-5 gene. In some embodiments, the genome of the mouse comprises a human Siglec-5 gene and lacks an endogenous murine Siglec-5 gene. In some embodiments, the genome of the mouse comprises a human Siglec-5 gene and a non-functional murine Siglec-5 gene.

In some embodiments, the human Siglec-5 gene comprises all intronic and exonic sequences of the Siglec-5 gene encoded on chromosome 19 in the human genome. An exemplary polynucleotide comprising all intronic and exonic sequences of the Siglec-5 gene encoded on chromosome 19 in the human genome is shown in SEQ ID NO: 16. In some embodiments, the human Siglec-5 gene comprises the coding sequence for the human Siglec-5 protein/polypeptide. In some embodiments, the human Siglec-5 protein/polypeptide is encoded by a nucleic acid comprising the sequence of SEQ ID NO: 16. In some embodiments, the human Siglec-5 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 16.

In some embodiments, the human Siglec-5 gene comprises a flanking sequence at the 5' end of the coding sequence for the human Siglec-5 polypeptide. In some embodiments, the human Siglec-5 gene comprises a flanking sequence at the 3' end of the coding sequence for the human Siglec-5 polypeptide. In some embodiments, the human Siglec-5 gene comprises a flanking sequence at the 5' end and 3' end of the coding sequence for the human Siglec-5 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-5 gene in one or more cells of the transgenic non-human animal. In some embodiments, the one or more human transcriptional regulatory elements direct expression of the human Siglec-5 gene and one or more additional genes in one or more cells of the transgenic non-human animal. In some embodiments, the one or more additional genes are one or more (e.g., one or more, two or more, three or more, four or more, five or more, or all six) of the human CD33, Siglec-7, Siglec-9, Siglec-11, Siglec-14, and/or Siglec-16 genes. In some embodiments, the one or more human transcriptional regulatory elements direct coordinate expression of the human Siglec-5 gene and the one or more additional genes in one or more cells of the transgenic non-human animal. In some embodiments, the one or more cells of the transgenic non-human animal are one or more of myeloid cells, natural killer (NK) cells, T cells, and/or microglia.

An exemplary amino acid sequence of human Siglec-5 is set forth below as SEQ ID NO: 4:

```
          10         20         30         40         50
  MLPLLLLPLL WGGSLQEKPV YELQVQKSVT VQEGLCVLVP CSFSYPWRSW 60         70         80         90        100
  YSSPPLYVYW FRDGEIPYYA EVVATNNPDR RVKPETQGRF RLLGDVQKKN 110        120        130        140        150
  CSLSIGDARM EDTGSYFFRV ERGRDVKYSY QQNKLNLEVT ALIEKPDIHF 160        170        180        190        200
  LEPLESGRPT RLSCSLPGSC EAGPPLTFSW TGNALSPLDP ETTRSSELTL 210        220        230        240        250
  TPRPEDHGTN LTCQMKRQGA QVTTERTVQL NVSYAPQTIT IFRNGIALEI 260        270        280        290        300
  LQNTSYLPVL EGQALRLLCD APSNPPAHLS WFQGSPALNA TPISNTGILE 310        320        330        340        350
  LRRVRSAEEG GFTCRAQHPL GFLQIFLNLS VYSLPQLLGP SCSWEAEGLH 360        370        380        390        400
  CRCSFRARPA PSLCWRLEEK PLEGNSSQGS FKVNSSSAGP WANSSLILHG 410        420        430        440        450
  GLSSDLKVSC KAWNIYGSQS GSVLLLQGRS NLGTGVVPAA LGGAGVMALL 460        470        480        490        500
  CICLCLIFFL IVKARRKQAA GRPEKMDDED PIMGTITSGS RKKPWPDSPG 510        520        530        540        550
  DQASPPGDAP PLEEQKELHY ASLSFSEMKS REPKDQEAPS TTEYSEIKTS

K
```

In some embodiments, a human Siglec-5 gene of the present disclosure encodes a polypeptide comprising the sequence of SEQ ID NO: 4. In some embodiments, a human Siglec-5 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 4.

In some embodiments, a human Siglec-5 gene of the present disclosure encodes an N-terminal truncation, a C-terminal truncation, or a fragment of a polypeptide comprising the sequence of SEQ ID NO: 4. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, but fewer than 501, consecutive amino acids of SEQ ID NO: 4.

In some embodiments, the human Siglec-5 gene encodes a polypeptide comprising one or more (e.g., one or more, two or more, three or more, four or more, or five) mutations selected from: a valine to alanine mutation at a position corresponding to position 72 of SEQ ID NO: 4; a methionine to valine mutation at a position corresponding to position 215 of SEQ ID NO: 4; a phenylalanine to serine mutation at a position corresponding to position 322 of SEQ ID NO: 4; an arginine to tryptophan mutation at a position corresponding to position 358 of SEQ ID NO: 4; and a proline to alanine mutation at a position corresponding to position 499 of SEQ ID NO: 4.

Human Siglec-7 Gene

In some embodiments, the genome of a transgenic non-human animal of the present disclosure comprises a human Siglec-7 gene. In some embodiments, the genome of the transgenic non-human animal comprises an inactivating mutation in the endogenous Siglec-7 gene. In some embodiments, the genome of the transgenic non-human animal comprises a non-functional endogenous Siglec-7 gene. In some embodiments, the genome of the transgenic non-human animal comprises a human Siglec-7 gene and lacks an endogenous Siglec-7 gene. In some embodiments, the genome of the transgenic non-human animal comprises a human Siglec-7 gene and a non-functional endogenous Siglec-7 gene. In some embodiments, the transgenic non-human animal is a mouse. In some embodiments, the genome of the mouse comprises an inactivating mutation in the endogenous murine Siglec-7 gene. In some embodiments, the genome of the mouse comprises a non-functional murine Siglec-7 gene. In some embodiments, the genome of the mouse comprises a human Siglec-7 gene and lacks an endogenous murine Siglec-7 gene. In some embodiments, the genome of the mouse comprises a human Siglec-7 gene and a non-functional murine Siglec-7 gene.

In some embodiments, the human Siglec-7 gene comprises all intronic and exonic sequences of the Siglec-7 gene encoded on chromosome 19 in the human genome. An exemplary polynucleotide comprising all intronic and exonic sequences of the Siglec-7 gene encoded on chromosome 19 in the human genome is shown in SEQ ID NO: 17. In some embodiments, the human Siglec-7 gene comprises the coding sequence for the human Siglec-7 protein/polypeptide. In some embodiments, the human Siglec-7 protein/ polypeptide is encoded by a nucleic acid comprising the sequence of SEQ ID NO: 17. In some embodiments, the human Siglec-7 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 17.

In some embodiments, the human Siglec-7 gene comprises a flanking sequence at the 5' end of the coding sequence for the human Siglec-7 polypeptide. In some embodiments, the human Siglec-7 gene comprises a flanking sequence at the 3' end of the coding sequence for the human Siglec-7 polypeptide. In some embodiments, the human Siglec-7 gene comprises a flanking sequence at the 5' end and 3' end of the coding sequence for the human Siglec-7 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-7 gene in one or more cells of the transgenic non-human animal. In some embodiments, the one or more human transcriptional regulatory elements direct expression of the human Siglec-7 gene and one or more additional genes in one or more cells of the transgenic non-human animal. In some embodiments, the one or more additional genes are one or more (e.g., one or more, two or more, three or more, four or more, five or more, or all six) of the human CD33, Siglec-5, Siglec-9, Siglec-11, Siglec-14, and/or Siglec-16 genes. In some embodiments, the one or more human transcriptional regulatory elements direct coordinate expression of the human Siglec-7 gene and the one or more additional genes in one or more cells of the transgenic non-human animal. In some embodiments, the one or more cells of the transgenic non-human animal are one or more of myeloid cells, natural killer (NK) cells, T cells, and/or microglia.

Siglec-7 is variously referred to as a Siglec-7 molecule, Sialic acid-binding Ig-like lectin 7, AIRM1, CD328, CDw328, D-Siglec, QA79, SIGLEC19P, SIGLECP2, p75, and p75/AIRM1.

An exemplary amino acid sequence of human Siglec-7 is set forth below as SEQ ID NO: 5:

```
            10         20         30         40         50
    MLLLLLLPLL WGRERVEGQK SNRKDYSLTM QSSVTVQEGM CVHVRCSFSY 60         70         80         90        100
    PVDSQTDSDP VHGYWFRAGN DISWKAPVAT NNPAWAVQEE TRDRFHLLGD 110        120        130        140        150
    PQTKNCTLSI RDARMSDAGR YFFRMEKGNI KWNYKYDQLS VNVTALTHRP 160        170        180        190        200
    NILIPGTLES GCFQNLTCSV PWACEQGTPP MISWMGTSVS PLHPSTTRSS 210        220        230        240        250
    VLTLIPQPQH HGTSLTCQVT LPGAGVTTNR TIQLNVSYPP QNLTVTVFQG 260        270        280        290        300
    EGTASTALGN SSSLSVLEGQ SLRLVCAVDS NPPARLSWTW RSLTLYPSQP 310        320        330        340        350
    SNPLVLELQV HLGDEGEFTC RAQNSLGSQH VSLNLSLQQE YTGKMRPVSG 360        370        380        390        400
    VLLGAVGGAG ATALVFLSFC VIFIVVRSCR KKSARPAADV GDIGMKDANT 410        420        430        440        450
    IRGSASQGNL TESWADDNPR HHGLAAHSSG EEREIQYAPL SFHKGEPQDL

460
    SGQEATNNEY SEIKIPK
```

In some embodiments, the Siglec-7 is a preprotein that includes a signal sequence. In some embodiments, the Siglec-7 is a mature protein. In some embodiments, the mature Siglec-7 protein does not include a signal sequence. In some embodiments, the mature Siglec-7 protein is expressed on a cell. In some embodiments, the mature Siglec-7 protein is expressed on a cell, such as the surface of a cell.

Human Siglec-7 proteins, contain several domains, including without limitation, a signal sequence located at amino acid residues 1-18 of SEQ ID NO: 5, an extracellular immunoglobulin-like variable-type (IgV) domain located at amino acid residues 39-122 of SEQ ID NO: 5, two Ig-like C2-type domains located at amino acid residues 150-233 and 240-336 of SEQ ID NO: 5, a transmembrane domain located at amino acid residues 354-376 of SEQ ID NO: 5, an ITIM motif 1 located at amino acid residues 435-440 of SEQ ID NO: 5, and an ITIM motif 2 located at amino acid residues 459-463 of SEQ ID NO: 5. As one of skill in the art will appreciate, the beginning and ending residues of the domains of the present disclosure may vary depending upon the computer modeling program used or the method used for determining the domain.

In some embodiments, a human Siglec-7 gene of the present disclosure encodes a polypeptide comprising the sequence of SEQ ID NO: 5. In some embodiments, a human Siglec-7 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 5.

In some embodiments, a human Siglec-7 gene of the present disclosure encodes an N-terminal truncation, a C-terminal truncation, or a fragment of a polypeptide comprising the sequence of SEQ ID NO: 5. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, but fewer than 467, consecutive amino acids of SEQ ID NO: 5.

In some embodiments, a human Siglec-7 gene of the present disclosure encodes a polypeptide comprising the sequence of SEQ ID NO: 6. In some embodiments, a human Siglec-7 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 6.

In some embodiments, a human Siglec-7 gene of the present disclosure encodes an N-terminal truncation, a C-terminal truncation, or a fragment of a polypeptide comprising the sequence of SEQ ID NO: 6. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, but fewer than 374, consecutive amino acids of SEQ ID NO: 6.

In some embodiments, a human Siglec-7 gene of the present disclosure encodes a polypeptide comprising the sequence of SEQ ID NO: 7. In some embodiments, a human Siglec-7 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 7.

In some embodiments, a human Siglec-7 gene of the present disclosure encodes an N-terminal truncation, a C-terminal truncation, or a fragment of a polypeptide comprising the sequence of SEQ ID NO: 7. N-terminal truncations, C-terminal truncations, or fragments may comprise least 10, at least 25, at least 50, at least 75, at least 100, at least 125, but fewer than 145, consecutive amino acids of SEQ ID NO: 7.

In some embodiments, a human Siglec-7 gene of the present disclosure encodes a polypeptide comprising the sequence of SEQ ID NO: 8. In some embodiments, a human Siglec-7 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 8.

In some embodiments, a human Siglec-7 gene of the present disclosure encodes an N-terminal truncation, a C-terminal truncation, or a fragment of a polypeptide comprising the sequence of SEQ ID NO: 8. N-terminal truncations, C-terminal truncations, or fragments may comprise least 10, at least 25, at least 50, at least 75, at least 100, at least 125, but fewer than 145, consecutive amino acids of SEQ ID NO: 8.

In some embodiments, the human Siglec-7 gene encodes a polypeptide comprising a leucine to proline mutation at a position corresponding to position 215 of SEQ ID NO: 5.

Human Siglec-9 Gene

In some embodiments, the genome of a transgenic non-human animal of the present disclosure comprises a human Siglec-9 gene. In some embodiments, the genome of the transgenic non-human animal comprises an inactivating mutation in the endogenous Siglec-9 gene. In some embodiments, the genome of the transgenic non-human animal comprises a non-functional endogenous Siglec-9 gene. In some embodiments, the genome of the transgenic non-human animal comprises a human Siglec-9 gene and lacks an endogenous Siglec-9 gene. In some embodiments, the genome of the transgenic non-human animal comprises a human Siglec-9 gene and a non-functional endogenous Siglec-9 gene. In some embodiments, the transgenic non-human animal is a mouse. In some embodiments, the genome of the mouse comprises an inactivating mutation in the endogenous murine Siglec-9 gene. In some embodiments, the genome of the mouse comprises a non-functional murine Siglec-9 gene. In some embodiments, the genome of the mouse comprises a human Siglec-9 gene and lacks an endogenous murine Siglec-9 gene. In some embodiments, the genome of the mouse comprises a human Siglec-9 gene and a non-functional murine Siglec-9 gene.

In some embodiments, the human Siglec-9 gene comprises all intronic and exonic sequences of the Siglec-9 gene encoded on chromosome 19 in the human genome. An exemplary polynucleotide comprising all intronic and exonic sequences of the Siglec-9 gene encoded on chromosome 19 in the human genome is shown in SEQ ID NO: 18. In some embodiments, the human Siglec-9 gene comprises the coding sequence for the human Siglec-9 protein/polypeptide. In some embodiments, the human Siglec-9 protein/polypeptide is encoded by a nucleic acid comprising the sequence of SEQ ID NO: 18. In some embodiments, the human Siglec-9 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 18.

In some embodiments, the human Siglec-9 gene comprises a flanking sequence at the 5' end of the coding sequence for the human Siglec-9 polypeptide. In some embodiments, the human Siglec-9 gene comprises a flanking sequence at the 3' end of the coding sequence for the human Siglec-9 polypeptide. In some embodiments, the human Siglec-9 gene comprises a flanking sequence at the 5' end and 3' end of the coding sequence for the human Siglec-9 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-9 gene in one or more cells of the transgenic non-human animal. In some embodiments, the one or more human transcriptional regulatory elements direct expression of the human Siglec-9 gene and one or more additional genes in one or more cells of the transgenic non-human animal. In some embodiments, the one or more additional genes are one or more (e.g., one or more, two or more, three or more, four or more, five or more, or all six) of the human CD33, Siglec-5, Siglec-7, Siglec-11, Siglec-14, and/or Siglec-16 genes. In some embodiments, the one or more human transcriptional regulatory elements direct coordinate expression of the human Siglec-9 gene and the one or more additional genes in one or more cells of the transgenic non-human animal. In some embodiments, the one or more cells of the transgenic non-human animal are one or more of myeloid cells, natural killer (NK) cells, T cells, and/or microglia.

Siglec-9 is variously referred to as a Siglec-9 molecule, Sialic acid-binding Ig-like lectin 9, CD329 antigen, CD329; CDw329, FOAP-9, and OBBP-LIKE.

Siglec-9 is an immunoglobulin-like receptor primarily expressed on myeloid lineage cells, including without limitation, macrophages, neutrophils, NK cells, dendritic cells, osteoclasts, monocytes, and microglia. In some embodiments, Siglec-9 forms a receptor-signaling complex with CD64. In some embodiments, Siglec-9 signaling results in the downstream inhibition of PI3K or other intracellular signals.

An exemplary amino acid sequence of human Siglec-9 is set forth below as SEQ ID NO: 9:

expressed on a cell. In some embodiments, the mature Siglec-9 protein is expressed on a cell, such as the surface of a cell.

Human Siglec-9 proteins contain several domains, including without limitation, a signal sequence located at amino acid residues 1-17 SEQ ID NO: 9, an extracellular immunoglobulin-like variable-type (IgV) domain located at amino acid residues 20-140 of SEQ ID NO: 9, two Ig-like C2-type domains located at amino acid residues 146-229 and 236-336 of SEQ ID NO: 9, a transmembrane domain located at amino acid residues 348-370 of SEQ ID NO: 9, an ITIM motif located at amino acid residues 431-436 of SEQ ID NO: 9, and SLAM-like motif located at amino acid residues 454-459 of SEQ ID NO: 9. As one of skill in the art will appreciate, the beginning and ending residues of the domains of the present disclosure may vary depending upon the computer modeling program used or the method used for determining the domain.

In some embodiments, a human Siglec-9 gene of the present disclosure encodes a polypeptide comprising the sequence of SEQ ID NO: 9. In some embodiments, a human Siglec-9 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 9.

In some embodiments, a human Siglec-9 gene of the present disclosure encodes an N-terminal truncation, a C-terminal truncation, or a fragment of a polypeptide comprising the sequence of SEQ ID NO: 9. N-terminal truncations, C-terminal truncations, or fragments may comprise least 10, at least 25, at least 50, at least 75, at least 100, at least 125, at least 150, at least 175, at least 200, at least 225,

```
        10         20         30         40         50
MLLLLLPLLW GRERAEGQTS KLLTMQSSVT VQEGLCVHVP CSFSYPSHGW 60         70         80         90        100
IYPGPVVHGY WFREGANTDQ DAPVATNNPA RAVWEETRDR FHLLGDPHTK 110        120        130        140        150
NCTLSIRDAR RSDAGRYFFR MEKGSIKWNY KHHRLSVNVT ALTHRPNILI 160        170        180        190        200
PGTLESGCPQ NLTCSVPWAC EQGTPPMISW IGTSVSPLDP STTRSSVLTL 210        220        230        240        250
IPQPQDHGTS LTCQVTFPGA SVTTNKTVHL NVSYPPQNLT MTVFQGDGTV 260        270        280        290        300
STVLGNGSSL SLPEGQSLRL VCAVDAVDSN PPARLSLSWR GLTLCPSQPS 310        320        330        340        350
NPGVLELPWV HLRDAAEFTC RAQNPLGSQQ VYLNVSLQSK ATSGVTQGVV 360        370        380        390        400
GGAGATALVF LSFCVIFVVV RSCRKKSARP AAGVGDTGIE DANAVRGSAS 410        420        430        440        450
QGPLTEPWAE DSPPDQPPPA SARSSVGEGE LQYASLSFQM VKPWDSRGQE

460
ATDTEYSEIK IHR
```

In some embodiments, the Siglec-9 is a preprotein that includes a signal sequence. In some embodiments, the Siglec-9 is a mature protein. In some embodiments, the mature Siglec-9 protein does not include a signal sequence. In some embodiments, the mature Siglec-9 protein is at least 250, at least 275, at least 300, at least 325, at least 350, at least 375, at least 400, at least 425, at least 450, but fewer than 463, consecutive amino acids of SEQ ID NO: 9.

In some embodiments, a human Siglec-9 gene of the present disclosure encodes a polypeptide comprising the sequence of SEQ ID NO: 10. In some embodiments, a human Siglec-9 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 10.

In some embodiments, a human Siglec-9 gene of the present disclosure encodes an N-terminal truncation, a C-terminal truncation, or a fragment of a polypeptide comprising the sequence of SEQ ID NO: 10. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, but fewer than 479, consecutive amino acids of SEQ ID NO: 10.

In some embodiments, the human Siglec-9 gene encodes a polypeptide comprising one or more (e.g., one or more, two or more, three or more, four or more, five or more, six or more, or seven) mutations selected from: a lysine to glutamate mutation at a position corresponding to position 100 of SEQ ID NO: 9; a serine to asparagine mutation at a position corresponding to position 125 of SEQ ID NO: 9; a lysine to glutamine mutation at a position corresponding to position 131 of SEQ ID NO: 9; an asparagine to lysine mutation at a position corresponding to position 147 of SEQ ID NO: 9; an alanine to glutamate mutation at a position corresponding to position 315 of SEQ ID NO: 9; an alanine to aspartate mutation at a position corresponding to position 316 of SEQ ID NO: 9; and a valine to alanine mutation at a position corresponding to position 349 of SEQ ID NO: 9.

Human Siglec-11 Gene

In some embodiments, the genome of a transgenic non-human animal of the present disclosure comprises a human Siglec-11 gene. In some embodiments, the genome of the transgenic non-human animal comprises an inactivating mutation in the endogenous Siglec-11 gene. In some embodiments, the genome of the transgenic non-human animal comprises a non-functional endogenous Siglec-11 gene. In some embodiments, the genome of the transgenic non-human animal comprises a human Siglec-11 gene and lacks an endogenous Siglec-11 gene. In some embodiments, the genome of the transgenic non-human animal comprises a human Siglec-11 gene and a non-functional endogenous Siglec-11 gene. In some embodiments, the transgenic non-human animal is a mouse. In some embodiments, the genome of the mouse comprises an inactivating mutation in the endogenous murine Siglec-11 gene. In some embodiments, the genome of the mouse comprises a non-functional murine Siglec-11 gene. In some embodiments, the genome of the mouse comprises a human Siglec-11 gene and lacks an endogenous murine Siglec-11 gene. In some embodiments, the genome of the mouse comprises a human Siglec-11 gene and a non-functional murine Siglec-11 gene.

In some embodiments, the human Siglec-11 gene comprises all intronic and exonic sequences of the Siglec-11 gene encoded on chromosome 19 in the human genome. An exemplary polynucleotide comprising all intronic and exonic sequences of the Siglec-11 gene encoded on chromosome 19 in the human genome is shown in SEQ ID NO: 19. In some embodiments, the human Siglec-11 gene comprises the coding sequence for the human Siglec-11 polypeptide. In some embodiments, the human Siglec-11 protein/polypeptide is encoded by a nucleic acid comprising the sequence of SEQ ID NO: 19. In some embodiments, the human Siglec-11 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 19.

In some embodiments, the human Siglec-11 gene comprises a flanking sequence at the 5' end of the coding sequence for the human Siglec-11 polypeptide. In some embodiments, the human Siglec-11 gene comprises a flanking sequence at the 3' end of the coding sequence for the human Siglec-11 polypeptide. In some embodiments, the human Siglec-11 gene comprises a flanking sequence at the 5' end and 3' end of the coding sequence for the human Siglec-11 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-11 gene in one or more cells of the transgenic non-human animal. In some embodiments, the one or more human transcriptional regulatory elements direct expression of the human Siglec-11 gene and one or more additional genes in one or more cells of the transgenic non-human animal. In some embodiments, the one or more additional genes are one or more (e.g., one or more, two or more, three or more, four or more, five or more, or all six) of the human CD33, Siglec-5, Siglec-7, Siglec-9, Siglec-14, and/or Siglec-16 genes. In some embodiments, the one or more human transcriptional regulatory elements direct coordinate expression of the human Siglec-11 gene and the one or more additional genes in one or more cells of the transgenic non-human animal. In some embodiments, the one or more cells of the transgenic non-human animal are one or more of myeloid cells, natural killer (NK) cells, T cells, and/or microglia.

An exemplary amino acid sequence of human Siglec-11 is set forth below as SEQ ID NO: 11:

```
          10         20         30         40         50
MVPGQAPQS  PEMLLLPLLL  PVLGAGSLNK  DPSYSLQVQR  QVPVPEGLCV 60         70         80         90        100
IVSCNLSYPR  DGWDESTAAY  GYWFKGRTSP  KTGAPVATNN  QSREVEMSTR
```

```
                    -continued
         110        120        130        140        150
    DRFQLTGDPG KGSCSLVIRD AQREDEAWYF FRVERGSRVR HSFLSNAFFL 160        170        180        190        200
    KVTALTKKPD VYIPETLEPG QPVTVICVFN WAFKKCPAPS FSWTGAALSP 210        220        230        240        250
    RRTRPSTSHF SVLSFTPSPQ DHDTDLTCHV DFSRKGVSAQ RTVRLRVAYA 260        270        280        290        300
    PKDLIISISH DNTSALELQG NVIYLEVQKG QFLRLLCAAD SQPPATLSWV 310        320        330        340        350
    LQDRVLSSSH PWGPRTLGLE LRGVRAGDSG RYTCRAENRL GSQQQALDLS 360        370        380        390        400
    VQYPPENLRV MVSQANRTVL ENLGNGTSLP VLEGQSLRLV CVTHSSPPAR 410        420        430        440        450
    LSWTRWGQTV GPSQPSDPGV LELPPIQMEH EGEFTCHAQH PLGSQHVSLS 460        470        480        490        500
    LSVHYPPQLL GPSCSWEAEG LHCSCSSQAS PAPSLRWWLG EELLEGNSSQ 510        520        530        540        550
    GSFEVTPSSA GPWANSSLSL HGGLSSGLRL RCKAWNVHGA QSGSVFQLLP 560        570        580        590        600
    GKLEHGGGLG LGAALGAGVA ALLAFCSCLV VFRVKICRKE ARKRAAAEQD 610        620        630        640        650
    VPSTLGPISQ GHQHECSAGS SQDHPPPGAA TYTPGKGEEQ ELHYASLSFQ 660        670        680        690
    GLRLWEPADQ EAPSTTEYSE IKIHTGQPLR GPGFGLQLER EMSGMVPK
```

In some embodiments, a human Siglec-11 gene of the present disclosure encodes a polypeptide comprising the sequence of SEQ ID NO: 11. In some embodiments, a human Siglec-11 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 11.

In some embodiments, a human Siglec-11 gene of the present disclosure encodes an N-terminal truncation, a C-terminal truncation, or a fragment of a polypeptide comprising the sequence of SEQ ID NO: 11. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 675, but fewer than 698, consecutive amino acids of SEQ ID NO: 11.

In some embodiments, a human Siglec-11 gene of the present disclosure encodes a polypeptide comprising the sequence of SEQ ID NO: 12. In some embodiments, a human Siglec-11 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 12.

In some embodiments, a human Siglec-11 gene of the present disclosure encodes an N-terminal truncation, a C-terminal truncation, or a fragment of a polypeptide comprising the sequence of SEQ ID NO: 12. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, but fewer than 602, consecutive amino acids of SEQ ID NO: 12.

Human Siglec-14 Gene

In some embodiments, the genome of a transgenic non-human animal of the present disclosure comprises a human Siglec-14 gene. In some embodiments, the genome of the transgenic non-human animal comprises an inactivating mutation in the endogenous Siglec-14 gene. In some embodiments, the genome of the transgenic non-human animal comprises a non-functional endogenous Siglec-14 gene. In some embodiments, the genome of the transgenic non-human animal comprises a human Siglec-14 gene and lacks an endogenous Siglec-14 gene. In some embodiments, the genome of the transgenic non-human animal comprises a human Siglec-14 gene and a non-functional endogenous Siglec-14 gene.

In some embodiments, the human Siglec-14 gene comprises all intronic and exonic sequences of the Siglec-14 gene encoded on chromosome 19 in the human genome. An exemplary polynucleotide comprising all intronic and exonic sequences of the Siglec-14 gene encoded on chromosome 19 in the human genome is shown in SEQ ID NO: 20. In some embodiments, the human Siglec-14 gene comprises the coding sequence for the human Siglec-14 polypeptide. In some embodiments, the human Siglec-14 protein/polypeptide is encoded by a nucleic acid comprising the sequence of SEQ ID NO: 20. In some embodiments, the human Siglec-14 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 20.

In some embodiments, the human Siglec-14 gene comprises a flanking sequence at the 5' end of the coding sequence for the human Siglec-14 polypeptide. In some embodiments, the human Siglec-14 gene comprises a flanking sequence at the 3' end of the coding sequence for the human Siglec-14 polypeptide. In some embodiments, the human Siglec-14 gene comprises a flanking sequence at the 5' end and 3' end of the coding sequence for the human Siglec-14 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-14 gene in one or more cells of the transgenic non-human animal. In some embodiments, the one or more human transcriptional regulatory elements direct expression of the human Siglec-14 gene and one or more additional genes in one or more cells of the transgenic non-human animal. In some embodiments, the one or more additional genes are one or more (e.g., one or more, two or more, three or more, four or more, five or more, or all six) of the human CD33, Siglec-5, Siglec-7, Siglec-9, Siglec-11, and/or Siglec-16 genes. In some embodiments, the one or more human transcriptional regulatory elements direct coordinate expression of the human Siglec-14 gene and the one or more additional genes in one or more cells of the transgenic non-human animal. In some embodiments, the one or more cells of the transgenic non-human animal are one or more of myeloid cells, natural killer (NK) cells, T cells, and/or microglia.

An exemplary amino acid sequence of human Siglec-14 is set forth below as SEQ ID NO: 13:

```
              10         20         30         40         50
       MLPLLLLPLL WGGSLQEKPV YELQVQKSVT VQEGLCVLVP CSFSYPWRSW 60         70         80         90        100
       YSSPPLYVYW FRDGEIPYYA EVVATNNPDR RVKPETQGRF RLLGDVQKKN 110        120        130        140        150
       CSLSIGDARM EDTGSYFFRV ERGRDVKYSY QQNKLNLEVT ALIEKPDIHF 160        170        180        190        200
       LEPLESGRPT RLSCSLPGSC EAGPPLTFSW TGNALSPLDP ETTRSSELTL 210        220        230        240        250
       TPRPEDHGTN LTCQVKRQGA QVTTERTVQL NVSYAPQNLA ISIFFRNGTG 260        270        280        290        300
       TALRILSNGM SVPIQEGQSL FLACTVDSNP PASLSWFREG KALNPSQTSM 310        320        330        340        350
       SGTLELPNIG AREGGEFTCR VQHPLGSQHL SFILSVQRSS SSCICVTEKQ 360        370        380        390
       QGSWPLVLTL IRGALMGAGF LLTYGLTWIY YTRCGGPQQS RAERPG
```

In some embodiments, a human Siglec-14 gene of the present disclosure encodes a polypeptide comprising the sequence of SEQ ID NO: 13. In some embodiments, a human Siglec-14 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 13.

In some embodiments, a human Siglec-14 gene of the present disclosure encodes an N-terminal truncation, a C-terminal truncation, or a fragment of a polypeptide comprising the sequence of SEQ ID NO: 13. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, but fewer than 396, consecutive amino acids of SEQ ID NO: 13.

Human Siglec-16 Gene

In some embodiments, the genome of a transgenic non-human animal of the present disclosure comprises a human Siglec-16 gene. In some embodiments, the genome of the transgenic non-human animal comprises an inactivating mutation in the endogenous Siglec-16 gene. In some embodiments, the genome of the transgenic non-human animal comprises a non-functional endogenous Siglec-16 gene. In some embodiments, the genome of the transgenic non-human animal comprises a human Siglec-16 gene and lacks an endogenous Siglec-16 gene. In some embodiments, the genome of the transgenic non-human animal comprises a human Siglec-16 gene and a non-functional endogenous Siglec-16 gene.

In some embodiments, the human Siglec-16 gene comprises all intronic and exonic sequences of the Siglec-16 gene encoded on chromosome 19 in the human genome. An exemplary polynucleotide comprising all intronic and exonic sequences of the Siglec-16 gene encoded on chromosome 19 in the human genome is shown in SEQ ID NO: 21. In some embodiments, the human Siglec-16 gene comprises the coding sequence for the human Siglec-16 polypeptide. In some embodiments, the human Siglec-16 protein/polypeptide is encoded by a nucleic acid comprising the sequence of SEQ ID NO: 21. In some embodiments, the human Siglec-16 protein/polypeptide is encoded by a nucleic acid comprising a sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identical to the sequence of SEQ ID NO: 21.

dinate expression of the human Siglec-16 gene and the one or more additional genes in one or more cells of the transgenic non-human animal. In some embodiments, the one or more cells of the transgenic non-human animal are one or more of myeloid cells, natural killer (NK) cells, T cells, and/or microglia.

An exemplary amino acid sequence of human Siglec-16 is set forth below as SEQ ID NO: 14:

```
          10         20         30         40         50
   MLLLPLLLPV LGAGSLNKDP SYSLQVQRQV PVPEGLCVIV SCNLSYPRDG 60         70         80         90        100
   WDESTAAYGY WFKGRTSPKT GAPVATNNQS REVAMSTRDR FQLTGDPGKG 110        120        130        140        150
   SCSLVIRDAQ REDEAWYFFR VERGSRVRHS FLSNAFFLKV TALTQKPDVY 160        170        180        190        200
   IPETLEPGQP VTVICVFNWA FKKCPAPSFS WTGAALSPRR TRPSTSHFSV 210        220        230        240        250
   LSFTPSPQDH DTDLTCHVDF SRKGVSAQRT VRLRVASLEL QGNVIYLEVQ 260        270        280        290        300
   KGQFLRLLCA ADSQPPATLS WVLQDRVLSS SHPWGPRTLG LELPGVKAGD 310        320        330        340        350
   SGRYTCRAEN RLGSQQRALD LSVQYPPENL RVMVSQANRT VLENLRNGTS 360        370        380        390        400
   LRVLEGQSLR LVCVTHSSPP ARLSWTWGEQ TVGPSQPSDP GVLQLPRVQM 410        420        430        440        450
   EHEGEFTCHA RHPLGSQRVS LSFSVHCKSG PMTGVVLVAV GEVAMKILLL 460        470        480
   CLCLILLRVR SCRRKAARAA LGMEAADAVT D
```

In some embodiments, the human Siglec-16 gene comprises a flanking sequence at the 5' end of the coding sequence for the human Siglec-16 polypeptide. In some embodiments, the human Siglec-16 gene comprises a flanking sequence at the 3' end of the coding sequence for the human Siglec-16 polypeptide. In some embodiments, the human Siglec-16 gene comprises a flanking sequence at the 5' end and 3' end of the coding sequence for the human Siglec-16 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human Siglec-16 gene in one or more cells of the transgenic non-human animal. In some embodiments, the one or more human transcriptional regulatory elements direct expression of the human Siglec-16 gene and one or more additional genes in one or more cells of the transgenic non-human animal. In some embodiments, the one or more additional genes are one or more (e.g., one or more, two or more, three or more, four or more, five or more, or all six) of the human CD33, Siglec-5, Siglec-7, Siglec-9, Siglec-11, and/or Siglec-14 genes. In some embodiments, the one or more human transcriptional regulatory elements direct coor- In some embodiments, a human Siglec-16 gene of the present disclosure encodes a polypeptide comprising the sequence of SEQ ID NO: 14. In some embodiments, a human Siglec-16 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 14.

In some embodiments, a human Siglec-16 gene of the present disclosure encodes an N-terminal truncation, a C-terminal truncation, or a fragment of a polypeptide comprising the sequence of SEQ ID NO: 14. N-terminal truncations, C-terminal truncations, or fragments may comprise least 10, at least 25, at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, but fewer than 481, consecutive amino acids of SEQ ID NO: 14.

Gene Combinations

In some embodiments, the genome of a transgenic non-human animal of the present disclosure comprises two or more, three or more, four or more, five or more, six or more, or all seven of the human CD33, Siglec-5, Siglec-7, Siglec-9, Siglec-11, Siglec-14, and/or Siglec-16 genes.

In some embodiments, the genome of transgenic non-human animal comprises one or more polynucleotides encoding two or more human genes. In some embodiments, the two or more human genes are encoded on separate polynucleotides. In some embodiments, the two or more human genes are encoded on a single polynucleotide. In some embodiments, the one or more polynucleotides are bacterial artificial chromosomes (BACs).

In some embodiments, the genome of the transgenic non-human animal comprises two of the human CD33, Siglec-5, Siglec-7, Siglec-9, Siglec-11, Siglec-14, and Siglec-16 genes. In some embodiments, the genome of the transgenic non-human animal comprises the human CD33 and Siglec-5 genes; the human CD33 and Siglec-7 genes; the human CD33 and Siglec-9 genes; the human CD33 and Siglec-11 genes; the human CD33 and Siglec-14 genes; the human CD33 and Siglec-16 genes; the human Siglec-5 and Siglec-7 genes; the human Siglec-5 and Siglec-9 genes; the human Siglec-5 and Siglec-11 genes; the human Siglec-5 and Siglec-14 genes; the human Siglec-5 and Siglec-16 genes; the human Siglec-7 and Siglec-9 genes; the human Siglec-7 and Siglec-11 genes; the human Siglec-7 and Siglec-14 genes; the human Siglec-7 and Siglec-16 genes; the human Siglec-9 and Siglec-11 genes; the human Siglec-9 and Siglec-14 genes; the human Siglec-9 and Siglec-16 genes; the human Siglec-11 and Siglec-14 genes; the human Siglec-11 and Siglec-16 genes; or the human Siglec-14 and Siglec 16 genes. In some embodiments, the two human genes are encoded on one or more BACs. In some embodiments, the two human genes are encoded on a single BAC. In some embodiments, the genome of the transgenic non-human animal comprises the human Siglec-5 and Siglec-14 genes. In some embodiments, the genome of the transgenic non-human animal comprises the human Siglec-11 and Siglec-16 genes.

In some embodiments, the genome of the transgenic non-human animal comprises three of the human CD33, Siglec-5, Siglec-7, Siglec-9, Siglec-11, Siglec-14, and Siglec-16 genes. In some embodiments, the genome of the transgenic non-human animal comprises the human CD33, Siglec-5, and Siglec-7 genes; the human CD33, Siglec-5, and Siglec-9 genes; the human CD33, Siglec-5, and Siglec-11 genes; the human CD33, Siglec-5, and Siglec-14 genes; the human CD33, Siglec-5, and Siglec-16 genes; the human CD33, Siglec-7, and Siglec-9 genes; the human CD33, Siglec-7, and Siglec-11 genes; the human CD33, Siglec-7, and Siglec-14 genes; the human CD33, Siglec-7, and Siglec-16 genes; the human CD33, Siglec-9, and Siglec-11 genes; the human CD33, Siglec-9, and Siglec-14 genes; the human CD33, Siglec-9, and Siglec-16 genes; the human CD33, Siglec-11, and Siglec-14 genes; the human CD33, Siglec-11, and Siglec-16 genes; the human CD33, Siglec-14, and Siglec-16 genes; the human Siglec-5, Siglec-7, and Siglec-9 genes; the human Siglec-5, Siglec-7, and Siglec-11 genes; the human Siglec-5, Siglec-7, and Siglec-14 genes; the human Siglec-5, Siglec-7, and Siglec-16 genes; the human Siglec-5, Siglec-9, and Siglec-11 genes; the human Siglec-5, Siglec-9, and Siglec-14 genes; the human Siglec-5, Siglec-9, and Siglec-16 genes; the human Siglec-5, Siglec-11, and Siglec-14 genes; the human Siglec-5, Siglec-11, and Siglec-16 genes; the human Siglec-5, Siglec-14, and Siglec-16 genes; the human Siglec-7, Siglec-9, and Siglec-11 genes; the human Siglec-7, Siglec-9, and Siglec-14 genes; the human Siglec-7, Siglec-9, and Siglec-16 genes; the human Siglec-7, Siglec-11, and Siglec-14 genes; the human Siglec-7, Siglec-11, and Siglec-16 genes; the human Siglec-7, Siglec-14, and Siglec-16 genes; the human Siglec-9, Siglec-11, and Siglec-14 genes; the human Siglec-9, Siglec-11, and Siglec-16 genes; the human Siglec-9, Siglec-14, and Siglec-16 genes; or the human Siglec-11, Siglec-14, and Siglec-16 genes. In some embodiments, the three human genes are encoded on one or more BACs. In some embodiments, the three human genes are encoded on a single BAC. In some embodiments, the genome of the transgenic non-human animal comprises the human CD33, Siglec-7, and Siglec-9 genes.

In some embodiments, the genome of the transgenic non-human animal comprises four of the human CD33, Siglec-5, Siglec-7, Siglec-9, Siglec-11, Siglec-14, and Siglec-16 genes. In some embodiments, the genome of the transgenic non-human animal comprises the human CD33, Siglec-5, Siglec-7, and Siglec-9 genes; the human CD33, Siglec-5, Siglec-7, and Siglec-11 genes; the human CD33, Siglec-5, Siglec-7, and Siglec-14 genes; the human CD33, Siglec-5, Siglec-7, and Siglec-16 genes; the human CD33, Siglec-5, Siglec-9, and Siglec-11 genes; the human CD33, Siglec-5, Siglec-9, and Siglec-14 genes; the human CD33, Siglec-5, Siglec-9, and Siglec-16 genes; the human CD33, Siglec-5, Siglec-11, and Siglec-14 genes; the human CD33, Siglec-5, Siglec-11, and Siglec-16 genes; the human CD33, Siglec-5, Siglec-14, and Siglec-16 genes; the human CD33, Siglec-7, Siglec-9, and Siglec-11 genes; the human CD33, Siglec-7, Siglec-9, and Siglec-14 genes; the human CD33, Siglec-7, Siglec-9, and Siglec-16 genes; the human CD33, Siglec-7, Siglec-11, and Siglec-14 genes; the human CD33, Siglec-7, Siglec-11, and Siglec-16 genes; the human CD33, Siglec-7, Siglec-14, and Siglec-16 genes; the human CD33, Siglec-9, Siglec-11, and Siglec-14 genes; the human CD33, Siglec-9, Siglec-11, and Siglec-16 genes; the human CD33, Siglec-9, Siglec-14, and Siglec-16 genes; the human CD33, Siglec-11, Siglec-14, and Siglec-16 genes; the human Siglec-5, Siglec-7, Siglec-9, and Siglec-11 genes; the human Siglec-5, Siglec-7, Siglec-9, and Siglec-14 genes; the human Siglec-5, Siglec-7, Siglec-9, and Siglec-16 genes; the human Siglec-5, Siglec-7, Siglec-11, and Siglec-14 genes; the human Siglec-5, Siglec-7, Siglec-11, and Siglec-16 genes; the human Siglec-5, Siglec-7, Siglec-14, and Siglec-16 genes; the human Siglec-5, Siglec-9, Siglec-11, and Siglec-14 genes; the human Siglec-5, Siglec-9, Siglec-11, and Siglec-16 genes; the human Siglec-5, Siglec-9, Siglec-14, and Siglec-16 genes; the human Siglec-5, Siglec-11, Siglec-14, and Siglec-16 genes; the human Siglec-7, Siglec-9, Siglec-11, and Siglec-14 genes; the human Siglec-7, Siglec-9, Siglec-11, and Siglec-16 genes; the human Siglec-7, Siglec-9, Siglec-14, and Siglec-16 genes; the human Siglec-7, Siglec-11, Siglec-14, and Siglec-16 genes; or the human Siglec-9, Siglec-11, Siglec-14, and Siglec-16 genes. In some embodiments, the four human genes are encoded on one or more BACs. In some embodiments, the four human genes are encoded on two BACs. In some embodiments, the four human genes are encoded on a single BAC.

In some embodiments, the genome of the transgenic non-human animal comprises five of the human CD33, Siglec-5, Siglec-7, Siglec-9, Siglec-11, Siglec-14, and Siglec-16 genes. In some embodiments, the genome of the transgenic non-human animal comprises the human CD33, Siglec-5, Siglec-7, Siglec-9, and Siglec-11 genes; the human CD33, Siglec-5, Siglec-7, Siglec-9, and Siglec-14 genes; the human CD33, Siglec-5, Siglec-7, Siglec-9, and Siglec-16 genes; the human CD33, Siglec-5, Siglec-7, Siglec-11, and Siglec-14 genes; the human CD33, Siglec-5, Siglec-7, Siglec-11, and Siglec-16 genes; the human CD33, Siglec-5, Siglec-7, Siglec-14, and Siglec-16 genes; the human CD33, Siglec-5, Siglec-9, Siglec-11, and Siglec-14 genes; the human CD33, Siglec-5, Siglec-9, Siglec-11, and Siglec-16 genes; the human CD33, Siglec-5, Siglec-9, Siglec-14, and Siglec-16 genes; the human CD33, Siglec-5, Siglec-11, Siglec-14, and Siglec-16 genes; the human CD33, Siglec-7, Siglec-9, Siglec-11, and Siglec-14 genes; the human CD33, Siglec-7, Siglec-9, Siglec-11, and Siglec-16 genes; the human CD33, Siglec-7, Siglec-9, Siglec-14, and Siglec-16 genes; the human CD33, Siglec-7, Siglec-11, Siglec-14, and Siglec-16 genes; the human CD33, Siglec-9, Siglec-11, Siglec-14, and Siglec-16 genes; the human Siglec-5, Siglec-7, Siglec-9, Siglec-11, and Siglec-14 genes; the human Siglec-5, Siglec-7, Siglec-9, Siglec-11, and Siglec-16 genes; the human Siglec-5, Siglec-7, Siglec-9, Siglec-14, and Siglec-16 genes; the human Siglec-5, Siglec-7, Siglec-11, Siglec-14, and Siglec-16 genes; the human Siglec-5, Siglec-9, Siglec-11, Siglec-14, and Siglec-16 genes; or the human Siglec-7, Siglec-9, Siglec-11, Siglec-14, and Siglec-16 genes. In some embodiments, the five human genes are encoded on one or more BACs. In some embodiments, the five human genes are encoded on two BACs. In some embodiments, the five human genes are encoded on a single BAC.

In some embodiments, the genome of the transgenic non-human animal comprises six of the human CD33, Siglec-5, Siglec-7, Siglec-9, Siglec-11, Siglec-14, and Siglec-16 genes. In some embodiments, the genome of the transgenic non-human animal comprises the human CD33, Siglec-5, Siglec-7, Siglec-9, Siglec-11, and Siglec-14 genes; the human Siglec-5, Siglec-7, Siglec-9, Siglec-11, Siglec-14, and Siglec-16 genes; the human CD33, Siglec-7, Siglec-9, Siglec-11, Siglec-14, and Siglec-16 genes; the human CD33, Siglec-5, Siglec-9, Siglec-11, Siglec-14, and Siglec-16 genes; the human CD33, Siglec-5, Siglec-7, Siglec-11, Siglec-14, and Siglec-16 genes; the human CD33, Siglec-5, Siglec-7, Siglec-9, Siglec-14, and Siglec-16 genes; or the human CD33, Siglec-5, Siglec-7, Siglec-9, Siglec-11, and Siglec-16 genes. In some embodiments, the six human genes are encoded on one or more BACs. In some embodiments, the six human genes are encoded on a single BAC.

In some embodiments, the genome of the transgenic non-human animal comprises the human CD33, Siglec-5, Siglec-7, Siglec-9, Siglec-11, Siglec-14, and Siglec-16 genes. In some embodiments, the seven human genes are encoded on one or more BACs. In some embodiments, the seven human genes are encoded on three BACs. In some embodiments, the seven human genes are encoded on a single BAC.

In some embodiments, the transgenic non-human animal is a rodent (e.g., a mouse or rat). In some embodiments, the transgenic non-human animal is a mouse. In some embodiments, the genome of the transgenic mouse comprises one or more (e.g., one or more, two or more, three or more, four or more, etc.) non-functional murine genes. In some embodiments, the one or more non-functional murine genes are one or more of the murine CD33 gene, the murine Siglec-5 gene, the murine Siglec-7 gene, the murine Siglec-9 gene, the murine Siglec-11 gene, and any combination thereof. In some embodiments, the genome of the transgenic mouse comprises a non-functional murine CD33 gene, a non-functional murine Siglec-5 gene, a non-functional murine Siglec-7 gene, a non-functional murine Siglec-9 gene, and a non-functional murine Siglec-11 gene.

Methods

Certain aspects of the present disclosure relate to methods of screening candidate agents that bind to and/or modulate the function and/or activity of at least one of the human genes in the transgenic non-human animals; to methods of screening candidate agents to determine their effect on one or more activities and/or functions associated with expression of at least one of the human genes in the transgenic non-human animals; to methods of recapitulating a human Siglec immune system in a non-human animal; and to methods of generating a non-human animal disease model comprising a human Siglec repertoire.

Transgenic non-human animals of the present disclosure may be generated by any method known in the art. In some embodiments, the method comprises introducing one or more polynucleotides encoding two or more of the human CD33, Siglec-5, Siglec-7, Siglec-9, Siglec-11, Siglec-14, and Siglec-16 genes into one or more cells of an animal (e.g., by pronuclear injection of purified polynucleotides into the zygote of an animal) to generate a founder transgenic non-human animal. In some embodiments, the one or more polynucleotides are one or more bacterial artificial chromosomes (BACs). Once founder transgenic non-human animals are produced whose genome comprises two or more of the human CD33, Siglec-5, Siglec-7, Siglec-9, Siglec-11, Siglec-14, and Siglec-16 genes, the founder animals may be bred, inbred, outbred, or crossbred to produce progeny (colonies) of the particular non-human animal Examples of such breeding strategies may include, but are not limited to, outbreeding of the founder animals with more than one integration site in order to establish separate lines; inbreeding of separate lines in order to produce compound transgenic that express the transgenes at higher levels due to the effects of additive expression of each transgene; crossing of heterozygous transgenic animals to produce transgenic animals homozygous for a given integration site in order to both augment expression and eliminate the need for screening of animals by DNA analysis; crossing of separate homozygous lines to produce compound heterozygous or homozygous lines; and breeding animals to different inbred genetic backgrounds so as to examine effects of modifying alleles on expression of the transgenes and the physiological effects of expression.

Transgenic non-human animals are produced by introducing one or more transgenes into the germline of the transgenic animal. Methods of introducing DNA into cells are generally available and well-known in the art, and different methods of introducing transgenes may be used (See e.g., Hogan et al. *Manipulating the Mouse Embryo: A Laboratory Manual Cold Spring Harbor Laboratory*, $2^{nd}$ edition, Cold Spring Harbor Laboratory (1994); U.S. Pat. Nos. 5,602,229; 5,175,384; 6,066,778; and 6,037,521). Technology used in developing transgenic animals include pronuclear microinjection (See e.g., Gordon, J. W. (1980) *PNAS* 77,7380-7384; U.S. Pat. No. 4,873,191), homologous recombination (targeted transgenesis by transferring embryonic stem cells into blastocysts; Thompson et al. (1989) *Cell* 56: 313-321), RNA interference (RNAi)/CRISPR-Cas/TALENs for silencing of specific gene function, retrovirus gene transfer into germ lines (See e.g., Van der Putten et al. (1985) *PNAS* 82: 6148-6152), electroporation of embryos (See e.g., Lo. (1983) *Mol. Cell. Biol.* 3: 1803-1814), and sperm-mediated gene transfer (See e.g., Lavitrano et al. (1989) *Cell* 57: 717-723).

Generally, the zygote is the best target for microinjection. In mice, for example, the male pronucleus reaches the size of approximately 20 μm in diameter, which allows reproducible injection of 1-2 pL of DNA solution. The use of zygotes as a target for gene transfer has a major advantage because, in most cases, the injected DNA will be incorporated into the host genome before the first cleavage. Consequently, nearly all cells of the transgenic non-human animal will carry the incorporated transgene(s). Generally, this will result in the efficient transmission of the transgene to offspring of the founder since 50% of the germ cells will harbor the transgene. The pronuclear microinjection method of producing a transgenic animal results in the introduction of linear DNA sequences into the chromosomes of the fertilized eggs. Bacterial artificial chromosome (BAC) containing the genes of interest, or an alternative plasmid construct containing the genes of interest, is injected into pronuclei (i.e., fertilized eggs at a pronuclear state). The manipulated pronuclei are subsequently injected into the uterus of a pseudopregnant female. Mice generated using this method can have on or multiple copies of the transgenes, which can be assayed by any method known in the art (e.g., by southern blot technology).

The transgenic non-human animals of the present disclosure may also be generated by introducing one or more targeting vectors into embryonic stem (ES) cells. ES cells may be obtained by culturing pre-implantation embryos in vitro under appropriate conditions (See e.g., Evans et al. (1981) *Nature* 292: 154-6; Bradley et al. (1984) *Nature* 309: 255-8; Gossler et al. (1986) *PNAS* 83: 9065-9; Robertson et al. (1986) *Nature* 322: 445-8). Transgenes may be efficiently introduced into ES cells by DNA transfection using a variety of methods known in the art, including, without limitation, electroporation, calcium phosphate co-precipitation, protoplast or spheroplast fusion, lipofection, polymer-based transfections, and DEAE-dextran-mediated transfection. Transgenes may also be introduced into ES cells by retrovirus-mediated transduction of by micro-injection. Such transfected ES cells may thereafter colonize an embryo following their introduction into the blastocoel of a blastocyst-stage embryo and contribute to the germ line of the resulting chimeric animals (See e.g., Jaenisch, (1988) *Science* 240: 1468-74). Prior to the introduction of transfected ES cells in the blastocoel, the transfected ES cells may be subjected to various selection protocols to enrich for ES cells that have integrated the transgenes if the transgenes provide a means for such a selection. Alternatively, PCR amplification may be used to screen for ES cells that have integrated the transgenes. This technique obviates the need for growth of the transfected ES cells under appropriate selective conditions prior to transfer in to the blastocoel.

Retroviral infection may also be used to introduce transgenes into a non-human animal Examples of suitable retroviruses may include, but are not limited to, human immunodeficiency virus (HIV), murine Moloney leukemia virus (MoMuLV), murine Moloney sarcoma virus (MSV), Harvey sarcoma virus (HaSV), spleen necrosis virus (SNV), Rous sarcoma virus (RSV) and Friend virus (See also, WO95/02697). The developing non-human embryo may be cultured in vitro to the blastocyst stage. During this time, blastomeres may be targets for retroviral infection. Efficient infection of the blastomeres may be obtained by enzymatic treatment to remove the zona pellucida. The viral vector system used to introduce the transgenes is typically a replication-defective retrovirus carrying the transgenes. Transfection is easily and efficiently obtained by culturing the blastomeres on a monolayer of virus-producing cells. Alternatively, infection can be performed at a later stage. Virus or virus-producing cells may be injected into the blastocoel. Most of the founder animals will be mosaic for the transgenes since incorporation occurs only in a subset of the cells which formed the transgenic non-human animal. Furthermore, the founder animal may contain retroviral insertion of the transgenes at a variety of positions in the genome; these generally segregate in the offspring. In addition, it is also possible to introduce transgenes into the germ line by intrauterine retroviral infection of the midgestation embryo.

Viral vectors may be used to produce a transgenic animal. In some embodiments, the viral vectors are replication-defective viral vectors (i.e., they are unable to replicate autonomously in the target cell). Generally, the genome of the replication defective viral vectors which are used lack at least one region which is necessary for the replication of the virus in the infected cell. These regions may either be eliminated (in whole or in part) or be rendered non-functional by any technique known in the art. These may include, for example, the total removal, substitution, partial deletion, or addition of one or more bases to an essential (for replication) region. Such techniques may be performed in vitro or in situ, using the techniques of genetic manipulation or by treatment with one or more mutagenic agents. In some embodiments, the replication-defective virus retain the sequences of its genome which are necessary for encapsidating the viral particles. Methods of producing viral vectors comprising one or more transgenes are known in the art.

Methods of Screening Candidate Agents

Certain aspects of the present disclosure relate to methods of screening candidate agents in any of the transgenic non-human animals described herein.

In some embodiments, the method comprises administering one or more candidate agents to a transgenic non-human animal of the present disclosure, and determining whether the one or more candidate agents bind to and/or modulates the function and/or activity of at least one of the two or more human CD33, Siglec-5, Siglec-7, Siglec-9, Siglec-11, Siglec-14, and/or Siglec-16 genes in the transgenic non-human animal.

In some embodiments, the method comprises administering one or more candidate agents to a transgenic non-human animal of the present disclosure, and determining the effect of the one or more candidate agents on one or more activities and/or functions associated with expression of at least one of the two or more human genes in the transgenic non-human animal. In some embodiments, the one or more candidate agents inhibits one or more activities and/or functions associated with expression of two or more (e.g., two or more, three or more, four or more, five or more, six or more, etc.) of the human CD33, Siglec-5, Siglec-7, Siglec-9, Siglec-11, Siglec-14, and/or siglec-16 genes in the transgenic non-human animal.

In some embodiments, the one or more candidate agents are any of 1 or more, 2 or more, 3 or more, 4 or more, 5 or more, 6 or more, 7 or more, 8 or more, 9 or more, or 10 or more candidate agents. In some embodiments, the one or more candidate agents are administered once to the transgenic non-human animal. In some embodiments, the candidate agents are administered two or more (e.g., two or more, three or more, four or more, five or more, six or more, seven or more, eight or more, nine or more, or ten or more) times to the transgenic non-human animal. In some embodiments, the one or more candidate agents are administered at the same dose two or more times in the transgenic non-human animal. In some embodiments, the one or more candidate agents are administered at two or more different doses two or more times in the transgenic non-human animal.

In some embodiments, the one or more candidate agents are two or more candidate agents. In some embodiments, the two or more candidate agents are administered at the same time to the transgenic non-human animal. In some embodiments, the two or more candidate agents are administered sequentially to the transgenic non-human animal. In some embodiments, the two or more candidate agents target one or more of the human CD33, Siglec-5, Siglec-7, Siglec-9, Siglec-11, Siglec-14, and/or Siglec-16 genes. In some embodiments, the two or more candidate agents target the same human gene (e.g., a first and second candidate agent target a single human gene; a first, second, and third candidate agent target a single human gene, etc.) In some embodiments, the two or more candidate agents target two or more of the human genes (e.g., the first candidate agent targets a first human gene, the second candidate agent targets a second human gene; the first candidate agent targets a first human gene, the second candidate agent targets a second human gene, the third candidate agent targets a third human gene, etc.). In some embodiments, the one or more candidate agents are three or more candidates agents, and at least two of the three or more candidate agents target the same human gene (e.g., a first and second candidate agent target a first human gene, a third candidate agent targets a second human gene, etc.).

Examples of candidate agents may include, but are not limited to, compounds that specifically inhibit Siglec synthesis and/or release, antisense molecules directed to one or more Siglecs, short interfering RNA (siRNA) molecules directed to one or more nucleic acids encoding one or more Siglecs, antibodies (e.g., monospecific antibodies, bispecific antibodies) that bind to one or more Siglecs, soluble Siglec receptors (e.g., soluble Siglec receptors that bind one or more Siglec ligands), Siglec-Fc fusion proteins, Siglec immunoadhesins, compounds that specifically inhibit one or more Siglec activities such as small molecule inhibitors and/or peptide inhibitors, compounds that specifically inhibit one or more Siglecs from binding to one or more ligands, Siglec structural analogs, RNA or DNA aptamers that binds one or more Siglecs, compounds that inhibit the synthesis of one or more Siglec ligands (e.g., sialic acid-containing glycans present on proteins or other molecules), compounds that promote Siglec ligand degradation, and compounds that directly degrade one or more Siglec ligands. In some embodiments, the one or more candidate agents are one or more antibodies.

In some embodiments, the effect of the one or more candidate agents is one or more of reducing cell surface levels of one or more polypeptides encoded by the human CD33, Siglec-5, Siglec-7, Siglec-9, Siglec-11, Siglec-14, or Siglec-16 genes; competing for binding with a natural ligand of one or more polypeptides encoded by the human CD33, Siglec-5, Siglec-7, Siglec-9, Siglec-11, Siglec-14, or Siglec-16 genes; reducing T cell proliferation and/or phagocytosis; increasing the survival of macrophages, neutrophils, NK cells, and/or dendritic cells; inducing CCR7 and/or F-actin in microglia, macrophages, neutrophils, NK cells, and/or dendritic cells; increasing expression of one or more inflammatory cell surface markers on macrophages, neutrophils, and/or NK cells; suppressing myeloid-derived suppressor cell (MDSC) proliferation, activation, and/or function; reducing IL-10 secretion from one or more myeloid cells; inducing SYK and/or ERK activation and/or phosphorylation; and any combination thereof.

In some embodiments, the one or more candidate agents inhibits one or more activities and/or functions associated with expression of two or more (e.g., two or more, three or more, four or more, five or more, six or more, etc.) of the human CD33, Siglec-5, Siglec-7, Siglec-9, Siglec-11, Siglec-14, and/or siglec-16 genes in the transgenic non-human animal. In some embodiments, the one or more activities and/or functions are one or more of immune cell suppression; decreased expression of one or more pro-inflammatory cytokines, optionally wherein the one or more pro-inflammatory cytokines are selected from a group consisting IFN-a4, IFN-beta, IL-1β, IL-1alpha, TNF-α, IL-6, IL-8, CRP, IL-20 family members, LIF, IFN-gamma, OSM, CNTF, GM-CSF, IL-11, IL-12, IL-17, IL-18, CRP, MCP-1, and MIP-1-beta; decreased expression of one or more pro-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; increased expression of one or more anti-inflammatory cytokines, optionally wherein the one or more anti-inflammatory cytokines are selected from the group consisting of IL4, IL10, IL13, IL35, IL16, TGF-beta, IL1ra, G-CSF, and soluble receptors for TNF, IFN-beta1a, IFN-beta1b, and IL6; increased expression of one or more anti-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; inhibition of extracellular signal-regulated kinase (ERK) phosphorylation; decreasing tyrosine phosphorylation on one or more cellular proteins, optionally, wherein the one or more cellular proteins comprise ZAP-70 and the tyrosine phosphorylation occurs on Tyr-319 of ZAP-70; decreased expression of C—C chemokine receptor 7 (CCR7); inhibition of microglial cell chemotaxis toward CCL19-expressing and CCL21-expressing cells; decreasing T cell proliferation induced by one or more cells selected from the group consisting of dendritic cells, bone marrow-derived dendritic cells, monocytes, microglia, M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells; inhibition of osteoclast production, decreased rate of osteoclastogenesis, or both; decreasing survival of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; decreasing proliferation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting migration of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting one or more functions of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting maturation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibition of one or more types of clearance selected from the group consisting of apoptotic neuron clearance, nerve tissue debris clearance, non-nerve tissue debris clearance, bacteria clearance, other foreign body clearance, disease-causing protein clearance, disease-causing peptide clearance, and tumor cell clearance; optionally wherein the disease-causing protein is selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; inhibition of phagocytosis of one or more of apoptotic neurons, nerve tissue debris, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; inhibition of tumor cell killing by one or more of microglia, macrophages, neutrophils, NK cells, dendritic cells, bone marrow-derived dendritic cells, neutrophils, T cells, T helper cells, or cytotoxic T cells; inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; inhibition of anti-tumor cell metastasis activity of one or more of microglia, macrophages, neutrophils, NK cells, dendritic cells, bone marrow-derived dendritic cells, neutrophils, T cells, T helper cells, or cytotoxic T cells; inhibition of one or more ITAM motif containing receptors, optionally wherein the one or more ITAM motif containing receptors are selected from the group consisting of TREM1, TREM2, Sirp beta, FcgR, DAP10, and DAP12; inhibition of signaling by one or more pattern recognition receptors (PRRs), optionally wherein the one or more PRRs are selected from the group consisting of receptors that identify pathogen-associated molecular patterns (PAMPs), receptors that identify damage-associated molecular patterns (DAMPs), and any combination thereof; inhibition of one or more receptors comprising the motif D/Ex0-2YxxL/IX6-8YxxL/I (SEQ ID NO: 22); inhibition of signaling by one or more Toll-like receptors; inhibition of the JAK-STAT signaling pathway; inhibition of nuclear factor kappa-light-chain-enhancer of activated B cells (NFκB); de-phosphorylation of an ITAM motif containing receptor; decreased expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; decreasing expression of one or more ITAM-dependent genes, optionally wherein the one more ITAM-dependent genes are activated by nuclear factor of activated T cells (NFAT) transcription factors; promoting differentiation of one or more of immunosuppressor dendritic cells, immunosuppressor macrophages, immunosuppressor neutrophils, immunosuppressor NK cells, myeloid derived suppressor cells, tumor-associated macrophages, tumor-associated neutrophils, tumor-associated NK cells, and regulatory T cells; rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; increasing the number of tumor-promoting myeloid/granulocytic immune-suppressive cells in a tumor, in peripheral blood, or other lymphoid organ; enhancing tumor-promoting activity of myeloid-derived suppressor cells; increasing expression of tumor-promoting cytokines in a tumor or in peripheral blood, optionally wherein the tumor-promoting cytokines are TGF-beta or IL-10; increasing tumor infiltration of tumor-promoting FoxP3+ regulatory T lymphocytes; enhancing tumor-promoting activity of myeloid-derived suppressor cells (MDSC); decreasing activation of tumor-specific T lymphocytes with tumor killing potential;

decreasing infiltration of tumor-specific NK cells with tumor killing potential; decreasing the tumor killing potential of NK cells; decreasing infiltration of tumor-specific B lymphocytes with potential to enhance immune response; decreasing infiltration of tumor-specific T lymphocytes with tumor killing potential; increasing tumor volume; increasing tumor growth rate; increasing metastasis; increasing rate of tumor recurrence; decreasing efficacy of one or more immune-therapies that modulate anti-tumor T cell responses, optionally wherein the one or more immune-therapies are immune-therapies that target one or more target proteins selected from the group consisting of PD1/PDLL, CTLA4, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, and any combination thereof, or cancer vaccines; inhibition of PLCγ/PKC/calcium mobilization; inhibition of PI3K/Akt, Ras/MAPK signaling; and any combination thereof.

In some embodiments, the transgenic non-human animal suffers from a disease, disorder, and/or injury. In some embodiments, administering the one or more candidate agents reduced or eliminates one or more signs and/or symptoms of the disease, disorder, and/or injury. In some embodiments, the disease, disorder, and/or injury is one or more of autoimmunity, susceptibility to infection, cancer, proliferative disorders, and/or neurodegenerative disorders.

In some embodiments, the disease, disorder, and/or injury is one or more of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV infection, and Haemophilus influenza infection.

Methods of Recapitulating a Human Siglec Immune System

Certain aspects of the present disclosure relate to a method of recapitulating a human Siglec immune system in a non-human animal. In some embodiments, the method comprises generating a transgenic non-human animal whose genome comprises two or more of the human CD33, Siglec-5, Siglec-7, Siglec-9, Siglec-11, Siglec-14, and/or Siglec-16 genes. In some embodiments, the two or more human genes are coordinately expressed in one or more cells of the transgenic non-human animal. In some embodiments, the one or more cells of the transgenic non-human animal are one or more of myeloid cells, natural killer (NK) cells, T cells, microglia, and any combinations thereof. In some embodiments, the transgenic non-human animal comprising a recapitulated human Siglec immune system is any of the transgenic non-human animals described herein. Methods of generating transgenic non-human animals are known in the art (e.g., by any of the methods described herein).

Without wishing to be bound by theory, it is thought that recapitulating a human Siglec immune system in a non-human animal comprises the coordinate expression of multiple (i.e., two or more) human Siglec genes in the non-human animal that mimics the cell-type specificity (e.g., myeloid lineages: monocytes, macrophages dendritic cells, microglia, etc.) and gene expression (e.g., expression levels, cellular localization of the proteins at the cell surface, etc.) observed in the corresponding human cells. Furthermore, without wishing to be bound by theory, it is thought coordinate expression of multiple human Siglec proteins in non-human animals would allow these proteins to form heteromers (e.g., heterodimers, etc.) in the myeloid cells of the non-human animals, and that the myeloid cells expressing the human Siglec genes would respond to the ligands of the human Siglec proteins equivalently to human cells with respect to ITIM signaling, as well as the suppressive/activating functions of the human Siglec proteins, thus recapitulating the human Siglec immune system in a non-human animal.

Methods of Generating Non-human Animal Disease Models with a Human Siglec Repertoire Certain aspects of the present disclosure relate to methods of generating non-human disease models comprising a human Siglec repertoire. In some embodiments, the method comprises introducing one or more genetic determinants of a disease into the genome of any of the transgenic non-human animals described herein.

In some embodiments, the disease is one or more of cancer (e.g., melanoma, acute myeloid leukemia, etc.), proliferative disorders, infectious diseases (e.g., bacterial infections), and/or neurodegenerative diseases. In some embodiments, the neurodegenerative diseases are one or more of dementia, frontotemporal dementia (FTD), Alzheimer's disease, Parkinson's disease, amyotrophic lateral sclerosis (ALS), Huntington's disease, taupathy disease, and/or multiple sclerosis. In some embodiments, the disease is Alzheimer's disease.

In some embodiments, the one or more genetic determinants are introduced into the genome of the transgenic non-human animal by genetic manipulation. Methods of genetically manipulating animals are known in the art, including, for example, by the introduction of plasmids/cosmids, knock in/knock out technology, through the use of transposons/retrotransposons, the use of viruses (e.g., adenovirus, adeno-associated virus, herpes virus, Rous sarcoma virus, HIV, etc.), the use of the CRISPR/Cas system, the use of TALENs, the use of Zinc finger nucleases, etc.

In some embodiments, the one or more genetic determinants are introduced into the genome of the transgenic non-human animal by mating. In some embodiments, the transgenic non-human animal is mated with an animal that is heterozygous or homozygous for the one or more genetic determinants. In some embodiments, progeny from this mating are screened to identify animals comprising the one or more genetic determinants as well as two or more of the human CD33, Siglec-5, Siglec-7, Siglec-9, Siglec-11, Siglec-14 and/or Siglec-16 genes. Methods of screening animals to identify animals comprising the one or more genetic determinants and the two or more human genes are known in the art (e.g., by PCR analysis, southern blot analysis, western blot analysis, FACS analysis, etc.).

In some embodiments, the one or more genetic determinants are one or more polynucleotides comprising a mutation. In some embodiments, the one or more mutations are one or more inactivating mutations. Examples of inactivating mutations may include, but are not limited to, deletions, insertions, point mutations, and rearrangements. In some embodiments, the one or more genetic determinants are one or more polynucleotides encoding one or more polypeptides comprising a mutation. In some embodiments, the one or more polypeptides comprising a mutation are one or more of amyloid precursor protein (APP), presenilin 1 (PS1), presenilin 2 (PS2), alpha-synuclein, serine/threonine-protein kinase PINK1, parkin, leucine-rich repeat serine/threonine protein kinase 2 (LRRK2), protein deglycase (DJ-1), probable cation-transporting ATPase 13A2 (ATP13A2), superoxide dismutase (SOD1), TAR DNA-binding protein 43 (TARDBP), RNA-binding protein FUS, translation endoplasmic reticulum ATPase (VCP), microtubule-associated protein tau, progranulin, protein C9orf72, charged multivesicular body protein 2b (CHMP2B), and any combinations thereof. In some embodiments, the polypeptide comprising a mutation is amyloid precursor protein (APP).

The present disclosure will be more fully understood by reference to the following Examples. They should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this disclosure and scope of the appended claims.

EXAMPLES

Example 1

Generation of Transgenic Mice Harboring Human CD33, Siglec-7, and Siglec-9

The amino acid sequence of human CD33 is set forth below in SEQ ID NO: 1. Human CD33 contains a signal sequence located at amino acid residues 1-17 of SEQ ID NO: 1, an extracellular immunoglobulin-like variable-type (IgV) domain located at amino acid residues 19-135 of SEQ ID NO: 1, an Ig-like C2-type domain located at amino acid residues 145-228 of SEQ ID NO: 1, a transmembrane domain located at amino acid residues 260-282 of SEQ ID NO: 1, an ITIM motif 1 located at amino acid residues 338-343 of SEQ ID NO: 1, and an ITIM motif 2 located at amino acid residues 356-361 of SEQ ID NO: 1. The structure of CD33 is depicted in FIG. 1.

CD33 amino acid sequence (SEQ ID NO: 1):

```
         10         20         30         40         50
 MPLLLLLPLL WAGALAMDPN FWLQVQESVT VQEGLCVLVP CTFFHPIPYY 60         70         80         90        100
 DKNSPVHGYW FREGAIISRD SPVATNKLDQ EVQEETQGRF RLLGDPSRNN 110        120        130        140        150
 CSLSIVDARR RDNGSYFFRM ERGSTKYSYK SPQLSVHVTD LTHRPKILIP 160        170        180        190        200
 GTLEPGHSKN LTCSVSWACE QGTPPIFSWL SAAPTSLGPR TTHSSVLIIT 210        220        230        240        250
 PRPQDHGTNL TCQVKFAGAG VTTERTIQLN VTYVPQNPTT GIFPGDGSGK 260        270        280        290        300
 QETRAGVVHG AIGGAGVTAL LALCLCLIFF IVKTHRRKAA RTAVGRNDTH 310        320        330        340        350
 PTTGSASPKH QKKSKLHGPT ETSSCSGAAP TVEMDEELHY ASLNFHGMNP

360
 SKDTSTEYSE VRTQ
```

The amino acid sequence of human Siglec-7 is set forth below in SEQ ID NO: 5. Human Siglec-7 contains a signal sequence located at amino acid residues 1-18 SEQ ID NO: 5, an extracellular immunoglobulin-like variable-type (IgV) domain located at amino acid residues 39-122 of SEQ ID NO: 5, two Ig-like C2-type domains located at amino acid residues 150-233 and 240-336 of SEQ ID NO: 5, a transmembrane domain located at amino acid residues 354-376 of SEQ ID NO: 5, an ITIM motif 1 located at amino acid residues 435-440 of SEQ ID NO: 5, and an ITIM motif 2 located at amino acid residues 459-463 of SEQ ID NO: 5.

Siglec-7 amino acid sequence (SEQ ID NO: 5):

```
         10         20         30         40         50
 MLLLLLLPLL WGRERVEGQK SNRKDYSLTM QSSVTVQEGM CVHVRCSFSY 60         70         80         90        100
 PVDSQTDSDP VHGYWFRAGN DISWKAPVAT NNPAWAVQEE TRDRFHLLGD
```

```
           110         120         130         140         150
PQTKNCTLSI RDARMSDAGR YFFRMEKGNI KWNYKYDQLS VNVTALTHRP 160         170         180         190         200
NILIPGTLES GCFQNLTCSV PWACEQGTPP MISWMGTSVS PLHPSTTRSS 210         220         230         240         250
VLTLIPQPQH HGTSLTCQVT LPGAGVTTNR TIQLNVSYPP QNLTVTVFQG 260         270         280         290         300
EGTASTALGN SSSLSVLEGQ SLRLVCAVDS NPPARLSWTW RSLTLYPSQP 310         320         330         340         350
SNPLVLELQV HLGDEGEFTC RAQNSLGSQH VSLNLSLQQE YTGKMRPVSG 360         370         380         390         400
VLLGAVGGAG ATALVFLSFC VIFIVVRSCR KKSARPAADV GDIGMKDANT 410         420         430         440         450
IRGSASQGNL TESWADDNPR HHGLAAHSSG EEREIQYAPL SFHKGEPQDL

460
SGQEATNNEY SEIKIPK
```

Figure 2:
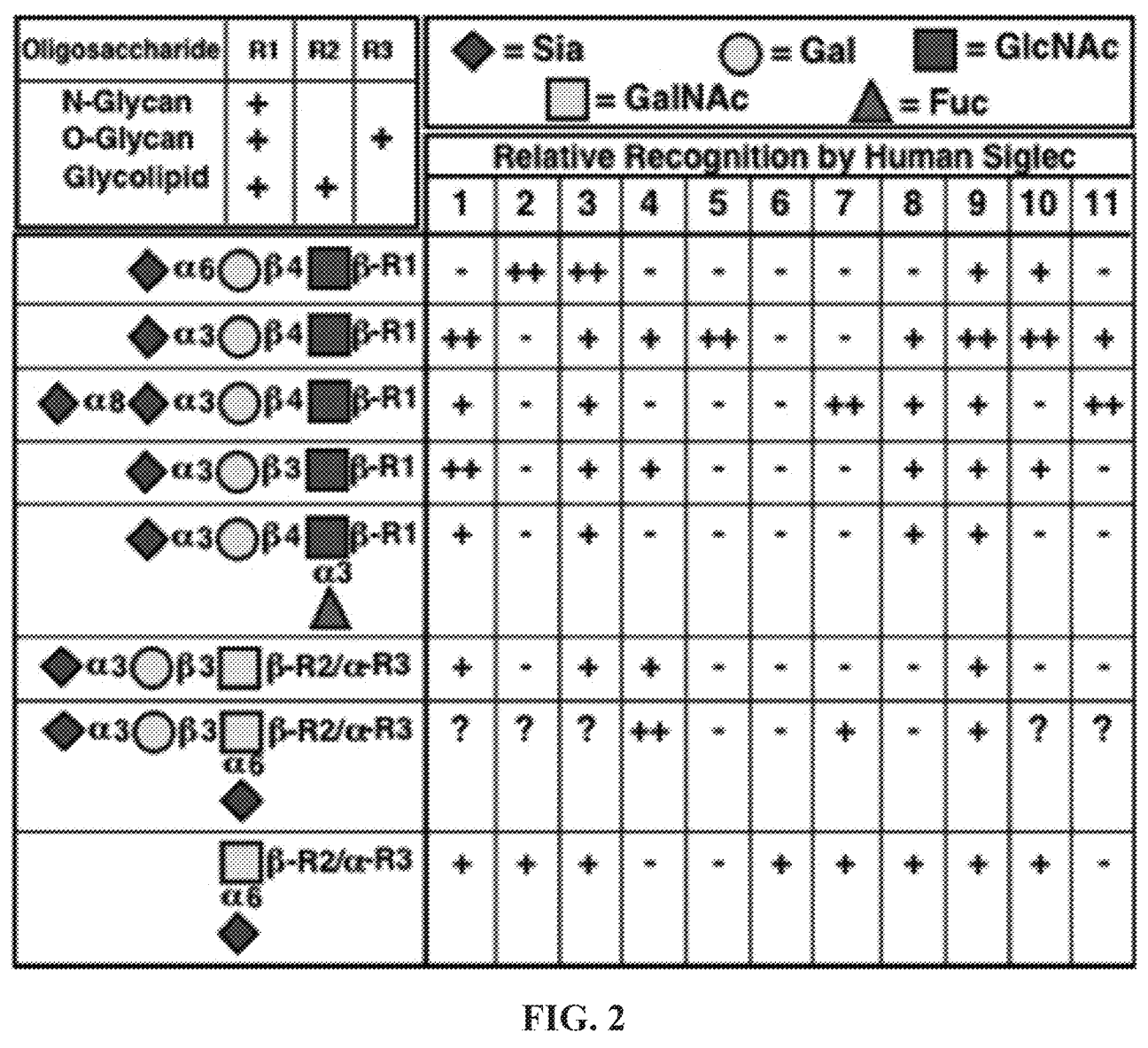
Figure 3:
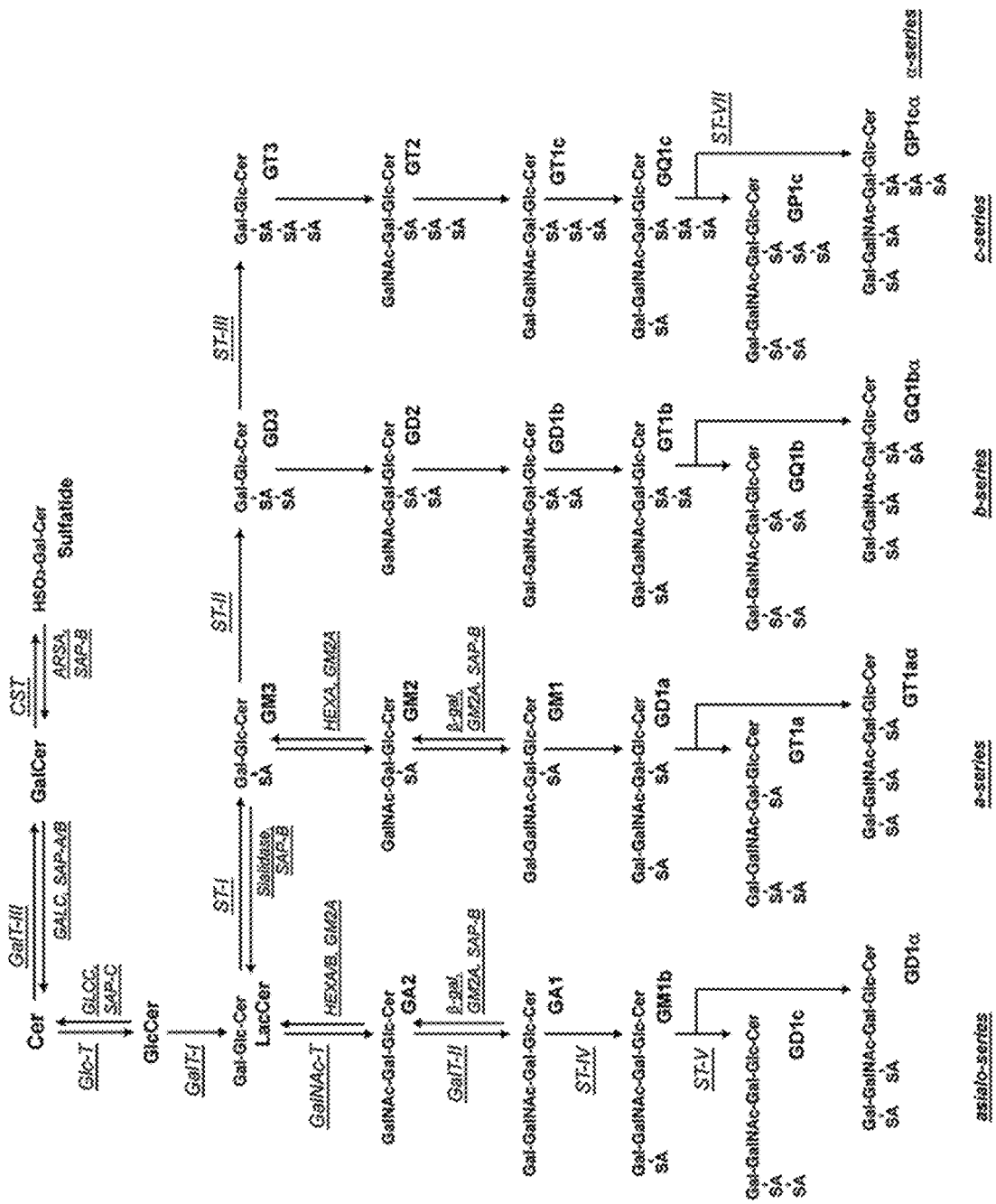
FIG. 3 shows the structure and metabolism of gangliosides in mammalian brain. The nomenclature of gangliosides in the figure follows the system of Svennerholm (1964) J. Lipid Res. 5:145-155 (Ariga T et al. (2008) J. Lipid Res. 49:1157-1175).

The purpose of the following example was to generate transgenic mice that coordinately express multiple human Siglec proteins. The genomes of the mice were engineered to contain multiple human Siglec transgenes under the control of their native human gene regulatory elements by introducing into the mouse genome Bacterial Artificial Chromosomes (BACs) encompassing the human locus containing the indicated Siglec genes and their regulatory network. Exemplary ligands bound by human Siglec proteins are depicted in FIG. 2 and FIG. 3. Without wishing to be bound by theory, it was believed that such mice would express the Siglec genes in a human pattern of gene expression, the expressed proteins would function appropriately, and the transgenic mice would allow for the development of therapeutics targeting the human proteins.

Methodologies

Identifying BACs of interest: Bacterial Artificial Chromosomes (BACs) harboring the human Siglec genes CD33, Siglec-7, and Siglec-9 with all intronic and exonic sequences were identified using the UCSC genome browser and the CloneDB from NCBI. BAC clones were further selected to identify those clones harboring a minimum of at least 10 kilobases of 5' and 3' flanking sequences in addition to the indicated Siglec genes to maximize the likelihood of identifying BAC clones that include the relevant human gene regulatory sequences in addition to human CD33, Siglec-7, and Siglec-9.

Isolating and purifying BAC clones: BAC clones meeting all of the selection requirements were obtained from Invitrogen/Life Technologies/Fisher Scientific as bacterial stab cultures. The cultures were grown, and BAC DNA was isolated and purified using standard techniques. Agarose gel electrophoresis after restriction digestion was used to confirm size and intactness of the inserts.

Generating transgenic animals: Mice harboring BAC clones of interest were generated by injecting the purified BAC DNA into mouse C57BL6/j zygotes by standard pronuclear injection techniques. Zygotes were returned to females, and the resulting pups were genotyped for the presence of the transgenes. Founder animals harboring the transgenes were then bred to non-transgenic animals, and progeny were screened for expression of the transgenes using standard techniques.

Generating murine CD33 knockout transgenic animals: Transgenic mice carrying the human CD33, Siglec-7, and Siglec-9 transgenes were bred with murine CD33-deficient mice that harbored a deletion within the mouse CD33 gene to obtain mice that carried the human CD33 transgene (as well as the human Siglec-7 and Siglec-9 transgenes), and were heterozygous for the murine CD33 knockout allele. The resulting mice were then bred with the same murine CD33-deficient mice to obtain mice carrying the human CD33 transgene (as well as the human Siglec-7 and Siglec-9 transgenes), but lacked the mouse CD33 gene (the mice were homozygous for the murine CD33 knockout allele). Mouse breeding and genotyping were carried out using standard techniques.

FACS analysis: Mice carrying the human CD33, Siglec-7, and Siglec-9 transgenes were analyzed by FACS analysis using standard techniques. Briefly, peripheral blood was obtained from 4-8 week old transgenic animals, and peripheral blood cells were subjected to multi-color flow cytometry panel staining Cells were incubated with the cell viability dye and indicated antibodies for 30 minutes on ice, washed twice with cold FACS buffer, and fixed with 4% PFA. The stained and fixed cells were then applied to a BD FACS CANTO II cytometer, data were acquired, and the resulting data was analyzed with FlowJo software.

For experiments testing the expression of human CD33 and Siglec-9, peripheral blood cells were stained with a cell viability dye and the following antibodies: anti-mouse CD11b (BD Biosciences, M1/70, 1:100), anti-mouse NK1.1 (Affymetrix, PK136, 1:100), anti-human Siglec-9 (Biolegend, K8, 1:20), and anti-human CD33 (Affymetrix, HIM3-4, 1:20).

For experiments testing the expression of human CD33, Siglec-7, and Siglec-9, peripheral blood cells were stained with a cell viability dye (Aqua dye) and the following antibodies: anti-mouse CD3, anti-mouse CD11b, anti-mouse NK1.1, anti-mouse Ly6G, anti-mouse Ly6C, anti-human CD33, and anti-human Siglec-7 or anti-human Siglec 9. Peripheral blood mononuclear cells (PBMCs) were FACS sorted to obtain T cells (CD-3 positive, NK1.1-negative), NK cells (CD3-negative, NK1.1-positive), myeloid cells (CD3-negative, NK1.1-negative), CD11b+ cells (CD11b-positive), monocytic myeloid-derived suppressor cells (Mo-MDSCs; CD11 b-positive, Ly6G-negative, Ly6C-positive), or granulocytic MDSCs/neutrophils (G-MDSCs/neutrophils; CD11b-positive, Ly6G-positive, Ly6C-positive).

Results

To obtain mice coordinately expressing multiple human Siglec genes, Bacterial Artificial Chromosomes (BACs) harboring key human Siglec genes with sufficient flanking sequences were identified using the UCSC genome browser and the CloneDB from NCBI. Three BAC clones (BACRP11-891J20, CTD-3187F8, and BACRP11-795H8) were identified that were predicted to contain the coding sequences for the human genes CD33, Siglec-7, and Siglec-9. Each BAC was tested by PCR analysis to confirm the proper human sequences of interest; however, BAC clone CTD-3187F8 failed to show a signal corresponding to the presence of the correct 5' end of the BAC, while BAC clone BACRP11-795H8 failed to show the presence of the appropriate human CD33 sequence.

Figure 4:
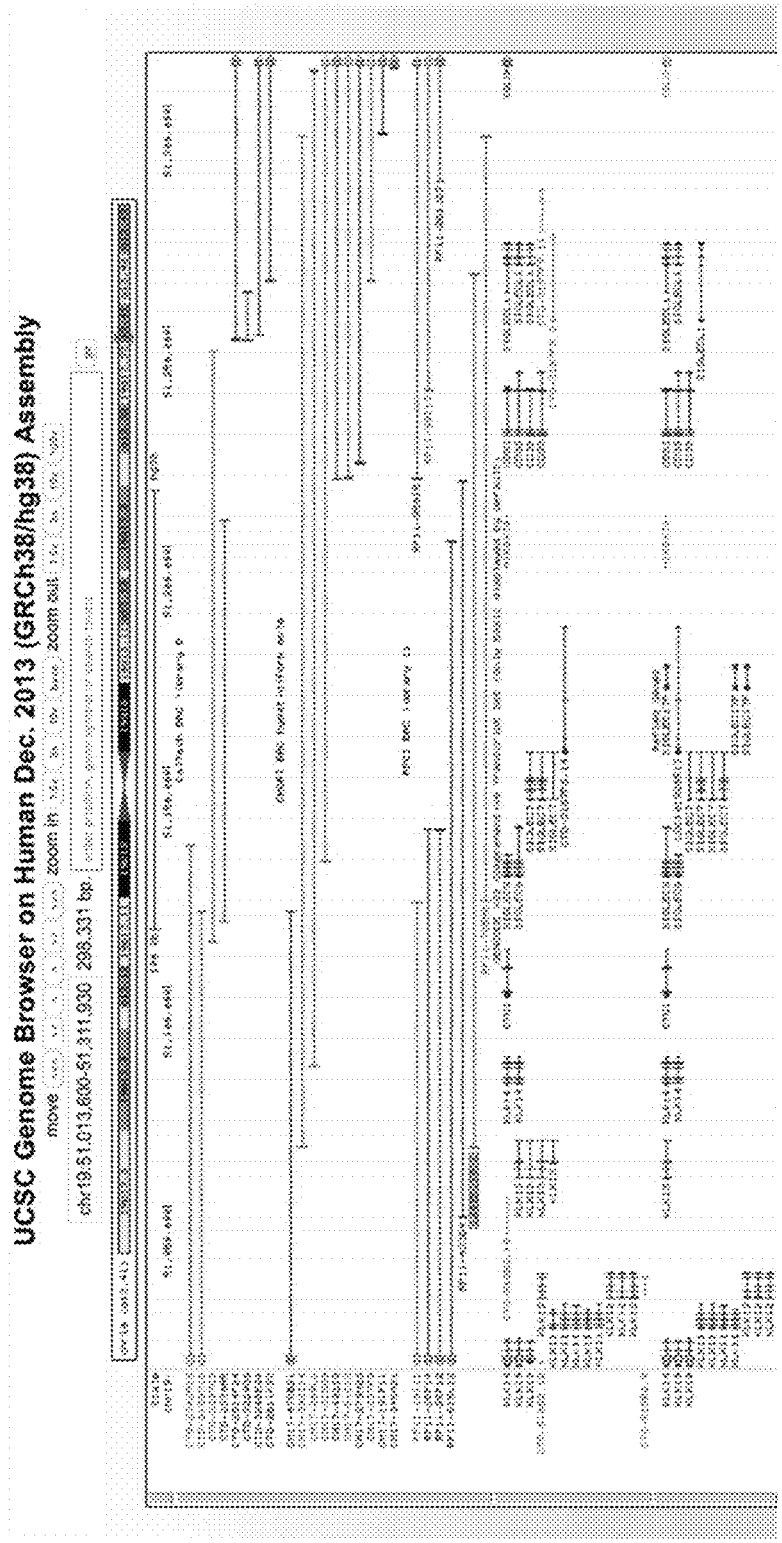
FIG. 4 shows a UCSC genome browser map of the genes, including CD33, Siglec-7, and Siglec-9, on a region of human Chromosome 19 that are included in the bacterial artificial chromosome (BAC) BACRP11-891J20, as labelled.
Figure 5:
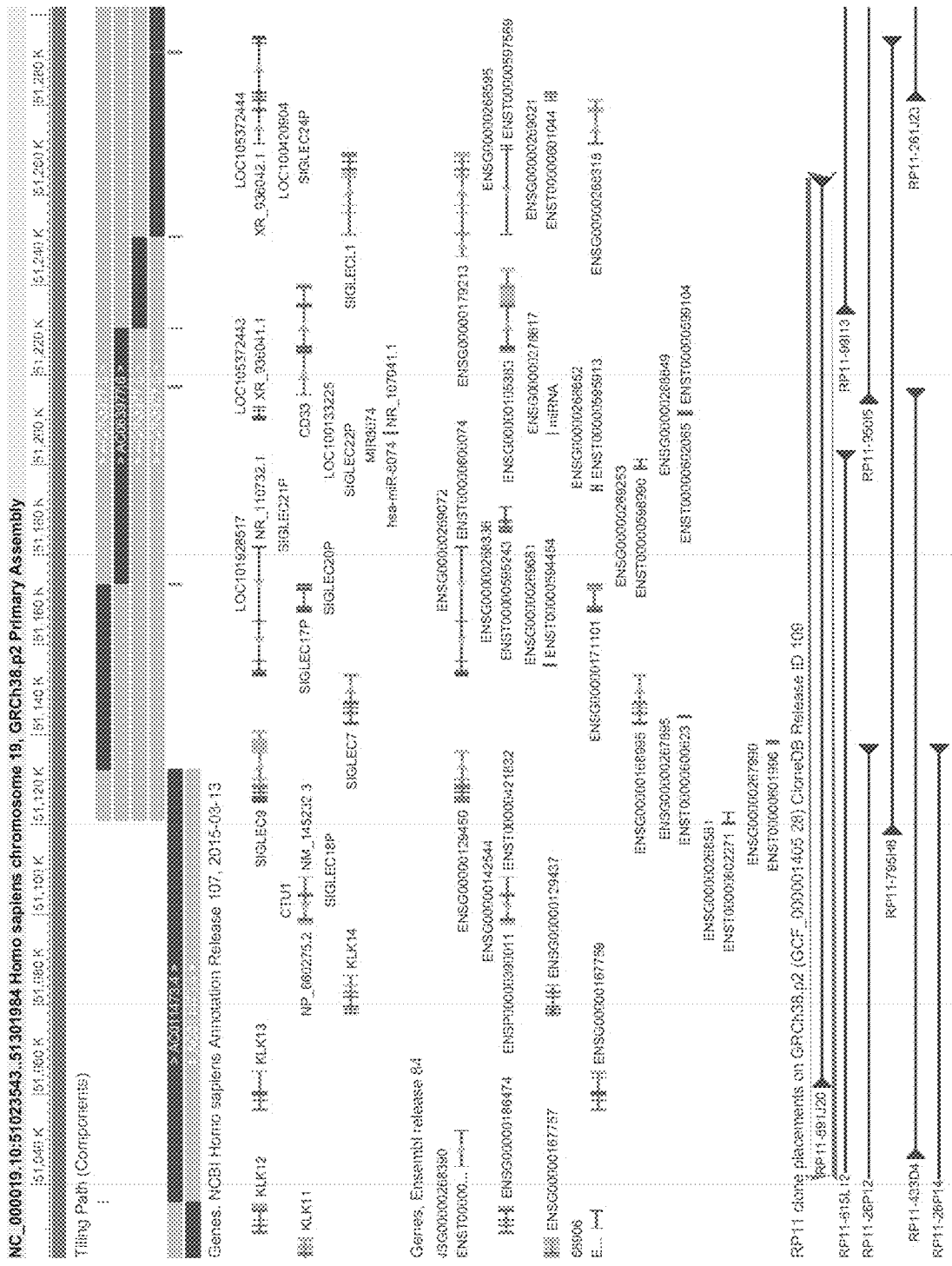
FIG. 5 shows a CloneDB map of the genes, including CD33, Siglec-7, and Siglec-9, on a region of human Chromosome 19 that are included in the bacterial artificial chromosome (BAC) BACRP11-891J20, as labelled.
Figure 6:
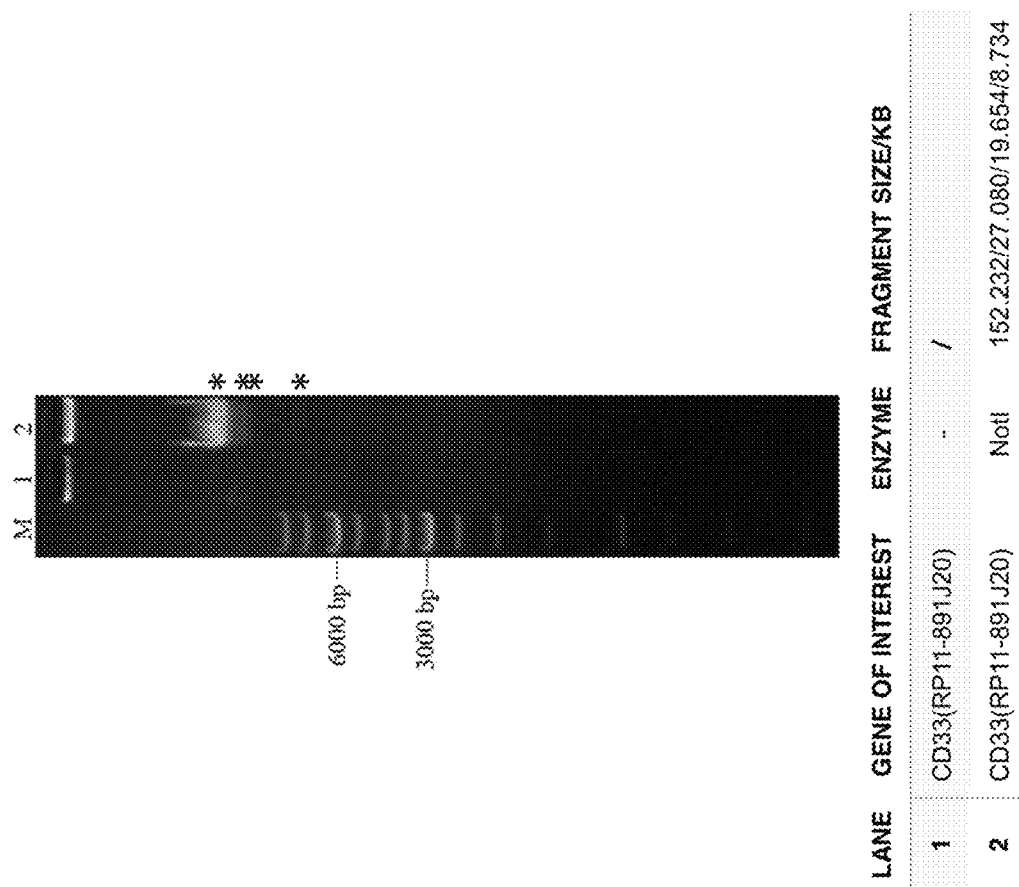
FIG. 6 shows the NotI restriction enzyme digestion of BACRP11-891J20. Asterisks indicate DNA fragments corresponding to the restriction fragments predicted for digestion of chromosomal DNA carrying human CD33, human Siglec-7, and human Siglec-9.

Maps of the human chromosomal region of interest encompassed by BACRP11-891J20 are shown in FIG. 4 (from the UCSC genome browser) and FIG. 5 (from the CLONEDB NCBI browser). The chromosomal DNA within BACRP11-891J20 spanned 196,887 nucleotides of the human genome, covering nucleotide positions 51,063,322-51,262,208 on human chromosome 19, based on the hg38 build of the UCSC genome browser (the human Siglec genes are found within a cluster on chromosome 19). Clone BACRP11-891J20 was tested via restriction digest/gel electrophoresis, the intactness and expected size of the human DNA insert was confirmed (FIG. 6).

Figure 7A:
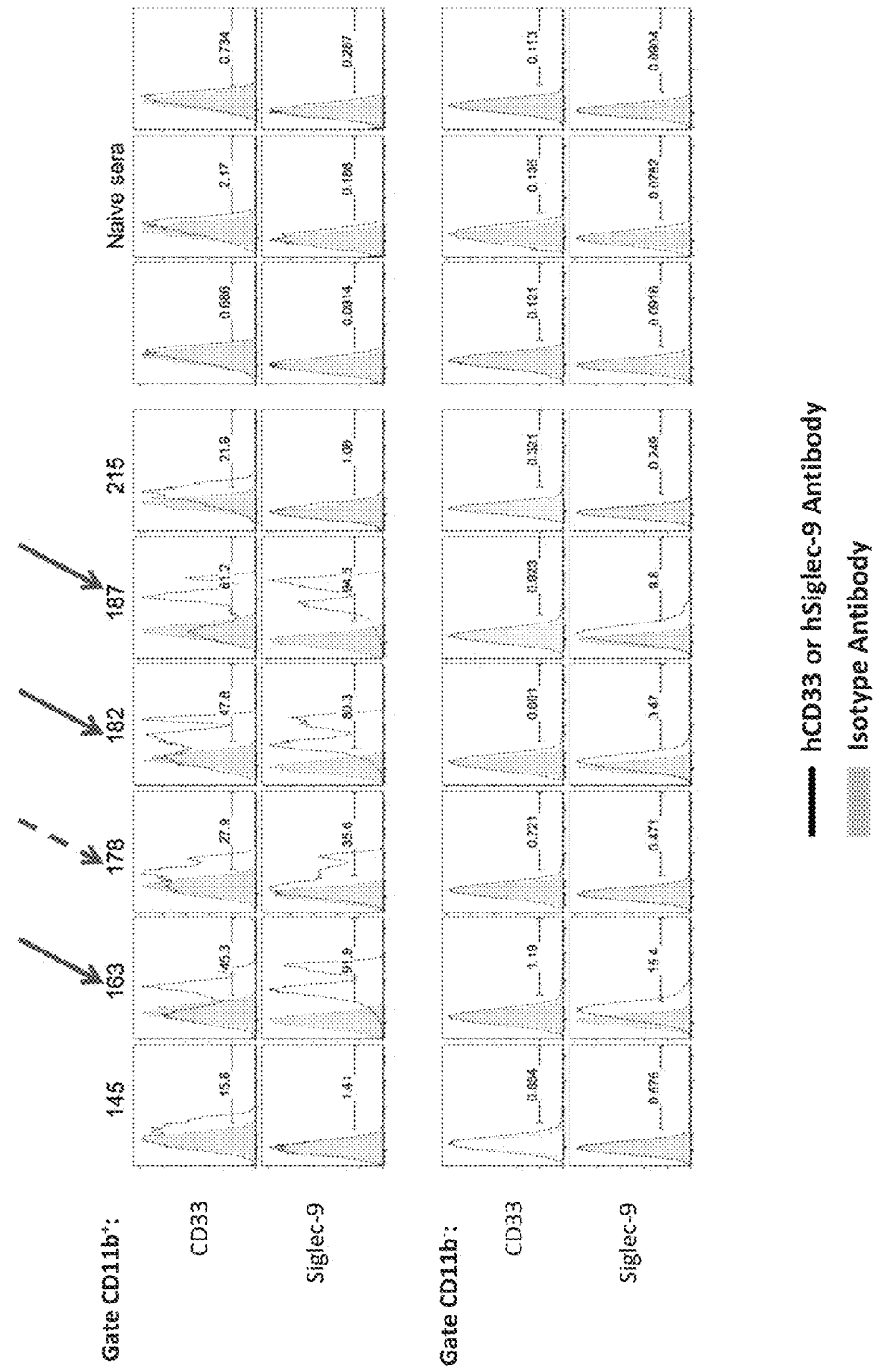
FIGS. 7A-7B show human CD33 and human Siglec-9 expression on cells isolated from BACRP11-891J20 transgenic mice.
Figure 7B:
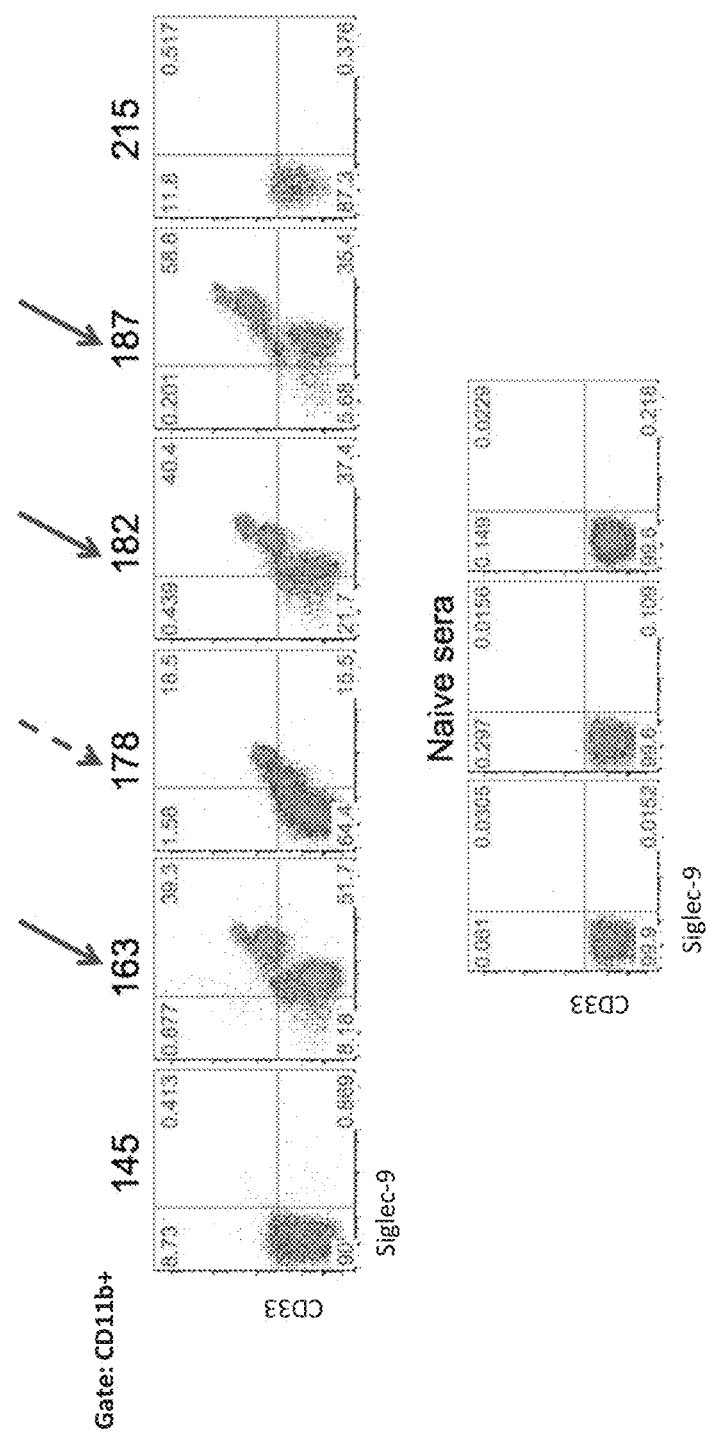

Transgenic mice harboring BACRP11-891J20 were generated by pronuclear injection of the BAC DNA into C57BL6/j zygotes. The resulting pups were genotyped to identify founder animals harboring the human transgenes (mouse #s 145, 163, 178, 182, 187, and 215). These animals were then analyzed by FACS analysis to monitor human CD33 and Siglec-9 protein expression on CD11b-positive and CD11b-negative cells (FIG. 7A). Expression of both human CD33 and Siglec-9 was observed on CD11b-positive cells from founder animals 163, 178, 182, and 187 (FIGS. 7A and 7B). Little to no expression of human CD33 and Siglec-9 were observed on CD11b-negative cells from these animals. Expression of human CD33 (but little to no expression of Siglec-9) was observed on CD11b-positive cells from founder animals 145 and 215. Expression levels of human CD33 and Siglec-9 varied across founder animals, with some animals showing high, medium, or low levels of human CD33 and Siglec-9 expression.

Taken together, this data suggested that transgenic animals were successfully generated that both carried human genes from the Siglec locus and were capable of coordinately expressing genes from this locus.

Example 2

Analysis of Human CD33, Siglec-7, and Siglec-9 Transgene Expression in Select Murine Cell Yypes Methodologies FACS analysis: Mice carrying the human CD33, Siglec-7, and Siglec-9 transgenes were analyzed by FACS analysis using standard techniques. Briefly, peripheral blood was obtained from 4-8 week old transgenic animals, and peripheral blood cells were subjected to multi-color flow cytometry panel staining Cells were incubated with the cell viability dye and indicated antibodies for 30 minutes on ice, washed twice with cold FACS buffer, and fixed with 4% PFA. The stained and fixed cells were then applied to a BD FACS CANTO II cytometer, data were acquired, and the resulting data was analyzed with FlowJo software.

For experiments testing the expression of human CD33, Siglec-7, and Siglec-9, peripheral blood cells were stained with a cell viability dye (Aqua dye) and the following antibodies: anti-mouse CD3, anti-mouse CD11b, anti-mouse NK1.1, anti-mouse Ly6G, anti-mouse Ly6C, anti-human CD33, and anti-human Siglec-7 or anti-human Siglec 9. Peripheral blood mononuclear cells (PBMCs) were FACS sorted to obtain T cells (CD-3 positive, NK1.1-negative), NK cells (CD3-negative, NK1.1-positive), myeloid cells (CD3-negative, NK1.1-negative), CD11b+ cells (CD11b-positive), monocytic myeloid-derived suppressor cells (Mo-MDSCs; CD11 b-positive, Ly6G-negative, Ly6C-positive), or granulocytic MDSCs/neutrophils (G-MDSCs/neutrophils; CD11b-positive, Ly6G-positive, Ly6C-positive).

BMDMs: Bone marrow-derived macrophages (BMDMs) were generated in vitro using standard techniques. Briefly, total bone marrow was cultured in DMEM supplemented with 10% bovine calf serum, 5% horse serum, and 6 ng/mL recombinant human CSF-1 (R&D Systems). Cells were cultured for 5-6 days, and adherent cells were detached with 1 mM EDTA in PBS. Cells were stained with the following antibodies: anti-mouse CD11b, anti-mouse CD40, anti-mouse GR1 (BD Pharmingen), anti-mouse F4/80 (Caltag Laboratories), anti-human CD33, and anti-human Siglec-7 or anti-human Siglec-9, and analyzed by FACS analysis as described above.

BMDCs: Bone marrow-derived dendritic cells (BMDCs) were generated in vitro using standard techniques. Briefly, total bone marrow was cultured in DMEM supplemented with 10% bovine calf serum, 5% horse serum, and 6 ng/mL GM-CSF (R&D Systems). Cells were cultured for 5-6 days, and adherent cells were detached with 1 mM EDTA in PBS. Cells were stained with the following antibodies: anti-mouse CD11b, anti-mouse CD40, anti-mouse GR1 (BD Pharmingen), anti-mouse F4/80 (Caltag Laboratories), anti-human CD33, and anti-human Siglec-7 or anti-human Siglec-9, and analyzed by FACS analysis as described above.

Brain microglia: Brain microglia were isolated from the transgenic animals using standard techniques (e.g., Bennett et al. (2016) *PNAS* 113(12): e1738-46). Cells were stained with a cell viability dye (Aqua dye) and the following antibodies: anti-mouse CD11b, anti-mouse CD45, anti-mouse F4/80 (Caltag Laboratories), and anti-human CD33, and analyzed by FACS analysis as described above.

Human NK and myeloid cells: Human NK and myeloid cells were isolated from the peripheral blood of an anonymous donor according to standard techniques.

Results

Figure 9:
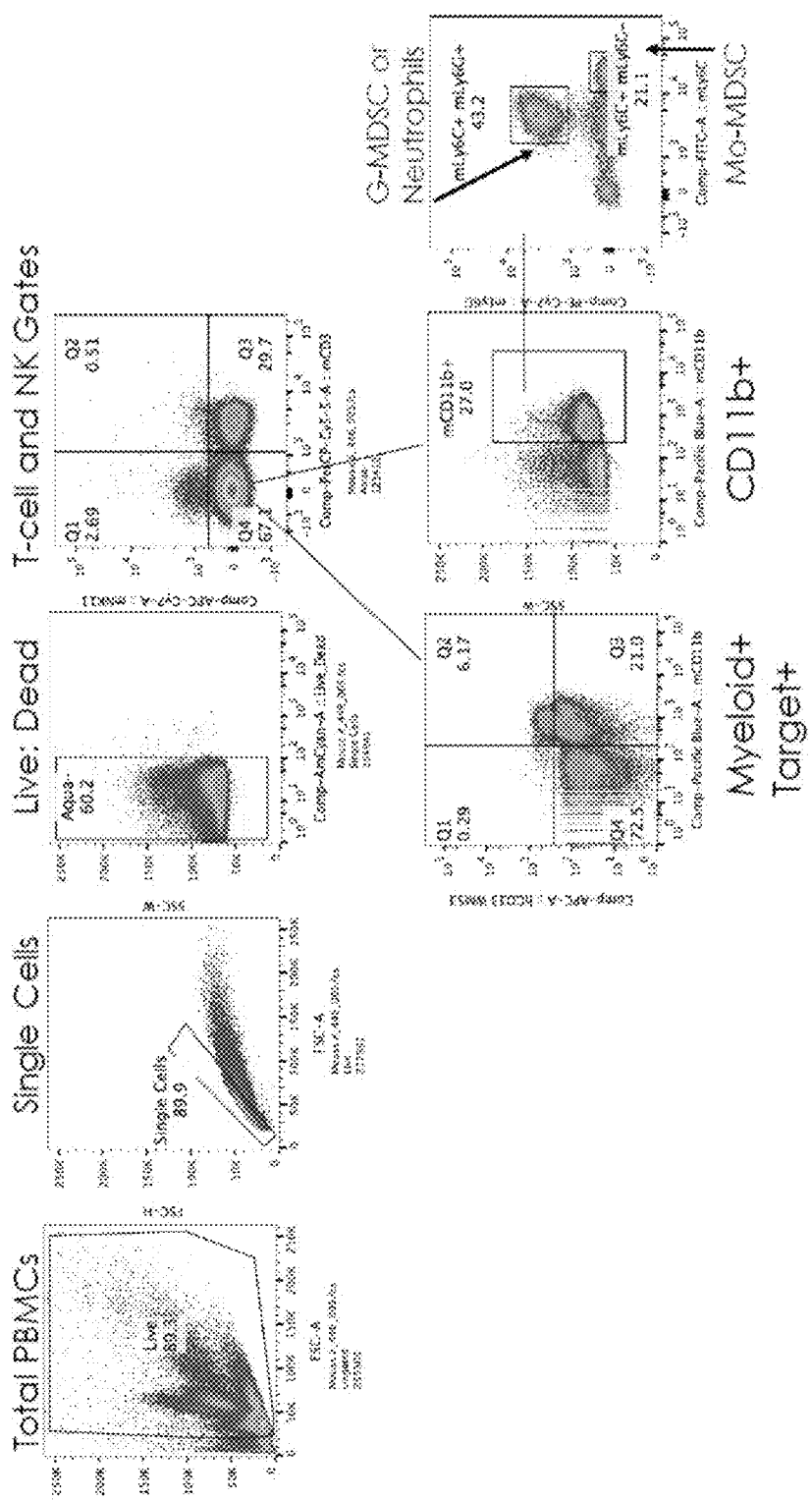
FIG. 9 shows the FACS gating strategy for the analysis of peripheral blood cells.

The transgenic founder animals from Example 1 were then crossed to non-transgenic mice. Pups resulting from this breeding scheme were genotyped to identify progeny animals harboring the human transgenes, and cells isolated from these animals were tested for protein expression of human CD33, Siglec-7 and Siglec-9 by FACS analysis. To characterize mouse cell subpopulations that expressed the human transgenes, cells isolated from these mice were also stained with antibodies to specifically identify particular immune cell subpopulations. The panel of antibodies used to sort for particular mouse cell subpopulations is summarized in FIG. 8. The cell isolation strategy used in these experiments is summarized in FIG. 9.

Human CD33 expression was positive on up to 50% of CD11b-positive myeloid cells in mice from the higher expression mouse #187 founder line (mouse #457 and #464), while CD33 was expressed on only a minority of the CD11-b-positive myeloid cells in mice from the lower expression mouse #182 founder line (mouse #446, #447, and

Figure 10:
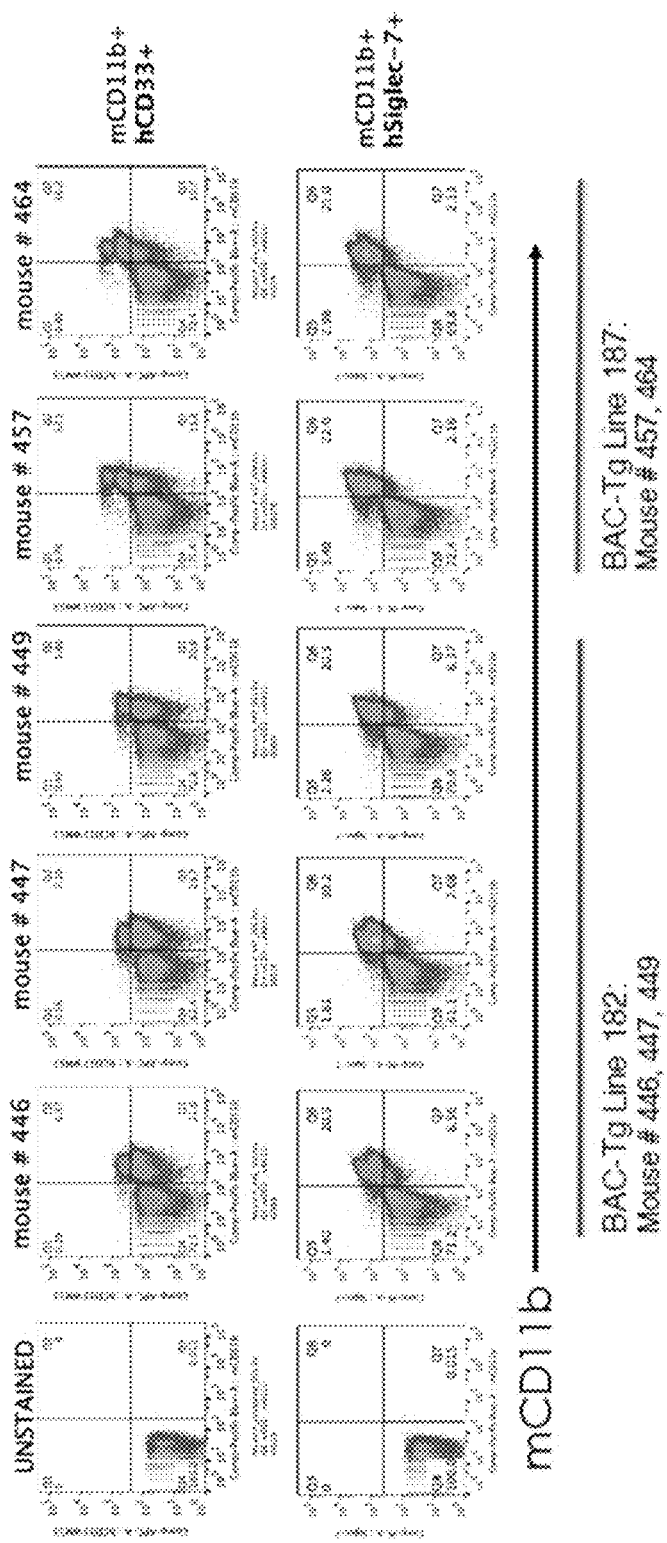
FIG. 10 shows results of FACS analysis demonstrating the expression pattern of human CD33 and human Siglec-7 on CD11b-positive primary myeloid cells from peripheral blood of BACRP11-891J20 transgenic mice.

449) (FIG. 10). Human Siglec-7 expression was positive on all CD11b-positive myeloid cells in mice from the higher expression mouse #187 founder line (mouse #457 and #464), and was expressed in a majority of such cells in mice from the lower expression mouse #182 founder line (mouse #446, #447, and #449) (FIG. 10).

Figure 11:
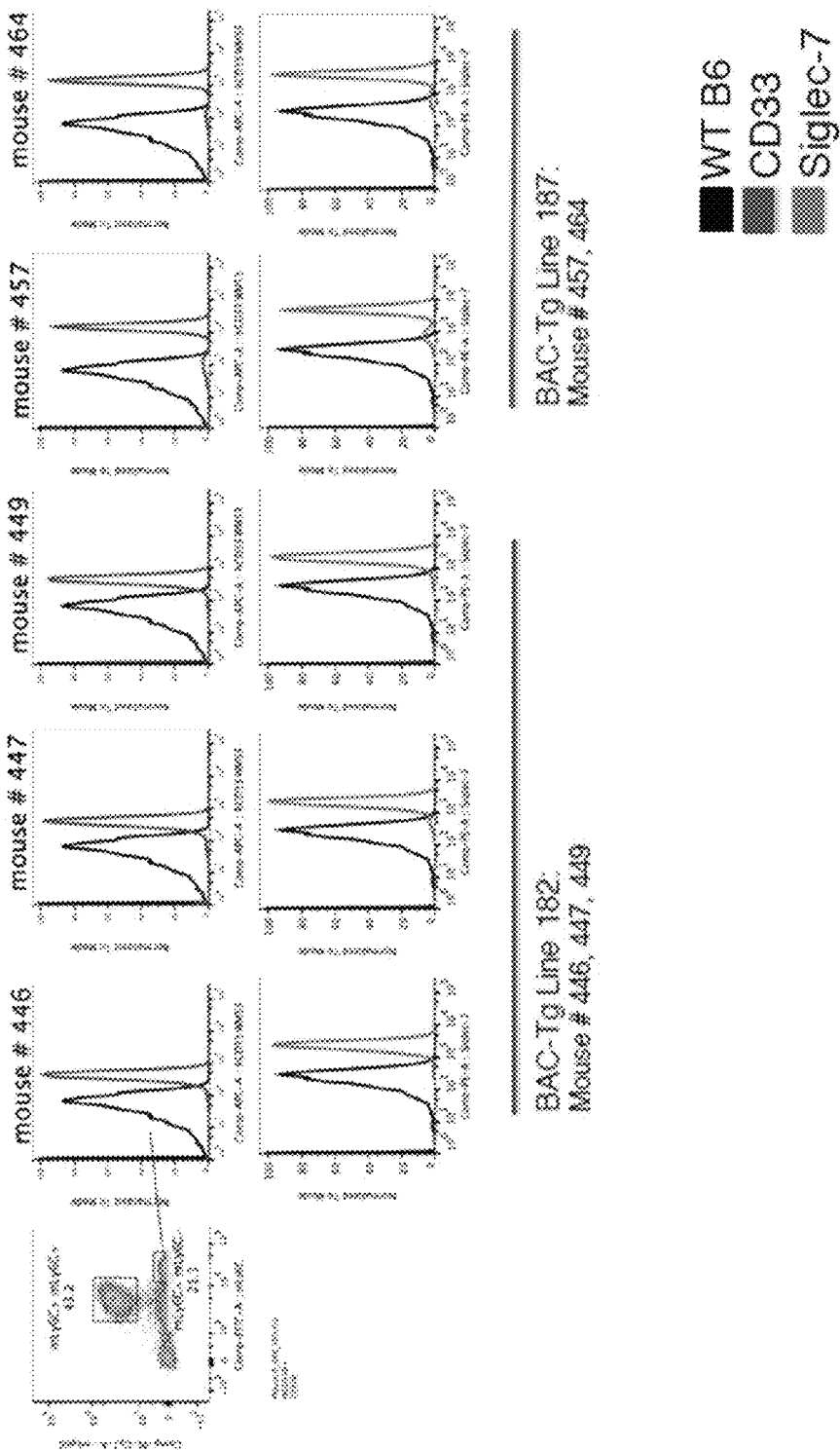
FIG. 11 shows results of FACS analysis demonstrating the expression pattern of human CD33 (purple line) and human Siglec-7 (green line) on primary monocyte-myeloid-derived suppressor cells (Mo-MDSCs) from peripheral blood of non-transgenic and BACRP11-891J20 transgenic mice. The black line indicates wild-type (WT) B6 non-transgenic mice.

Human CD33 expression was positive on most monocytic myeloid-derived suppressor cells (Mo-MDSCs) in mice from the higher expression mouse #187 founder line (mouse #457 and #464), and all such cells in mice from the lower expression mouse #182 founder line (mouse #446, #447, and #449) (FIG. 11). Human Siglec-7 expression was also positive on most Mo-MDSCs in mice from the higher expression mouse #187 founder line (mouse #457 and #464), and all such cells in mice from the lower expression mouse #182 founder line (mouse #446, #447, and #449) (FIG. 11).

Figure 12:
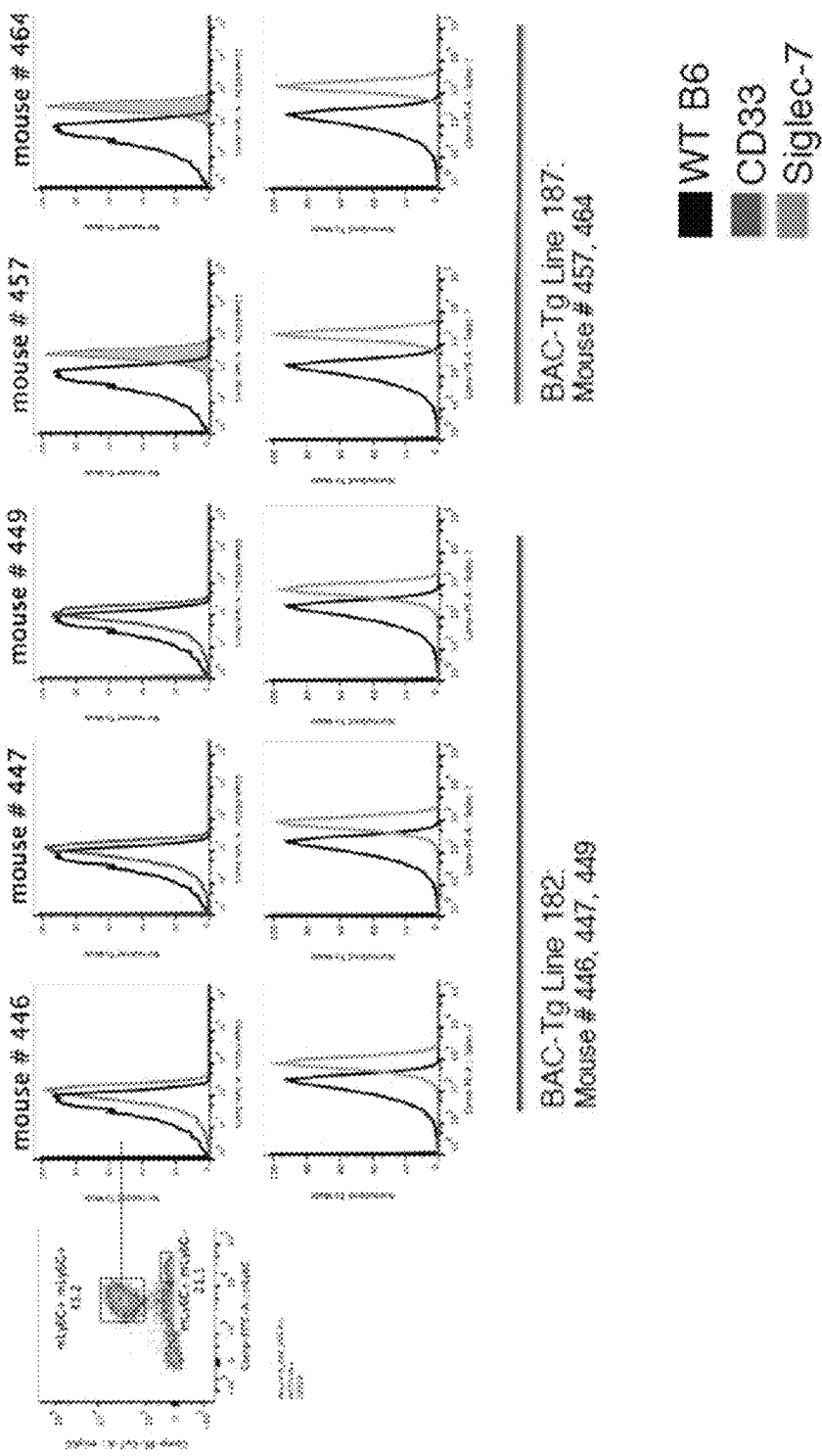
FIG. 12 shows results of FACS analysis demonstrating the expression pattern of human CD33 (red line) and human Siglec-7 (blue line) on primary granulocyte-myeloid-derived suppressor cells/neutrophils (G-MDSCs/neutrophils) from peripheral blood of non-transgenic and BACRP11-891J20 transgenic mice. The black line indicates wild-type (WT) B6 non-transgenic mice.

Human CD33 expression was very low on most granulocytic MDSCs/neutrophils (G-MDSCs) in mice from both the higher expression mouse #187 founder line (mouse #457 and #464) and lower expression mouse #182 founder line (mouse #446, #447, and #449) (FIG. 12). Human Siglec-7 expression was high on most G-MDSCs/neutrophils in mice from the higher expression mouse #187 founder line (mouse #457 and #464), and moderately expressed on such cells in mice from the lower expression mouse #182 founder line (mouse #446, #447, and #449) (FIG. 12).

Figure 13:
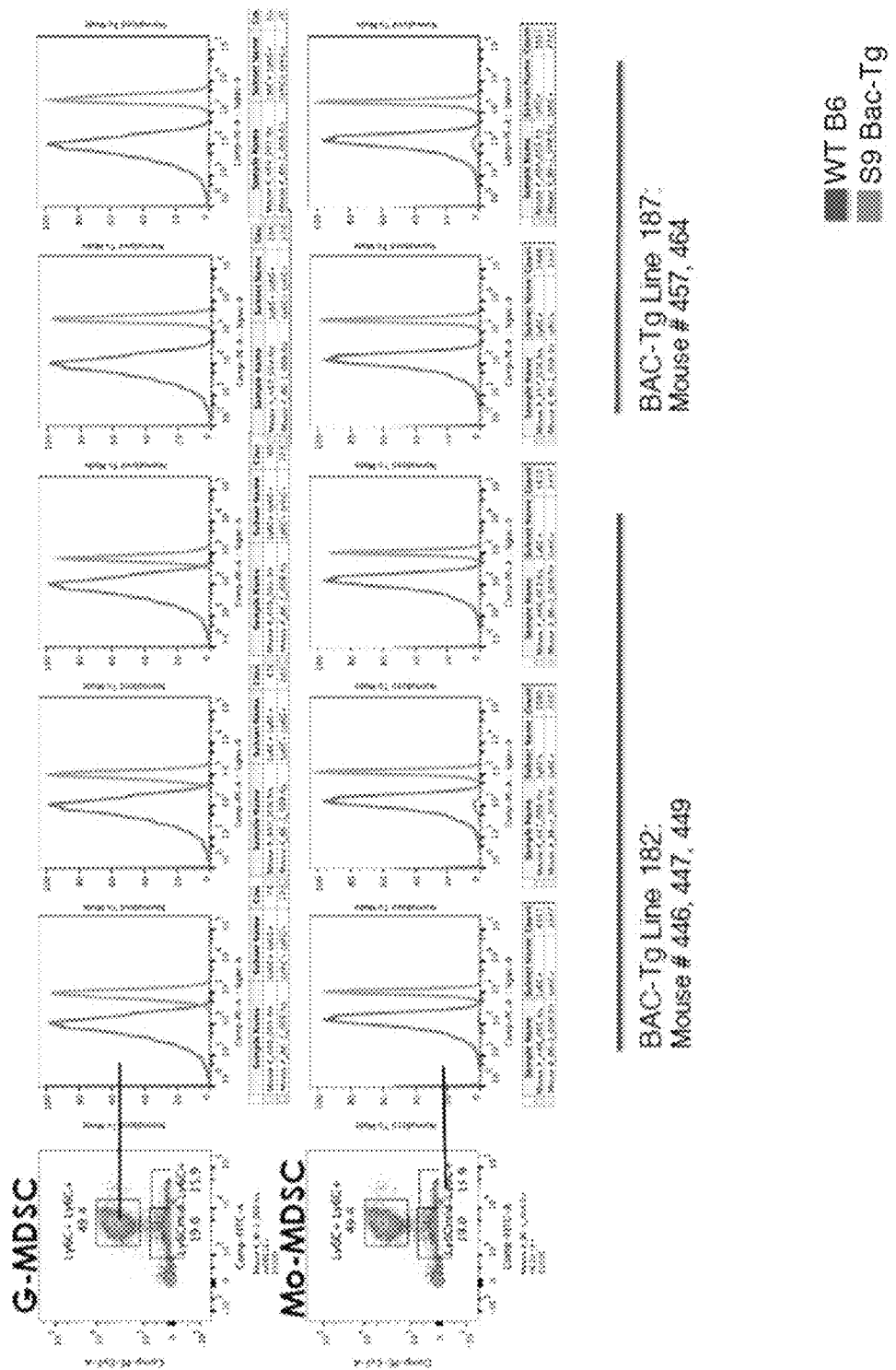
FIG. 13 shows results of FACS analysis demonstrating the expression pattern of human Siglec-9 on primary monocyte-myeloid-derived suppressor cells (MDSCs) and primary granulocyte-myeloid-derived suppressor cells/neutrophils (G-MDSCs/neutrophils) from peripheral blood of control non-transgenic mice (red line) and BACRP11-891J20 transgenic mice (blue line).

Human Siglec-9 expression was high on CD11 b-positive myeloid cells in mice from the higher expression mouse #187 founder line (mouse #457 and #464), but moderate in mice from the lower expression mouse #182 founder line (mouse #446, #447, and #449). Similar results were observed for human Siglec-9 expression on Mo-MDSCs and G-MDSCs/neutrophils (FIG. 13).

Figure 14A:
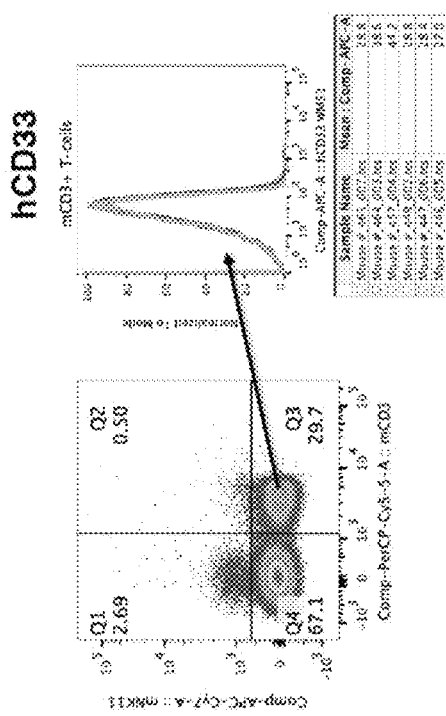
FIGS. 14A-14C show results of FACS analysis demonstrating the expression pattern of human CD33 (FIG. 14A), human Siglec-7 (FIG. 14B), and human Siglec-9 (FIG. 14C) on primary T cells from peripheral blood of BACRP11-891J20 transgenic mice.
Figure 14B:
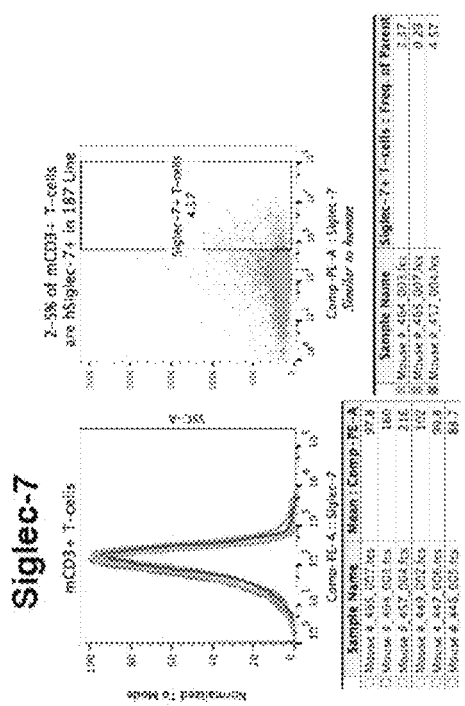
Figure 14C:
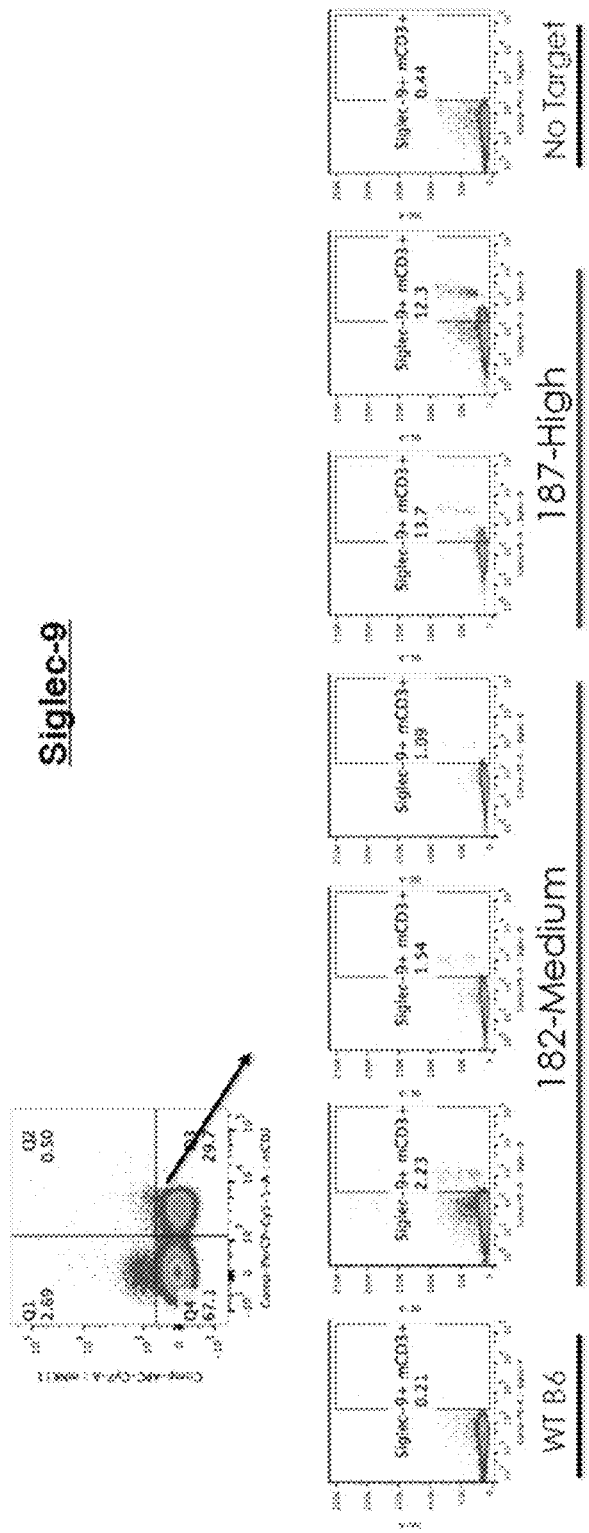

Human CD33 expression was negative on T cells in mice from both the higher expression mouse #187 founder line and lower expression mouse #182 founder line (FIG. 14A). Human Siglec-7 expression was observed on approximately 5% of T cells in mice from the higher expression mouse #187 founder line, while no human Siglec-7 expression was observed on T cells in mice from the lower expression mouse #182 founder line (FIG. 14B). Surprisingly, the expression pattern of human CD33 and Siglec-7 on T cells in mice from the higher expression mouse #187 founder line recapitulated the pattern of human expression of these proteins in T cells. Human Siglec-9 expression was observed on 10-15% of T cells in mice from the higher expression mouse #187 founder line, and minimal human Siglec-7 expression was observed on T cells in mice from the lower expression mouse #182 founder line (FIG. 14C).

Figure 15A:
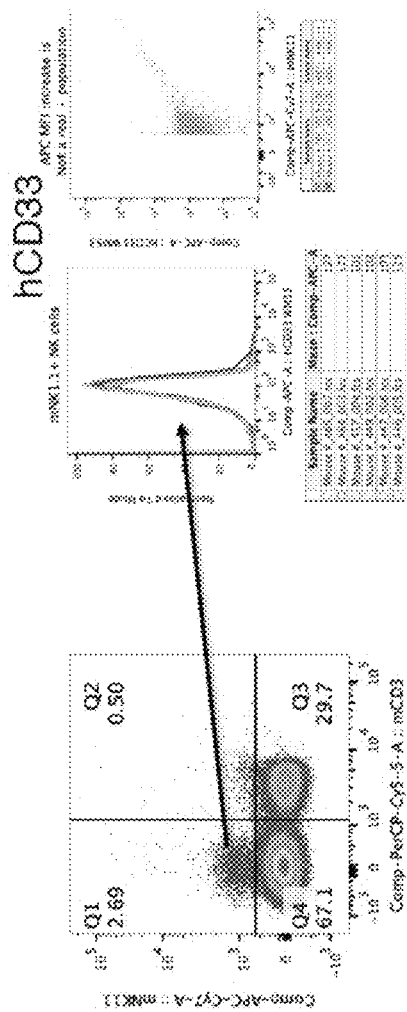
FIGS. 15A-15C show results of FACS analysis demonstrating the expression pattern of human CD33 (FIG. 15A) on primary natural killer (NK) cells from peripheral blood of BACRP11-891J20 transgenic mice, the expression pattern of human Siglec-7 (FIG. 15B) on primary natural killer (NK) cells from peripheral blood of control non-transgenic mice (blue line) and BACRP11-891J20 transgenic mice (red line), and the expression pattern of human Siglec-9 (FIG. 15C) on primary natural killer (NK) cells from peripheral blood of control non-transgenic mice (red line) and BACRP11-891J20 transgenic mice (blue line).
Figure 15B:
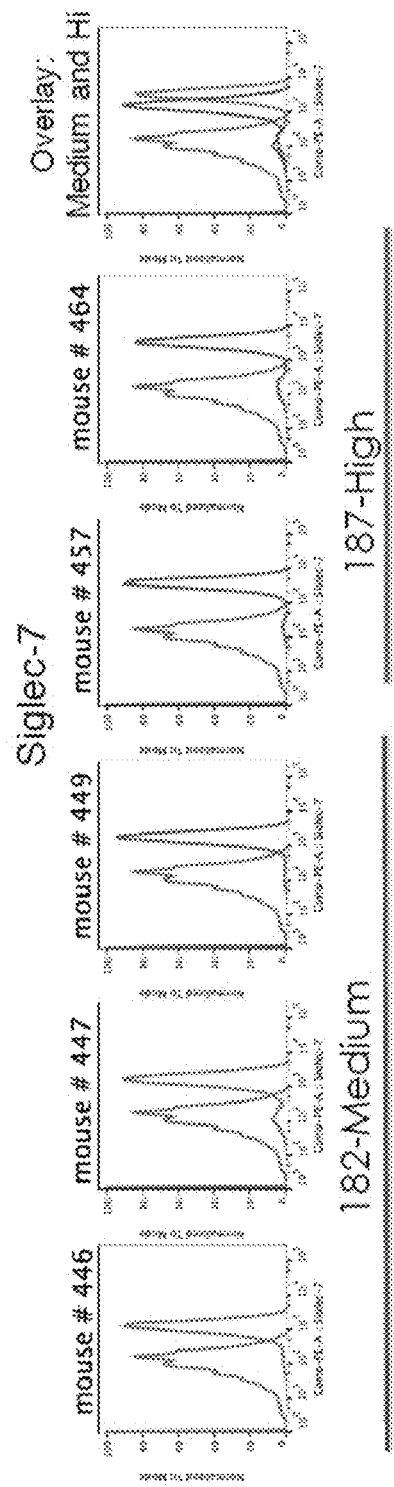
Figure 15C:
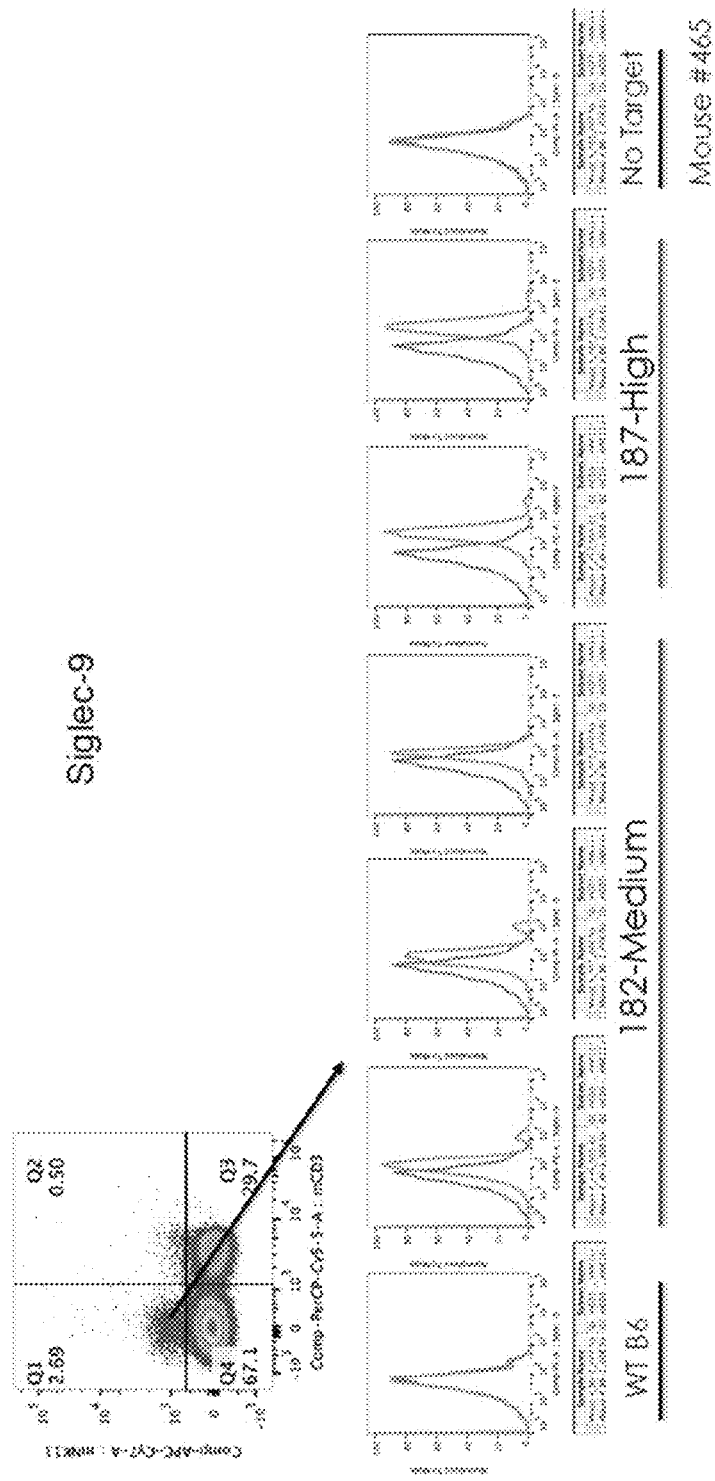

Human CD33 expression was negative on NK cells in mice from both the higher expression mouse #187 founder line, and the lower expression mouse #182 founder line (FIG. 15A). Human Siglec-7 (FIG. 15B) and Siglec-9 (FIG. 15C) were highly expressed on NK cells in mice from the higher expression mouse #187 founder line, and were moderately expressed in mice from the lower expression mouse #182 founder line. Surprisingly, the expression pattern of all three human transgenes recapitulated the pattern of human expression of these genes on NK cells.

A summary of the results of human CD33, Siglec-7, and Siglec-9 expression in the various subpopulations of peripheral blood cells is provided in Table A below.

TABLE A summary of expression results from peripheral blood cells

|  | Mice from higher expression founder line (187) | | | Mice from lower expression founder line (182) | | |
| --- | --- | --- | --- | --- | --- | --- |
|  | hCD33 | hSiglec-7 | hSiglec-9 | hCD33 | hSiglec-7 | hSiglec-9 |
| Myeloid cells | >50% of cells | All cells | High | Small subset of cells | Majority of cells | Medium |
| Mo-MDSCs | High on most cells | High on most cells | High | Medium on all cells | Medium on all cells | Medium |
| G-MDSCs/ neutrophils | High | High on most cells | High | Very low | Medium | Medium |
| T cells | Negative | ~5% of cells | 10-15% of cells | Negative | Negative | Minimal |
| NK cells | Negative | High | High | Negative | Moderate | Moderate |

Figure 16:
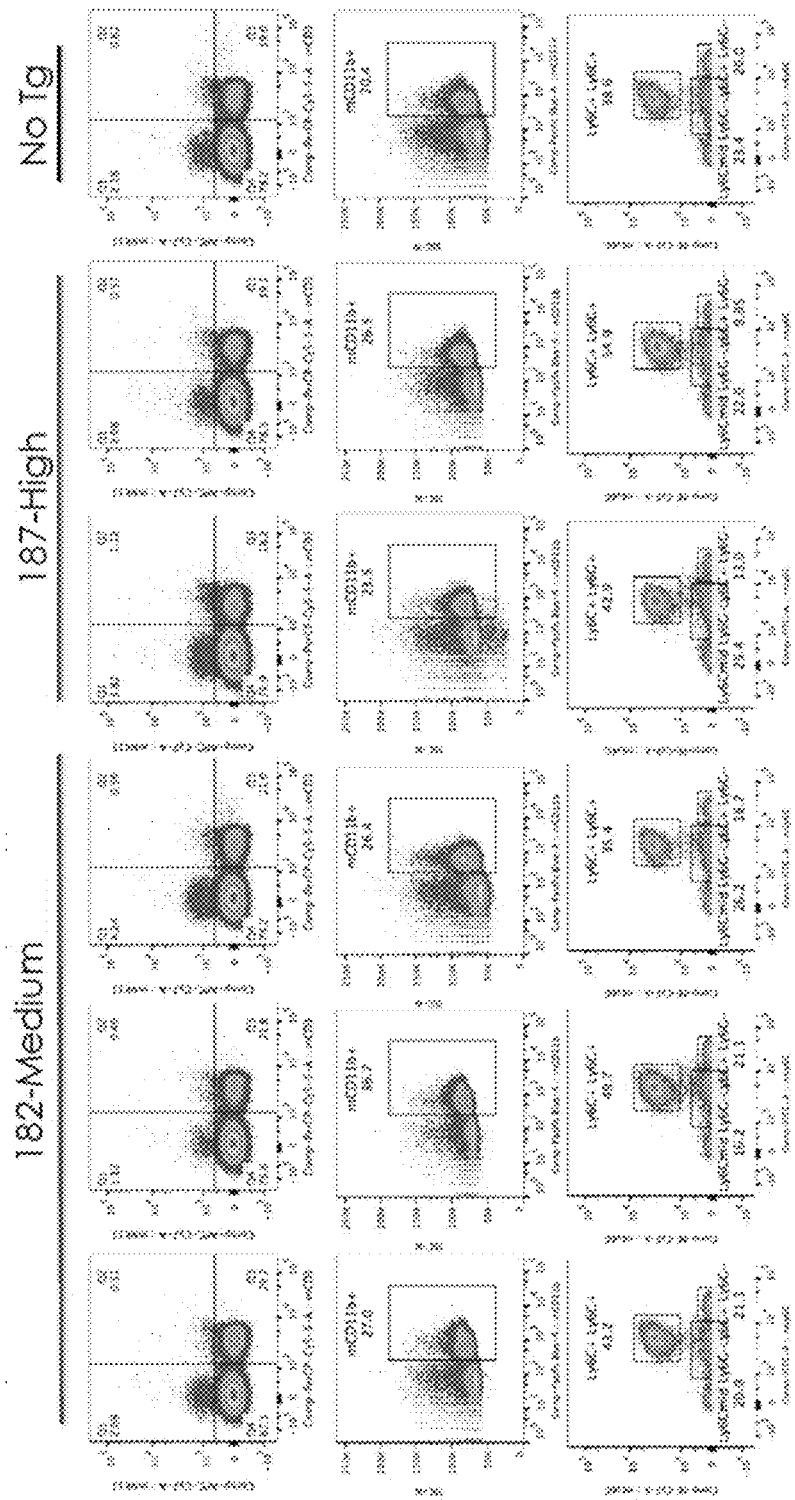
FIG. 16 shows results of FACS analysis comparing the immune cell populations in the periphery of control non-transgenic and BACRP11-891J20 transgenic mice.

The overall percentages of peripheral blood cells did not appear to be altered in the transgenic 187 or 182 founder mouse lines relative to a non-transgenic mouse (FIG. 16). Specifically, no gross alterations in the number of T cells, NK cells, myeloid cells, CD11b-positive cells, Mo-MDSCs, or G-MDSCs/neutrophils were observed in peripheral blood tested from the higher expression mouse #187 founder line or the lower expression mouse #182 founder line (FIG. 16).

Figure 17:
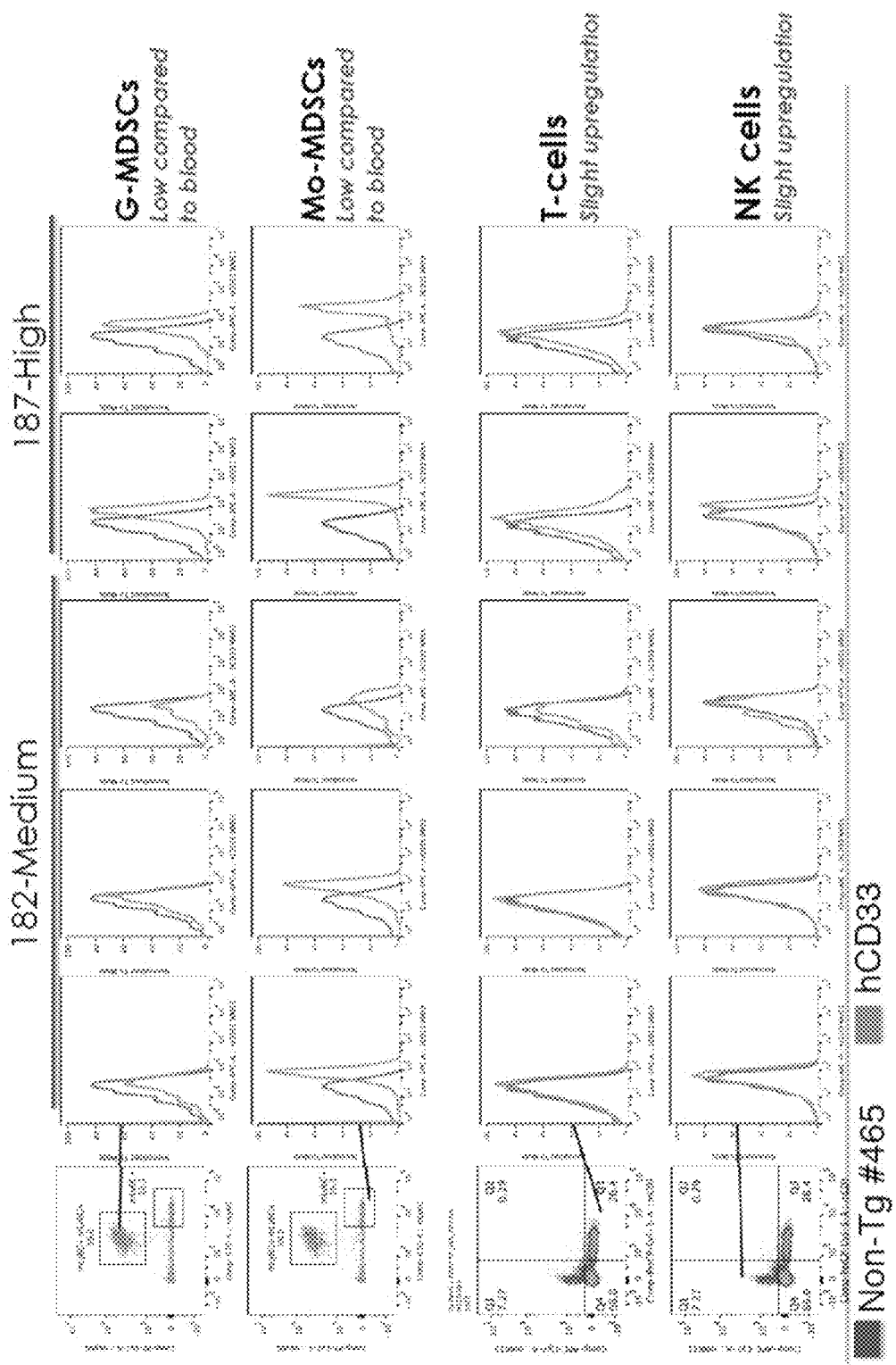
FIG. 17 shows results of FACS analysis demonstrating the expression pattern of human CD33 on primary G-MDSCs, primary Mo-MDSCs, primary T cells and primary NK cells from the spleens of control non-transgenic mice (red line) and BACRP11-891J20 transgenic mice (blue line).
Figure 18:
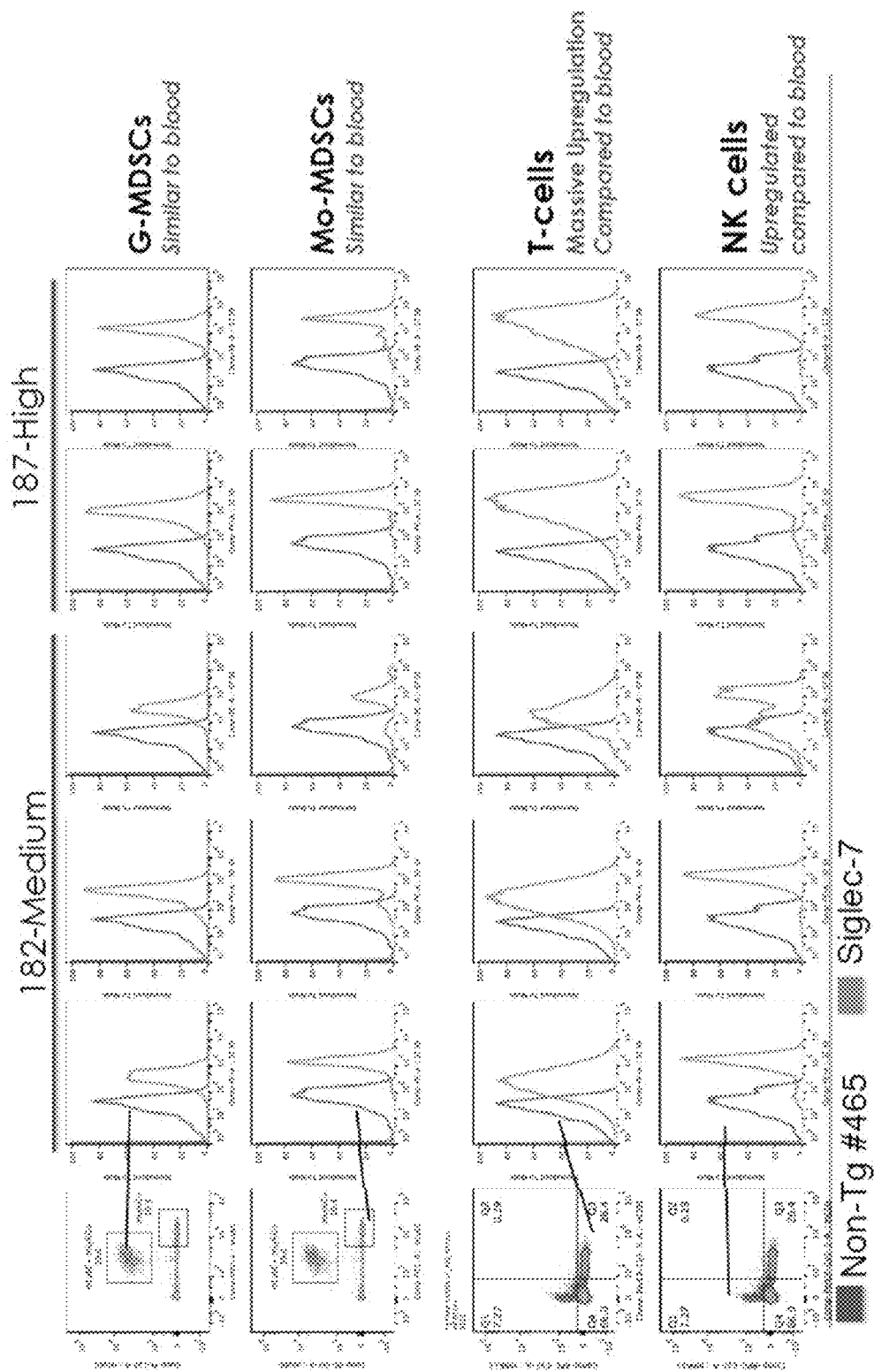
FIG. 18 shows results of FACS analysis demonstrating the expression pattern of human Siglec-7 on primary G-MDSCs, primary Mo-MDSCs, primary T cells and primary NK cells from the spleens of control non-transgenic mice (red line) and BACRP11-891J20 transgenic mice (blue line).
Figure 19:
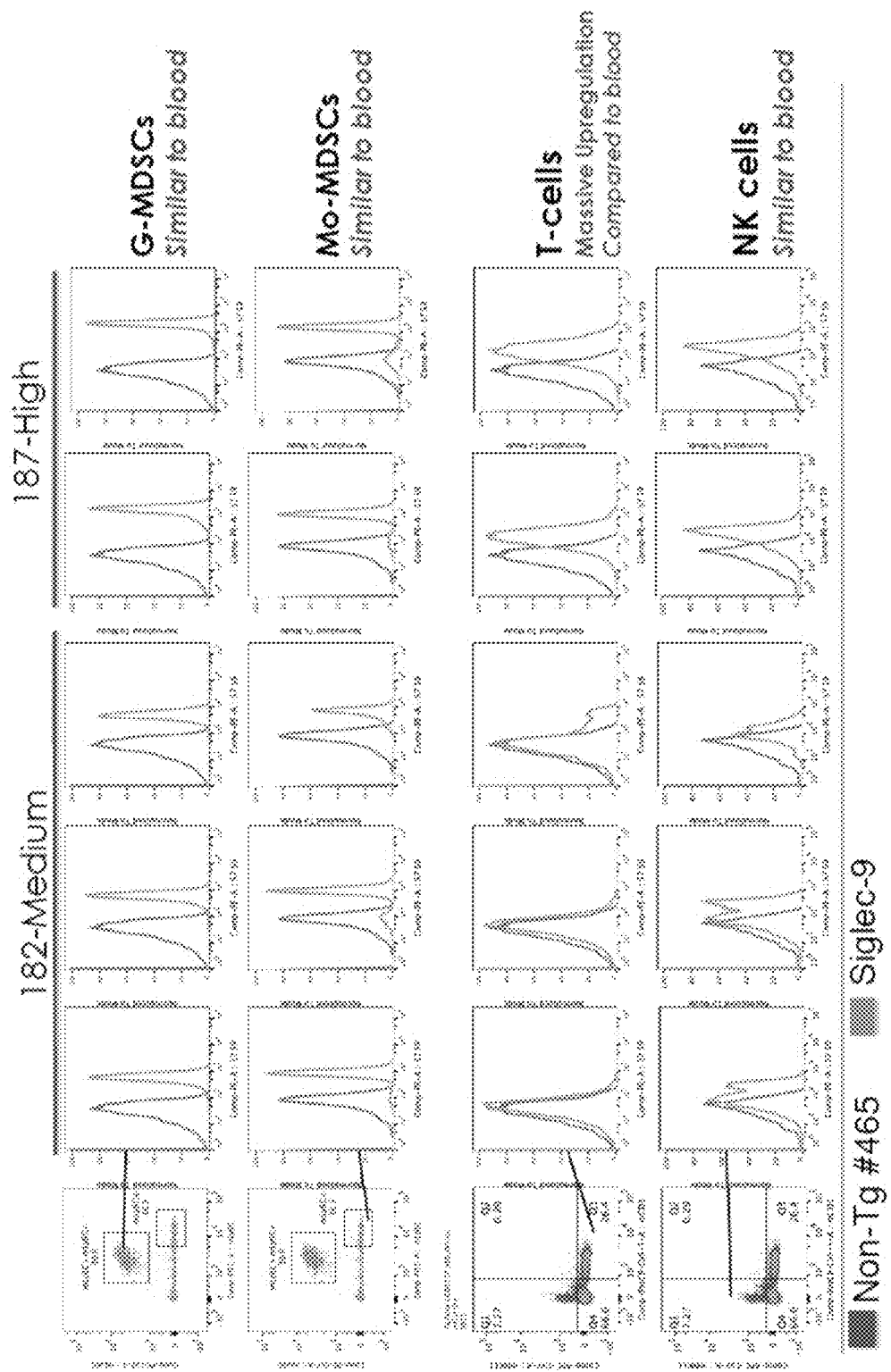
FIG. 19 shows results of FACS analysis demonstrating the expression pattern of human Siglec-9 on primary G-MDSCs, primary Mo-MDSCs, primary T cells and primary NK cells from the spleens of control non-transgenic mice (red line) and BACRP11-891J20 transgenic mice (blue line).

Human CD33 expression levels on splenic immune cells were comparable to those of their counterparts in peripheral blood (FIG. 17). Human CD33 levels were mildly reduced on splenic MDSCs relative to peripheral blood MDSCs, and CD33 remained low or absent on T and NK cells (FIG. 17). Human Siglec-7 expression levels on MDSCs isolated from the spleen were similar to that observed on MDSCs from peripheral blood, but expression of Siglec-7 was greatly increased on splenic T cells, and to a lesser extent splenic NK cells, than their counterparts in peripheral blood (FIG. 18). Human Siglec-9 expression on splenic MDSCs and NK cells was similar to the expression observed on their counterparts in peripheral blood, but Siglec-9 expression was greatly increased on splenic T cells relative to peripheral blood T cells (FIG. 19). A summary of the relative expression of human CD33, Siglec-7, and Siglec-9 on splenic vs. peripheral blood cells is provided in Table B below.

TABLE B

Relative transgene expression in splenic cells

|  | hCD33 | hSiglec-7 | hSiglec-9 |
| --- | --- | --- | --- |
| Mo-MDSCs | Low compared to blood | Similar to blood | Similar to blood |
| G-MDSCs/ neutrophils | Low compared to blood | Similar to blood | Similar to blood |
| T cells | Slightly upregulated compared to blood | Massively upregulated compared to blood | Massively upregulated compared to blood |
| NK cells | Slightly upregulated compared to blood | Upregulated compared to blood | Similar to blood |

Figure 20:
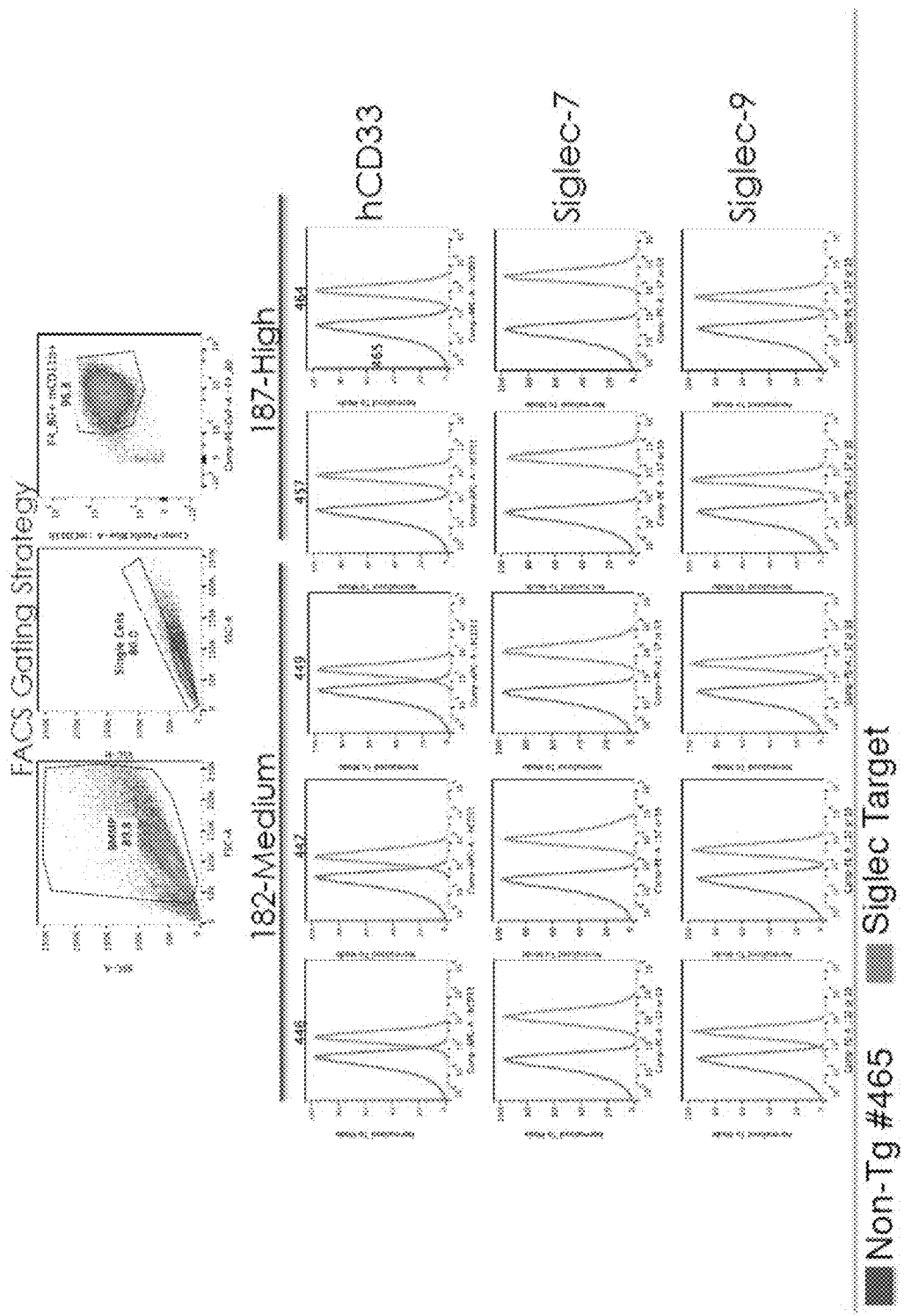
FIG. 20 shows results of FACS analysis demonstrating the expression pattern of human CD33, human Siglec-7, and human Siglec-9 on primary bone marrow-derived macrophages (BMDMs) from control non-transgenic mice (red line) and BACRP11-891J20 transgenic mice (blue line).
Figure 21:
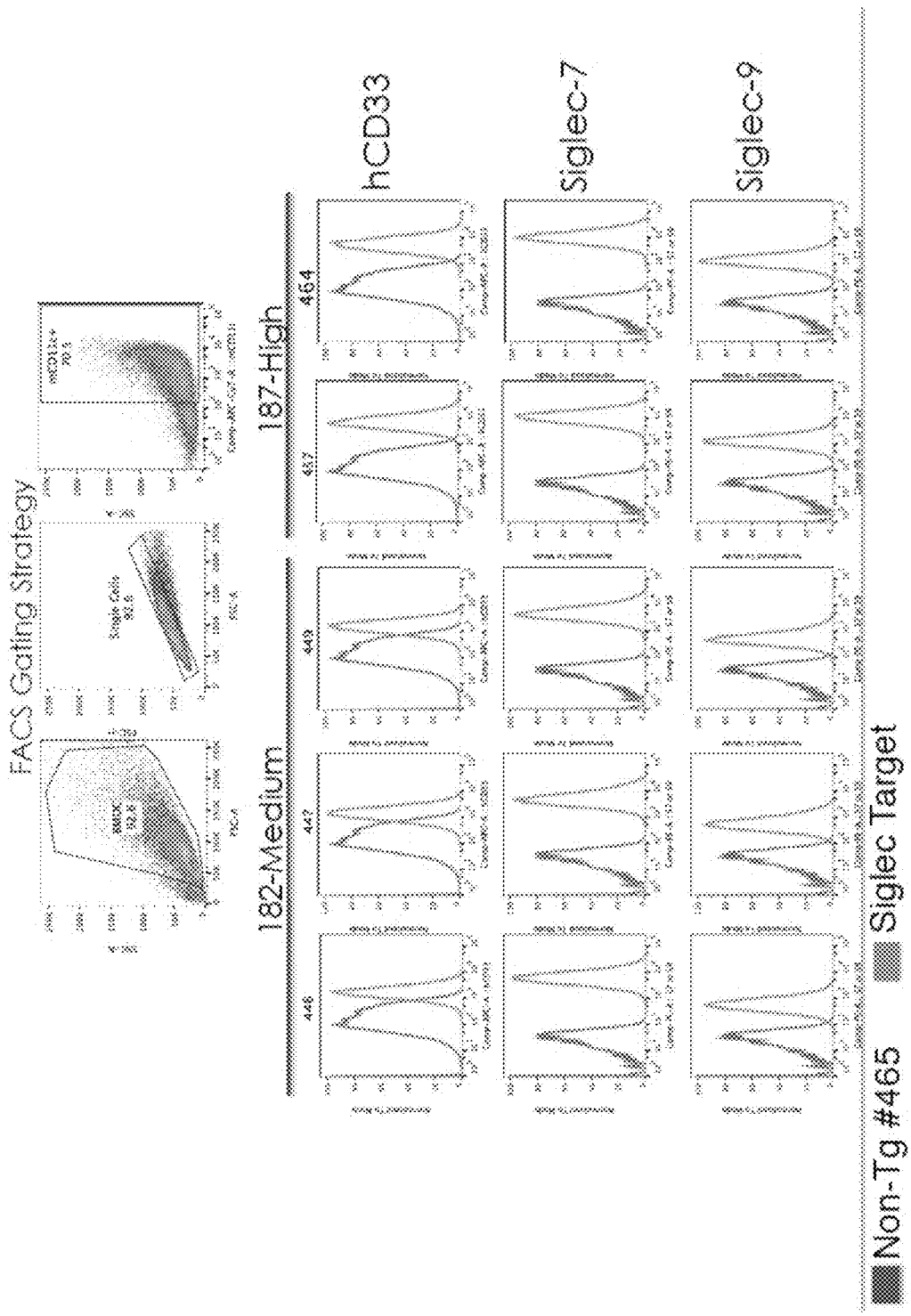
FIG. 21 shows results of FACS analysis demonstrating the expression pattern of human CD33, Siglec-7, and Siglec-9 on primary bone marrow-derived dendritic cells (BMDCs) from control non-transgenic mice (red line) and BACRP11-891J20 transgenic mice (blue line).

Transgenic mouse BMDMs (FIG. 20) and BMDCs (FIG. 21) from either the higher expression mouse #187 founder line or the lower expression mouse #182 founder line expressed high levels of human CD33, human Siglec-7, and human Siglec-9.

Figure 23:
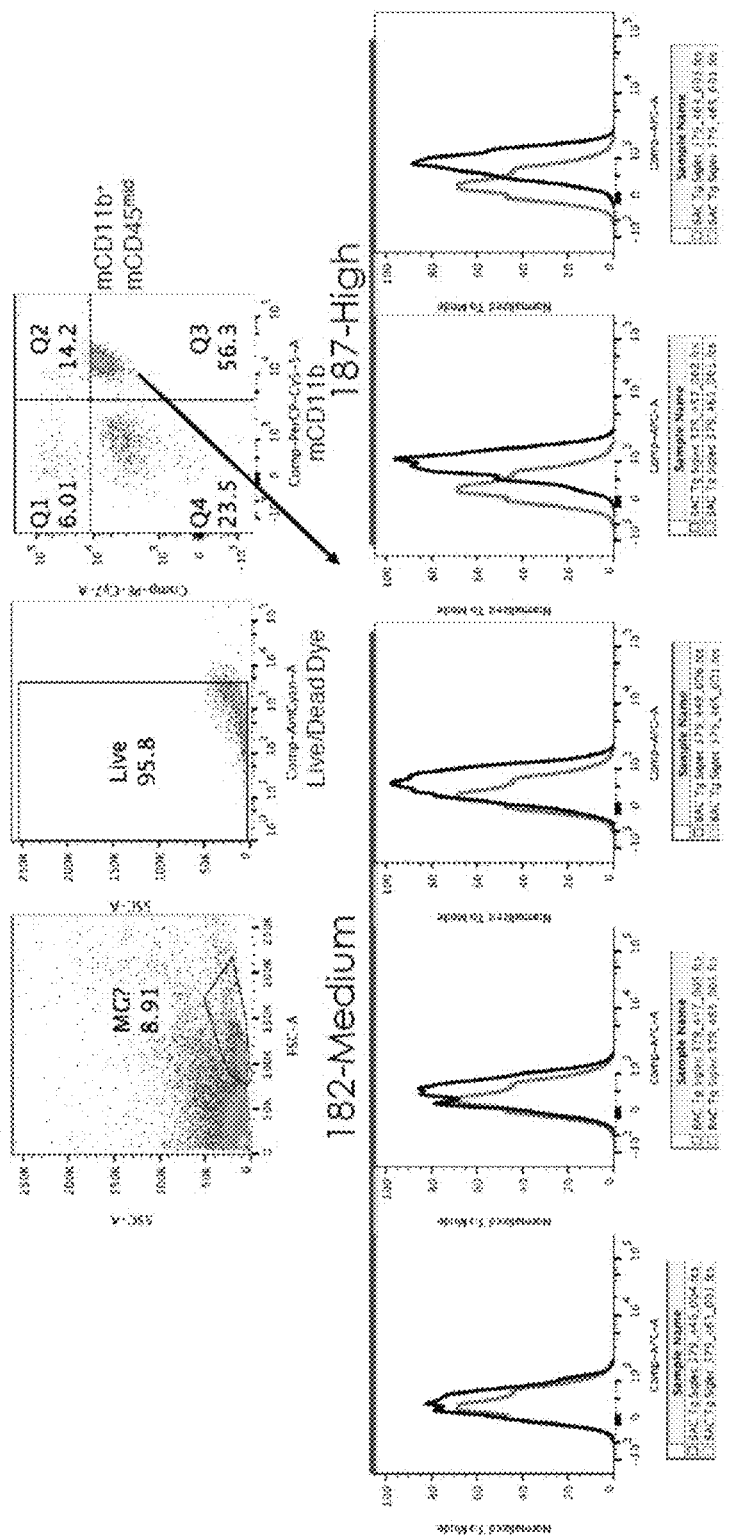
FIG. 23 shows results of FACS analysis demonstrating the expression pattern of human CD33 on primary brain microglia from BACRP11-891J20 transgenic mice.

Next, experiments were conducted to determine the expression of human CD33 on brain microglia isolated from rederived transgenic animals from the higher expression mouse #187 founder line or the lower expression mouse #182 founder line. The FACS panel design used to stain mouse brain microglia is summarized in FIG. 22. Brain microglia isolated from mice derived from the lower expression mouse #182 founder line showed little to no human CD33 expression, while human CD33 expression was apparent in brain microglia isolated from mice derived from the higher expression mouse #187 founder line (FIG. 23).

Figure 24A:
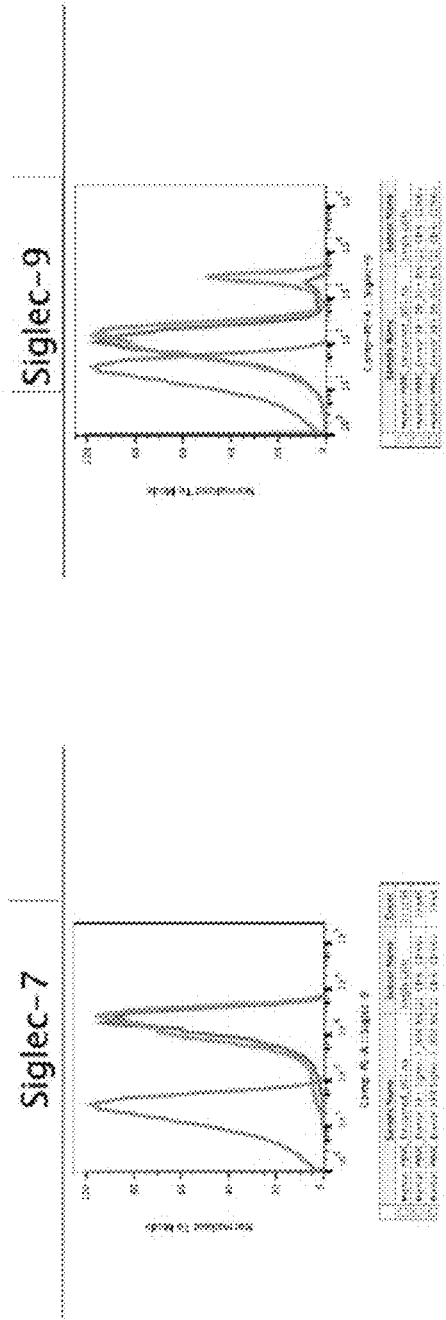
FIGS. 24A-24B show results of FACS analysis demonstrating the expression pattern of human Siglec-7 and human Siglec-9 on primary NK cells from peripheral blood of either a human patient (FIG. 24A) or BACRP11-891J20 transgenic mice (FIG. 24B).
Figure 24B:
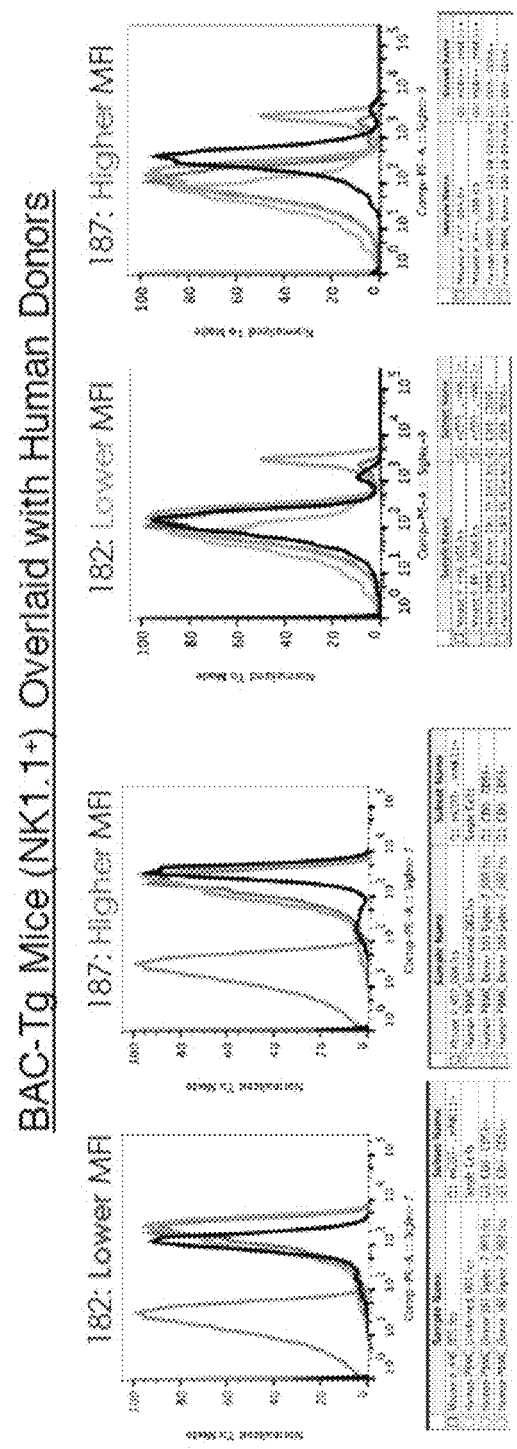
Figure 25A:
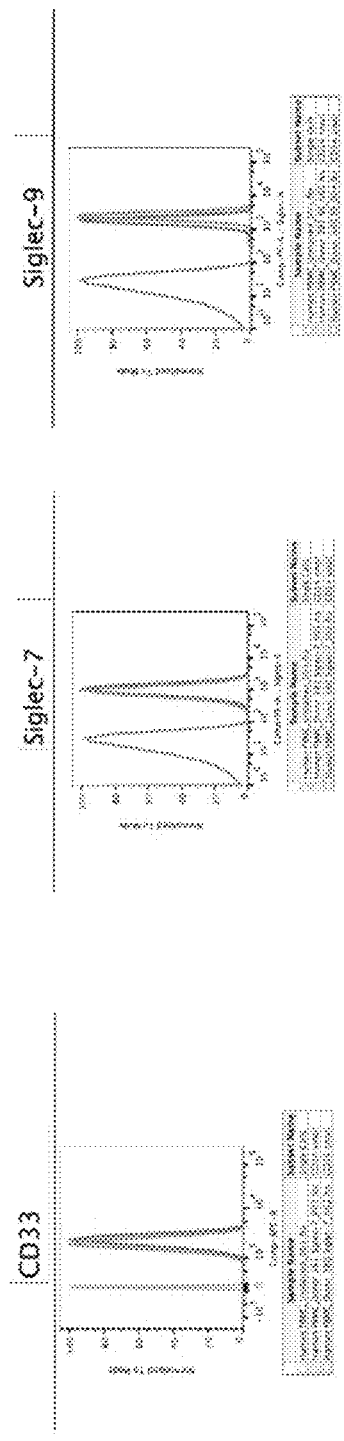
FIGS. 25A-25B show results of FACS analysis demonstrating the expression pattern of human CD33, human Siglec-7, and human Siglec-9 on primary myeloid cells from peripheral blood of either a human patient (FIG. 25A) or BACRP11-891J20 transgenic mice (FIG. 25B).
Figure 25B:
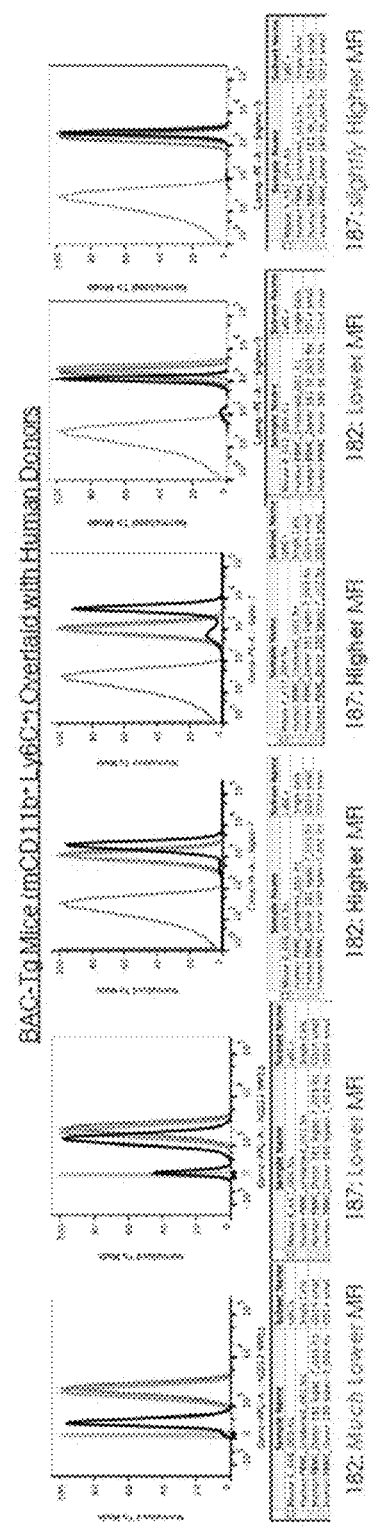

Finally, expression levels of human CD33, human Siglec-7, and human Siglec-9 were directly compared between human primary cells and primary cells isolated from the higher expression mouse #187 founder line or the lower expression mouse #182 founder line. Surprisingly, expression levels of human Siglec-7 and human Siglec-9 were comparable between NK cells isolated from the human donor (FIG. 24A) and NK cells isolated from either the higher expression mouse #187 founder line or the lower expression mouse #182 founder line (FIG. 24B) Similarly, expression levels of human CD33, human Siglec-7, and human Siglec-9 were comparable between myeloid cells isolated from the human donor (FIG. 25A) and myeloid cells isolated from either the higher expression mouse #187 founder line or the lower expression mouse #182 founder line (FIG. 25B).

Taken together, this data suggested that transgenic animals had been generated which coordinately expressed the human CD33, human Siglec-7, and human Siglec-9 genes. Moreover, this data suggested that these transgenic animals not only coordinately expressed the human genes, but expressed them at or near the same levels, and on the same cell types, as was observed in primary cells isolated from a human donor. The data provided herein suggested that, for the first time, transgenic animals had been developed which had been "humanized for the Siglec locus. Without wishing to be bound by theory, these transgenic animals harboring a "humanized" Siglec system will allow for the study and development of novel therapeutics that interact with and target human Siglec proteins, opening the door for the improvement of treatment strategies for diseases in which the human Siglecs may be involved (e.g., neurodegenerative diseases, proliferative diseases, etc.)

Example 3

Generation of Transgenic Mice Harboring Human Siglec-5 and Siglec-14

Methodologies

Identifying BACs of interest: Bacterial Artificial Chromosomes (BACs) harboring the human Siglec genes Siglec-5 and Siglec-14 with all intronic and exonic sequences were identified using the UCSC genome browser and the CloneDB from NCBI. BAC clones were further selected to identify those clones harboring a minimum of at least 10 kilobases of 5' and 3' flanking sequences in addition to the indicated Siglec genes to maximize the likelihood of identifying BAC clones that include the relevant human gene regulatory sequences in addition to human Siglec-5 and Siglec-14.

Isolating and purifying BAC clones: BAC clones meeting all of the selection requirements were isolated and purified as described in Example 1.

Generating transgenic animals: Mice harboring BAC clones of interest were generated as described in Example 1.

Isolating primary cells: Primary cells from mice and humans were isolated as described in Examples 1 and 2. Bone marrow cells were cultured to differentiate dendritic cells for 7 days.

FACS analysis: Mice carrying the human Siglec-5 and Siglec-14 transgenes were analyzed by FACS analysis using standard techniques. Briefly, peripheral blood was obtained from 4-8 week old transgenic animals, and peripheral blood cells were subjected to multi-color flow cytometry panel staining. Cells were incubated with the cell viability dye and the following antibodies: anti-mouse cD11b (BD Biosciences, M1/70, 1:100), anti-mouse CD3, anti-mouse NK1.1, and anti-human Siglec-5 (Biolegend, 1A5, 1:20). Alternatively, peripheral blood, spleen, and bone marrow-derived cells were subjected to multi-color flow cytometry panel staining. Cells were incubated with the cell viability dye and the following antibodies: anti-mouse cD11b (BD Biosciences, M1/70, 1:100), anti-mouse CD3 (Affymetrix, 145-2C11, 1:100), anti-mouse CD11b (Biolegend, 1A8, 1:200), and anti-human Siglec-5 (Biolegend, 1A5, 1:20). Bone marrow-derived cells were additionally stained with anti-human Siglec-7. The cells were stained for 30 minutes on ice, washed twice with cold FACS buffer, and fixed with 4% PFA. The stained and fixed cells were then applied to a BD FACS CANTO II cytometer, data were acquired, and the resulting data was analyzed with FlowJo software.

Results

To obtain mice coordinately expressing multiple human Siglec genes, Bacterial Artificial Chromosomes (BACs) harboring key human Siglec genes with sufficient flanking sequences were identified using the UCSC genome browser and the CloneDB from NCBI. Three BAC clones (BACCTD-2026P14, BACRP11-145E6, and BACRP11-105H4) were identified that were predicted to contain the coding sequences for the human genes Siglec-5 and Siglec-14. Each BAC was tested by PCR analysis to confirm the proper human sequences of interest; however, BAC clone BACRP11-145E6 failed to show a signal corresponding to the presence of Siglec-14, while BAC clone BACRP11-105H4 could not be successfully isolated.

Figure 26:
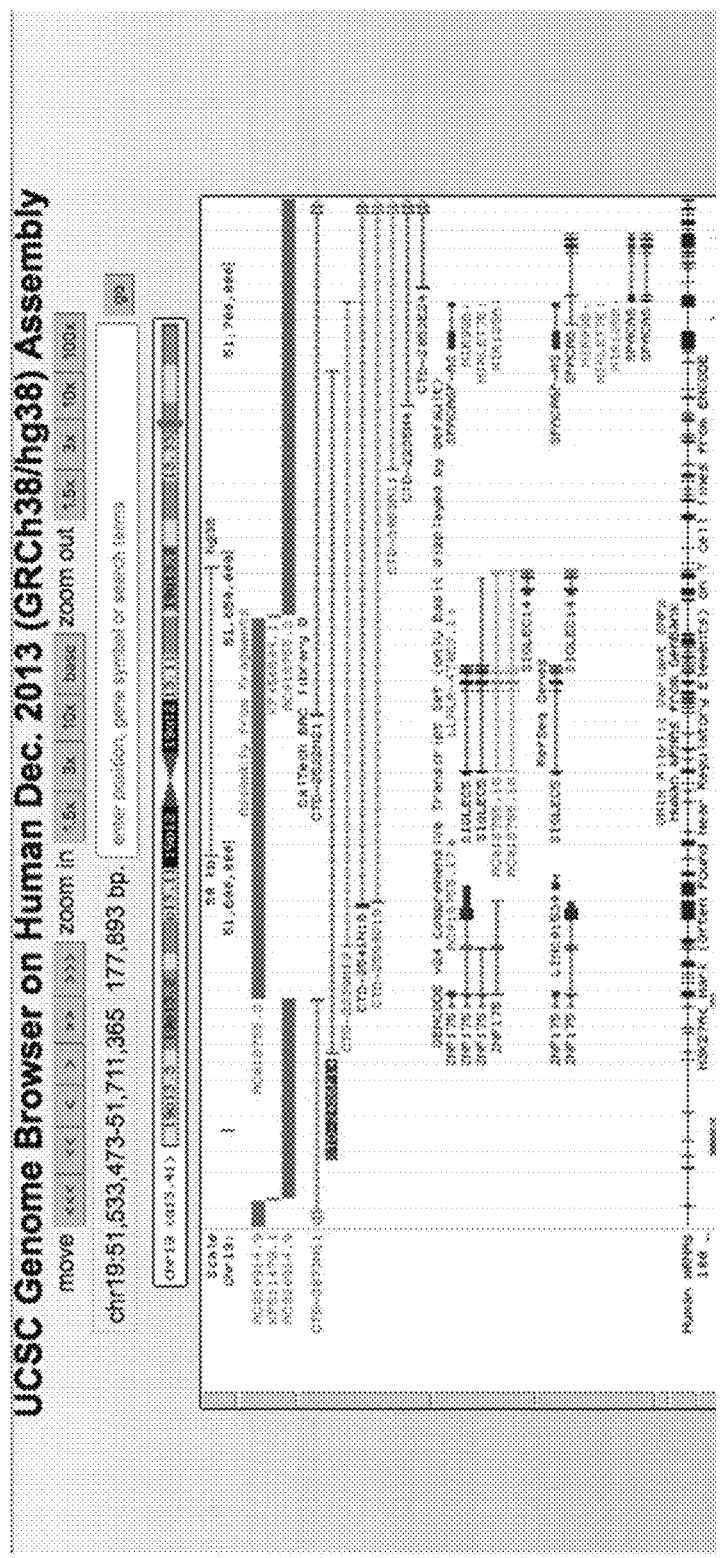
FIG. 26 shows a UCSC genome browser map of the genes, including Siglec-5 and Siglec-14, on a region of human Chromosome 19 included in the bacterial artificial chromosome (BAC) BACCTD-2026P14.
Figure 27:
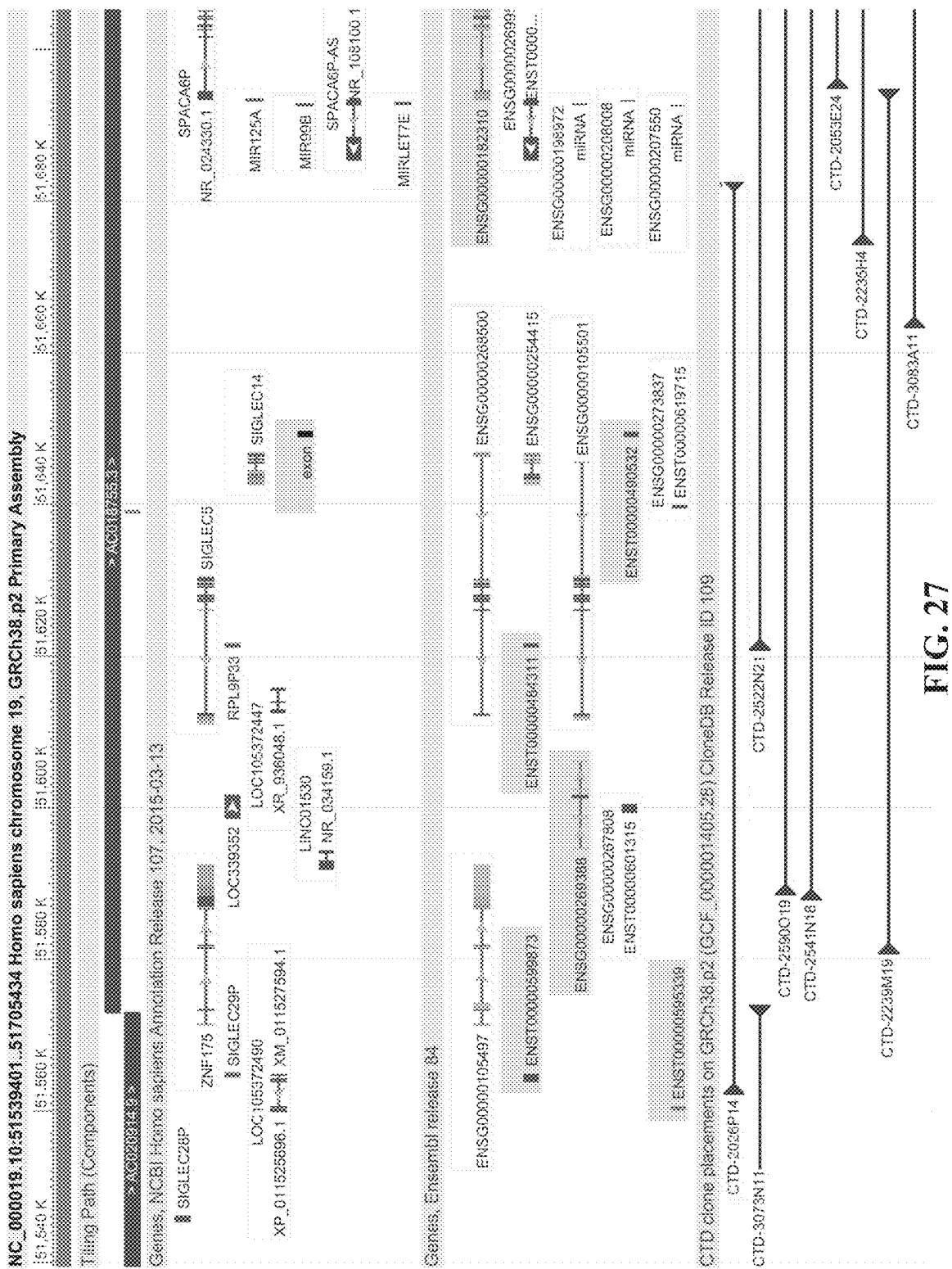
FIG. 27 shows a CloneDB map of the genes, including Siglec-5 and Siglec-14, on a region of human Chromosome 19 included in the bacterial artificial chromosome (BAC) BACCTD-2026P14.

Maps of the human chromosomal region of interest encompassed by BACCTD-2026P14 are shown in FIG. 26 (from the UCSC genome browser) and FIG. 27 (from the CLONEDB NCBI browser). The chromosomal DNA within BACCTD-2026P14 spanned 118,595 nucleotides of the human genome, covering nucleotide positions 51,563,112-51,681,716 on human chromosome 19, based on the hg38 build of the UCSC genome browser (the human Siglec genes are found within a cluster on chromosome 19). Sequences within the Siglec-5 gene were amplified by PCR and sequenced by the Sanger method to confirm the presence of the gene in BACCTD-2026P14.

Figure 28:
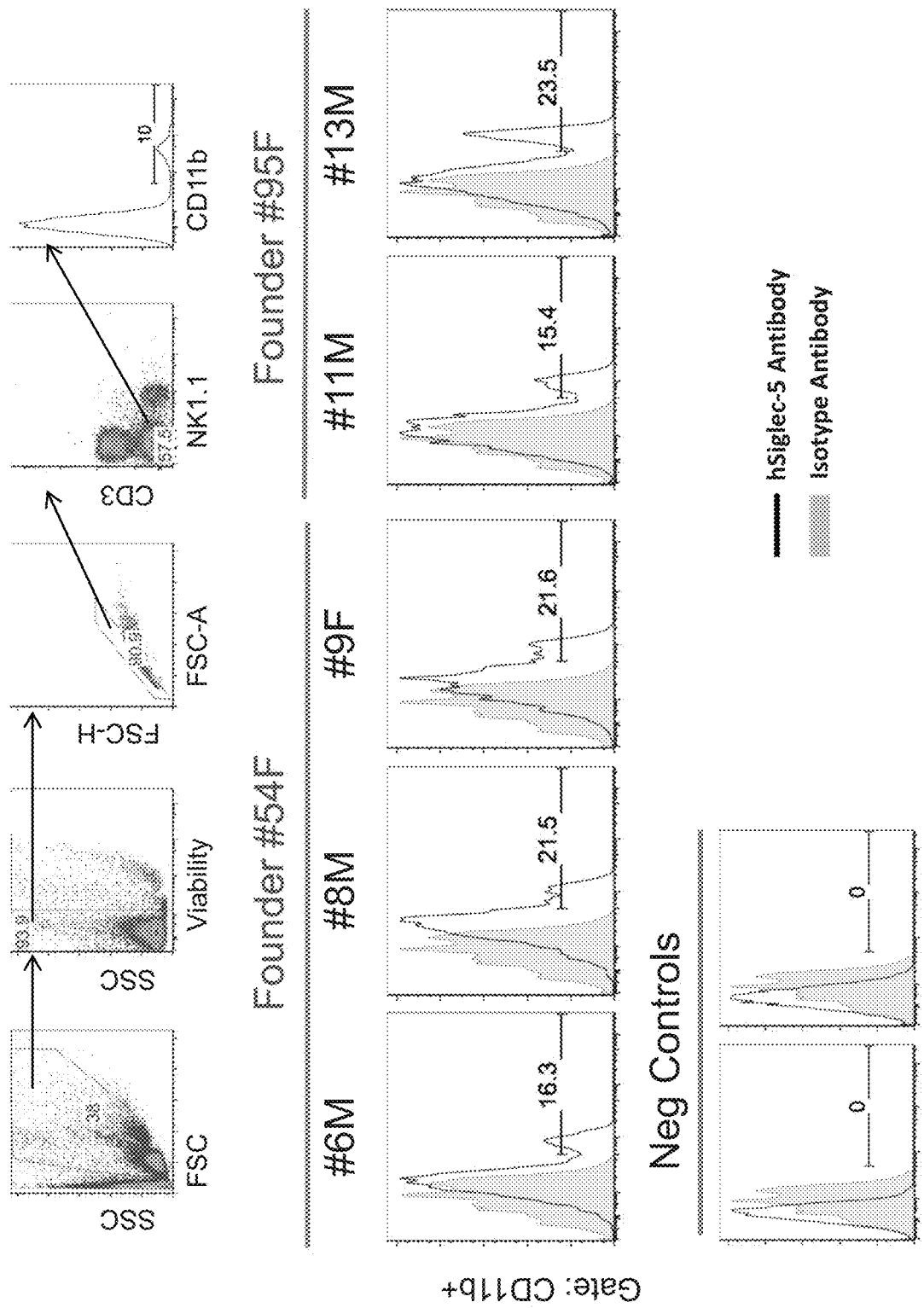
FIG. 28 shows results of FACS analysis demonstrating the expression pattern of human Siglec-5 on CD11b-positive primary cells from peripheral blood of BACCTD-2026P14 transgenic mice (#6M, #8M, #9F, #11M, and #13m) and control non-transgenic mice (Neg Controls).

Transgenic mice harboring BACCTD-2026P14 were generated by pronuclear injection of the BAC DNA into C57BL6/j zygotes. The resulting pups were genotyped to identify founder animals harboring the human transgenes (mouse #s 54 and 95). These founder animals were then bred to non-transgenic animals, and progeny animals (mouse #s 6, 8, 9, 11, and 13) were then analyzed by FACS analysis to monitor human Siglec-5 protein expression on CD11b-positive cells (FIG. 28). Expression of human Siglec-5 was observed on 10-20% of the CD11b-positive cells from mice derived from both of the founder animals, whereas control non-transgenic animals were negative for human Siglec-5 (FIG. 28).

Figure 29:
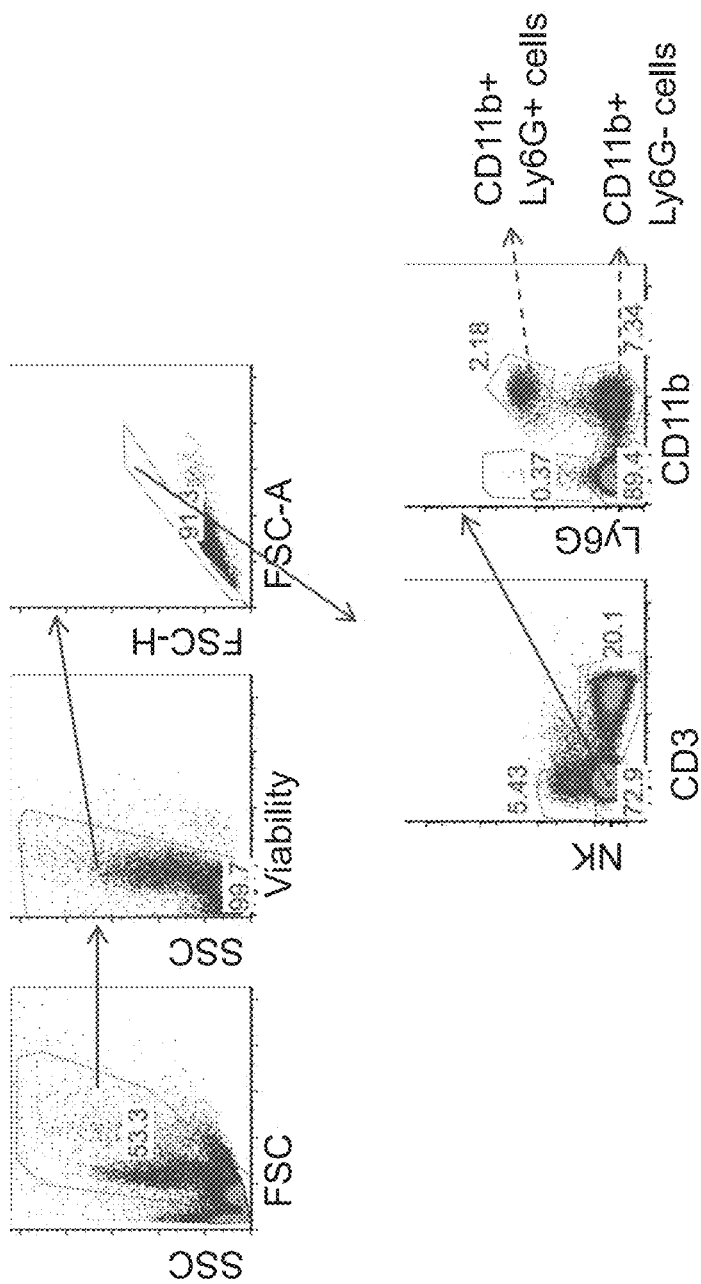
FIG. 29 shows the FACS gating strategy for the analysis of peripheral blood and spleen cells.

Transgenic mouse #13 (from founder animal #95) was then bred to generate progeny animals. Pups resulting from this breeding scheme were genotyped to identify progeny animals harboring the human transgenes, and cells isolated from these animals were tested for protein expression of human Siglec-5 by FACS analysis. To characterize mouse cell subpopulations that expressed the human Siglec-5, cells isolated from these mice were also stained with antibodies to specifically identify particular immune cell subpopulations. The cell isolation strategy used in these experiments is summarized in FIG. 29.

Figure 30:
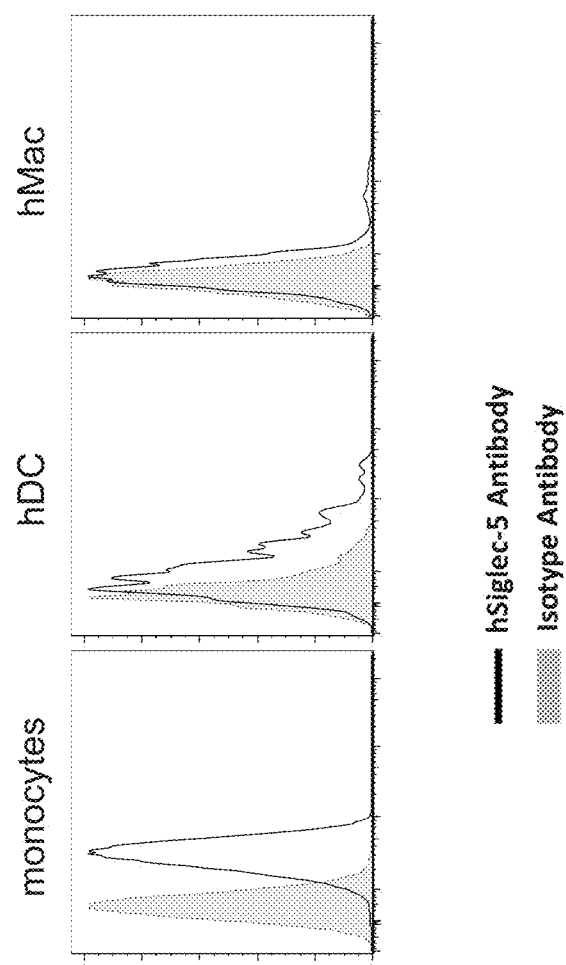
FIG. 30 shows results of FACS analysis demonstrating the expression pattern of human Siglec-5 on primary monocytes, dendritic cells (hDC), and macrophages (hMac) from peripheral blood of a human patient stained with an isotype control antibody (grey) or an anti-human Siglec-5 antibody (black line).
Figure 31:
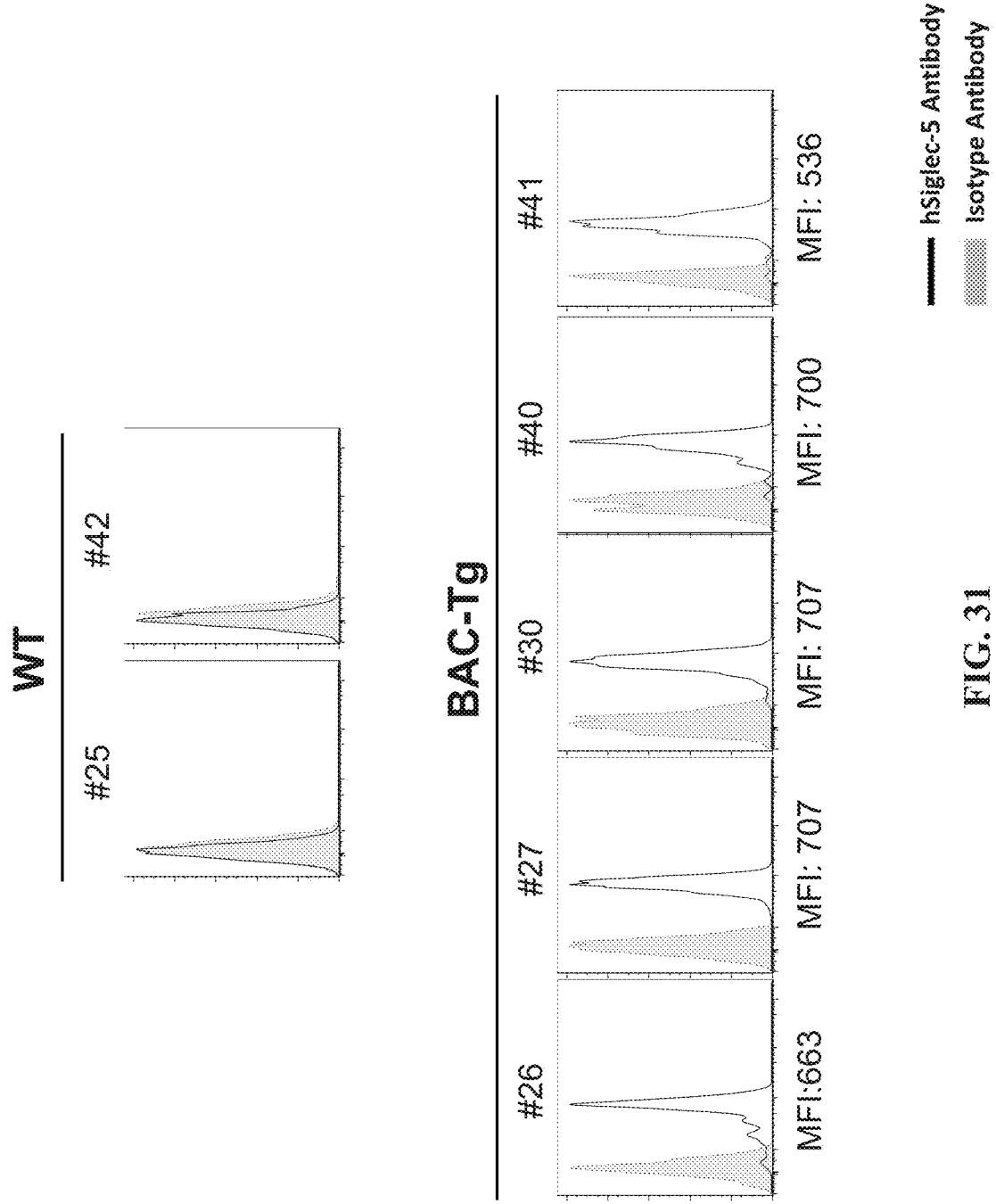
FIG. 31 shows results of FACS analysis demonstrating the expression pattern of human Siglec-5 on CD11b$^+$/Ly6G$^+$ primary cells from peripheral blood of control non-transgenic mice (#25 and #42) and BACCTD-2026P14 transgenic mice (#26, #27, #30, #40, and #41) stained with an isotype control antibody (grey) or an anti-human Siglec-5 antibody (black line).
Figure 32:
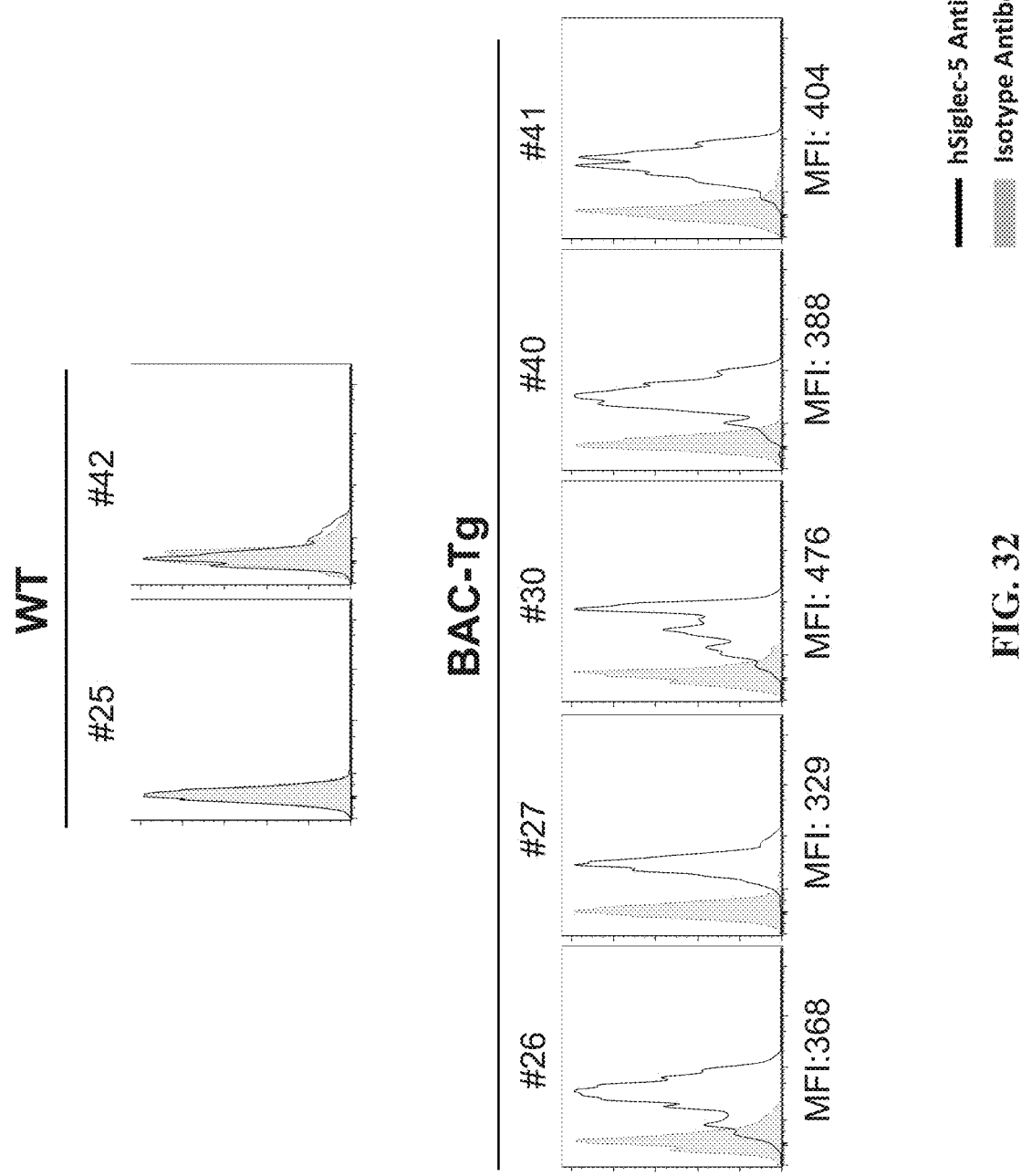
FIG. 32 shows results of FACS analysis demonstrating the expression pattern of human Siglec-5 on CD11b$^+$/Ly6G$^+$ primary cells from the spleen of control non-transgenic mice (#25 and #42) and BACCTD-2026P14 transgenic mice (#26, #27, #30, #40, and #41) stained with an isotype control antibody (grey) or an anti-human Siglec-5 antibody (black line).
Figure 33:
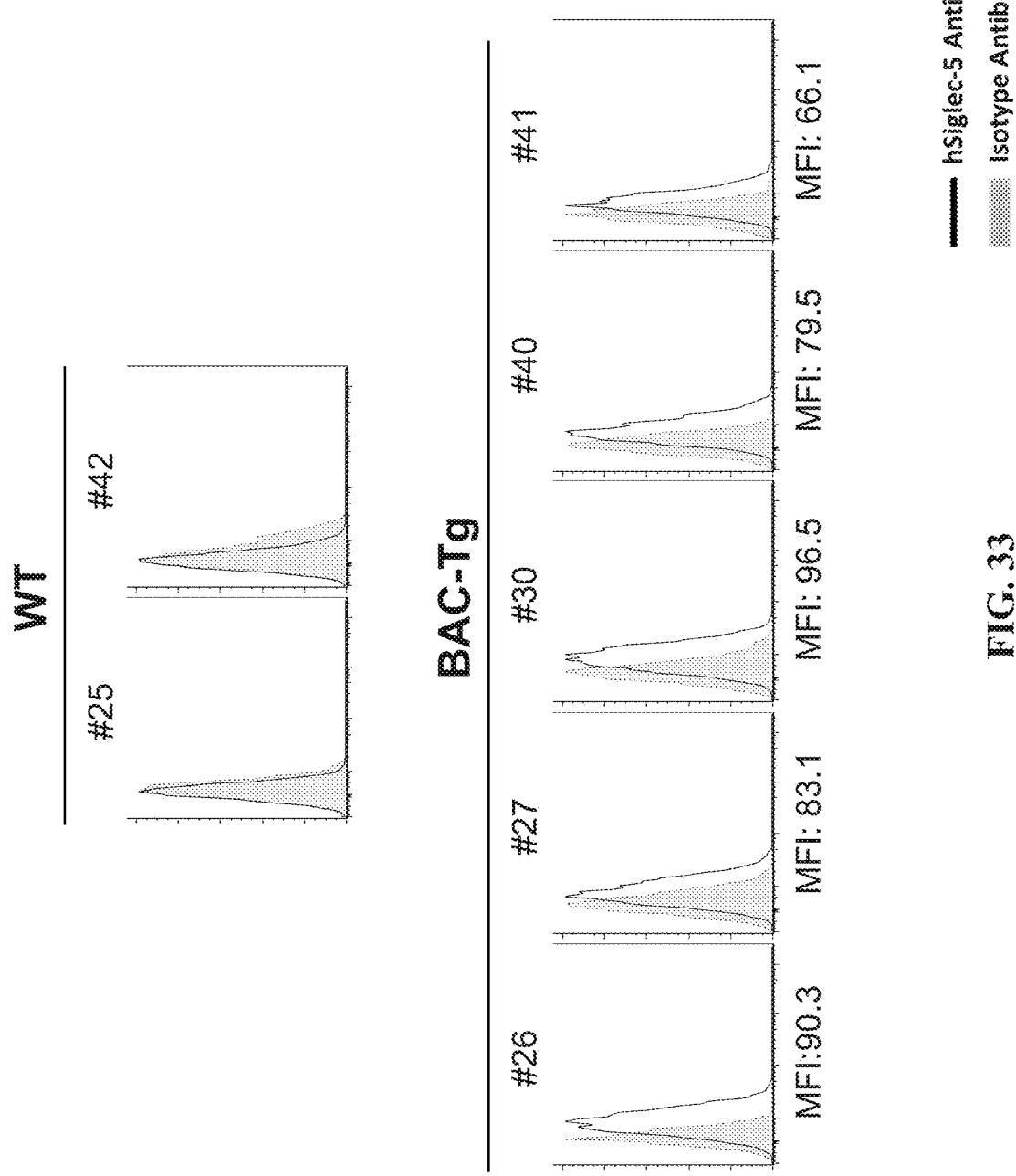
FIG. 33 shows results of FACS analysis demonstrating the expression pattern of human Siglec-5 on CD11b$^+$/Ly6G primary cells from peripheral blood of control non-transgenic mice (#25 and #42) and BACCTD-2026P14 transgenic mice (#26, #27, #30, #40, and #41) stained with an isotype control antibody (grey) or an anti-human Siglec-5 antibody (black line).
Figure 34:
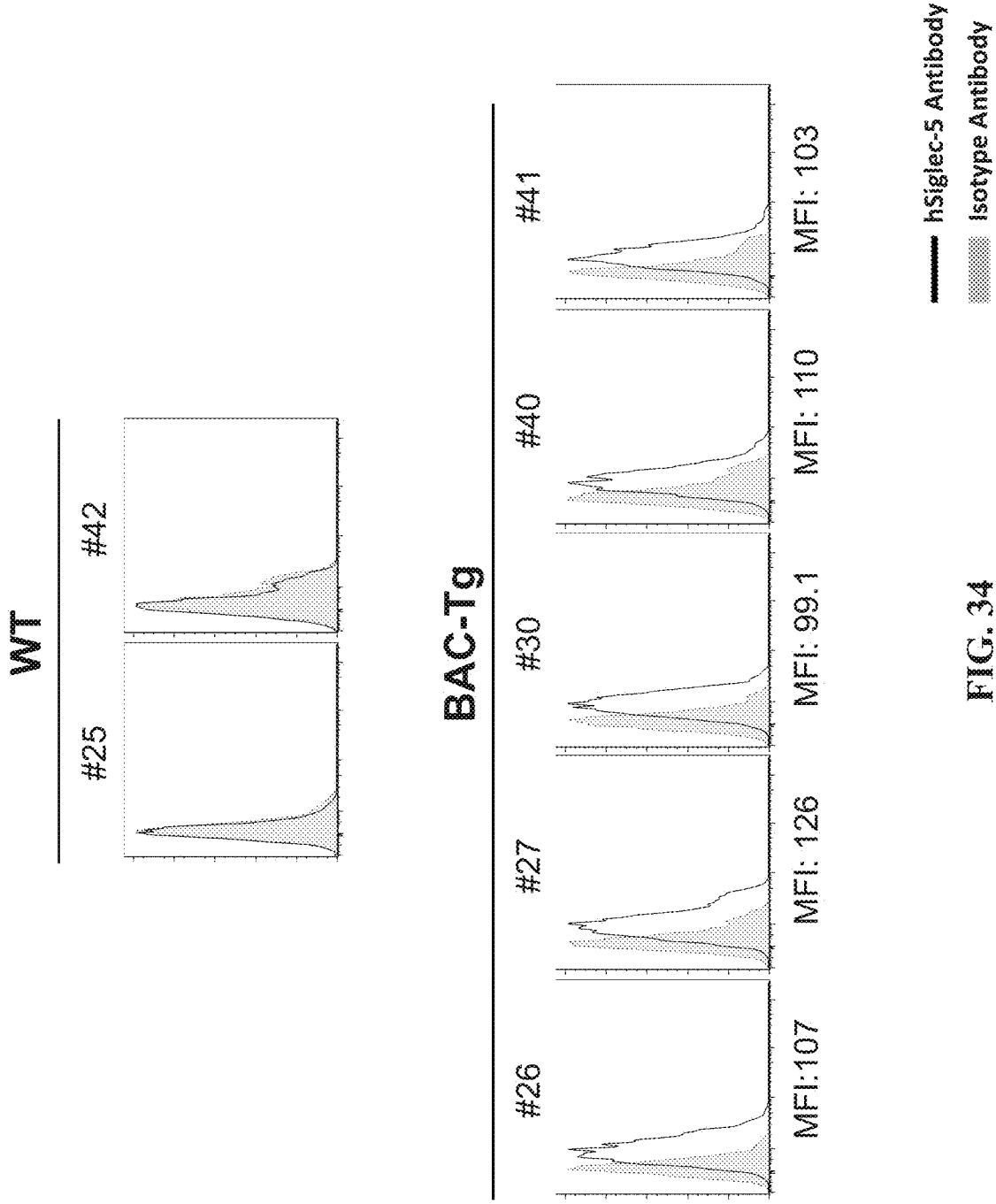
FIG. 34 shows results of FACS analysis demonstrating the expression pattern of human Siglec-5 on CD11b$^+$/Ly6G primary cells from the spleen of control non-transgenic mice (#25 and #42) and BACCTD-2026P14 transgenic mice (#26, #27, #30, #40, and #41) stained with an isotype control antibody (grey) or an anti-human Siglec-5 antibody (black line).

Monocytes, dendritic cells, and macrophages isolated from a human patient expressed Siglec-5 on their surface (FIG. 30). The expression of human Siglec-5 on relevant mouse immune cells was tested to determine whether these transgenic mice expressed human Siglec-5 in a similar pattern to the expression of Siglec-5 on human immune cells. Human Siglec-5 expression was positive on CD11b+/Ly6G+ cells from peripheral blood (FIG. 31) and spleens (FIG. 32) in mice from the mouse #95 founder line (mouse #26, #27, #30, #40, and #41), and negative on non-transgenic control mice. Similarly, human Siglec-5 expression was positive on CD11b+/Ly6G cells from peripheral blood (FIG. 33) and spleens (FIG. 34). This data showed that Siglec-5 was successfully expressed on these immune cell types in all of the transgenic mice tested.

Figure 35A:
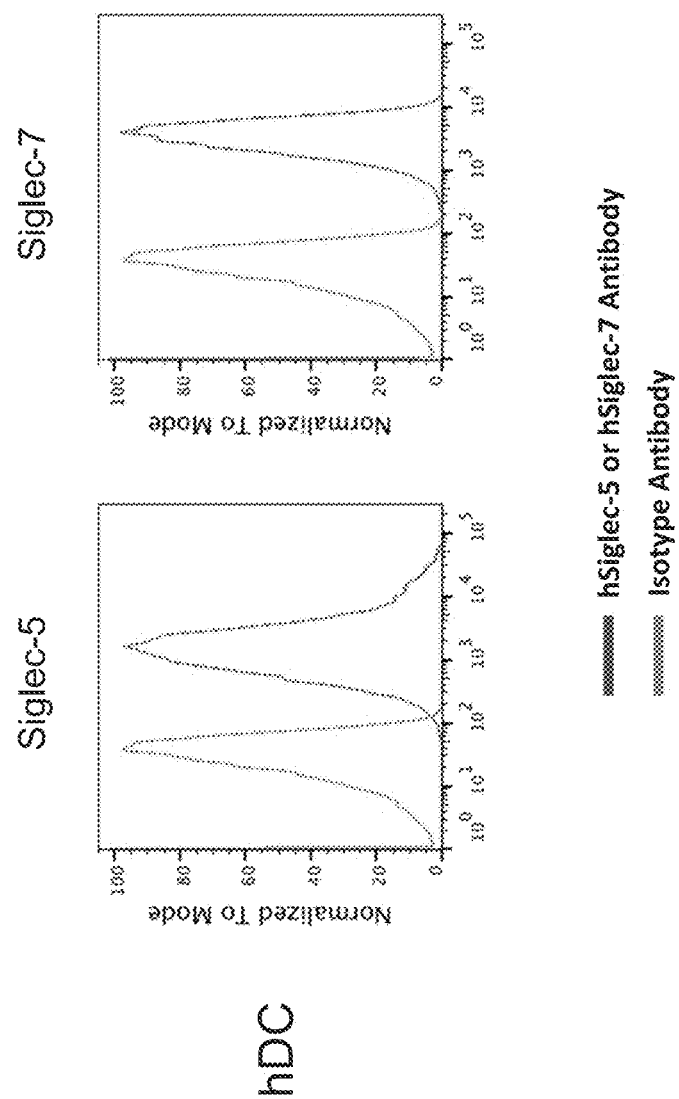
FIGS. 35A-B show human Siglec-5 and human Siglec-7 expression patterns on dendritic cells isolated from mice and humans.
Figure 35B:
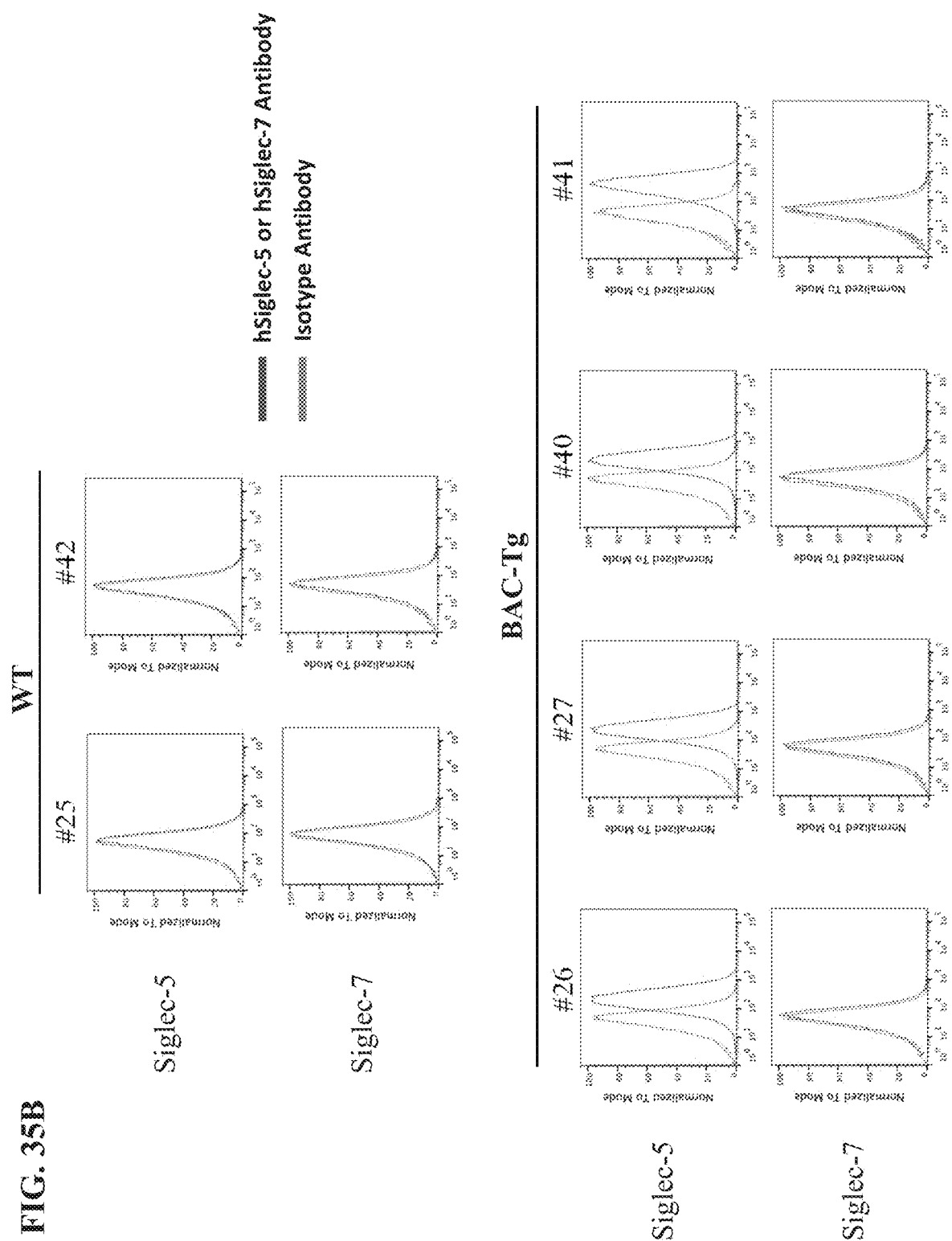

Finally, the expression pattern of human Siglec-5 on dendritic cells in the transgenic mice was tested. Dendritic cells isolated form a human patient expressed both Siglec-5 and Siglec-7 on their surface (FIG. 35A). Bone-marrow derived dendritic cells (BM-DCs) in mice from the mouse #95 founder line (mouse #26, #27, #30, #40, and #41) were also observed to express human Siglec-5 on their surface, while BM-DCs in non-transgenic control mice were Siglec-5 negative (FIG. 35B). None of the mice had observable expression of human Siglec-7, as these mice did not carry a human Siglec-7 transgene.

Taken together, this data suggested that transgenic animals were successfully generated that carried the human Siglec-5 and Siglec-14 genes. Further, these transgenic mice were capable of expressing human Siglec-5 on a number of relevant immune cell types, similar to the expression of Siglec-5 observed on human immune cells.

Example 4

Generation of Transgenic Mice Harboring Human Siglec-11 and Siglec-16

Methodologies

Identifying BACs of interest: Bacterial Artificial Chromosomes (BACs) harboring the human Siglec genes Siglec-11 and Siglec-16 with all intronic and exonic sequences were identified using the UCSC genome browser and the CloneDB from NCBI. BAC clones were further selected to identify those clones harboring a minimum of at least 10 kilobases of 5' and 3' flanking sequences in addition to the indicated Siglec genes to maximize the likelihood of identifying BAC clones that include the relevant human gene regulatory sequences in addition to human Siglec-5 and Siglec-14.

Isolating and purifying BAC clones: BAC clones meeting all of the selection requirements were isolated and purified as described in Example 1.

Generating transgenic animals: Mice harboring BAC clones of interest were generated as described in Example 1.

Results

Figure 36:
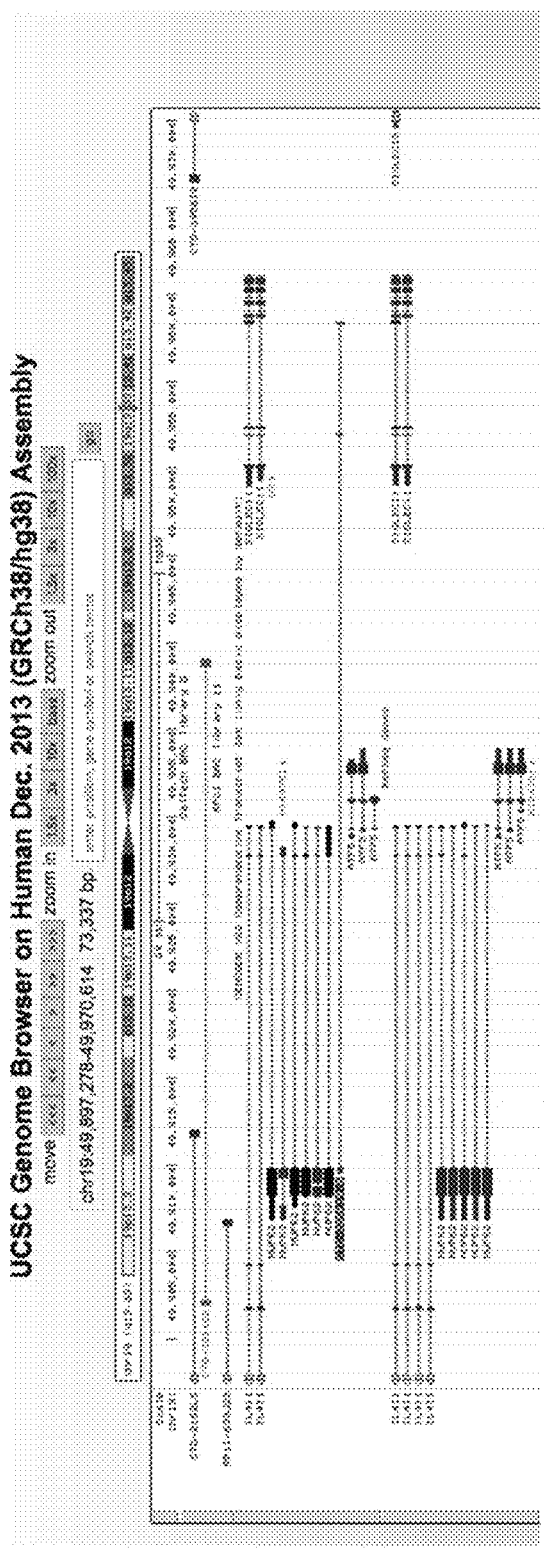
FIG. 36 shows a UCSC genome browser map of the genes, including Siglec-11 and Siglec-16, on a region of human Chromosome 19 containing the bacterial artificial chromosome (BAC) BACCTC-326K19.

To obtain mice coordinately expressing multiple human Siglec genes, Bacterial Artificial Chromosomes (BACs) harboring key human Siglec genes with sufficient flanking sequences were identified using the UCSC genome browser and the CloneDB from NCBI. One BAC clone (BACCTC-326K19) was identified that was predicted to contain the coding sequences for the human genes Siglec-11 and Siglec-16. Maps of the human chromosomal region of interest encompassing BACCTC-326K19 are shown in FIG. 36 (from the UCSC genome browser). The chromosomal DNA within BACCTC-326K19 spanned 118,595 nucleotides of the human genome, covering nucleotide positions 49,893, 498-50,039,937 on human chromosome 19, based on the hg38 build of the UCSC genome browser (the human Siglec genes are found within a cluster on chromosome 19). Sequences at the ends of the BAC clone were confirmed, as was the presence of the 5' end of the human Siglec-11 gene sequence.

Transgenic mice harboring BACCTC-326K19 were generated by pronuclear injection of the BAC DNA into C57BL6/j zygotes. The resulting pups were genotyped to identify founder animals harboring the human transgenes. These founder animals were then bred to non-transgenic animals, and progeny animals were then analyzed to monitor expression of human Siglec-11 and Siglec-16.

---

SEQUENCES
All polypeptide sequences are presented N-terminal to C-terminal unless otherwise noted.

Human CD33 polypeptide - isoform 1 (SEQ ID NO: 1)
MPLLLLLPLLWAGALAMDPNFWLQVQESVTVQEGLCVLVPCTFFHPIPYYDKNSPVHGYWFRE
GAIISRDSPVATNKLDQEVQEETQGRFRLLGDPSRNNCSLSIVDARRRDNGSYFFRMERGSTKYS
YKSPQLSVHVTDLTHRPKILIPGTLEPGHSKNLTCSVSWACEQGTPPIFSWLSAAPTSLGPRTTHSS
VLIITPRPQDHGTNLTCQVKFAGAGVTTERTIQLNVTYVPQNPTTGIFPGDGSGKQETRAGVVHG
AIGGAGVTALLALCLCLIFFIVKTHRRKAARTAVGRNDTHPTTGSASPKHQKKSKLHGPTETSSC
SGAAPTVEMDEELHYASLNFHGMNPSKDTSTEYSEVRTQ Human CD33 polypeptide - isoform 2 (SEQ ID NO: 2)
MPLLLLLPLLWAGALAMDPNFWLQVQESVTVQEGLCVLVPCTFFHPIPYYDKNSPVHGYWFRE
GAIISRDSPVATNKLDQEVQEETQGRFRLLGDPSRNNCSLSIVDARRRDNGSYFFRMERGSTKYS
YKSPQLSVHVTDLTHRPKILIPGTLEPGHSKNLTCSVSWACEQGTPPIFSWLSAAPTSLGPRTTHSS
VLIITPRPQDHGTNLTCQVKFAGAGVTTERTIQLNVTYVPQNPTTGIFPGDGSGKQETRAGVVHG
AIGGAGVTALLALCLCLIFFIVKTHRRKAARTAVGRNDTHPTTGSASPVR Human CD33 polypeptide - isoform 3 (SEQ ID NO: 3)
MPLLLLLPLLWADLTHRPKILIPGTLEPGHSKNLTCSVSWACEQGTPPIFSWLSAAPTSLGPRTTH
SSVLIITPRPQDHGTNLTCQVKFAGAGVTTERTIQLNVTYVPQNPTTGIFPGDGSGKQETRAGVV
HGAIGGAGVTALLALCLCLIFFIVKTHRRKAARTAVGRNDTHPTTGSASPKHQKKSKLHGPTETS
SCSGAAPTVEMDEELHYASLNFHGMNPSKDTSTEYSEVRTQ

```
SEQUENCES
All polypeptide sequences are presented N-terminal to C-terminal unless otherwise noted.

Human Siglec-5 polypeptide (SEQ ID NO: 4)
MLPLLLLPLLWGGSLQEKPVYELQVQKSVTVQEGLCVLVPCSFSYPWRSWYSSPPLYVYWFRD
GEIPYYAEVVATNNPDRRVKPETQGRFRLLGDVQKKNCSLSIGDARMEDTGSYFFRVERGRDVK
YSYQQNKLNLEVTALIEKPDIHFLEPLESGRPTRLSCSLPGSCEAGPPLTFSWTGNALSPLDPETTR
SSELTLTPRPEDHGTNLTCQMKRQGAQVTTERTVQLNVSYAPQTITIFRNGIALEILQNTSYLPVL
EGQALRLLCDAPSNPPAHLSWFQGSPALNATPISNTGILELRRVRSAEEGGFTCRAQHPLGFLQIF
LNLSVYSLPQLLGPSCSWEAEGLHCRCSFRARPAPSLCWRLEEKPLEGNSSQGSFKVNSSSAGPW
ANSSLILHGGLSSDLKVSCKAWNIYGSQSGSVLLLQGRSNLGTGVVPAALGGAGVMALLCICLC
LIFFLIVKARRKQAAGRPEKMDDEDPIMGTITSGSRKKPWPDSPGDQASPPGDAPPLEEQKELHY
ASLSFSEMKSREPKDQEAPSTTEYSEIKTSK Human Siglec-7 polypeptide - isoform 1 (SEQ ID NO: 5)
MLLLLLLPLLWGRERVEGQKSNRKDYSLTMQSSVTVQEGMCVHVRCSFSYPVDSQTDSDPVHG
YWFRAGNDISWKAPVATNNPAWAVQEETRDRFHLLGDPQTKNCTLSIRDARMSDAGRYFFRME
KGNIKWNYKYDQLSVNVTALTHRPNILIPGTLESGCFQNLTCSVPWACEQGTPPMISWMGTSVS
PLHPSTTRSSVLTLIPQPQHHGTSLTCQVTLPGAGVTTNRTIQLNVSYPPQNLTVTVFQGEGTAST
ALGNSSSLSVLEGQSLRLVCAVDSNPPARLSWTWRSLTLYPSQPSNPLVLELQVHLGDEGEFTCR
AQNSLGSQHVSLNLSLQQEYTGKMRPVSGVLLGAVGGAGATALVFLSFCVIFIVVRSCRKKSAR
PAADVGDIGMKDANTIRGSASQGNLTESWADDNPRHHGLAAHSSGEEREIQYAPLSFHKGEPQD
LSGQEATNNEYSEIKIPK Human Siglec-7 polypeptide - isoform 2 (SEQ ID NO: 6)
MLLLLLLPLLWGRERVEGQKSNRKDYSLTMQSSVTVQEGMCVHVRCSFSYPVDSQTDSDPVHG
YWFRAGNDISWKAPVATNNPAWAVQEETRDRFHLLGDPQTKNCTLSIRDARMSDAGRYFFRME
KGNIKWNYKYDQLSVNVTDPPQNLTVTVFQGEGTASTALGNSSSLSVLEGQSLRLVCAVDSNPP
ARLSWTWRSLTLYPSQPSNPLVLELQVHLGDEGEFTCRAQNSLGSQHVSLNLSLQQEYTGKMRP
VSGVLLGAVGGAGATALVFLSFCVIFIVVRSCRKKSARPAADVGDIGMKDANTIRGSASQGNLT
ESWADDNPRHHGLAAHSSGEEREIQYAPLSFHKGEPQDLSGQEATNNEYSEIKIPK Human Siglec-7 polypeptide - isoform 3 (SEQ ID NO: 7)
MLLLLLLPLLWGRERVEGQKSNRKDYSLTMQSSVTVQEGMCVHVRCSFSYPVDSQTDSDPVHG
YWFRAGNDISWKAPVATNNPAWAVQEETRDRFHLLGDPQTKNCTLSIRDARMSDAGRYFFRME
KGNIKWNYKYDQLSVNVTE Human Siglec-7 polypeptide - isoform 4 (SEQ ID NO: 8)
MLLLLLLPLLWGRERVEGQKSNRKDYSLTMQSSVTVQEGMCVHVRCSFSYPVDSQTDSDPVHG
YWFRAGNDISWKAPVATNNPAWAVQEETRDRFHLLGDPQTKNCTLSIRDARMSDAGRYFFRME
KGNIKWNYKYDQLSVNVTG Human Siglec-9 polypeptide - isoform 1 (SEQ ID NO: 9)
MLLLLLPLLWGRERAEGQTSKLLTMQSSVTVQEGLCVHVPCSFSYPSHGWIYPGPVVHGYWFRE
GANTDQDAPVATNNPARAVWEETRDRFHLLGDPHTKNCTLSIRDARRSDAGRYFFRMEKGSIK
WNYKHHRLSVNVTALTHRPNILIPGTLESGCPQNLTCSVPWACEQGTPPMISWIGTSVSPLDPSTT
RSSVLTLIPQPQDHGTSLTCQVTFPGASVTTNKTVHLNVSYPPQNLTMTVFQGDGTVSTVLGNGS
SLSLPEGQSLRLVCAVDAVDSNPPARLSLSWRGLTLCPSQPSNPGVLELPWVHLRDAAEFTCRAQ
NPLGSQQVYLNVSLQSKATSGVTQGVVGGAGATALVFLSFCVIFVVVRSCRKKSARPAAGVGD
TGIEDANAVRGSASQGPLTEPWAEDSPPDQPPPASARSSVGEGELQYASLSFQMVKPWDSRGQE
ATDTEYSEIKIHR Human Siglec-9 polypeptide - isoform 2 (SEQ ID NO: 10)
MLLLLLPLLWGRERAEGQTSKLLTMQSSVTVQEGLCVHVPCSFSYPSHGWIYPGPVVHGYWFRE
GANTDQDAPVATNNPARAVWEETRDRFHLLGDPHTKNCTLSIRDARRSDAGRYFFRMEKGSIK
WNYKHHRLSVNVTALTHRPNILIPGTLESGCPQNLTCSVPWACEQGTPPMISWIGTSVSPLDPSTT
RSSVLTLIPQPQDHGTSLTCQVTFPGASVTTNKTVHLNVSYPPQNLTMTVFQGDGTVSTVLGNGS
SLSLPEGQSLRLVCAVDSNPPARLSLSWRGLTLCPSQPSNPGVLELPWVHLRDAAEFTCRAQ
NPLGSQQVYLNVSLQSKATSGVTQGVVGGAGATALVFLSFCVIFVVVRSCRKKSARPAAGVGD
TGIEDANAVRGSASQILNHFIGFPTFLGLGFEFLLNLRDLCCHPDSEFYVYHFSHFRLIKNIAGEIV
WSLEGKILWLLDVSDFFHWFFLICVG Human Siglec-11 polypeptide - isoform 1 (SEQ ID NO: 11)
MVPGQAQPQSPEMLLLPLLLPVLGAGSLNKDPSYSLQVRQVPVPEGLCVIVSCNLSYPRDGWD
ESTAAYGYWFKGRTSPKTGAPVATNNQSREVEMSTRDRFQLTGDPGKGSCSLVIRDAQREDEA
WYFFRVERGSRVRHSFLSNAFFLKVTALTKKPDVYIPETLEPGQPVTVICVFNWAFKKCPAPSFS
WTGAALSPRRTRPSTSHFSVLSFTPSPQDHDTDLTCHVDFSRKGVSAQRTVRLRVAYAPKDLIISI
SHDNTSALELQGNVIYLEVQKGQFLRLLCAADSQPPATLSWVLQDRVLSSSHPWGPRTLGLELR
GVRAGDSGRYTCRAENRLGSQQQALDLSVQYPPENLRVMVSQANRTVLENLGNGTSLPVLEGQ
SLRLVCVTHSSPPARLSWTRWGQTVGPSQPSDPGVLELPPIQMEHEGEFTCHAQHPLGSQHVSLS
LSVHYPPQLLGPSCSWEAEGLHCSCSSQASPAPSLRWWLGEELLEGNSSQGSFEVTPSSAGPWAN
SSLSLHGGLSSGLRLRCKAWNVHGAQSGSVFQLLPGKLEHGGLGLGAALGAVAALLAFCSC
LVVFRVKICRKEARKRAAAEQDVPSTLGPISQGHQHECSAGSSQDHPPPGAATYTPGKGEEQELH
YASLSFQGLRLWEPADQEAPSTTEYSEIKIHTGQPLRGPGFGLQLEREMSGMVPK Human Siglec-11 polypeptide - isoform 2 (SEQ ID NO: 12)
MVPGQAQPQSPEMLLLPLLLPVLGAGSLNKDPSYSLQVRQVPVPEGLCVIVSCNLSYPRDGWD
ESTAAYGYWFKGRTSPKTGAPVATNNQSREVEMSTRDRFQLTGDPGKGSCSLVIRDAQREDEA
```

SEQUENCES

All polypeptide sequences are presented N-terminal to C-terminal unless otherwise noted.

```
WYFFRVERGSRVRHSFLSNAFFLKVTALTKKPDVYIPETLEPGQPVTVICVFNWAFKKCPAPSFS
WTGAALSPRRTRPSTSHFSVLSFTPSPQDHDTDLTCHVDFSRKGVSAQRTVRLRVAYAPKDLIISI
SHDNTSALELQGNVIYLEVQKGQFLRLLCAADSQPPATLSWVLQDRVLSSSHPWGPRTLGLELR
GVRAGDSGRYTCRAENRLGSQQQALDLSVQYPPENLRVMVSQANRTVLENLGNGTSLPVLEGQ
SLRLVCVTHSSPPARLSWTRWGQTVGPSQPSDPGVLELPPIQMEHEGEFTCHAQHPLGSQHVSLS
LSVHWKLEHGGGLGLGAALGAGVAALLAFCSCLVVFRVKICRKEARKRAAAEQDVPSTLGPISQ
GHQHECSAGSSQDHPPPGAATYTPGKGEEQELHYASLSFQGLRLWEPADQEAPSTTEYSEIKIHT
GQPLRGPGFGLQLEREMSGMVPK
```

Human Siglec-14 polypeptide (SEQ ID NO: 13)
```
MLPLLLLPLLWGGSLQEKPVYELQVQKSVTVQEGLCVLVPCSFSYPWRSWYSSPPLYVYWFRD
GEIPYYAEVVATNNPDRRVKPETQGRFRLLGDVQKKNCSLSIGDARMEDTGSYFFRVERGRDVK
YSYQQNKLNLEVTALIEKPDIHFLEPLESGRPTRLSCSLPGSCEAGPPLTFSWTGNALSPLDPETTR
SSELTLTPRPEDHGTNLTCQVKRQGAQVTTERTVQLNVSYAPQNLAISIFFRNGTGTALRILSNG
MSVPIQEGQSLFLACTVDSNPPASLSWFREGKALNPSQTSMSGTLELPNIGAREGGEFTCRVQHP
LGSQHLSFILSVQRSSSSCICVTEKQQGSWPLVLTLIRGALMGAGFLLTYGLTWIYYTRCGGPQQS
RAERPG
```

Human Siglec-16 polypeptide (SEQ ID NO: 14)
```
MLLLPLLLPVLGAGSLNKDPSYSLQVRQVPVPEGLCVIVSCNLSYPRDGWDESTAAYGYWFKG
RTSPKTGAPVATNNQSREVAMSTRDRFQLTGDPGKGSCSLVIRDAQREDEAWYFFRVERGSRVR
HSFLSNAFFLKVTALTQKPDVYIPETLEPGQPVTVICVFNWAFKKCPAPSFSWTGAALSPRRTRPS
TSHFSVLSFTPSPQDHDTDLTCHVDFSRKGVSAQRTVRLRVSLELQGNVIYLEVQKGQFLRLLC
AADSQPPATLSWVLQDRVLSSSHPWGPRTLGLELPGVKAGDSGRYTCRAENRLGSQQRALDLS
VQYPPENLRVMVSQANRTVLENLRGNTSLRVLEGQSLRLVCVTHSSPPARLSWTWGEQTVGPS
QPSDPGVLQLPRVQMEHEGEFTCHARHPLGSQRVSLSFSVHCKSGPMTGVVLVAVGEVAMKILL
LCLCLILLRVRSCRRKAARAALGMEAADAVTD
```

Human CD33 genomic sequence (SEQ ID NO: 15)
```
tctgctcacacaggaagccctggaagctgcttcctcagacatgccgctgctgctactgctgcccctgctgtgggcaggtgagtggctgtggggagagg
ggttgtcgggctgggccgagctgaccctcgtttccccacaggggccctggctatggatccaaatttctggctgcaagtgcaggagtcagtgacggtac
aggagggtttgtgcgtcctcgtgccctgcacttctttccatcccataccctactacgacaagaactccccagttcatggttactggttccgggaagga
gccattatatccagggactctccagtggccacaaacaagctagatcaagaagtacaggaggagactcagggcagattccgcctccttgggatcccag
taggaacaactgctccctgagcatcgtagacgccaggaggagggataatggttcatacttctttcggatggagaggaagtaccaaatacagttaca
aatctccccagctctctgtgcatgtgacaggtgaggcacaggcttcagaagtggccgcaaggaagttcatgggtactgcagggcagggctgggatgg
gaccctggtactgggaggggtttagggtaaagcctgtcgtgcttagcgggggtacagaggttgaccagaggttgatcttctctcaggccctcacctggaccc
tccctcctgattctgcatccctctttctcctcactagacttgacccacaggcccaaaatcctcatccctggcactctagaaccccggccactccaaaa
acctgacctgctctgtgtcctgggcctgtgagcagggaacacccccgatcttctcctggttgtcagctgccccacctccctgggcccaggactact
cactcctcggtgctcataatcacccccacggccccaggaccacggcaccaacctgacctgtcaggtgaagttcgctggagctggtgtgactacggagag
aaccatccagctcaacgtcacctgtaagtgctgggccaggatgctgggtccctgagggtgtaggggagacaggatgggctggtgctggggacattta
gtgtcctggaggcctggctgagttcgggagccagaagacatgagccctgtcccttctgcatttctgtggtttctggcaggagtaaggggaaatgcct
accctttatctcatctctaccccaactgaaggaaatcctctcttcctctcctagatgttccacagaacccaacaactggtatctttccaggagatggc
tcaggtaggaaggagcctcccgcctggggctgttactgacattgagtctgtgtcaggtttggtcagatctggactttcagagtcaaatgttcagagg
caaggcctgcagttagacacgggtagacatcaggcaccttggaaaaggaatttggggatgactagcaacttccccctttgcccatccaaataatgctc
tttgtctccctcctgtctctgaatgtcttgggtgatttttattttttaattgatatgtaataatagtacatatttatggatggcatagtgatgtttccat
actaataatgtatagtaatcagatcagggtaatagcatatccatcatcttgaacatttattatttcattgttgttgggaacattcaatatcccttc
tagctatttgaagctatctattattgttaagcatagtcatcctacagtggtatagaacaccagaacttattcttcctttccaggtgtaatctagtatc
ctttaacaaatctctctccttatcattgttccctaacctttcccagccttattattctctgttctacttttttacttctatgaaatcaacttcttgta
gcttccacttatgagtgagaacatggtattcaactttctgttcctagctattttcatttaacatatgtcctctagttcaatctatgttatagtga
ataacaagatttcattattttttatggctgaatgataatccattgtgtatatacgccacatttcctttatttattcatctgtgttggacacttaggt
ttatttcatatcttcctattgtggataatgctgcaataaacattgaggtgcagacgtttcttcaatatactgattcctttcctttctataaatgccc
agtagtgggttgctggatcatatggtagttctattttgtagttttttgagaaatttccatactcttctccatagtggttatactagtttacattctgg
tcaaaagtatataagagttccctcttctctacatcctccaccatcatttgttttaattttcatcttttttttatcatagtcctcccaactggggtgatgt
acctcattgtggttttgatttgcatttcctggtgattggtgacgttgagcattttcatatacacttgttggccatctgtatatctttcttgagaa
atgtctactcagataatttgcccatttttaaatgagattgggtttctttgccattgagatgtatgagttcctcgtatgttctggatatgaatcacttg
tcagatgaatagctgacaaatattttctcctattctgtaggttgccttttcactctgttggttgtttccttttctgcatagaagcttttttagcttgata
tcatctcatttattttacttttgctttttgttgcttgtgctagtgaggtcttactcataaaatattttccagaccaatgtcctaaagcattttcccctat
gttttttttctagtattttttaaatttttgtgtcttatattcaggtcttttgatccatttgaattgattttttgtataggacgagaggtgtgagtctaatg
tcattcttctgcatatggcaccagttttcccagcatcatttattaaagaaactgctctttcctcaatgagtgttcttcatgcatttgtcaaaattcag
ttggctgtagatcgtggattaatttcggtgttctctattatgtattattggtgtatgtatctgcttttatgccaatatcatgctgttttggttactac
agcttttagttttgaaatcttaaattttgaaattttgaaattttctagttttgaaattttgaaatcttgtagtgtgatacctccagcttctgttt
ttttgcttgggattgcttttgaccattcaggctattttagttccatatgaattttaagattgttcctcttactctgtgaagaattacattgatatt
ttgatagagccaggtttgaatctgtagattcttttgggtagtaataatcatttagcaatattaattcatctgatgagtaaggaatgtcttttccatttg
tttgtatcctcttcagtttatttcctcagtgttttgtagttttcttattaaggcttgtcacctccttggttaaatttattcctaggtatacttcatt
ctcttatagctattgtaaatgtgattgccttcctgatttattttcagctaattcattgtgtgtagaaatgctactgattttttgtatattgattttgca
tcctgcaaatttactaaattcatttgtcagttctgagagtttttgttgagactcttgttttttgttttgtttttgttgtttggttttgtttttg
agatggaatttcaccatgttggccaagtcggtcttgatctcctggcctcaagcaatctgcccactttggcctcctaaagtgctggaattacaggcatg
agccaccacgcctggccaagtctttaggttttgtatgttatttgcagagacaatttgacttccgcctttccagtttggatggttttattttctttct
cttgcctaattgctctggctaggacttttcagtactatgtaaaataagagtcataacagtggacatccagttcctagaggaaaagattttcagctttttct
ccattcagtatgatgttagccatgggtttgtcatatggccttttttgtgttgaggtacttccttctataccttaatttattgagagtttctatcat
gaaacaatattgaatttttaacacatgcttttttattctgcaactattttaggtgatcatacggtttatgtccttcctgttgacatatgtaaacatt
tattgatttgcatatgttgaatcattcttgcctttctgggattaatccactttcatcatgtgatgttatcttttttgatgtattgttggatttgattttg
ctactatttttgttgaatattttttgcatctatgttcatcagggatattggcctctagttttcttttttattgtcctccttctgattttggtgtcatgg
ttatgctggccttgtagaatgagttaggaagagttgcctccacttcaattttttggaatagtttgagaagagttggcataatttttttttctttaaag
gttcagtaaagttcagcactgaagccatccagcccctggaattttcttgttggggggccttttattattcattcaatctcattacttgttgtttgtct
gctgaagttttctataccttcttgattcaatctcggtagattatatgtgtccaggaacttatccatttcttctagacttttcaaatttgttggcatatt
```

SEQUENCES
All polypeptide sequences are presented N-terminal to C-terminal unless otherwise noted.

```
gttcatagtagtgtctaagatcctgtgtatttctgtggtaaccattgtgacatcttcttttttatttatgattttattaattttatgtcttctgtct
ctttcttagtttagctaatgattgtcaattttattattttttccaaaaagcgaacttgttcattgatttttttttaatttcatttatttctgctctga
tctttatgatttcttcattgtgctgattttggatttggtttgttcttgcttctctagtttcttgaaatgcacagttaaatggtttacttgaaatttgt
ctaattgtttgatgtaggcatttatttctctcaagttgtctcttaaaactgttttttgctgtgtcccataggttttggtatatttattctatttttta
tttatttttgagaaatttttaaatatcattcttaatttcttccttcactattggtcatttagaatcattttgtttcatttctgtgtatttgtatagttt
gcatgtttcccttggtattgattttttagttttattcaattgtagtcaaataagatacttgatacattttggtttttaaaaattttttggcacttgtttt
gtgttctaacatatggtcgatccttgggaatgttgcacatgctgatgaaaccatgtgtattctgcagctgtcggttgaaatgttctgtaaatatctta
ggttcatttggtatatggtgcagtttaaatccaacgtttatttgttaatcttgtctagatgatttgttcaatgctgagagtggggcgttgaagtcctc
aactattattgtattggagtctatctctcccttatatctaataatatttgctttacatatctgggtgctctggtgttgtgtgcatatgtatttacag
ttgttatattatagtgctgaactgacccctttataataatataatgtccttctttgtctctttacagcttttgacttgtagtccgttttgtctgagat
aagtatagctattcctgcttcctttcattcccacttgggtagaatatcttttttccatctcttccttttcagtctatgtgtgtcttctaggtgagataa
gtttcttgtaagcagtatatagctgtgttggtagaagggctgaggcagggcttgcttgtctgacataatgtaaaagagtcttggaacatgtcctgggt
ccagggtctcaaaccctcgtggcctatgaacaccaagctctgtgcctaagggtggaaggctgcctgccacactgcaatctaagcccagggcataa
aacccctcgtggcttggaaagaatccagggctctgggcataaaaccccctcatagcctctggaatgtgtccagacttgctggccccttgctccttgctc
tcccaggatcataaattgattgtatcttgagtgaaaagaacttgttctccattatttcaagtagcagagcatatgctaaaccgtcacagctatgcttg
atgcaccgctacctttctaccccaaagtcctcacgttctcacttgtctatccccacttctgcacgtcctcaccacctgcttctttgtttgattaccaa
taaatagtgtgggctcccagagctcggggcctcacagcctccatactagcgtcggcccctggactcactttatgtactattaacttgtcttgtctc
attcctttgactccgctggacttcgtggccccacggcctagtgttggatctgatcaccccaacaagctgagtctagattttcttttcattcattcag
gcagtccatatattttaaatgggacaatttaatccattttacatacacattattattaatagggttattttcatttcattgattgttttctgattgtttt
atatattcctggttccttacttccccctcttattgtttcttttttgtggttggctgatgttttttttttttttgtagtgataagatttgattccttttctc
tttcttcttttgtgtatgggctgtcagtgagttttaagttcacgtgttttttgccttttcacttccagatgtaagactcccttgagcatttcttttcttt
ttcttctcttatttattttttattatttttttttttgagaaagtgtctcactctgtcgcccaggcaggagtgcagtggcatgatcacggctcactatagt
ctcgacctcctgggcttaagcaatcttcctgccttaacctcccaagtagctgggactacaggcatgtgccaccacgcccagctaattttttgtgttttct
tgtagaggtagggtgttgccatttgcctaagctggtctcaaattaaagagctcaagtggtccacctgcctgccttcacctcccaatgtgctgggatta
taggcatgagccacactgtgcctggcccttgagcatttcttgtaaggccagtctaagagtgattagaattcccttagtttttgcttatctatgaaat
atttttatttctccttcttttctgaaagatagcttttctgggtatagtatttttgactgttaagttttttatcttcagtactttgagtatgtcatccc
attctatcctggcctatataatgttactgctgagaaactcactgttagtctaataaggataatcctatatgtgactagatactttttacctttgctgttt
ttacaattctttacttgactttttgacaattttggcataatgagctttggagaggacttgcttgggttgaatattttgagagtagttttgagcttcctgga
cctggatgtccttctagttcccaaggcttgggaagttttcacctattactggattaaatatgttttctacaccttttccattctcttctcctcctgga
aataccataatgtgaatatttgcttgattgtgtcccatgagtcctgtaggtttccttcgttctattttattctcttattttttacctgcctgtgttatt
tcagaagatctgtcttcaagttcagaaattattttttcttcttgacctagcctgttgttgaagctctcgattgcggtttttttatttcatttattgagt
tctcagctgtaggagttctgctttgttcttttatataatatctatctctcgtttcaagtcatgaattaaaacaatgggacacaggt
gcccaactacttggctgacctgggggcatatctgctggaggtgccaacatggctgtttcagggctgagatgaagctgaatgactcttggctggcct
aggtgtgttttttgccaggagtagcactcagagctttatctagggtttgggatgtgagtgtaagactgctcagctggcctagggggtgtaccagccagt
ggtagcccatggggctgtttctcaggcctggaatgcaagcacattctgcctggggtcatgtctaaaagggttggctcacaaggctgtttctcaggccc
taattgtgggagagtggccttttgggcaggccagagtcatgtccacagaaggcgtctgccacgtaaggctgtttctcagagcctgtgtgtgagcaca
taaccactaccccagcctggggatgtatcaactctttgttggctcagaggtctctccccattcaggtgagcatgcacagtagtttggccaactcaattg
tgtgttcgcctgagtgggactataagacctttcctccagctggaagtacgggcagcaggggttggtttctctgctgttcagggccagagtcccagcc
aatcctgggcccaggctccatgcagctctaattgtggtattcagccactactgcaggtttagtggaatgaagatgcacaatgataaagaggtgcatgc
cactgccccagaggaggggtgcactccagagatggctgtgtgctccaagatggttctgtgttgtagcagcttgcccgcagggggcggttagggagttg
ggagtgcacaccaaatgctccatgcagctgtgtgaattcctggcagctcttccaactgtgctcagagcttgtgaggactgtaagattaacctgtagta
aggaatgtaggtatctgcagtggcactggaggttggttggattcctctgcttatcatttcccacaaggggaaatccttcctgtctctgggacaaacc
aatctgggctggggagatggagctgcaaagcccgggtgcctccatgctgccctcctgggtttccaattaccacaggtaactctccactccttgctgc
actacactactctccctctcgacactccactcaaatctttgctgtggttttcattgccttggtccttttcttgtctcgggtgacacggggaggagagc
tccaggcacctccggtgagccattttgctccaatgggggcatttttttttaatagttttatttttcagagtagttttttgtttcacagcaaaattgag
tggaatcttctagtcgctgatcatcttgggagcatttataaatgaaccttattttttcatgaaagaatttgagcagaagatactaagacttcccgtatgc
cctctacccttacacatagtttccccggccatcagcatccccatcagagtggtacatttgttacagtcaataaaactacattgacatatcattgtca
cctgaagcccatagtttacattaaagttcactcttggtgttgtaacagcttttaaaaatgtataatgacatgaatccaccatgagagtat
catatagaatagtcacacttccctaaaaatctctttagggcattttttttctactgttccataccctcaacccttagccctggcctctgtccaaagaccag
tgctctctccactgccctattccaattaatatggcatctggcacctcagtggacagtgagcccagtgagagcaggaacagttccctcagtagtggtt
atcaaactgttaacaatgatgctcagagacacgcccctgactctgagtgttgggaccctagaaggcacagccaggcaggtccaggagaactgtctgggt
ctaagaaggtctgagaaccaccctccctgccccaccctgcttccaggccctttttaaggccaaaaggaccaccttttgaccctaagtgatggggccagtg
ggaagaaagaagagacaaggcctatcagcattccagtgcttttctctctctcatccaagaggctcagagcttcacgtccttcagggggctatgtctg
aggtcatttcagaaagacccagggtggagaggaacctgagtcctaggagagatgatgtttgtgcaccagagagagggtgggacaagaggtgtca
ggtgcactgtgtacttcatctcatggtcgtggtcaatattgatgtctatgatgggtgggaagatctaggagctaaacccattttggaggtgaagtca
ccctctctacatgctggagaggaggatacacatacctgtttatctagattagaattcaccccaaatcttttttgtctgcagggaaacaagagaccag
agcaggagtggttcatggggccattggaggagctggtgttacaccgtcctgctgctctttgtctctgcctcatcttcttcatgtgagcattttctctg
gtcaggcatgggccagaggtgaagaggtggacctggtgtagaagggtcctggagggctgtgagggctggaaaagggcagggggtgtgatgatga
cagaatccagcctgtgccactgggataggcgtgggtctattccagggccctgatctcagatgtccaaggagtgggaggtagagggagacccttgtgac
taagtcttgtttgagggctcctggattaatcccacccttttacctgccaaagtccctcattccaggctcataacaatggcccacagcctgagaaaacc
aggctcaaagaccctggtgtctcccatcagagtgaagacccacaggaggaaagcagccaggacagcagtgggcaggaatgacaccaccctaccacag
ggtcagcctccccggtgagtgatggggcatcctggcatccagtctgtcctgcagacacctcctcccaatgtggccaccgtcatgcccccattcagcat
ttccagaactgagcttattgtctttcctcctgtttaacagtgtaggttttaatattttcaggtacgttgaggccaacagatcaggagatgatggcca
ttgaaagatagtttcttggccgggcacagtgtttcacacctgcaatcccagcacctttggaggccaaggcgggcggatcacgaggtcaggagattga
gactatcctggctaacatggtgaaaccccgtctctactaaaaatacaaaaaattagccagatgtggtggctggcgcctgtagtcccagctacttggga
ggctgaggcaggagaatggtatgaacccgggaggcagacttgtagtgagccgacatagcacctgccactgcactccagcctgggtgacagagagagactct
gtcccaaaagaaaaaaaaatagtttcttattcaccgttcccgagagggcacaccacaccatgcaaggccatatggaagagcaccagggtcagtcag
gaagcagagggagcaaggagaaaatgggacaagagccttcactgtggctttcatggaaaagaatgggcaagacagggtaagcaagctaggcaggttta
ggattggctactagaacaatttcagcagactctggggtataggagttgtctctagttgtctggtacatggccctgggtttattaaggaggattgtgg
tctggagtgtaagagctcaataaaggatccagctggtagtgtgggctttagattgactggtttgcacatgaaaggtgcacttgtatgcaagtccttta
ttagctctagaaatctactatctttgggaaaggcagtctctcaaggagtcagtgcccagatgtgcaaaacatcagaaaacacttggttgacacaccc
ctaaacatacttctcctgatgggttctccatctcgctgatggcactcttgtcccattacccaaccagaacatgcccctcctgtcccagtcctcc
atctcttcctgtgccagtatgctacgatgcatgtctgagcttcctctgaacacggcttaacacaaccactcctgagccgagagcccctcttactcctt
attctgctgcagcctcacctcccatttctcctctccagaacattagcatcacctccctaaaaggtcattgtcccatcattcccaagtttgaaatgcac
tgcttctctacacactcctgaaagattggcattccaacaacttggtctggcattttggagcaggaaaaccagagtcccctcagtgctatgctcccccaac
attagccactcaatcacctcaagcagggcaagcttttctcatctcagaatcattgctgggctgccccctcctcctcatatgcctaatagctacctgccc
```

SEQUENCES
All polypeptide sequences are presented N-terminal to C-terminal unless otherwise noted.

```
aactccagtgcatccttcaagctctgattttttttttaatttatttaactctgactaaagtgaacaccacagtaaagttttgaacacagggtcaacc
agcacccattcattctgaaatatctatataatcccatttgccaattgctctggtgcctgccattctgtatttttataaacacacagtttacaaat
ataaaatattcctcctatcgggggcttaacatttattggggaaagggatgaaaataatgaacaaataagcagtgcaaatatacatgaaataggcatga
aataagtgctatggcaggaaatgaaatgggagaacggattggacagtcctgggggccaaagaatggcctttgggcaaacacctgcagaaagaaagtga
gtacagtatgagcagtagagaatcatcaaggaagcagcaagtaccatggctctgaggccggaacacatctgatgttttagagaaacaaagtaggacag
tgtggataaggcagagttacgtcgtgtggggggtggagtgtggactgaacaatggtaggtaggaaatgaggttgaagagacataggagctgcaaatattgc
aggatcctaagtccatcatagttattgatgcgtttagagcagaagagtgacatgaactgacactcattttagtgggagtcactctggctgctctgtga
gaaactctagtatgtagtatagaagagaagataccagaatagaagatacacagataatcaagccaagagatgactgactcagacttagtcccaagtaa
gaataatgaatctgatgtggagaaattgggttccggatacatcttgaaggtggagtcaacagtatttgcaagtggagtgatggagtgcatgcaaggca
tgagcaaagatagctcacgggctctgctcgataagtgtctcagatgtcataggtgggtccacagatatcatagatgtcatggatgtccaagaagaccc
catagatgtcatagatgtctatagatgccaatgatgatgttcatgtggttaactcagaattcaaacttaaaaaatcaaattgccaatgattaaaattg
ccatccttgaaggagaagtctattttcaagtgtatatcaaacattattttggttaccgtaagtttgaggtgcctctgagacatccatgtggagatgac
aagtagcaggcaagtgtctggagctcagaagagggctccacgtgggagacacagaggtgggagcttccctatcaacatccaataatcgatgaatcta
caaagaagagaagggggccacagacacagccctggaaccctccagcatttaatgttagggagatgaggtgtaaatggtgagaaagctgagaatgaata
ggagccaatgaccaggaaattgcaggctgtagtgttggtggccaaggagaagatgggctttcatggaggagaggttggtcatttgtttcaaatgctggt
aagtctggtaagatggaatctgagaaatggctatttgaatgtagctaagtggtatgacagcaaagcagatctgattttttctgctggaggaagatctct
tgactagagagagttcaagagagaatgggaggagaagaggcagaaactgtgagttgaaggactcttttgagaaacactgccccaaatctagaaccaag
aaatgggcctgcaccagcaaatggttgtaccctgtagacttgccatttctccagcatctgctcctgtgtctcttatgataccatgttccctgtttgtg
taggggctttgcaccacttgaactaactgcattcccatagcttccccctaccacaccatgagctccacaaggaaaagcctgggtttattagacctccat
cattctactctctcctgttcatctgcacactgtcacaatttgcaattaccagtctgtttctgtcttcatccctcgcagtactggaaatcacagggccc
ctgctctgctctgctccctcctgaggatccagtgcccagcacataggaggtcccagagacctgggaccgagttcagggtcaacagatgtgtgactttg
gaaattcctaagctctctgagacctagtacctggtctgtaaaatggattaaaataatagatgccaaagatgatgtcagtgtagctgcccagaattat
ccacattagtctctgtgagtattcaagaagatgcgaatcaatcaatacgtgctacatgtttagataagtaagtagagccttaattaattaaca
tttgatgaaagaatgaaagagtgaataaatgttctgtcagagtcaaatttacttcattgaccctcttttgccttctcctggtcccctcctcactgccc
tgctctaaccccctttctttcctctccataagaaacaccagaagaagtccaagttacatggccccactgaaacctcaagctgttcaggtgccgcccta
ctgtggagatggatgaggagctgcattatgcttccctcaactttcatgggatgaatccttccaaggacacctccaccgaatactcagaggtcaggacc
cagtgaggaacccacaagagcatcaggctcagctagaagatccacatcctctacaggtcggggaccaaaggctgattcttggagatttaacaccccac
aggcaatgggtttatagacattatgtgagtttcctgctatattaacatcatcttagactttgcaagcagagagtcgtggaatcaaatctgtgctcttt
catttgctaagtgtatgatgtcacacaagtcctcaaccttccatgtctccattttcttctctgtgaagtaggtataagaagtcctatctcataggga
tgctgtgagcattaaataaaggtacacatggaaaacaccagtc
```

Human Siglec-5 genomic sequence (SEQ ID NO: 16)
```
gtgcgcgtccacagctctcactcaccctccggcttcctgtcgggctttctcagcccccaccccacgtttggacatttggagcatttccttccctgaca
gccggacctgggactgggctggggccctggcggatggagacatgctgcccctgctgctgctgcccctgctgtgggggggtgagtgagctgagggagga
gggacaggcacaggggtgagaaggggggctggagctgcagctgagcttctgtgtcccccagggtccctgcaggagaagccagtgtacgagctgcaag
tgcagaagtcggtgacggtgcagagggcctgtgcgtcctttgtgccctgctccttctcttaccccctggagatcctggtattcctctccccccactctac
gtctactggttccgggacggggagatcccatactacgctgaggttgtggccacaaacaacccagacagaagagtgaagccagagaccccagggccgatt
ccgcctccttggggatgtccagaagaagaactgctccctgagcatcggagatgccagaatggaggacacgggaagctatttcttccgcgtggagagag
gaagggatgtaaaatatagctaccaacagaataagctgaacttggaggtgacaggtatggcagggaccccaggagaggaccctgggacgtggagaccc
ccgtatgagaacagggacaggagttgggcaggggcggctggaggaggctggggcagtcggggcctggcgcactctcgggggtca
caccttacgtcctcaagccccctgggggccaggtatctccctgtctcctcctcagccctgatagagaaacccgacatccacttctgcgaaggcctctggag
tccggccgccccacaaggctgagctgcagcctccaggatcctgtgaagcgggaccacctctcacattctcctggacggggaatgccctcagcccct
ggaccccgagaccaccccgctcctcggagctcaccctcaccccccaggcccgaggaccatggcaccaacctcacctgtcagatgaaacgccaaggagctc
aggtgaccacggagagaactgtccagctcaatgtctcctgtgagtggtgctggagacacgagctgagtcctcaaggggcagtgggagtgaggggtgtgtg
tgtgtgtgtgtgtgtgtgtgtgtgtgtaaggaagacagagagaaacaaaacaataacttgagaaaccttgtgtggatctaagccttgggatctgcg
gggagtgagacaggacagccttccccgcttggtgggtttctgtggctcctcttttgggtacctcctgggcccatgccatctcactcctcactgctgaa
gccaagtttatatctttttatcccagatgctccacagaccatcaccatcttcaggaacgcatagggtaggaaagacctcctctctgaagctgggacct
gcctctgggtctgtctctgagcagaggtagagaatcagagcttgaatgcaaatcagattgggaagagcaagaatgagaattactgcctttcgggcttcc
accttctgtgagccccatgtgcaggcacatatgcacacacgcacatacacacgcacacatgcacacgcacacacacacgcacacacacatgcat
atacaccacacacatacacatgcaatacaccacacacacacgcacatacacacacacatgcacacaggcacacatgcacacacaccacacacatatgc
acacacacacatacaccacacaggcacatgcacatacacgcacacatgcacatacaccacacacacatatgcagatacacccacacacgcacacat
gtacgtacacccgcacacgcacacacacacagtgcacactcatgcactcatgcaaagcagtgaacagactttagaccccaccccatctccc
atccctcctgtggtctggttctttccacagtcactaaggaccactccatgccctctcatctcagtcagcccagctctgtggttcttctctcacccctt
ccactcctgcatcctcagtctttatttcctgtcacattagcggactgtatttcccaacgccaccggggggctctctgtcctctctccaccacagtccagg
catgtaccagtgagatattgagcctcctctggagacatgagactcagacacttttggtcagtttcctgagtgtgcaaaggccagcctttgaaccagg
atgcaatcaagccagcataggccagggaggagagggagatgtcatctggatcctgggaaggagggaaggataggactgtcagcctccctggcccca
tctctctttccccaccctttctctccccaaagccctagaagatcctgcaaaacacctcatacctctccggtcctggagggccaggctctgcggctgctctg
tgatgctcccagcaaccccctgcacacctgagctggttccagggctccctgccctgaacgccacccccatctccaataccgggatcttggacttc
gtcgagtaaggtctgcagaagaaggaggcttcacctgccgcgctcagcacccgctgggcttcctgcaaatttttctgaatctctcagtttactgtgag
tgtggggcagctggagcaggaactgcatggtattaaagaaggaagaggcccctgctgagttctgtcctcctccccacagcccctcccacagttgct
gggccccctcctgctcctgggaggctgagggtctgcactgcagatgctccttcgagccccggccggcccccccctctgtgctgggctgaggagaagac
cgctgaggggaacagcagccagggctcattcaaggtcaactccagctcagctgggccctgggccaacagctccctgatcctccacgggggctcagc
tccgacctcaaagtcagctgcaaggcctggaacatctatgggtcccagagcggctctgtcctgctgctgcaaggtcaggggggcgtattgcagagggca
ggggcctgagggaggggcatggatcccagagtgatggatggtgggagagagaggctggactggtggtggggagacagggttcttcatctcctgtctg
agcagggccctggacaagttgcccagcaggtggggaggacaagagtctgagtcctgggagtgagttattgcacgcccctcttttctgcagggagatcg
aacctcgggacaggagtggttcctgcagcccttggtggtgctggtgcatgggcctgctctgtatctgctgtgggcctcatcttcttttttaatgtaagt
cttggtcccaggaaggtacaggtggtgtttgtagggagtaggagagactgaatctcagaaacacagagctaaggccagagggtggtgatgtgtctt
gtggttccagatgctcaggagtctgaggcaggaggatcacttgatcatggaggttgaggctgcagtgagccaggattgtgccaatgcactccatcctg
ggcctcagagtgagagaccctgtcttaaaagaaaaacaaaacaaaacaaaaagcagaactgagtagatccagagaggtcttctttctttttttcttt
ctaatagcttttattgagatacatgttttgtacaattcatccactgaaagtgtacgagtcaatggctttaagtatattgacagagtttatgcatctgtca
ccaaaatcaattttagaacattttcatcagcctaaagtgaaaaacgaagacataaagaaaacctttgacccccttagctatcactcctgcttcttcccc
cagccctaacctattccatgtctctgtggatttgtctgtcctgaagttgcagttgtacttttgtgtgaatgaaatcacgcgatatgtggtcctttgcgg
ctggcttcttttcactcggcctaatgttttcaagattcatctatgttgtagcatgcatcgatacttcattccttttttgttttcaaataatattccatta
tataaatggaacgcatttgatttgtgggttcagctgttgacgggtactttgggttgcctctgcttcttggctatgatgcataacactgctatgaccatt
cctgccatggttttgtgtgtaagaggggggtctatatgatggaaattcagtccatggccaccctgaccaaatccctggttatccaggaggatggagccc
tcactccgaagtcaggaaggtctccgagtttagttccggggcctggatggcttcattgtcattttcaccatcttagcatgggatgggacaacccgcta
```

```
acccgtgcctgggtggtcccagctgcactgtgctggtttctttccttagagtgaaagcccgcaggaagcaagcagctgggagaccagagaaatggat
gatgaagacccccattatgggtaccatcacctcggtgagtggtttggggatctctcatgtgcatgtccactcggaaagtccaggctgagctcttcagc
attccaccaaacccactcctccctcatcacctgggagttctcttctctcctgttctcccccttcatatcccagagccaggaaatcattatgtcccatt
caaccttctttgttttgtttgtttgtttgttttgagatggagtttcactcttgttacccaggctggagtgcaatggtgcgatcttggctcact
gcaaactccacctcccaggttcaagcgattctcctgcctcagcctcccaagtagctgggattacaggcgcacaccaccatgcccggctaattttgta
tttttagtagagacgggattttgccatgttaggcaggcagttcttgaactcctgacctcaggtgatccgcccgcctcggcctcccaaagtgctgggat
tacaggcgtaagccaccgcgcccggccaccaaccttctttctaaaagtaaaactaacttgtccttgctcatcttccctccccacctctactgaccac
agagcctgcctcacttcctccctgcctccatctctcattccaaacttcaggctgccagaatcatcgcccaaaactattacttcccaggcagcctgga
gtttcaatgttgttgttgtttgttcctgttgcttagagaatcaggccatgttccttgcccacaccaggtggccacttcagcctgtttctgtcctct
gatcctgcccgtggcctggccacgctggccttctgtctccatacggacctgctgtcctacaactttgagcccttgcaagtatagtttcttccacctt
tccttccctgtttccaccagactacctcatctaatccttccagctctaatctcagtatctgctactctagtcatttccctccctgttgatatctgccc
cttctcttctgtgtttacagccctacatgcatccccgtccccatcacacatcaccactgccttacctgtctccacccactcatcatatctgtagaat
tctttttttatttttatttttttggagacggagtcctgctctgtcacccaggctggagtgcactggcgcaacctcggctcactgcaacctctgcctccc
aggctcaagcaattctcctgcctcagcctcccaagtagctgggattacaggcatgcaccacctggctaattttttgtattttagtagagacggggttt
caccatgttggccagggtggtctcgaactcctgacctcaggtgatctgcctgcctcagcctcccaaagtgctgggattacaggtgtgagccaccgcgt
gcggccaatatctgtggaattcttgaaggacaggggctggggcttcttagcccctgcagttttctctcctgctgtttctgtccagcgtgtctcctct
cctcttttataaaattgatctagtgttgccccgaacgaattgtccaaatgcttagttcatgaccaagctgtcatgactggaacaagcatcatttact
tttacttttcactttggttcataatatgataaataactgcaaacccaccatccaacctaagacctaacacattggtgataacttgtatccacctgtg
ttgctccctgatccattcccagtaaccactgttgtgaatcttgtcttcctagtgttgtcacatatatgtaggcttatgccactatttagttttaattg
tttatgaatctacagagggtatcatgttccacgcacacttcttggacttgctttgtagactcaacattgtattatgattcattcatgttgtataaagt
tgcagttgtattcatttttcctgcttataatatatatattttttgagacagggtctgactccattgcccaggttggagtgcagtggtgcgatctcggc
tcattgcaacctccacctcccgggttcaagcaactctcctgcctcagcttcctgagtagctgggattacaggcatgtaccaccacgcaaggctcattt
ttgcatttttagtagcgatgggggtttcaccatgttggccagtctggtcttgatccacccttgacctcccaaagtgctgggattataggtgtgacg
gcttataatattatattttatgattgtgtctatcacctaagctcatattgatgcacacttgagttgtttccatttgagccgttctgaacattcttatc
cttgtctcaccgtactaacacacacgagctttcctttagcatcacctaaagattgagttgccgcatcgctgggcatgtgaatgggcatctttacaagg
tcatgaaaaatggctttccaaagcaattatatccatttatactctcatctatgcctaggaaatcttgttgttctgtaatctctccaacttgcttttct
cagttttggaggctattttactatctctatggtattggtttgcatttcctcggttaccagtgaagatgaaaaatctctctctgctttcatcttcta
taaaacacctggtcacatctggatcccattttcctattgggtgtttgactttttcttaatgaatttgttggagggctttatacatttttacactattt
ttctcattgtatgtgttgtaaatataaatatcttctcccaatgcgtagcttgtcttcacttcttaaagtgatcttcaatgaacataagttcctagttg
taatataatcatattcacaaatcctctcttttctattgagtaccttttggatctcattaaaaaaaatttcacccatcctaagattagaaagatattca
aatatagtttctactaaaagtttttatgcttttattttttaattttgtgggtacatattagatgtatatatttatggggtacatgaactgtttcaataga
ggcatgcagtgtgaaataaacacttcatgaagaattgggtacccagcccctcaagccttgatccgttgagttgcaaacaatccagaagcaacctaagt
gtccatcaatagatgaatggataaagaaaatgttgtgcatatacacaatggagtactattcagccataaaaaagaatgagatccagtcatttgcaaca
acatggatgaactggagatcattatgttaagtgaaataaggcaggcacagaaagacaaacattgcatgttctcacatatttgtgggatctaagaata
aaaaaaaattgaactgatggacatagagagtatgcttttcttttgacattaagtactcactctgtctggggttgactttgtgtatggtgtatagtg
ttgatccatatatgttttctccttcatttctgaatagtccttctccctctccattgagcaacatgccaattctgccatgtattaaaattctatatatt
tgtcggtctctttctgtggtctctattctactccaatagtcaatttttactgtccctgagtcatcactgtctataaattcaaaaataagtcctgatata
gagtacagcaaaacctcttccttaatctccttcaatagtatcttgaccattcttggtccttttttttttttcactttaatgttagaatcaggttgtcaa
ggcccgggcgcggtggctcacgcctgtaatcccagcactttgggaggccgaggtgggtggatcacgaggtcaggagatcgagaccatcctggctcacac
ggtgaaacccgtctttactaaaaatacaaaaaaaaaaaaattagccaggcgtggtggtcccagcctactactcgggaggctgaggca
ggagaatggcgtgaacctgggaggcagagcttgcagtgagccggagatcgcgccagtgcactccagcctgggtgacagaacacgactccgtctcaaaac
aaaacaaaacaaaaacaaaaagcaaaacaaaacaaaacaaaaagaatcaggttgtcaaattccaaaaaatacattgaatctatagctcaatgtgg
aaaaaatttacttgtttagaaattcatgccttcttatccatgacagtaggtctttctctctctattcctttaaatattttttaagtgttttaaagagat
aatgtagagtttcttcacacaggtctataattctctcagtaaatgcagcaagtaaaactcatttttaattgatttcattttccttccaacttgccaagctc
ccttattagttcaaataactagtatatagaaattgaagtattttaaataaatttttttcaattaaaacaaaatcaaattaggccaggttggtggc
tcatgcctgtaatcccagaactttgggaggctgaggcaggaggatctcttgaggccaggagttcaaggccagggggataacacagtgagccctccatct
ctacaaaaagaaaaaaaatcacacattgatcttgggtattatttagaatgttttgggatttcaaattagatgattatatcatctgcaaaataataaca
gtttatttcttcccttttgtcctaagcacttctttccttttttcttgtttcaatatgctgggtgagattggtcaaagttgagtagacatagtgaccat
gggcatctttgctactgctgattttgaaggaaatgcacccaatatcctgccacttggttctgtgaacttttcatcaggttaaggaagttccttctat
cactaaataagttttatcctaaacttctgttgtatttttgaatgcatctactgataggattttttcctacttaatctgttaccatggggaatgaca
attaaagattttctggtatgaaactactcctgcattcctgggagaaaaccatattattcatagcattttttaatactccagtaggttgtttgatca
tcttttgctcagcacttttgcgtctatatgcatggtcaaatacacttgtcatttccttttttcctcctgtttcttctgtttgggtatcaagataagat
tgagaaattggggactagtctctcttttttctactgtctggaagagtgtgtataaaactgaaatgactttgtttcctgaatgattgatagatgtcactta
tcaaactacctgggcctggtggcgtcactatgtgcaattttcctaattttaatcattttatgtattcttcagcgagctttattctagggacgtgttcct
ttcacctaagttatatatatatatattttgacaaaaggatatgggtggcattcttttgtctttatattatttgttttttgtcgagattacttccct
tttagaaatattcctgacattggttatttgtgacttcttctttttttctagctaaatcttgttaattgctttccctattttattatcagtttcaagg
aaccaacttttgggattgtagaattttctcactgtatctttgttttcgttttattgattttttactctcattttctcagcaccttccttctacttgtt
ttggtttattctgatgatcttttgataaattttttaagctggatacttagctttctctagtgtctatattttcattctctataaaacgtaagttagggataaa
tttctctcagaatttcatttttcatcccattgcacaaattttgatatgtattattttgaataacattcagttgtgatattgttaaaacaacattgtgat
ttcttctttgaatcttaaattatttgggattaaaaaattccaaaggtatgaagattttaaacatcttttcataattaaattctaagtagatgcttttgg
tcagaatacatggttttatgatatctacttttaaaattttgttgagacttgatctgtggcctgtatacaatgaatttttgtaaatgtttccctgtgtgc
ttaagaataatgtatgtttttagccgggtgcggtggctcatacctgtaatcccagcacttttgggaggccgaggtgggcagatcacaaggtcaggagtt
caagaccagcctggccaatatggtgaaaccccgtctctactaaaaatataaaaaattacctgggcatggtggcaggcacctgtagtcccagc
tactcaggaggctgaggcaggagaatcgtgtgaacccaggaggtggaggttgcagtgagccaagatcgtgccactgcactccagcctgggcgacaatg
tatatttttatttcttaaattaacagtccagtgtgttaattgtaatgttcaaatccaaatcttcagatgtcaacagatcttccaacatgtcaatac
ttgagagaggtgtgttgaaatcttacattatgataatgtatttgtcaatttcttactgtaattctaacaattgtgtttcttatttttgatgtacttttt
aaattaaaaaccatatattttagaaaagcattatatcttctcagtgaactgaacattttatcaaacatagtaattcttttctcttcatagtggtgcttttt
tttttttttttttttttttttttggagacagagtctcactctgtcacccaggcggcagtgcagtggcacgatctcggctcactgcaacttccacctcctgg
```

SEQUENCES
All polypeptide sequences are presented N-terminal to C-terminal unless otherwise noted.

```
gttcaagcaattctcctgcttcagcctcctgagtagctgggattacaggtgcccgccaccatgcccaggtaattttttgtattttttagtggagacaggg
tttatcatgttgaccgggctggtcttgaacctcctgggctcaagtgatctgcccacctcgtcctcccaaagtgctgggattacaggtgtgagccactg
tgcccggctcataatgatgcttttttgctttaaagtctgttcgactggatgttttttttttttttttttttttttaggcagggtctcactcactcatg
cgggctggaatgaagcggcatgtggatcttaatatagctactctagtttcttattgattagttagatgcctgatacttttttcattttctcccatcctc
ccaacatttttatgtatttatgctctaccagtgattttttgtaaacagtatataaccaggttttaaaaaatccaatttgacatcccttgttgagtttact
ctgctggtatttattatggttactgacatatgtggatttctttctactattttaccttttactttcacttagtcccactttttcaatattcatttt
ctccttctcttacttagaagcttaatatcttgccgggcacagtgatgcatacctgtaattccagctacttgggagggtgaggtaggagcatcgcttgag
cccaggactttgaatctagtatgagcaacatagcaagactctcgcctcaaaaaaaaattaatatctctgtcttacatctaacaaaaagaattttggtg
cgcttttatatctcttggcctctcttccttcaactcttttacaatgttgatattttctacaaatgtgcagttttttgttctgtgttattatgaacatact
tagcattttctcattatttgattttttaaaaaatatacagctacacattttgttgaggtattttgtcacctttctattccatacttatcacagatttt
ctgttcttcttttctctttctctctttttattttgaatttcttccccccagtggttttcagtttgggttcctcaaggcttctgaagacttatatgcctgg
aaatatattttatcccccttacattttaattttatttggcaggatatacattctaaaattaaagtgattttccttttggtgcttttaaactccaccccact
gtttcttgcatttagtattgctgttaagacatcttacgtcattcttaatctcacatatttgtaggtaatccactcattttccctggaaacttttataa
ttttctctttggttctgatattcttaagatccactgtcctgtgtctaggcatgggattcccctgcatctttttttcttgcactcgtggggccctttcagc
tgaggtgtttcatcttcttttaactctggaaattttgtttccactattttttcaaatattttttcctttctactttttttttttttaaggtggagt
cttgctctgtcgcccaggctggagtgcagtggcgcgatctcctctcactgcaagctccgcctcccgggttcacgccattctcctgcctcagccctccg
agtagttgggactacaggcgcccgccaccatgcccggctaatttttgtatttttagtagagacgggggtttcaccgtcttagccaggatggtcttgat
ctcctgacccttgtgatccgccagcctcggcctcccaaagtactggcatgagccaccacacccggcctatttcttttttatcttatttgaaaactatta
ttatctaaatgttcaagtgttttttttttttgttttttttttgacagtctcactctgtgcccagctgggagtgcagtggcacaatctcggctcac
tgcaatctctgcctcctgggttcaagtgaatcttgtgcctcagcctcccgagtagctgggattacaggtgcacatcatcacgcctggctaattttttgt
atttttttagagacaggattttgccatgtcggccaagctgatcttgaactcctgacctcaagtgatctgcctgccttggccttccaaagtgctaggat
tacaggcatgagccaccacgcctggccagttttctatttctatcttccatctatcttaacctttttctcatatgttctagtcttcatccttccctact
tccttttagggatacttctgacggcccttctagctcactaatttgccctcaattatagtcattctattctccatcccatccattgggctcttcctat
gatattttttcagatatttccacatggcctttttgcatcaagtacacaattacataattccttattatgtttcacattcattttgcatgcacactttg
ttattgacaaagttttcttatgcttgttttcatgctgctaatattgccacatcttttagtgcatgtaatatgctcagtttagcttcttgaccaaagcg
tcctagtacttgtgcttctagtggtctatcaggttctgttggtttgcttttcttcaaaggtgcccagccttctgagctgtgagctcacattccctgg
ggttattggctactctggcagtgtttcttgaatgagggaagggcagatgctggcctgtgtcaggcttactgagccaaagaaatgacagggacgccggg
cacggtggctcacgcctataatcccagcacttttgggaggccgaggtgggcagatcacctgaggtcgggagtttgaggccagcccaaccaacatggaga
aactccgtctctactaaaaatacaaaattagccaggtgtggtggcacatgcctgtaatcccagctactcgggaggctgaggcaggggaatctcttgaa
cctgggaggtggaggttgcagtgagccgagatcatgccattgcactccagcctgggcaacaacagtgaagcatcgtctcaaaaaaagagaaatgactg
ggacaagccccagggtggatcccctcaagaacccaaaccacacccaaccagtcccacttcctatcacccagtcaaggcagcttaagtcatccctccat
cttcagaccctcgtggagaagcaacattggtcaaggactctcgttgcattgtgatccaccagcccttggagtttggagtgggagaaaatggcaaggaga
atgtcaaagaccagtgagcttccacctccgttctccttctcctcacccccagtgggcctctggtgcttacccaacacatgcctgttggacactggcaca
tcataatcctgtccatactctgaattctgcagtgagggggcagacaatgtttgtcccactggaaggggtagaggagagaaaggagcagaattcaagtatg
tttgggctaaccatcctctcaacaagccagctgtccccccgccagttctcccacccctttcttcaaatgagccttaactttccctagggatatc
agtgtgattgattgatcataaattgatttgtaaagttttgttcacccaggagctccatctttagttccatcattggtaggtcttggagaacagagccg
gtgtatgaattcactccttttgacaagaactatggtagagagagcttttgttttctccttttatttttacctttaaccattctgcacactttcatgccatag
gcagaatggtaaagcgaggcacagcatggtccctggagtttgacgtcctgcattcaggttctagattcacccacttgcaagctgtgtgacctttggata
agctaatgaaccctctctgttttttttgttttctcctataagaaattgggttattaatatgctagtatctgtctcggattgttacaaggagtgcttagtaa
agtggcaagctcacagggagctcacttataactgttacccagtattacttttccttctgtctaacaaggaactgcatgacggggaggtatttgggtgg
tttcagtctgctttatgtcctcatttatacgaacggcatctagcccaaagaaagcactcagcaaagagctattgagtgaaagggtgaacatactgcat
tgtcctatttactaatctgagctgtgccttttctttcagttgtcaatttcaccctttttatttcatataccgcacacctattgatagacatatgtctt
tatttcttccttgcctgcataatgctggtgtgcataccactttttcattttattcatctttcttgtgcctaatataagcagctctctccagaaag
tctatttttttctgacacaatgaagccatttttccctaactgcggagtccttttaaaaaaactgtatggccaggtgtggtggctcacacctgtaatcc
caccactctggaaggctaagctgggccagtcgcttagcccaggagtttgagaccaacctgggtaacgtggcgaaaccctgtctttacaaaaattagct
gggcatggtggcttgtgcctgtggtctcagctactcaggaagctgaggtgggaggattgcttgagccagggacgggaggttgcagtgagacgaaatca
caccactgccctccagcctggatgacagagtgaaactctgtctcaaaaagaaaacttctgagctactgtttgaagactcacgttgctttcaacatatt
ttccatagcgtgatgggtagggatatgggtgaaggtgggagaggaaaaattgcttacttgtatctggttaccatctttgctggggacaggatctgc
tccattttgtttctctttcatggaaactgggtccaggatcagaattgccatctcttttctggttttgcacataagacaccttgtaacctatgccgaagg
tatacatttgcttcatcaataatccgctcctcctgcctaggtcagggtctatgtctgatttctcacactgtacgtgcccagaacctgaaacaggggag
acagggctgagttcgaatcctggcctcgccatgtattagatgaataaccctgggcaagctacttaacctctctccacctcagtttccctgtgtgtaag
gtggggataattagaatatctttttatactgttgtgggtttttttttggtgatgattcaatgtgattagtaagtcctcaatatggtctgatcaatcata
gtattacaaaattttgaaagaatgagcgaatagttgagttcacaggaaatgtatatgacagggtggggccgggatttgaacccagccctgtctgccct
gtgccggttcctgggcacgtacagtgtgagaaatcagacatagaccctgacctaggcagcctatggcctgtccttaggaggagtggattataaaagga
tgaattgataaatgtcacatcagcccaacttccctgtgggaaccattgttgtattttctcttatttggtgttgaggtctctctttggggagtggtc
ataaaatctagcccggccttgaatgggaaccccagagatctggccatcatgttcacagtgtgactttcacagaatactccttttatcctggcacaccac
ctgctgcctgagtgcccagcctgtgaccccctctcacagcaaacttgtttatcctggcagattccttgcagctttcctatgacctgtgtccggttta
ttcccaccaagacagctattctctaggagagccttgaccagaaagaaggtgaggttcaggtctgttgggcgggtgggacacagaggagacagcacaac
aaaacacatgaaataacagaagcagtttattactcacaggtcccagagaagataagcacagcaagcctggaagggcgaatggaaaggagggaactga
ccaggacgcaagtgctcatccagtgggtagggggcaagagagagagagagagaagaacccatgagccaaagccttaattagagtccagggcata
atctaagcaggcttcccacagggagttctaactggggggttttagagctagcaggcaggagttctgtggagccacactgtgactgagaggtggttgctgc
agtatatctgcgcagcctatgagggacacaggagtcaatacgtaagtcaagtaggttgtagctgtatgtcccataggggagctggtcacaaggagatgg
ttgtataaggcagacatttggattaaccacctttggggaactgggaggaggtagagaattgaaatttgtgtccaggtgactaagccctgcttctggcat
gagaaagtccaacttacattcaaaataaatcccaaggcaacatataaatatataagaactcattattctacacctgcctctttattcctactgtgacacc
tttccttcccctttactcagggttccaggaagaagccctggccagacagcccgggagatcaagcatctcctcctgggggatgccctccctggaagaa
caaaaggagctccattatgcctcccttagtttttctgagatgaagtcgagggagcctaaggaccaggagccccaagcaccacggagtactcggagat
caagacaagcaagtgaggatttgcccagagttcagtcctggctgggaggagccacagcctgtctggggaaaggacaagtcagggaccacttgctgaag
cacgaagagcccttgtggcaatgttaacattaactgatgtttaagtgctccaagcagatggaattagagaggtgggctcaaatctaggccctggcact
gtcatcaagcaattcactgcatccctctgtgcctcagtttccattcccatttcatagagatcatgcatgctacctcaaaggttgttgtgaacattaaa
gaaatcaacacatggaaatcaaccaacatgggtcctggaacagggcgttgtgctcagtgcttctgtgtctctcttccttgaatagaaaggtcctgctg
gcaagttctctcaaggctgggatgaccaggcacaaaaaacagggcagcaatatgttggtgtcactccccttcccaaaactcttcgaagactccctag
gaaagaccagccctcagcctggcacttggttcatgatgtgggatcttatatccttgccagagtcatatctttgcccacttttacctgcaatccttgc
atcatattccttgctccagtcctcatttatgagacccataggaatccttccaacagcaaagagttgagtctaactctttcctgcccaaacccat
tcacggccccctggccttagacaatatatcacaagcatctcccctgacacataaagtc
```

SEQUENCES
All polypeptide sequences are presented N-terminal to C-terminal unless otherwise noted.

Human Siglec-7 genomic sequence (SEQ ID NO: 17)
```
gcagttcctgagagaagaaccctgaggaacagacgttccctcgcggccctggcacctccaacccagatatgctgctgctgctgctgcccctgct
ctggggagggagagggtggaaggacagaagagtaaccgaaggattactcgctgacgatgcagagttccgtgaccgtcaagagggcatgtgtgtcc
atgtgcgctgctccttctcctacccagtggacagccagactgactctgacccagttcatggctactggttccgggcagggaatgatataagctggaag
gctccagtggccacaaacaacccagcttgggcagtgcaggaggaaactcgggaccgattccacctccttggggacccacagaccaaaaattgcaccct
gagcatcagagatgccagaatgactgagtgatgcggggagatacttcttcgtatggagaaaggaaatataaaatggaattataaatatgaccagctctctg
tgaacgtgacaggtaaggcacgggctccaagagaggccaaaggcaaatgtgatgagggctttagggcacggctgagacgggacacatgtcctgggagg
gggcggggtgatggactcaggagaggagctggaccagagcctgagcttccccaggaccgcaccttggatgcccctcctgatcctgcaggccctcc
cctcaccagccctgacccacaggcctgacatcctcatcctgcctctgacgctggcattgtggcatgtgggccttatgactccttgttttggggcctg
tcctaggcatggccggggtttagcaccatcccaggcctctcccaccagatgccagaagcacccactccacccatgcagtgagacaataacaattatc
tccacacattgttaaacgtcctgggggggttaagtcctccccagttgagagccttaggtctacacaacccgtgactctctcaggccaggccagggagg
aagcacttcctggcgcaaaccaagggcagcagaggcacctgagcctggacagggagactcagcacacggcccctccatctctcatgccctgaggtcct
cggagatccacatttagatgctcaaaagacaggagggacctccacgatggtccgagggcggggagggcaggacctacgtgtctggtgcaggccctggt
gctccagggaagcccggaggtaggaggtgggacacggtctcttctcctccctgggtgggtctctgagcttcagggttccttcactctg
tgcagagggaaccagttcctatagcatgtgggtttgtagtttctctttcgtgctgggttgaggtctccagctcctctccagccctctccagccccct
gtgggtcccacagccctgccctcctctcctcccacttctctgctcacacaaggagcccaggaaccctctgtctcagagatgctgctgcctctcttg
tgggcaaatgaagagagggacagtcggggctgggctgagcctcatttcccacagcgtcccaggccccactgtcaagatacaggctggaggtgctgga
gttggtgatggtgcaggagggctagtgcgtctctgtgccctgcagtgtcttaaccctattacaactgaactgactgactctagccctgtccatggatgct
ggtttaagaaagggatcaatatacaatggaataatccagtggccacaaacatcccaaatggaaaagtgcaggagacacggggccgattccacctcctt
ggggacctgaagaccaacaactgctccctgagcatcagagatgccaggaaggggatttgaggaactactacttccaggtggagagaggacagataag
atggaattacaaaacgaagcagctctctgtgaatgtgacagataaggcacaggctccaggagacaccacagggaaggtcatgggggtggcagcgaaa
gcctgggatggggcccctgccctggagagggctgagggtgaagcgagttgggctcagggcagaagctgaaccagagcctgagcttccccagggctg
taccatggatcctctgtcctgatcctgagtcccccctctcttcaccagccttgacccacaggccaacatccttatcccgggtacgctggagtctggct
gcttccagaatctgacctgctctgtgccctgggcctgtgagcaggggacgcccctatgatctcctggatggggacctctgtgtcccccctgcacccc
tccaccacccgctcctcagtgctcaccctcatcccacagcccagcaccacggcaccagcctcacctgtcaggtgaccttgcctggggccggcgtgac
cacgaacaggaccatccaactcaatgtgtcctgtgagtgctgagccaggacgccctggtccctgatgaggggggacgtccctgagggcagaggatgg
ggtcagggctcgacactgggtgctgggtcccagaatctgggctggttgtgggatcaggaggacgctggctccgccttccccatttatgcagctcctgg
ggagacagggccagtgtccccagccctcacagtgatgcaggtctccatgtctttctgtcccagaccctcctcagaacttgactgtgactgtcttccaa
ggagaaggcacaggtaggatggagccccctccctggggctggggagcagggccttcagctcagggcagggccaggtccctcctcatcctggactcac
cctggtgatatgagactccttgtagttgaaaccaggcctcctccccatccttagcctctgtggccacctgagcacctgtcctcttcccccactccc
ctcagactcttgcacacacaccctcctcagccctgcagcaggacagggggaaatacatatagcaggagcagcctttgggcctcttatcttccatctc
ctgaatatgccacctaactcgtctctttatttttacccaatagttttgagctacgttcttttggatacatgctataatcacgtgggcaaaaattttaaa
ttcacagtaaaatgtgtccccagaatcaaccagggtctgtccaggctgtcctgagccttggtttgtgcacctggaagatctcagaggtggttttgatgt
cagcagtgagactgtttgcaccctcttctagggatgtgtgtgattccactgtctgaatagtctctgattttgtggcatctcctaatggaagatcatgg
cactaattttatcctacggcacgaacactgcaatgaataatgttgtatctactcccacaaggaatatctaagtgtataggataaattcctaaaagcac
attttaccagtgtcatatgttcttctgatttttgaaagatatggtgaagttgtcctcaaataaaggtgggcaagtttacattcccaacagtgagcggt
gaacataagtatgtccctgcaccagcctacatcactctctgttccattcccagtctcattctgtatccttcctccctgtttcaatcactttgtctct
ttgaaccctccaactttttctctacagcatccacagctctggggaacagctcatctctttcagtcctagagggccagtctctgcgcttggtctgtgctg
ttgacagcaatccccctgccaggctgagctggacctggaggagtctgacctgtaccccctcacagccctcaaacccctctggtactggagactgcaagtg
cacctggggggatgaaggggaattcacctgtcgagctcagaactctctggtccccagcacgttcctgaacctctccctgcaacaggagtacacagg
tgggtaagggaggggctggaggaggagaacacacctgccccacccctcatgggccaccactgccctgagcttcaagggggagctcagctctggtctg
tgctcagctgtgaggcctggaacttccctgcaacccagggcactgctgtcctcttcctgccaggaaggtgtgtaaggcaggaagaggggaggagtgg
gtcttggagggggagctgggggcctggacaggtgtgttggggagacagtgcctgcttgctctgactagggtgacacaagcaaggcact
cacttctgggcacacgactaaaaaacaaaaaataaaacaactcagcaagcaagtgaaataatattggatgtgattatctttattaaaaactaaaaatt
attgcaaaataaatttgacagtgaatacaaatcaaaatttcaaatacaggcaggctgtgcttaccactctcatgcctcagtgacctcaggagttgtccc
ttcctcctccctcccattcttgcccttttgtttctgggaaggggggattagggtacccaagttgggggccttataggaagtgggaggagaagagaccag
ttcttggagttggatcaccaaaacaattccaatccatcctcaggcaggcctgtatcaggagtgtttgctggggggcggtcggggggagctggagc
cacagccctggtcttcctctccttctgtgtcatcttcattgtgtgagcactgacccctagggaggggaggagagatcctggggaggggcggactgggag
aggatccctgaagccagagctggaagggactgcatgggtcaagagcttggggcaagaatgagctcacgggtgcgtggcaagaatttcaagagcgccct
tgtctgtggggctccacatctgtggtgaaccttgggccccaccacccaggaggcaggagcctctgttttcaacactgggtctctgggactggaccac
cctcctcccacctcagttacccctccagcgccccaacaggaaaatacaggcaggggttggtctgcccactgcaccccgatctgaccacactgaaaggc
tctctggctctcttcactcagagtgaggtcctgcaggaagaaatcggcaaggccagcagcggacgtgggagacataggcatgaggatgcaaacaccat
cagggctcagcctctcaggtgagtgatatgggcgtctccacacccagcatccagctgggacatctcccacaggatggcctccaggatttctctgctt
atcatgccaaaattatctcctcatctcctcctcttcccaccatccagcttctcctgcaggattccccatcttgctgactgcatgacagtccctcct
acctactttctctcgggccaggcatggaggaggagttatctcctctctgtctccctttcttctctatagctccacattcaccaaatcttgtccattt
ttcctccctaagaatggctagcattgctccaccccccaccaatcctaaactctctcaatgctgaggcctgaggatctctgtcttgggacttcctcacct
ccctgcctcttgtgtccctgcctgatgggaggaatcattcagaagccatcactgatcagtttctttgcatctggacagctgttcccaccccaaca
ctgtctagagcagaagccagaaaatactatctggaaaggccagataggaaatattttggctttctggcctacacagtctcattgcagctcctcaact
ctactgatgtagcaggaaatcagccgtagaccatgtgtaaatgattagctggctgtgtgccagtaaaactttattataaaaacaagctgtgggtaga
attgtcccaagggctctagtttgacaagcctaacctagagaaaaagactcataactgcagccctgcaactctcgtctcttaaacatcta
cctctctagcagggctggaattagtgtgagatgagtgaggtcctggcctagcatgcaaaatttaagaaggtgccaaaatctcagtaattgtgatagt
tttaaaaaaactcttattttaggtttgggggtacatgtgcaggtttgttacatacataaactctggtcagaggggtttgtggtacagattattttgt
cacccaggtcctaagcctagtacccacagttattttttctgttcctctctctcctcccaccctccaccttcaagtgggcccccagtgtctgttgttc
tcttctttgtgttcatgagttctcatcatttagctctcactgataagtgagaacatgcagtatttggttttctgttcctgtgttcgtttgctaaggat
aatggcctccagctccatccatgttcccacaaaagacataatctccattcttttatggctgcacgatattccatggtgtatatgtaccatatttttct
ttatccattctgtcggatgggcatttaggttaatttcatatatttgctattgtgaatagtactacaatgaacatttgcttgtatgctctttatgg
tagaatgattttttattactctgagtataaaaccagtaatgtgattgctatgtcaaatgatagttctgcttttagctcttcaggaaattaccatactgc
tttccacagtggttgaactaatttacactcctgccgacagtataagtgttcccttttctctgcagccttgccagcctctgtgatttttttacttttt
aaaagtagccattctgactggtgtgagatgatatttcattgtggttctgatttgcgtttctctagtgatcagcgataatgagcttttctcatatgtc
tgttggccaaaatgtctgtttatgcttttgctcacttttttaatggggtttgttttcttttgaaattgtttaagttccttatagattgcctacta
ttgtcttccagagttttatagttttgagttttacatttaagttttaacccatctcgagttgattttttatatggggtataaggaagcagtcccactc
aatcttctgcatgtggctagacagttatcccagcaccatttattgaatcaggagtcctttcccccattgcttttttttgtcagctttgttgaagatcaa
attgttgtaggtgtgtggctttattttctgggctctctattccgttccattggtctatgtgtctgtttttgtaccactaccatgctgttttggttactg
```

-continued

SEQUENCES
All polypeptide sequences are presented N-terminal to C-terminal unless otherwise noted.

tagacttgtaatatagtttaaatttgggtaacgtgatgcctccaggttttcttttttgcttaggattgccttggctatttgggcacttttttggtttca
tatgaatttaaaattgttttttctagttctgtgaagaatctcattggtagtttgatagaaatagcattgaatgtataaatttctttgggcagtatgg
ccattttaatgattttgattcttttatccatgagcatagtatgttttccattttgtgtcacctttgattatttgagcagtgttttgtaattctcat
tgtagagttctttcacctccctggttagctgtatttctaaaaatttttattcttttttgtggcaattgtgaatgggattgtgttcctaatgtgactcttg
gcttggtagttcctgatgtatagaaatactagtgattttctatattgattttgtatcctgaaactttgctgaagttatttatcatttaagaagcttt
tgggctgggactacgagttttctagatatagaatcatgcatctgcaaagagggatagtttaaattcctctcttcctattttggatgctctttatttct
ttctcttgcctgattgctctggccagaatttccaatactacgtaaacaggagtggtgagagagggcatccttgtcttgtgctggctttcaaggggaa
tgctttcagcttttccatattcaatatgatgttggctctgcgttcaccatagatagctcttattattttgagatatgttcctttaatacctagttta
ctgagagttttttaacacgaagcgatgctgaattttatcaaaagccttttctgcatctattgagataatcatgtgtttttgtctttagttctgtttgtgt
ggtgaatcacatttattgatttgtgtatgttgaaccaacatgaagccgacttgatcatattggattaaccttctgatgtgctgatggattcagtttgc
aagtattttgttgaggattttttgcatcaatgttcatcaaggatattggcccgaagttttcttctttttgttgtgtcttcgccagattttggtatcagga
tgatactggcctcatagaatgagttagggaagagtcagtcttcctccgtatttgggaatagtttcagtaggaacagaaggaggctcagatctgacatt
tattgtgtgattgaagagccttccaggcagagggaggagcaaagcaaggcccaggcacaggaagaggaaaggagaggagccatgggacatctgtgtga
ttagacagagggaggcaggactgagagcaggaaatgactttggaggagttgagcctatgtgaattgtgtctgactgcacaggctactgtgagcatttg
gagagttttgagcagaaggacatgatcagacgagattgggtccgttcagggtggtatagctgtagaccagaagaacatgatcaactttcatttcatg
ggattcctctgccactgtgtgcagaagagaccgtgtgtgtggcaggggaaggagagagcataggaggtagacaggaggctggtgaacatcccaggca
gaaggtggtgttggctggaaccaagatagcagcagtggtagacatgactgtctcccagatgaattctgcagtggaacctactgggatttgttaatgaa
ttggaattagaatgtgagccacagaaagggagcaagaattacttccagatttttgccctgagcagtgggaagaatggaggtgccaatcattgaggctg
agaagattgcagaagaaatggattttgggaaagaaaaggaggagttcagattgaatagggttgagttttgtgtgtcttggacaagaacgcgggggtttg
aattataccactggatcaaagactatagtcaggagaaaggagtgggctggggtacagattgggagtcattagcctattgatggcatgaagcaaca
cagtggataagatcacaaggcaaaggtaaagaagaaaagaacccggggctgctctgatatttaaggtcagggagacctgaagcaattggcaaagaggt
tgccaagaaggtgaggtggacccagaaaagcatgatgtcctatagttgagtcaagaaggccttctgtgtagggaaggtgagcagctgggtcctctgct
gctgaaaagtccaggaaggagaagactgcaaggtggacattttagactcagccactttaagtggtagtcacagtgaccttgataagtagcagtgcttagac
ttggtatgtgtgtgaatattaatttgagtaatcaagagagaatctggcaagcaaaatcactgacagttccatggagcatcttctgcacagggagcag
cagggaaagggctgcgatgaaggaggaccctcccaggcagcctctgtcactctctgctgtgtgagtctgtattagtttcctgtggctgctgtgacaaat
taccatgcatttcctggcttccaacaacacacatggattaaagttctgaaggtcacaaccccaaaatgggtgtcactgggccaaaatcaaggcattgg
caggcagggctggttccttctggaggctccagggggaggatgcaatttctcaccctttctggcttctagaggcacctgcattccttggctcaagtccct
tcctctgtttgcaaggcaagtagcctggcatcttccaatctctctaagccctcctcctttccacttgtaaggactcctgtcattccactgggcccaccc
aaataatccaggataacctccccatgtcaatatccttaacctagctccatctgtaaagtcccttagcaatgtaacgtaacagattcacaggtttcag
gggattagggtatggacattttggggagcagttatacttcttatcagaggatataattctttgactgagttgtcctcccataccaccgaactgtga
gcttcctaagagcaggtgccccatccaaatcaaggccctgtaattctctctcacttagcctcttcctgcccatcttataattcacacatagatattcg
tttgtttgacagtcattttttgccaaattccctcaattaaaaagtgagtttcaggaggtcagggccaacacctactgtgtccaccacagtccatccagc
acccggatcagggcttcacacacagagggcccccagcaggactccaggctttgggttcagaaggaagggactggattgggtcccggcataacagggagt
ttgggtacgctacttcttcatggagttgttgcgggaagttaataagattaataaacaccaaacaagttgctcaataagtgttaaatattgcaggaaa
gtataaatgaaggagatttctataaaatgaacgtgggatagaggcaggaactcatgaagtttaattctatacagaggaatatatccgaaccaaccaac
cgatcaaacaacttgtgactctccctgccttatcctattttccactgctctgctctgcccttctctctctccattcagggtaacctgactgagtcc
tgggcagatgataaccccgacaccatggcctggctgcccactcctcaggggaggaaagagagatccagtatgcaccccctcagcttctcataagggga
gcctcaggacctatcaggacaagaagccaccaacaatgagtactcagagatcaagatccccaagtaagaaatgcagaggctcgggcttgtttgaggg
ttcacgacccctccagcaaggagtctgaggctgattccagtagaattagcagccctcaatgctgtgcaacaagacatcagaacttattcctcttgtc
taactgaaaatgcatgcctgatgaccaaactctcccttttcccccatccaatcggtccacactccccgccctggcctctggtacccaccattctcctctg
tacttctctaaggatgactactttagattccgaatatagtgagattgtaacgtg Human Siglec-9 genomic sequence (SEQ ID NO: 18)
tagggcctcctctaagtcttgagcccgcagtttcctgagagaagaacctgaggaacagacgttccctcgcgcgccctggcacctctaaccccagacatg
ctgctgctgctgctgcccctgctctggggagggagagggcggaaggacagacaagtaaactgctgacgatgcagagttccgtgacggtgcaggaagg
cctgtgtgtccatgtgccctgctccttctcctaccccctcgcatggctggatttaccctggcccagtagttcatggctactggttccgggaagggggcca
atacagaccaggatgctccagtggccacaaacaacccagctcgggcagtgtgggaggagactcgggaccgattccacctccttggggacccacatacc
aagaattgcaccctgagcatcagagatgccagaagaagtgatgcggggagatacttctttctgtatggagaaaggaagtataaaattggaattataaaca
tcaccggctctctgtgaatgtgacaggtaaggcacaggctccaggaaaggccacaggaaaggcatggggcggcagggaaaggctgggatggagcc
cctgccccaggagaggctttagggtgaagcgagttggctcagggcaggagctggaccagagcctgagctcccccagggctgcaccatggatcctctg
acctgatcctgagtccccctctcttcaccagccttgacccacaggcccaacatcctcatcccaggcaccctggagtccggctgcccccagaatctgac
ctgctctgtgccctgggcctgtgagcagggggacacccctatgatctctgatagggaccctccgtgtccccctggaccctccaccaccccgctcct
cggtgctcacctcatcccacagcccaggaccatggcgaccagcctcacctgtcaggtgacctttccctgggcccagcgtgaccagaacaagaccgtc
catctcaacgtgtcctgtgagtgctgggccgggacgcctgggtccctgatggggtgagcgtcaagcctggacactgggtgctgggtcccggaatctgg
gctggtggtggggtcaggaggacactggctctgccttccctgtttatgcggctcctggggacagacagggccagtgtcccagccctcacagtgatgc
gggtctccatgtctttctgtcccagacccgcctcagaacttgaccatgactgtcttccaaggagacgcacaggtaggatggagctccctccctgggg
ctggaggagcagggccttcaggtcaggatggggctggcttattcctcaacctggactcacttttggcaaacagggatgtccttgggtggggtgaactcaggg
ccctctgtatcctaggccccaaggccacttgttcccatcctccatcacctccttggactccccacacacccccctcagcctcaaacaagaa
gagggtggcattcacacagcaggaccaggctttgaggctccttctcatgtatctcctgaatacatctccaccttatctgtttatttctgatagttct
gatctaagtacttctggacaggtgataaatgtccatgggcaaaaattcaaattgcagagcaaaggctctcctccgatgcctgcccccctcccccagaac
caaccactgtccatccaggctgccctggctctcggttttgtacacctggaggattccaggttgtttgacgtccgtagtgagactgtccgcaccctcc
tctagggctgtgtgtgagtccactgcatggatggactctgattttgtggcatctcctaatggaagatcacggcactaatttcatcctacgcaggata
gaacaatcttgtatctacttccacaggaatatctaagcctgtgggttaagttcctaaaagcaaaatgtagctacattatatgttcttctttattttga
aagataagcccaaactgttctcgatgaagcgggagaagtttacattcccagcagtgagtggtgaaagtgtgtgtttccagaacttcagtctatgtct
gtgtgtcagttgctgtcatcagtctctttctgtatcctttcctttttctccagatctatgtatctctctgaccctctgtctctttttctacagtatcca
cagtcttgggaaatggctcatctctgtcactcccagagggccagtctctgcgcctggtctgtgcagttgatgcagttgacagcaatccccctgccagg
ctgagcctgagctggagaggcctgaccctgtgcccctcacagccctcaaaccctgggggtgctggagtgccttgggtgcacctgagggagtcagctga
attcacctgcagagctcagaaccctctcggctctcagcaggtctacctgaacgtctccctgcagagtgagtgcaccagtatgctggggagggggctgga
gaggagaacacacctcctccaccccttagtaactgctgagcgtggaccttcagagaggagctccgctctggtctgtgctcagctgtgaggtctggaact
tccctgggacccacagcaccactgtcctcttcctgccagggaaggtttgtggtgtggagagggcaggagtggatctcagaggggacaggatgggc
cggacaggtgttttagggagacaaggccctttctttcagggctgaactggagtcacacaactgagactacttgctttgaagcatcaattaaaaaaaa
gaaaaagcccagcaagtcagcaatcaaatgaaatcatattgcaatgcaataatcttttaaaaaaagtaaaaattgaatgcaaaacaaattcattaatg
gataaaatattaaaattgtgaaaaaaaacccaaaaggaatggctggcacttgcacgcctcactggcctcaggaagagtctctccatgtcctgctctc
tctcattcctgttctttgtgtctgaaaggggaagtggaaatagaagtctaggaccctcaggagtgggaggagaagagacccaattctctatgata
tatcacaaaaataactcccatctgtcaacaggcaaagccacatcaggagtgactcaggggggtggtcggggagctggagccacagccctggtcttcct
gtccttctgcgtcatcttcgttgtgtaagcatggaccctagagagggaggaggagagccctggggaggacaggctggaagctggatccctgaagc

SEQUENCES
All polypeptide sequences are presented N-terminal to C-terminal unless otherwise noted.

```
cagagctggagggacctggatgggtcaagagcttggggcaagaaggaggtcacaggtgcatggtgagaattccatgtgggcctgtgtttgaggagctt
tgagtctgtggcaaaccttggtacccactgtccaggagaagagacctctgttctcaaccttggggtctctaagactggaccactgcttt cccacctc
agtcaccctgcagtcccttaataggaaacacatggggg tacctggtctgcccaccgcaccccaatctgaccacactgaaaggctctctggtctcttc
actcagagtgaggtcctgcaggaagaaatcggcaaggccagcagcgggcgtgggagatacgggcatagaggatgcaaacgctgtcaggggttcagcct
ctcaggtgagtgatgtggactctccacagccagcatgtagcctggacacctcccacaggatgaccccaggactaatcagctgggcgtagccaaagtt
acctcctctctgttcttcctttctctgtagccccaaatcacaatgtttggttggtttcctcccctaagaacagcttttattgtctctgctccc ta
tcctgaccct tcattgctgaggcctgaggatctctgtctttttgttccctcacctgtctgcctgtctcctctccttt cctgcctgggggg actgtccag
aagacatcatcgtccagttcctctgcatttgaacagctgttccccaccccctcaataccgtttagagcagaagccagcaaatactatctgt cagggac
agatagaaactattttcggcttcatgggcacacagtctcattgcagctcctcaaatctgctgttgtagcaagaaagaagccatataccctgtgtaaa
caaatgaatatggctgtgtgccaataaaactattcacaaacataaagagtgggctggatatgactcagatactgtagtttgacaaccc ctgatctaga
gtaaaaatcccaaactctatagcctgcagcagtgcacattctgactttttttgttttttttttttttgttgttgttttttgagacagagtcttgc
tctgtcgcccaggctggagtgcagtggtgcgatctctgctcactgcaacttccacctt ccgggttcaagccattctcctgcctcagcctccggagtag
ctgggactacaggcgcctgccaccacgcccagctaattttttt gtattttttagtagagacggggtttcactgtgttagccaggatggtctcagtctcc
tgaccttgtgatctgcccacct tggcttcccgaagtgctgggattacaggcgtgagccactgtgaccggccacattctgacctttt aagcacctacct
ctccactagggcaagaacaaggg tgaagtgagtgaggctgttgcctcaagtgcattttt cgtttgtttgtttttgtttttgagatggagtctcgct
ctgtcacccaggatgtagtgcagtggcgcacaatcttggcttactgcaacctctgcctcctaggttcaagcgattctcctgcctcagcctcctgagtagc
tgggattaaaggtgcacaccaccacacctggctaatttt gtatttttagtagagacaggg tttcaccatgttggccaggctggtctcaaactcctgac
ctcaggtgatccgcctacctcagcctcctgaagagctgggattacagatgtgagccaccgcgcccatcctcactgtctgctctgactcacttctctc
tccatgtctcagggggccctgactgaaccttgggcagaagacagtccccc agaccagcctccccccagcttctgcccgctcctcagtgggggaaggag
agctccagtatgcatccctcagcttccagatggtgaagcttgggactcgcggggacaggaggccactgacaccgagtactcggagatcaagatccac
agatgagaaactgcagagactcaccctgattgagggatcacagccc ctccaggcaagggagaagtcagaggctgattcttgtagaattaacagccctc
aacgtgatgagctatgataacactatgaat tatgtgcagagtgaaaagcacacaggctttagagtcaaagtatctcaaacctgaatccacactgtgcc
ctcccttttatttttttaactaaaagacagacaaattccta
```

Human Siglec-11 genomic sequence (SEQ ID NO: 19)
```
cgaggctcctcctctgtggatggtcactgcccctccaccaggcttcctgctggaggagtttccttcccagccaggccggcccagaagccagatggtcc
cgggacaggcccagcccc agagcccagagatgctgctgctgccccctgctgctgccctggtgggggcgggtgagtgggtcggtggctggggg tcccag
gcagggctggggctgccgctgagcctctgcatctccccagggtccctgaacaaggatcccagttacagtcttcaagtgcagagg cagg tgccgg tgc
cggagggcctgtgtgtcatcgtgtcttgcaacctctcctaccccgggatggctgggacgagtctactgctgcttatggctactggttcaaaggacgg
accagcccaaagacgggtgctcctgtggcactaacaaccagagtcgagaggtggaaatgagcacccgggaccgattccagctcactgggga tccc gg
caaagggagctgctccttggtgatcagagacgcgcagagggaggatgaggcggtgacttctt cgggtggagagaggaagccgtgtgagacatagtt
tcctggacaatgcgttctttctaaaag taacagtatggaaatgggtgggaaccctgcctgtcacactgggagggacctggggacaggctatggg
ctgagcagagagggctctcagggacccctgcagcacaagaatctcccaccccggtctctgtcccagccctgactaagaagcctgatgtctacatcccg
agaccctggagcccgggcagccggtgacggtcatctgtgtgtttaactgggctttcaagaaatgtccagccccttctttctcctggacggggggctgcc
ctctcccctagaagaaccagaccaagcacctcccacttctcagtgctcagcttcacgcccagccccaggaccacgacaccgacctcacctgccatgt
ggacttctccagaaagggtgtgagcgcacagaggaccgtccgactccgtcctccgtgtggcctgtgatgtggcctgggagggtggggcgtgcagacagccccgg
tgggtggggaggtggaggagcccagcggacagtgagtggctcccagctcaggagcatccaggga gaggaaggctgtgggg tcccaggatgccgg tca
gccctggggagggggatgggaatggcgtctgatcctctgtccacatgtgtgagccctggagctggttgtcacttgtccatcctgggatgttcccacttt
cttttccctgagggagttttttccaggtgtgaggaacaaattgtccctccctgaagccagctcacaatcttgttgcagatgcccccaaagaccttatt
atcagcatttcacatgacaacagtcaggtactgagggcctcaggtgtcgggctggggctgggccagtcctccttt agggatgaaaaggcttcagggggtgagg
ggatgtggtcctctttgcagcccccccctcccaccccattctctctctccaccccc acccctctctcttt cctgtcttcagccctggaactccaggg aaa
cgtcatatatctggaagttcagaaaggccagttcctgcggctcctctgtgctgctgacagccagccccctgccacgctgagctgggtcctgcaggaca
gagtcctctcctcgtcccacccctggggccccagaaccctggggctggagctgcgtggggtaagggccggggattcagggcgctacacctgccgagcg
gagaacaggcttggctcccagcagcaaggcctctggacctctctgtgcagctg tgagtgtgcctgcaggggcctggagtccattgggagggcagagggat
acaggggctgggctcagggtcccagagctgaggggggtctt gaacccc aggcctcggggactgacctt cttacctgt gtagacc ctcatgcagtttgtg
tctgggactcagtgggtgattctgccctgcccttctatcccacccactt cccccaccct cagtgt ccaggatagttccctttacccagagggaagcccc
tggtctgtctagagccggtccc ctgtctccatttcagatcctccagagaacctgagagtgatggtttcccaagcaaacaggacaggtaggaaaggaga
cagaggagccaggg cctctcagtgccaaactgggggcccaggagtctggaagggctccccacacaggagggtccctgagccctcagtgcacgtcgattc
tgcctcttccttccctagtcctggaaaacctgggaacggcacatccctcccggtcctggaggg ccaaagcctgcgcctggtctgtgtcacccacagc
agcccccagccaggctgagctggaccggtggggacagaccgtgggcccctccagccctcagaccccggggtcctggagctgccacccattcaaat
ggagcacgaaggagagttcacctgccacgctcagcaccctctgggctcccagcacgtctctctcagcctctccgtgcactgtgagtggggg aaaggg g
acacctgggtcccaggaagggggccctgctgagtcctgtcctccctccccacagaccctccacagctgctgggcccctcctgctcctggaggctgag
ggtctgcactgcagctgctcctccaggccagcccggccc ctctctcgcgtggtggcttggggagg agctgctggagggg aacagcag tcagggg ctc
cttcgaggtcacccccagctcagccgggcctgggccaacagctccctgagcctccatggagggctcagctccggccctcaggctccgctgtaaggcct
ggaacgtccacggggcccagagtggctctgtcttccagctgctaccaggtgagggg actgtggggggctgaggttcagggagaaaggagacaggatcc
tagaaagatgaaggttcaaggttgtggggagagggtgtgggcgtggtgggaagggga tgggacaaagtccctgctctg tggctgg tagttgttgcggg
aaactgaggaacggagagagcaatatggagaacaggaggattgtttatttaaggtaagttccagcttagtggattt acattt caaaagctgagcatta
aataaagacaaagaagggg tttt tttt gttttttggttttttttttgagatggagtctcgctctgtcagcaaggctggagtgcagtggctcgatctcg
gctcactgcaacctctgcctcccggattcaagcaattctcctgcctcagccacctgagtagctgggattacaggcatgcgccaccacgcccagctaat
ttttttgtatttttagtttcactatgttggccaggctggtctcgaactcctgaccttgtgattcacgcacctggacctcccaaagtgctgggattaca
ggcgtgtgccaccgcgcccggctaaagcagtgtgttttataagcgcatttacaaaagtaaaacaaaagcggttaattatatagtgcataacttgtgcc
ttgtagctgtgtcaaaagaaaaacaagaactggttaaatacagacatttgtgaaacataattgtgcttaagaagcc aggg aaaggagtaacagtaaaa
gaatttgtcttttttttttttttttcttaaccttgctctggaaggggtgtgtctggagcccattccttt ggcctt ggctttttaaacagtgttatttat
acctgtccttgaagtgagcttgctaggcatagaaagacttgggtttttttgttttttttttaaccctt gccttgcctgttacttttt ggggagtgaa
tgaatgcatatttatttttt aaatttttgcctcagtttccccctttt gatgtttttt ataaaagaagttt aatagaaggcattactatttacttaattct
gcatgaagagacacttttttttcttt agacaaaggttgatattt tatgcagagccgtt agctgagtggtagtttgcctagctgctattgcctttatagtt
gattgaatgcttccaacaaggagagctaagagacaagggagtattcggcaacttcctagtatggcagaaccacttttattaaagtcttgaacc ctct
gcaaaatgaaaccagtccttaaagagagaatctggagaccacccttt ccaagtttgaactggaacatgggctaatt ttt ttatttttgcagtt att t
ttataattgcctttt cattgtcagcgattttt aggcagcagttagttagattgaacttttt acatt ttttttttttt ctgggctaggagtagtccaaagc
taacctgttctgatagataacattcttcatttttgtgggttgctgggccagtaaatctaatgcatttgctgtttt attagtgatgatttcaagtactg
cctgcaacctt atgatgcgttaagcatgtaaat aggagtgtgg tatcccatgacccatttt gtgcccaggtagctggcctat actattgaattatt
tttt caggggggt taatt tgtgtctttt caatttttt aattttatttttgtgtgtgtttgcattttttt aactttattatagacaggataccttt
aaagtttctccctgtt gcagtgggaataggaagaaagacggtctaatt gtttcaagcacacaggcccctgtccatttagctggcaactgttgatatgc
ccatggcctacagatccaacaaagactaggaggtgcttgccaagtatttggagctttcggctgatagtaggtgtgatttaaagaagagaaacagggaa
cggatttggatgaggtcatttgcattcatctttgccccgccacaaagtgtttcttagtgttttatcgtcatattgctgtcctaagcagtttagttctt
ttactgggtttgtaaaaacttttccccagcgagcaacacagtatttcctgataatagaagttttttaagagccagacgcttgaacttgtgggcgtcggt
```

-continued

SEQUENCES
All polypeptide sequences are presented N-terminal to C-terminal unless otherwise noted.

tcgggagaagagtcagttaaattattttgtggcattaacttttttgctttccaaggccattggtcttccgtgttagtccctccgcaaacatagtatga
ggaaatgcctaggctgccgacaatgtttttaggcagccgagcaaacaggttttctgctaaaggagtgggctctggtaacaggattacaggtgtgagcc
actgcgcccggccataagtacaagttcttttttttttttttttgagacggagtctcgctctgttgccctggctggagtgcagtggcgccatctctgc
tcactgcaagctccaactcccaggttcacgccattctcctgcctcagcctcccgagtagctgggactacaggcgcccgccaccaagcccggctaattt
ttttgtattttttactagagacaggttttcacagtgttagccaggatggtctcaatctcctgaccctgtgatctgtccacctcggcctcccaaagtgct
gggattacaggtgtgagccgccatgcccggcctgctaatttttcttttttatgagggctgctgccaacagattggccttttttttttaagcctatgttct
gcttccttttcttcctgagttatcctgctcctacagctggccagtgggactgggctacggcgtgggccccgcccctgtgcacgcacgcactgccat
ctatctttactgtttctttctgattttttctttttttccttttttcacacttacttttttgggctaggtaggatctgcacagccgtagtccacccctgggc
cgttataggcccagaggcttggtagatgcctgccgcaagttgtaagaattatgccttttcttttttttttttttttggcttttttttctggggccagtc
cccgccccgctcttttttccagatagagccaggctgaggagagggactaaaccccttggtgtgcctagctgcttggtgcctcgcttgttgctttcgctct
ttcccgttttgttctctggtcatggtttcatgtacatcttggtggtcacttttataagctggggtggcattcatgcctgcagctgccgcttgacgtcacc
ctgggcttgccctacaaatgctgtgtttaccatgcgctgattttcagcagcctcagggtcaaatagggtgtaaggccggaatgcttcacaaagttttt
tataaaactgacttgggctctcgtcagctctctgaagcacttttgaaattttttcgtatattaattgctttctttccaccagcttttatcccttgcaga
agtgtctcttggtacctttgcaaatgctgaagctgagttgcatcctctgggttccagttgggatcttggtatgagaactgaccttgagtgtatgcctg
agcattcactgcatctgctggtgcatggggttttagccaggggagagctgcctatgttactctcctgcgcttttttagtgttaaataacgttaggaaaa
gctgcctgcaatctggccaggttggactgtgtgtcagaaagacggattgcgtcagatctataagagcttgaggcttctccatgtaggagggagtatgg
tgtttccagttcagtagatcagtagctcagtagtcagaaagggctgatagatgaaggtgcgttgccccccacctccgaacctggccttggttattaca
ataagtgggtcctcacatctccctgacaggcatttgcatagctcgagcaggcatttgcatagctcaagcacggccagatctgagacagcctgcttgac
tattttgacttccttccctggcctttttgaggctccagtccttccccttcggggtcagactcagggcatgctagctcctgaatttggttcctggagggct
gttggcctcagtaaagggggggtaggctgggacatatggaggggaatttctgtttcctctggcagctgttgcaaaactggctctcttgctcttttctg
gggttttctttttaacttcgtgtcagtcggtgaagtcgtctcttacttttatttttggctcgggctacaagtgttttgcaataagctgctaaacagggc
ttgatccaggttagtcttgtctgtgctgtatttaaccatgaatcaatataaggaaattgatcgggatactcaggctgtcctcagaccccctatccaccat
ctttaatacatgcccaattgtttcctagtctacagtttcttcggtcagccatccaacatcaaaagaaagtcattctaattcaaagagagttctcaacc
tttgggggtttagcttaactttataatccctgcaaaaccttttcttaaagttttgtaacatgcacttcaatggagtaagttttgatggactttccttc
tattccttccttttacggcccagcacactcactcttcctctagttttcggccaactataccatctcctattacgggagttttcagaagctacttggcttt
ggagagttccttattcctgctacaactctgagctgtagggcagctcctattagccatacgcagatcaccactagtcttagttggcccacactttgct
cggagcacccagtccacactaagagaattgtgacttcccattttgtggctgatcagactaaaggcttcttcattttcacacactgttacacacttccc
cactcccagttcctaagttcctaattaggggtggtaagccactctcgccacctccagtttccttttcctaatcgacttagcaaaccattctccatcct
gtgatggttgggtgtgagtttcatccaaatcgacgagccactctcgctgcccccaaccctctgggtcggactgttaggcaccccgcaagaagtgat
cagcctccccttccatccctatgggatgggtcctgccttggtccccaaaaggttactgtggttcctgacgtacactgtttctgaaatcattctgtagc
tcctttcaggttttgttgtgctgctgggtagggcgccggctcagggagagctgattctcctccaggctgaagttcacccagtggcacctggggtc
acaggtctcctgaggcccgggctccagccccccagaggcaaaggaggcagtaaacctcgtctctgtgctcccttcgtggtcgccaaaaatgctgcggg
aaactgaggactggtgagaccgatacggagaacaggaggattgtttattttaggtgcaaaccggctcagtggactcgcatctaaaaagctgagcatga
aacaaagacagagcgaggtttttatgagcagacttacaaaagtaaaacagaggcagttaattttaggataggtgacataatttatagtatagcataac
ttgtggccttgcatagctggtggccttgtagctgtatcaaaaggaaaaaaaaagaactggctaaatacagacatttgtaaaacatagttatgcttaag
aagccagggaaaggagtaacagtaaaggaatttgttttttcttttcttgttttccttcaaccttgctctggaagggggtgtgtctggagcctattccttt
ggccttggcttttttaaacagtattatcttataactgtccttgaagtgagccttgctaagcagaggaaaagttgttctttttttaaccctttccttgcc
tgttactttcttggagtgaatgaatgcatattttattttttaaatttctgcctcagttggggatgaagaatccgagagctctaggtctgtgggaggaag
gggcaggagggtctcagggccaggagggcaccaccccaaaccctgctcccatgcagggaagctggagcatgggggaggacttggcctgggctgccc
tgggagctggcgtcgctgccctgctcgctttctgttcctgccttgtcgtcttcaggtaagcatcggagggcaggcaatgcagggtgtgggaagggtga
gggttctagaatcccagacagtcccagctgcaggaatctagatggggcagtgggtgtgagaactaggcctgggcaagaggatcagagcaggggtctg
ctccagagccctgatctgggccatctatgagggtccccagttctcactatggaagtcacccccgtggatatgtccccaccccactgggctctgcagcct
tccagcctctgctaagccatgtgggtagcagttttccccaggctctggaccagcctggaggctgaagggcactgcctcctccctccagggtgagatctg
caggaaggaagctcgcaagaggggcagcagctgagcaggacgtgccctccaccctgggaccccatctcccaggtgagagcccagcctctgtctgctgggg
ccctgcctgttcccctttccttgatggccatgggtagtcctcttggtgacttgcagaatcattgtgcccaaatagggttttgctcctgggtccccat
caatgcagtcccaagtcccatgatctgggaggcaccctcccccactgctccctacatcccctcccagaaccaagggcccccaggcctgtccatactct
gcctgtgctcagatccagtggaccctccacctcccactcctcatttcctcctgcatccccgactcctttgccctcctcctatctctcctcctcaaca
caggatgccagagagtccttcctcagatgactattgtcactacaacaagctgggtgcccccatcctcacttctgacaccaaccacagttgtggggtcc
ccacgaccactctgaggttggataaccccctaggactcgcaggactcactgagagctgtgatcctcggtgatgattttatagtgaccgatacagatg
aaaatcatggacaggaaggtgctcagggcaggtccaggagataccaaacccacagcttccggtggccttttccagggggagccatggggacagcacc
caattctcccagcaaggaagtgtgacagatgcacggagcatcagggcaccgctcacctgggaagctccaccaaacctgggtccagggttcactggggg
tgggtcacgcaggcatgggggacttgccactgacttcagttcctcagccctgcagagccaaactgatgctacgtaggccccgccgtaagtccagtg
ctggcgtaaactatgtggcctggcttgtgtgtccccaggtcaacagggatgcctctaccagcaggatattccaaggccctacattagaggttccttccca
gcacctgggcacaaacggttgaagctttctctgggcaagggaatccttttacttccagtaaccttttctttcttgagctcctagctcagtttcacaatt
gtgtccgagtagatcttccaaggtctttgaggtcagtccaggtccgagcaaatccctgtctttctcacacctcctccttcctgggcatccacttataa
tttgcaattagatagtaacttcattgactatagctttaatgtgtctacttcttcttccatactgcaagctgcctgagatcaggggtggtgtctcccta
gttccccgggaatatccagggctggcacagggagctgttccataaggcagcgggcactggagtcagagaaacctggacgtgaatcctggcctgac
cgctacttagatgtgcgggtttggggtatttactcagccttcattttctccatctgatcatggagacaatagtgtctccccagtggattgtgggagga
ttttatgagtctggattgtggtgaggattttatgagtctggcagtgaatttaccaagagctagatgttattgttctcaaatattttgctgaatgagtgaa
tgaatgaatgagtgaatgaatgagggcccagctgaccttgtggaatgagtaggtgaaacaggaaatactcaatttccagatcctcttgtgcatcctc
cttgctctcgcttagccccatgaccctaatttgacccccttttctcccctgcattcagggtcaccagcatgaatgctcggcaggcagctcccaagacc
acccgccccaggtgcagccacctacaccccggggaaggggaagagcaggagctccactatgcctccctcagcttccagggcctgaggctctgggag
cctgcggaccaggaggccccagcaccaccgagtactcggagatcaagatccacacaggacagccccctgaggggcccaggcttttgggcttcaattgga
gagggagatgtcaggggatggttccaaagtgaagaggtctccatggcaacaggacaccagcaagtgtgtgggagtcgcactggtgtgacggccagaact
ggactcagatttcagccccatccccaatgaagagcttgagtttgaagattatacttttttttgagacagggtctgactctgtcctccaggcagagtcc
agtggtgcaatctcagctcactgtagcctcaacctgccaggttgaagtgagcctcccattttcagcctcccaagtagctgggactacaattgtgagcca
ccatgccaggctcattgttatatttttagtagagacaggttttgccatgtttccctggctggtctcagactcctgggctcaagcaatctgcccgcct
ctgcctcccaaagtgctgggattacagacgtgagccaccacagctggctgaagattatactttcaattcagagcgagtttgaagatgacactttgagg
catcgtgtctatggttcattactacagaagctctctgatgtgtaaagcaccaaggcagggaggtgctctccagaacgagaag
ccagtcctggagtgttctgctgcaactgccattccccgttgatgaccatgctcttccttcagaagagggagagtgagaggaccaagtccaagtggtt
cccatttgaacatttaaaaaaaaaaaaaaggctgggcatggtggctcacgcctgtaatctcaacactttgggaggctgaagtgggtggatcacaagtc
aggagttcaagaccagcctgggcaagatggtgaaaccccatctctactaaaaatacaaaaattagccgggcatggtggcgggcgcctaaaatcccagc
tactcggagactaggcagagaattggttgaacccggggaggtggaggttgcagtgagccgagatcgtcccactgcactccagcctgggcaacagagtg
agactctgtttctaaataaataaatgaa

SEQUENCES
All polypeptide sequences are presented N-terminal to C-terminal unless otherwise noted.

Human Siglec-14 genomic sequence (SEQ ID NO: 20)
```
actcaccctccggcttcctgtcggggctttctcagcccacccacgtttggacatttggagcatttccttccctgacagccggacctgggactgggc
tggggccctggcggatggagacatgctgcccctgctgctgctgcccctgctgtgggggggtgagtgagctgagggaggagggacaggcacagggtga
gaaggggggctggagctgcagctgagcttctgtgtccccccagggtccctgcaggagaagccagtgtacgagctgcaagtgcagaagtcggtgacggt
gcaggagggcctgtgcgtccttgtgccctgctccttctcttacccctggagatcctggtattcctcctccccactctacgtctactggttccgggacg
gggagatcccatactacgctgaggttgtggccacaaacaacccagacagaagagtgaagccagagacccagggccgattccgcctcctttggggatgtc
cagaagaagaactgctccctgagcatcggagatgccagaatggaggacacgggaagctatttcttccgcgtggagagaggaaggggatgtaaaatatag
ctaccaacagaataagctgaacttggaggtgacaggtatggcaggaaccctaggagaggaccctgggacgtggagaccccgtatgagaacagggaca
ggagttgggcaggggcggctggaggaggtgtaggacttggggcaggtcggggcctgaggcctggccactctcgggtcacaccttacgtcctcaagcc
cctggggcccaggtatctccctgtctcctcctcagccctgatagagaaacccgacatccacttctggagcctctggagtccggccgccccacaaggc
tgagctgcagccttccaggatcctgtgaagcgggaccacctctcacattcctggacggggaatgccctcagcccctggaccccgagaccaccgc
tcctcggagctcaccctcaccccaggcccgaggaccatggcaccaacctcacctgtcaggtgaaacgcaaggagctcaggtgaccacggagagaac
tgtccagctcaatgtctcctgtgagtggtgctggggacacagctgagtcccaagggcagtgggagtgaggggggtgtgtgtgtgtgtgtgtgt
gtgtagaagagagagagagaaagagaatgataaccagggaaaactcgtgtgtgggcaggaaggacagcggtccccacctggtgggtttctgtggcccc
tcctggggtccctcccgggaccacgcccatccctcttgtcacctctgaagctggtgctgtatctttctatcccagatgctccacagaacctcgccatc
agcatcttcttcagaaatggcacaggcacaggtaggaaagaccctcttccctctggggctgtgatgggagccttctattagctcagggttcagcattg
ggagaggagaccctccctcaccctcagccctgggtctgggtccttcctgctcccaaccccccaatcccagtcactaagatcttgcacgaacagacc
tagtatttcttttggcttctccttttctctgctctcttttttcagattttattttttcattgtgagaaaatacacatagcacaaaatttgtcatcttag
ccattttaaagagtacagttcagcagtgtttaaatgtgttcacattgttgcaaaaccaaactgcagagctccttttatctggcaaaactgaaactttgt
acccactgaacagcgactttccacttccccctcctgccaccgagcagtcaccattctacttttctgtctctgtgagtttgagtactcaggacacgctg
ttcccttttcttgaatttctgcctgctccgatgtcctctgatgcatgccctgcttcatctctaactgatcgtcctttttgggagccttcgactttccc
acctcccacagctctgtcccagaaccagttcttccctccacattcctgactaatccgatctctccttgacctctgctgatgcctcccacaactt
atatccagccctttctctgaggcacagatctgcacatttagccacctccctcggatgcttctcggctcctccttccctgttgatcccagggctgttct
ggacatcgctgtagacagcaccctttctcatcagctgtttcatgagtccgcaagtcttaacacctttacttcaccaatcatcacttccctcctcatcc
ccttggttccaggcccagctcaagtctcgtgctcaaccctggcccattgcccagcctcctcccagcctccctgcctcctatcccacttctctccagt
ccgggacctacttggctccagcaggatcttttctagatccagtgctaactctgtttcccttgcttatagccccctcttgctttccaggataaagcccaa
ggccctcaatctggcacccaatgctccaaaagatctgagcctgcttctacctccattatcgtgtcttgggagctctgggtcctccctgacaggttgcg
gatctaggagcctcttcctcgtctgcctgtctcagttcttggcacgtctgcacctgagctgccatccacttctccttaatgtgagaactcctcctc
atctgtcttttctcagctcagccaccttctttctggtagcctgacctgatcaccaagtcctcatcctttcacccatgactagcccattctcagcactc
accacacagtcttgtctttcttcttgcagctcagtgggaggaatgagggagaatttgggcctcccagctccactcacctggctgtgcttctctcttccca
gccctgcggatcctgagcaatggcatgtcggtgcccatccaggagggccagtccctgttcctgcctgcgcacagttgacagcaaccccctgcctcact
gagctggttccggggagggaaaagccctcaatccttcccagacctcaatgtctgggacccctggagctgcctaacataggagctagagagggagggaat
tcacctgccgggttcagcatccgctgggctcccagcacctgtccttcatcctttctgtgcagagtgagttgcaggacaggtgctgagggtagacagcc
cggtgaggtattcaggttggtgggagggactgaggcctggtaacagcaccttaccttctcctttctcccaggaagctcctccttcctgcatatgtgtaa
ctgagaaacagcagggctcctggccccctcgtcctcacccctgatcagggggggctctcatggggggctggcttcctcctcacctatggcctcacctggatc
tactataccaggtgagccggactgcctgtctccaggaagctcctgagttccaggtggggctgagctgtcctgcccccaggacagctcagccccacctgg
aattagaactgaagtggctggtgctgatctgaggccatgttggctctgcaggtgtggaggccccagcagagcagggctgagaggcctggctgagcc
cctcccgctcaagacagaactgaggtgtggacacttagccctgtgggacacatgcaggacatcactgtcagctctttctggaagctcacatcccact
gactaccctcttttccttcctgcccataccatctacttattccctctgcttgtgagtcttgccccaccacacctgcatccccatctgcacccca
tccctctccacctgccatctatccctctccatccaccatctccagcctgtgaaggggaatgtacttctcggtcttataccccattaccattaccca
aaagttacctttttttttttttttttttgagacagagtctcactctgttgcacaggctggagttcagtggcacaatctccgttcactgcaacctc
cacctctgggttcaagcaattctcctgcctcagcctccctagtagctgggattacaggtgcctgccaccacatccagttaatttttttttttttgtat
gttagtagagatgggtttaccatgttggccaggtctgaaactcctgacctcaagcaatccactgcattggcctcccaaagtgctggcattacaggt
atgagccaccgtgcctggctgccaaaagttaccttcttaacacttgaatttctggtctcctcagcttcctatccataggacagagaggcagcat
ttgttttccagttaaaactctacctcattgtgattattatccaatacaattgttacaaaataagtaaaactttttatgaaacaatacaacataactgat
tttactctttaa
```

Human Siglec-16 genomic sequence (SEQ ID NO: 21)
```
actgcccctccaccaggcttcctgctggaggagtttccttcccagccaggccggcccagaagccagatggtcccgggacaggcccagccccagagccc
agagatgctgctgctgcccctgctgctgcccgtgctgggggcgggtgagtgggtcggtggctgggggtcccaggcaggggctggggctgccgctgagc
ctctgcatctcccccaggggtccctgaacaaggatcccccagttacagtcttcaagtgcagaggcaggtgccggtgccggagggcctgtgtgtcacgtgtc
ttgcaacctctcctaccccgggatggctgggacgagtctactgctgcttatgcgtactggttcaaaggatggaccagcccaaagacgggtgctcctg
tggccactaacaaccagagtcgagaggtggaaatgagcacccgggaccgattccagctcactgggatcccggcaaaggggagctgctccttggtgatc
agagacgcgcagagggaggatgaggcatggtacttctttcgggtggagagaggaagccgtgtgagacatagtttcgtgaacaatttgttctaaaagta
acaggtatggaatggggtgggaaccccctgcctgtcacactgggagagggaccctggggacaggctatgggctgagcagagagggcttcagggacccct
gcagcacaagaattccccacccggtctctgcccagccctgactcagaagcctgatgtctacatccccgagaccctggagcccggggcagccggtgac
ggtcatctgtgtgtttaactgggctttcaagaaatgtccagccccttcttttctcctggacgggggctgccctctccctagaagaaccagaccaagca
cctcccacttctcagtgctcagcttcacgcccagccccaggaccacgacaccgacctcacctgccatgtggacttctccagaaagggtgtgagcgca
cagaggaccgtccgactccgtgtggcctgtgagtgtggcctgggaggtgggggcgtgcagacagcccgtgggtgggagggtgaggagccagcag
gacagtgagtggctcccagctcaggagcatccagggagagggagctgcagccctggcagcctcagccctggaggggatggaaatggcgtc
tgatcctctgtccacatgtgtgagccctcgagctggttgtcacttgtccatcctgggatgttccacttttcttttccctgagggagtttttttccaggt
gtgaggaacaaattgtccctccctgaagccagctcacaatcttgttgcagatgccccaaagacccttattatcagcatttcacatgacaacacgtcag
gtactgagggccttcgggctggggctgggccagtcctctttagggatgaaaaggcttcagggggggtgagggggatgtggtcctctttgcagccccct
cccacccattctctctctccacccccaccctctctctttccctgtcttcagccctggaactccaggggaaacgtcatatatctggaagttcagaaaggc
cagttcctgcggctcctctgtgctgctgacagccagccccctgccacgctgagctgggtcctgcagagcagagtcctctcctcgtcccaccctgggg
cccagaaccctggggctggagctgcgtggggtaaggggccgggagttcagggcgctcacacctgccgagcggagaacaggcttggctcccagcagcgag
ccctggacctctctgtgcagtgtgagtgtgcctagcaggggcctggagtccattgggagggcagaggggatacaggggctgggctcagtgtcccagagc
tgaggggtcttgaaccccaggcctcggggactgaccttcttacctgtgtagaccctcatgcagtttgtgtctgggactcagtgggtgattctgccct
gcccttctatcccacccacttccccaccctcagtctccaggacgcttcccttttgcccagagggaagtccctggtccgtctagagccggtccctgtct
ccattttcagatcctccagagaacctgagagtgatggtttcccaagcaaacaggacaggtaggaaaaggagacagagggccctccagtgccaa
attggggcccaggtgtctggagggtcccatgcaggcgggtccctgagccctgagctgcacgtcgattctgcctcttccttccctagtcctggaaaa
cctgaggaacggcacatccctccgggtcctggagggccaaagcctgcgtctggtctgtgtcacacacagcagcccccagccaggctgagctggaccc
ggtggggacagaccgtgggccctcccagccctcagaccctggggtcctggagctgcctcgggttcaaatggagcacgaaggagagttcacctgccac
gctcggcacccgctgggctcccagcgcgtctctctcagcttctccgtgcactgtgagtggggaaaggggacacctgggtcccaggaaggggcccctgc
tgagtcctgtcctccctcccacagagccccccagctgctgggaccctcctgctcctgggaggctgagggtctgcactgcagctgctcctcccaaggc
```

SEQUENCES
All polypeptide sequences are presented N-terminal to C-terminal unless otherwise noted.

```
agcccggccccgtctctgccctggtggattggtggggagctgcggagggaaacagcagccaggactacttcaaggtcaccccagctcagccgggccc
tgggccaacagctccctgatcctccaaggggggggcttggctccaacctcaggctcacctttgaggcccagaaacgtccatggggcccagagctctctga
ttcctggcggacagtcagggtataggtggggaggcctgggctcaccaggtcctgcatccaggatgtaggaagggcctggagaaccaagttgcaata
agagaggaaggattcggaagtgtggtttagaaggtgaatgggccttatcccacttttccaggcaaatcagggcccatgacggggtggttctggtggc
tgttggggaggtggctatgaagatcctgcttctctgcctctgcctcatcctcctcaggtgagccctgccccagggaccaaggggaggggcggagaggg
caaaggatacaccgctgaatcccagaatctcaatcctgggggtacttggacagttaaagaggcctgtggccaggcagaggctgagttgatcgtgatga
ttccacacgggccagtgttgtcagtccccaactctggaccaatgtccaggctggggaggttcctgcttgtatcagggaggtcctgggggctaggcctg
ctctctctgcctcagtcccctccaaccccttagcagggcacaggggaggtgagtctgctgccctcttcaccccatccagccacactcacaggccctgg
tctcttcacccagagtgaggtcttgcaggaggaaggcagcaagggcagcattgggcatgaggctgcagacgctgtcacggactaatctccaggtgag
tgtcgtgggcctcttaccctccaacatcccgctggacacctcccctcgatggcccaaggactgctccactcaacttggccataactgactcatcac
ctccctttccaagcccacttctcttgttgagagcccatccctctgatgacatggtagcccatctctaacgtcagaacccgggtgtgggtgtccacc
ttgacctccctcctcctccagatcccaaaaatcactagcacttgtccctcctcctaagtacaggtcaccttggagccctttctccatcctggccc
ggtcatgcctgggcctcacctcttccctggtcgctgaacccacctcacctcttgcctccatctctcccaacagactccagactgcttccagatgcctc
ctcatccagttc
```

What is claimed is:

1. A transgenic mouse whose genome comprises two or more human genes, wherein the two or more human genes are selected from the group consisting of CD33, Siglec-5, Siglec-7, Siglec-9, Siglec-11, Siglec-14, and Siglec-16, wherein the two or more human genes are expressed in one or more cells of the transgenic mouse, and wherein the one or more cells are selected from the group consisting of myeloid cells, natural killer (NK) cells, T cells, microglia, and any combination thereof.

2. The transgenic mouse human animal of claim 1, wherein:

the genome comprises the human genes Siglec-5 and Siglec-14;
the genome comprises the human genes Siglec-11 and Siglec-16;
the genome comprises the human genes CD33, Siglec-7, and Siglec-9; or
the genome comprises the human genes CD33, Siglec-5, Siglec-7, Siglec-9, Siglec-11, Siglec-14, and Siglec-16.

3. The transgenic mouse of claim 1, wherein:
the two or more human genes comprise all intronic and exonic sequences of one or more of the two or more human genes;
the two or more human genes comprise at least one flanking sequence at the 5' and/or 3' end of one or more of the two or more human genes;
the two or more human genes comprise at least one flanking sequence at the 5' and/or 3' end of one or more of the two or more human genes, and the flanking sequence is at least 10,000 base pairs in length;
the two or more human genes comprise at least one flanking sequence at the 5' and/or 3' end of one or more of the two or more human genes, and the flanking sequence comprises one or more human transcriptional regulatory elements; or
the two or more human genes comprise at least one flanking sequence at the 5' and/or 3' end of one or more of the two or more human genes, the flanking sequence comprises one or more human transcriptional regulatory elements, and the one or more human transcriptional regulatory elements directs expression of one or more of the two or more human genes.

4. The transgenic mouse of claim 1, wherein:
the human CD33 gene encodes a polypeptide at least 95% identical to a polypeptide encoded by the nucleic acid sequence of SEQ ID NO: 15, or encodes a polypeptide at least 95% identical to a sequence selected from the group consisting of SEQ ID NOS: 1-3;
the human Siglec-5 gene encodes a polypeptide at least 95% identical to a polypeptide encoded by the nucleic acid sequence of SEQ ID NO: 16, or encodes a polypeptide at least 95% identical to SEQ ID NO: 4;
the human Siglec-7 gene encodes a polypeptide at least 95% identical to a polypeptide encoded by the nucleic acid sequence of SEQ ID NO: 17, or encodes a polypeptide at least 95% identical to a sequence selected from the group consisting of SEQ ID NOS: 5-8;
the human Siglec-9 gene encodes a polypeptide at least 95% identical to a polypeptide encoded by the nucleic acid sequence of SEQ ID NO: 18, or encodes a polypeptide at least 95% identical to SEQ ID NO: 9 or SEQ ID NO: 10;
the human Siglec-11 gene encodes a polypeptide at least 95% identical to a polypeptide encoded by the nucleic acid sequence of SEQ ID NO: 19, or encodes a polypeptide at least 95% identical to SEQ ID NO: 11 or SEQ ID NO: 12;
the human Siglec-14 gene encodes a polypeptide at least 95% identical to a polypeptide encoded by the nucleic acid sequence of SEQ ID NO: 20, or encodes a polypeptide at least 95% identical to SEQ ID NO: 13; or
the human Siglec-16 gene encodes a polypeptide at least 95% identical to a polypeptide encoded by the nucleic acid sequence of SEQ ID NO: 21, or encodes a polypeptide at least 95% identical to SEQ ID NO: 14.

5. The transgenic mouse of claim 1, wherein:
the myeloid cells are selected from the group consisting of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof;
the NK cells are selected from the group consisting of M1 NK cells, activated M1 NK cells, M2 NK cells, and any combination thereof;
the T cells are selected from the group consisting of T helper cells, cytotoxic T cells, regulatory T cells (Tregs), and any combination thereof; or
the microglia are selected from the group consisting of brain microglia microglial, M1 microglia, activated M1 microglia, M2 microglia, and any combination thereof.

6. The transgenic mouse of claim 1, wherein expression of the two or more human genes in the one or more cells of the transgenic mouse recapitulates the expression pattern of the two or more human genes in a corresponding human cell.

7. The transgenic mouse of claim 1, wherein the two or more human genes are co-expressed, and co-expression of the two or more human genes suppresses one or more myeloid immune cell functions.

8. The transgenic mouse of claim 7, wherein the one or more myeloid immune cell functions are selected from the group consisting of:
i. phagocytosis;
ii. antigen presentation;
iii. immune cell recruitment;
iv. immune cell maturation, migration, proliferation, differentiation, and/or survival;
v. modulation of adaptive immune cells such as B cells and T cells;
vi. expression and/or secretion of one or more cytokines and/or chemokines;
vii. tumor infiltration, tumor cell recognition, and/or tumor cell killing;
viii. releasing granules (degranulation) or neutrophil extracellular traps (NETs);
ix. anti-parasitic activities;
x. bactericidal activities;
xi. clearance of cellular debris and/or protein aggregates; and
xii. any combination thereof.

9. The transgenic mouse of claim 1, wherein expression of the two or more human genes humanizes the Siglec repertoire on the one or more cells of the transgenic mouse.

10. The transgenic mouse of claim 1, wherein the transgenic mouse comprises a genome comprising one or more non-functional murine genes, wherein the one or more non-functional murine genes are selected from the group consisting of murine CD33, murine Siglec-5, murine Siglec-7, murine Siglec-9, murine Siglec-11, and any combination thereof.

11. The transgenic mouse of claim 1, wherein the transgenic mouse is predisposed to develop one or more diseases, or the transgenic mouse is treated or interbred to generate one or more mouse disease models.

12. A method for recapitulating a human Siglec immune system in a mouse, the method comprising generating a transgenic mouse whose genome comprises two or more human genes, wherein the two or more human genes are selected from the group consisting of CD33, Siglec-5, Siglec-7, Siglec-9, Siglec-11, Siglec-14, and Siglec-16, wherein the two or more human genes are coordinately expressed in one or more cells of the transgenic mouse, and wherein the one of more cells selected from the group consisting of myeloid cells, natural killer (NK) cells, T cells, microglia, and any combination thereof.

13. A method of generating a mouse disease model with a human Siglec repertoire, the method comprising introducing one or more genetic determinants of a disease into the genome of the mouse of claim 1.

14. The method of claim 13, wherein:
the one or more genetic determinants are introduced into the genome of the mouse by mating;
the one or more genetic determinants are introduced into the genome of the mouse by mating with a disease model mouse; or
the one or more genetic determinants are introduced into the genome of the mouse by genetic manipulation.

15. The method of claim 13, wherein the genetic determinant is a polynucleotide encoding a polypeptide comprising one or more mutations, wherein the polypeptide is selected from the group consisting of amyloid precursor protein (APP), presenilin 1 (PS1), presenilin 2 (PS2), alpha-synuclein, serine/threonine-protein kinase PINK1, parkin, leucine-rich repeat serine/threonine protein kinase 2 (LRRK2), protein deglycase (DJ-1), probable cation-transporting ATPase 13A2 (ATP13A2), superoxide dismutase (SOD1), TAR DNA-binding protein 43 (TDP-43), RNA-binding protein FUS, huntingtin (HTT), translation endoplasmic reticulum ATPase (VCP), microtubule-associated protein tau (MAPT), progranulin, protein C9orf72, charged multivesicular body protein 2b (CHMP2B), and any combinations thereof.

16. A transgenic mouse whose genome comprises the human genes CD33, Siglec-7, and Siglec-9, wherein the human genes CD33, Siglec-7, and Siglec-9 are expressed in one or more cells of the transgenic mouse, and wherein the one or more cells are selected from the group consisting of myeloid cells, natural killer (NK) cells, T cells, microglia, and any combination thereof.

17. The transgenic mouse of claim 16, wherein the human CD33 gene encodes a polypeptide at least 95% identical to a polypeptide encoded by the nucleic acid sequence of SEQ ID NO:15, or encodes a polypeptide at least 95% identical to a sequence selected from the group consisting of SEQ ID NOS:1-3; the human Siglec-7 gene encodes a polypeptide at least 95% identical to a polypeptide encoded by the nucleic acid sequence of SEQ ID NO:17, or encodes a polypeptide at least 95% identical to a sequence selected from the group consisting of SEQ ID NOS:5-8; and the human Siglec-9 gene encodes a polypeptide at least 95% identical to a polypeptide encoded by the nucleic acid sequence of SEQ ID NO:18, or encodes a polypeptide at least 95% identical to SEQ ID NO:9 or SEQ ID NO:10.

18. The transgenic mouse of claim 16, wherein the transgenic mouse is predisposed to develop one or more diseases, or the transgenic mouse is treated or interbred to generate one or more mouse disease models.

* * * * *

SEQUENCE LISTING

<160> NUMBER OF SEQ ID NOS: 22

<210> SEQ ID NO 1
<211> LENGTH: 364
<212> TYPE: PRT
<213> ORGANISM: Homo sapiens

<400> SEQUENCE: 1

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
        50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly

```
                        245                 250                 255
Val Val His Gly Ala Ile Gly Gly Ala Gly Val Thr Ala Leu Leu Ala
                260                 265                 270

Leu Cys Leu Cys Leu Ile Phe Phe Ile Val Lys Thr His Arg Arg Lys
            275                 280                 285

Ala Ala Arg Thr Ala Val Gly Arg Asn Asp Thr His Pro Thr Thr Gly
        290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 2
<211> LENGTH: 310
<212> TYPE: PRT
<213> ORGANISM: Homo sapiens

<400> SEQUENCE: 2

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
        50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
210                 215                 220

Arg Thr Ile Gln Leu Asn Val Thr Tyr Val Pro Gln Asn Pro Thr Thr
                225                 230                 235                 240

Gly Ile Phe Pro Gly Asp Gly Ser Gly Lys Gln Glu Thr Arg Ala Gly
            245                 250                 255
```

```
Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Val Arg
305                 310

<210> SEQ ID NO 3
<211> LENGTH: 237
<212> TYPE: PRT
<213> ORGANISM: Homo sapiens

<400> SEQUENCE: 3

Met Pro Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
                20                  25                  30

Asn Leu Thr Cys Ser Val Ser Trp Ala Cys Glu Gln Gly Thr Pro Pro
            35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
        115                 120                 125

Gly Val Val His Gly Ala Ile Gly Gly Ala Gly Val Thr Ala Leu Leu
    130                 135                 140

Ala Leu Cys Leu Cys Leu Ile Phe Phe Ile Val Lys Thr His Arg Arg
145                 150                 155                 160

Lys Ala Ala Arg Thr Ala Val Gly Arg Asn Asp Thr His Pro Thr Thr
                165                 170                 175

Gly Ser Ala Ser Pro Lys His Gln Lys Lys Ser Lys Leu His Gly Pro
            180                 185                 190

Thr Glu Thr Ser Ser Cys Ser Gly Ala Ala Pro Thr Val Glu Met Asp
        195                 200                 205

Glu Glu Leu His Tyr Ala Ser Leu Asn Phe His Gly Met Asn Pro Ser
    210                 215                 220

Lys Asp Thr Ser Thr Glu Tyr Ser Glu Val Arg Thr Gln
225                 230                 235

<210> SEQ ID NO 4
<211> LENGTH: 551
<212> TYPE: PRT
<213> ORGANISM: Homo sapiens

<400> SEQUENCE: 4

Met Leu Pro Leu Leu Leu Leu Pro Leu Leu Trp Gly Gly Ser Leu Gln
1               5                   10                  15

Glu Lys Pro Val Tyr Glu Leu Gln Val Gln Lys Ser Val Thr Val Gln
                20                  25                  30
```

-continued

Glu Gly Leu Cys Val Leu Val Pro Cys Ser Phe Ser Tyr Pro Trp Arg
              35                  40                  45

Ser Trp Tyr Ser Ser Pro Pro Leu Tyr Val Tyr Trp Phe Arg Asp Gly
 50                  55                  60

Glu Ile Pro Tyr Tyr Ala Glu Val Val Ala Thr Asn Asn Pro Asp Arg
 65                  70                  75                  80

Arg Val Lys Pro Glu Thr Gln Gly Arg Phe Arg Leu Leu Gly Asp Val
                 85                  90                  95

Gln Lys Lys Asn Cys Ser Leu Ser Ile Gly Asp Ala Arg Met Glu Asp
              100                 105                 110

Thr Gly Ser Tyr Phe Phe Arg Val Glu Arg Gly Arg Asp Val Lys Tyr
              115                 120                 125

Ser Tyr Gln Gln Asn Lys Leu Asn Leu Glu Val Thr Ala Leu Ile Glu
 130                 135                 140

Lys Pro Asp Ile His Phe Leu Glu Pro Leu Glu Ser Gly Arg Pro Thr
 145                 150                 155                 160

Arg Leu Ser Cys Ser Leu Pro Gly Ser Cys Glu Ala Gly Pro Pro Leu
                 165                 170                 175

Thr Phe Ser Trp Thr Gly Asn Ala Leu Ser Pro Leu Asp Pro Glu Thr
              180                 185                 190

Thr Arg Ser Ser Glu Leu Thr Leu Thr Pro Arg Pro Glu Asp His Gly
              195                 200                 205

Thr Asn Leu Thr Cys Gln Met Lys Arg Gln Gly Ala Gln Val Thr Thr
 210                 215                 220

Glu Arg Thr Val Gln Leu Asn Val Ser Tyr Ala Pro Gln Thr Ile Thr
225                 230                 235                 240

Ile Phe Arg Asn Gly Ile Ala Leu Glu Ile Leu Gln Asn Thr Ser Tyr
                 245                 250                 255

Leu Pro Val Leu Glu Gly Gln Ala Leu Arg Leu Leu Cys Asp Ala Pro
              260                 265                 270

Ser Asn Pro Pro Ala His Leu Ser Trp Phe Gln Gly Ser Pro Ala Leu
              275                 280                 285

Asn Ala Thr Pro Ile Ser Asn Thr Gly Ile Leu Glu Leu Arg Arg Val
 290                 295                 300

Arg Ser Ala Glu Glu Gly Gly Phe Thr Cys Arg Ala Gln His Pro Leu
305                 310                 315                 320

Gly Phe Leu Gln Ile Phe Leu Asn Leu Ser Val Tyr Ser Leu Pro Gln
                 325                 330                 335

Leu Leu Gly Pro Ser Cys Ser Trp Glu Ala Glu Gly Leu His Cys Arg
              340                 345                 350

Cys Ser Phe Arg Ala Arg Pro Ala Pro Ser Leu Cys Trp Arg Leu Glu
              355                 360                 365

Glu Lys Pro Leu Glu Gly Asn Ser Ser Gln Gly Ser Phe Lys Val Asn
 370                 375                 380

Ser Ser Ser Ala Gly Pro Trp Ala Asn Ser Ser Leu Ile Leu His Gly
385                 390                 395                 400

Gly Leu Ser Ser Asp Leu Lys Val Ser Cys Lys Ala Trp Asn Ile Tyr
                 405                 410                 415

Gly Ser Gln Ser Gly Ser Val Leu Leu Leu Gln Gly Arg Ser Asn Leu
              420                 425                 430

Gly Thr Gly Val Val Pro Ala Ala Leu Gly Gly Ala Gly Val Met Ala
              435                 440                 445

Leu Leu Cys Ile Cys Leu Cys Leu Ile Phe Phe Leu Ile Val Lys Ala

```
                    450                 455                 460
Arg Arg Lys Gln Ala Ala Gly Arg Pro Glu Lys Met Asp Asp Glu Asp
465                 470                 475                 480

Pro Ile Met Gly Thr Ile Thr Ser Gly Ser Arg Lys Lys Pro Trp Pro
                485                 490                 495

Asp Ser Pro Gly Asp Gln Ala Ser Pro Pro Gly Asp Ala Pro Pro Leu
            500                 505                 510

Glu Glu Gln Lys Glu Leu His Tyr Ala Ser Leu Ser Phe Ser Glu Met
                515                 520                 525

Lys Ser Arg Glu Pro Lys Asp Gln Glu Ala Pro Ser Thr Thr Glu Tyr
            530                 535                 540

Ser Glu Ile Lys Thr Ser Lys
545                 550

<210> SEQ ID NO 5
<211> LENGTH: 467
<212> TYPE: PRT
<213> ORGANISM: Homo sapiens

<400> SEQUENCE: 5

Met Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
                20                  25                  30

Ser Val Thr Val Gln Glu Gly Met Cys Val His Val Arg Cys Ser Phe
            35                  40                  45

Ser Tyr Pro Val Asp Ser Gln Thr Asp Ser Asp Pro Val His Gly Tyr
50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
                100                 105                 110

Ala Arg Met Ser Asp Ala Gly Arg Tyr Phe Phe Arg Met Glu Lys Gly
                115                 120                 125

Asn Ile Lys Trp Asn Tyr Lys Tyr Asp Gln Leu Ser Val Asn Val Thr
130                 135                 140

Ala Leu Thr His Arg Pro Asn Ile Leu Ile Pro Gly Thr Leu Glu Ser
145                 150                 155                 160

Gly Cys Phe Gln Asn Leu Thr Cys Ser Val Pro Trp Ala Cys Glu Gln
                165                 170                 175

Gly Thr Pro Pro Met Ile Ser Trp Met Gly Thr Ser Val Ser Pro Leu
            180                 185                 190

His Pro Ser Thr Thr Arg Ser Ser Val Leu Thr Leu Ile Pro Gln Pro
            195                 200                 205

Gln His His Gly Thr Ser Leu Thr Cys Gln Val Thr Leu Pro Gly Ala
        210                 215                 220

Gly Val Thr Thr Asn Arg Thr Ile Gln Leu Asn Val Ser Tyr Pro Pro
225                 230                 235                 240

Gln Asn Leu Thr Val Thr Val Phe Gln Gly Glu Gly Thr Ala Ser Thr
                245                 250                 255

Ala Leu Gly Asn Ser Ser Ser Leu Ser Val Leu Glu Gly Gln Ser Leu
                260                 265                 270
```

-continued

```
Arg Leu Val Cys Ala Val Asp Ser Asn Pro Pro Ala Arg Leu Ser Trp
            275                 280                 285

Thr Trp Arg Ser Leu Thr Leu Tyr Pro Ser Gln Pro Ser Asn Pro Leu
290                 295                 300

Val Leu Glu Leu Gln Val His Leu Gly Asp Glu Gly Glu Phe Thr Cys
305                 310                 315                 320

Arg Ala Gln Asn Ser Leu Gly Ser Gln His Val Ser Leu Asn Leu Ser
            325                 330                 335

Leu Gln Gln Glu Tyr Thr Gly Lys Met Arg Pro Val Ser Gly Val Leu
        340                 345                 350

Leu Gly Ala Val Gly Gly Ala Gly Ala Thr Ala Leu Val Phe Leu Ser
    355                 360                 365

Phe Cys Val Ile Phe Ile Val Val Arg Ser Cys Arg Lys Lys Ser Ala
370                 375                 380

Arg Pro Ala Ala Asp Val Gly Asp Ile Gly Met Lys Asp Ala Asn Thr
385                 390                 395                 400

Ile Arg Gly Ser Ala Ser Gln Gly Asn Leu Thr Glu Ser Trp Ala Asp
            405                 410                 415

Asp Asn Pro Arg His His Gly Leu Ala Ala His Ser Ser Gly Glu Glu
        420                 425                 430

Arg Glu Ile Gln Tyr Ala Pro Leu Ser Phe His Lys Gly Glu Pro Gln
    435                 440                 445

Asp Leu Ser Gly Gln Glu Ala Thr Asn Asn Glu Tyr Ser Glu Ile Lys
450                 455                 460

Ile Pro Lys
465

<210> SEQ ID NO 6
<211> LENGTH: 374
<212> TYPE: PRT
<213> ORGANISM: Homo sapiens

<400> SEQUENCE: 6

Met Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
            20                  25                  30

Ser Val Thr Val Gln Glu Gly Met Cys Val His Val Arg Cys Ser Phe
        35                  40                  45

Ser Tyr Pro Val Asp Ser Gln Thr Asp Ser Asp Pro Val His Gly Tyr
    50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Phe Arg Met Glu Lys Gly
        115                 120                 125

Asn Ile Lys Trp Asn Tyr Lys Tyr Asp Gln Leu Ser Val Asn Val Thr
    130                 135                 140

Asp Pro Pro Gln Asn Leu Thr Val Thr Val Phe Gln Gly Glu Gly Thr
145                 150                 155                 160

Ala Ser Thr Ala Leu Gly Asn Ser Ser Ser Leu Ser Val Leu Glu Gly
                165                 170                 175
```

```
Gln Ser Leu Arg Leu Val Cys Ala Val Asp Ser Asn Pro Pro Ala Arg
            180                 185                 190

Leu Ser Trp Thr Trp Arg Ser Leu Thr Leu Tyr Pro Ser Gln Pro Ser
            195                 200                 205

Asn Pro Leu Val Leu Glu Leu Gln Val His Leu Gly Asp Gly Glu
210                 215                 220

Phe Thr Cys Arg Ala Gln Asn Ser Leu Gly Ser Gln His Val Ser Leu
225                 230                 235                 240

Asn Leu Ser Leu Gln Gln Glu Tyr Thr Gly Lys Met Arg Pro Val Ser
            245                 250                 255

Gly Val Leu Leu Gly Ala Val Gly Gly Ala Gly Ala Thr Ala Leu Val
            260                 265                 270

Phe Leu Ser Phe Cys Val Ile Phe Ile Val Val Arg Ser Cys Arg Lys
            275                 280                 285

Lys Ser Ala Arg Pro Ala Ala Asp Val Gly Asp Ile Gly Met Lys Asp
            290                 295                 300

Ala Asn Thr Ile Arg Gly Ser Ala Ser Gln Gly Asn Leu Thr Glu Ser
305                 310                 315                 320

Trp Ala Asp Asp Asn Pro Arg His His Gly Leu Ala Ala His Ser Ser
                    325                 330                 335

Gly Glu Glu Arg Glu Ile Gln Tyr Ala Pro Leu Ser Phe His Lys Gly
                    340                 345                 350

Glu Pro Gln Asp Leu Ser Gly Gln Glu Ala Thr Asn Asn Glu Tyr Ser
                    355                 360                 365

Glu Ile Lys Ile Pro Lys
    370

<210> SEQ ID NO 7
<211> LENGTH: 145
<212> TYPE: PRT
<213> ORGANISM: Homo sapiens

<400> SEQUENCE: 7

Met Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
            20                  25                  30

Ser Val Thr Val Gln Glu Gly Met Cys Val His Val Arg Cys Ser Phe
            35                  40                  45

Ser Tyr Pro Val Asp Ser Gln Thr Asp Ser Asp Pro Val His Gly Tyr
    50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Phe Arg Met Glu Lys Gly
            115                 120                 125

Asn Ile Lys Trp Asn Tyr Lys Tyr Asp Gln Leu Ser Val Asn Val Thr
            130                 135                 140

Glu
145
```

```
<210> SEQ ID NO 8
<211> LENGTH: 145
<212> TYPE: PRT
<213> ORGANISM: Homo sapiens

<400> SEQUENCE: 8

Met Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
            20                  25                  30

Ser Val Thr Val Gln Glu Gly Met Cys Val His Val Arg Cys Ser Phe
        35                  40                  45

Ser Tyr Pro Val Asp Ser Gln Thr Asp Ser Asp Pro Val His Gly Tyr
    50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Phe Arg Met Glu Lys Gly
        115                 120                 125

Asn Ile Lys Trp Asn Tyr Lys Tyr Asp Gln Leu Ser Val Asn Val Thr
    130                 135                 140

Gly
145

<210> SEQ ID NO 9
<211> LENGTH: 463
<212> TYPE: PRT
<213> ORGANISM: Homo sapiens

<400> SEQUENCE: 9

Met Leu Leu Leu Leu Leu Pro Leu Leu Trp Gly Arg Glu Arg Ala Glu
1               5                   10                  15

Gly Gln Thr Ser Lys Leu Leu Thr Met Gln Ser Ser Val Thr Val Gln
            20                  25                  30

Glu Gly Leu Cys Val His Val Pro Cys Ser Phe Ser Tyr Pro Ser His
        35                  40                  45

Gly Trp Ile Tyr Pro Gly Pro Val Val His Gly Tyr Trp Phe Arg Glu
    50                  55                  60

Gly Ala Asn Thr Asp Gln Asp Ala Pro Val Ala Thr Asn Asn Pro Ala
65                  70                  75                  80

Arg Ala Val Trp Glu Glu Thr Arg Asp Arg Phe His Leu Leu Gly Asp
                85                  90                  95

Pro His Thr Lys Asn Cys Thr Leu Ser Ile Arg Asp Ala Arg Arg Ser
            100                 105                 110

Asp Ala Gly Arg Tyr Phe Phe Arg Met Glu Lys Gly Ser Ile Lys Trp
        115                 120                 125

Asn Tyr Lys His His Arg Leu Ser Val Asn Val Thr Ala Leu Thr His
    130                 135                 140

Arg Pro Asn Ile Leu Ile Pro Gly Thr Leu Glu Ser Gly Cys Pro Gln
145                 150                 155                 160

Asn Leu Thr Cys Ser Val Pro Trp Ala Cys Glu Gln Gly Thr Pro Pro
                165                 170                 175

Met Ile Ser Trp Ile Gly Thr Ser Val Ser Pro Leu Asp Pro Ser Thr
```

```
            180                 185                 190
Thr Arg Ser Ser Val Leu Thr Leu Ile Pro Gln Pro Gln Asp His Gly
        195                 200                 205
Thr Ser Leu Thr Cys Gln Val Thr Phe Pro Gly Ala Ser Val Thr Thr
    210                 215                 220
Asn Lys Thr Val His Leu Asn Val Ser Tyr Pro Pro Gln Asn Leu Thr
225                 230                 235                 240
Met Thr Val Phe Gln Gly Asp Gly Thr Val Ser Thr Val Leu Gly Asn
                245                 250                 255
Gly Ser Ser Leu Ser Leu Pro Glu Gly Gln Ser Leu Arg Leu Val Cys
            260                 265                 270
Ala Val Asp Ala Val Asp Ser Asn Pro Pro Ala Arg Leu Ser Leu Ser
        275                 280                 285
Trp Arg Gly Leu Thr Leu Cys Pro Ser Gln Pro Ser Asn Pro Gly Val
    290                 295                 300
Leu Glu Leu Pro Trp Val His Leu Arg Asp Ala Ala Glu Phe Thr Cys
305                 310                 315                 320
Arg Ala Gln Asn Pro Leu Gly Ser Gln Gln Val Tyr Leu Asn Val Ser
                325                 330                 335
Leu Gln Ser Lys Ala Thr Ser Gly Val Thr Gln Gly Val Val Gly Gly
            340                 345                 350
Ala Gly Ala Thr Ala Leu Val Phe Leu Ser Phe Cys Val Ile Phe Val
        355                 360                 365
Val Val Arg Ser Cys Arg Lys Lys Ser Ala Arg Pro Ala Ala Gly Val
    370                 375                 380
Gly Asp Thr Gly Ile Glu Asp Ala Asn Ala Val Arg Gly Ser Ala Ser
385                 390                 395                 400
Gln Gly Pro Leu Thr Glu Pro Trp Ala Glu Asp Ser Pro Pro Asp Gln
                405                 410                 415
Pro Pro Pro Ala Ser Ala Arg Ser Ser Val Gly Glu Gly Glu Leu Gln
            420                 425                 430
Tyr Ala Ser Leu Ser Phe Gln Met Val Lys Pro Trp Asp Ser Arg Gly
        435                 440                 445
Gln Glu Ala Thr Asp Thr Glu Tyr Ser Glu Ile Lys Ile His Arg
    450                 455                 460

<210> SEQ ID NO 10
<211> LENGTH: 479
<212> TYPE: PRT
<213> ORGANISM: Homo sapiens

<400> SEQUENCE: 10

Met Leu Leu Leu Leu Pro Leu Leu Trp Gly Arg Glu Arg Ala Glu
1               5                   10                  15
Gly Gln Thr Ser Lys Leu Leu Thr Met Gln Ser Ser Val Thr Val Gln
                20                  25                  30
Glu Gly Leu Cys Val His Val Pro Cys Ser Phe Ser Tyr Pro Ser His
            35                  40                  45
Gly Trp Ile Tyr Pro Gly Pro Val Val His Gly Tyr Trp Phe Arg Glu
        50                  55                  60
Gly Ala Asn Thr Asp Gln Asp Ala Pro Val Ala Thr Asn Asn Pro Ala
65                  70                  75                  80
Arg Ala Val Trp Glu Glu Thr Arg Asp Arg Phe His Leu Leu Gly Asp
                85                  90                  95
```

```
Pro His Thr Lys Asn Cys Thr Leu Ser Ile Arg Asp Ala Arg Arg Ser
            100                 105                 110

Asp Ala Gly Arg Tyr Phe Phe Arg Met Glu Lys Gly Ser Ile Lys Trp
        115                 120                 125

Asn Tyr Lys His His Arg Leu Ser Val Asn Val Thr Ala Leu Thr His
    130                 135                 140

Arg Pro Asn Ile Leu Ile Pro Gly Thr Leu Glu Ser Gly Cys Pro Gln
145                 150                 155                 160

Asn Leu Thr Cys Ser Val Pro Trp Ala Cys Glu Gln Gly Thr Pro Pro
                165                 170                 175

Met Ile Ser Trp Ile Gly Thr Ser Val Ser Pro Leu Asp Pro Ser Thr
            180                 185                 190

Thr Arg Ser Ser Val Leu Thr Leu Ile Pro Gln Pro Gln Asp His Gly
        195                 200                 205

Thr Ser Leu Thr Cys Gln Val Thr Phe Pro Gly Ala Ser Val Thr Thr
    210                 215                 220

Asn Lys Thr Val His Leu Asn Val Ser Tyr Pro Pro Gln Asn Leu Thr
225                 230                 235                 240

Met Thr Val Phe Gln Gly Asp Gly Thr Val Ser Thr Val Leu Gly Asn
                245                 250                 255

Gly Ser Ser Leu Ser Leu Pro Glu Gly Gln Ser Leu Arg Leu Val Cys
            260                 265                 270

Ala Val Asp Ala Val Asp Ser Asn Pro Pro Ala Arg Leu Ser Leu Ser
        275                 280                 285

Trp Arg Gly Leu Thr Leu Cys Pro Ser Gln Pro Ser Asn Pro Gly Val
    290                 295                 300

Leu Glu Leu Pro Trp Val His Leu Arg Asp Ala Ala Glu Phe Thr Cys
305                 310                 315                 320

Arg Ala Gln Asn Pro Leu Gly Ser Gln Gln Val Tyr Leu Asn Val Ser
                325                 330                 335

Leu Gln Ser Lys Ala Thr Ser Gly Val Thr Gln Gly Val Val Gly Gly
            340                 345                 350

Ala Gly Ala Thr Ala Leu Val Phe Leu Ser Phe Cys Val Ile Phe Val
        355                 360                 365

Val Val Arg Ser Cys Arg Lys Lys Ser Ala Arg Pro Ala Ala Gly Val
    370                 375                 380

Gly Asp Thr Gly Ile Glu Asp Ala Asn Ala Val Arg Gly Ser Ala Ser
385                 390                 395                 400

Gln Ile Leu Asn His Phe Ile Gly Phe Pro Thr Phe Leu Gly Leu Gly
                405                 410                 415

Phe Glu Phe Leu Leu Asn Leu Arg Asp Leu Cys Cys His Pro Asp Ser
            420                 425                 430

Glu Phe Tyr Val Tyr His Phe Ser His Phe Arg Leu Ile Lys Asn Ile
        435                 440                 445

Ala Gly Glu Ile Val Trp Ser Leu Glu Gly Lys Ile Leu Trp Leu Leu
    450                 455                 460

Asp Val Ser Asp Phe Phe His Trp Phe Phe Leu Ile Cys Val Gly
465                 470                 475

<210> SEQ ID NO 11
<211> LENGTH: 698
<212> TYPE: PRT
<213> ORGANISM: Homo sapiens

<400> SEQUENCE: 11
```

-continued

```
Met Val Pro Gly Gln Ala Gln Pro Gln Ser Pro Glu Met Leu Leu Leu
1               5                   10                  15

Pro Leu Leu Leu Pro Val Leu Gly Ala Gly Ser Leu Asn Lys Asp Pro
                20                  25                  30

Ser Tyr Ser Leu Gln Val Gln Arg Gln Val Pro Val Pro Glu Gly Leu
        35                  40                  45

Cys Val Ile Val Ser Cys Asn Leu Ser Tyr Pro Arg Asp Gly Trp Asp
        50                  55                  60

Glu Ser Thr Ala Ala Tyr Gly Tyr Trp Phe Lys Gly Arg Thr Ser Pro
65                  70                  75                  80

Lys Thr Gly Ala Pro Val Ala Thr Asn Asn Gln Ser Arg Glu Val Glu
                85                  90                  95

Met Ser Thr Arg Asp Arg Phe Gln Leu Thr Gly Asp Pro Gly Lys Gly
                100                 105                 110

Ser Cys Ser Leu Val Ile Arg Asp Ala Gln Arg Glu Asp Glu Ala Trp
        115                 120                 125

Tyr Phe Phe Arg Val Glu Arg Gly Ser Arg Val Arg His Ser Phe Leu
130                 135                 140

Ser Asn Ala Phe Phe Leu Lys Val Thr Ala Leu Thr Lys Lys Pro Asp
145                 150                 155                 160

Val Tyr Ile Pro Glu Thr Leu Glu Pro Gly Gln Pro Val Thr Val Ile
                165                 170                 175

Cys Val Phe Asn Trp Ala Phe Lys Lys Cys Pro Ala Pro Ser Phe Ser
                180                 185                 190

Trp Thr Gly Ala Ala Leu Ser Pro Arg Arg Thr Arg Pro Ser Thr Ser
        195                 200                 205

His Phe Ser Val Leu Ser Phe Thr Pro Ser Pro Gln Asp His Asp Thr
210                 215                 220

Asp Leu Thr Cys His Val Asp Phe Ser Arg Lys Gly Val Ser Ala Gln
225                 230                 235                 240

Arg Thr Val Arg Leu Arg Val Ala Tyr Ala Pro Lys Asp Leu Ile Ile
                245                 250                 255

Ser Ile Ser His Asp Asn Thr Ser Ala Leu Glu Leu Gln Gly Asn Val
                260                 265                 270

Ile Tyr Leu Glu Val Gln Lys Gly Gln Phe Leu Arg Leu Leu Cys Ala
        275                 280                 285

Ala Asp Ser Gln Pro Pro Ala Thr Leu Ser Trp Val Leu Gln Asp Arg
290                 295                 300

Val Leu Ser Ser Ser His Pro Trp Gly Pro Arg Thr Leu Gly Leu Glu
305                 310                 315                 320

Leu Arg Gly Val Arg Ala Gly Asp Ser Gly Arg Tyr Thr Cys Arg Ala
                325                 330                 335

Glu Asn Arg Leu Gly Ser Gln Gln Ala Leu Asp Leu Ser Val Gln
                340                 345                 350

Tyr Pro Pro Glu Asn Leu Arg Val Met Val Ser Gln Ala Asn Arg Thr
        355                 360                 365

Val Leu Glu Asn Leu Gly Asn Gly Thr Ser Leu Pro Val Leu Glu Gly
370                 375                 380

Gln Ser Leu Arg Leu Val Cys Val Thr His Ser Ser Pro Pro Ala Arg
385                 390                 395                 400

Leu Ser Trp Thr Arg Trp Gly Gln Thr Val Gly Pro Ser Gln Pro Ser
                405                 410                 415
```

```
Asp Pro Gly Val Leu Glu Leu Pro Pro Ile Gln Met Glu His Glu Gly
            420                 425                 430

Glu Phe Thr Cys His Ala Gln His Pro Leu Gly Ser Gln His Val Ser
        435                 440                 445

Leu Ser Leu Ser Val His Tyr Pro Pro Gln Leu Leu Gly Pro Ser Cys
    450                 455                 460

Ser Trp Glu Ala Glu Gly Leu His Cys Ser Cys Ser Ser Gln Ala Ser
465                 470                 475                 480

Pro Ala Pro Ser Leu Arg Trp Trp Leu Gly Glu Glu Leu Leu Glu Gly
            485                 490                 495

Asn Ser Ser Gln Gly Ser Phe Glu Val Thr Pro Ser Ser Ala Gly Pro
            500                 505                 510

Trp Ala Asn Ser Ser Leu Ser Leu His Gly Gly Leu Ser Ser Gly Leu
        515                 520                 525

Arg Leu Arg Cys Lys Ala Trp Asn Val His Gly Ala Gln Ser Gly Ser
    530                 535                 540

Val Phe Gln Leu Leu Pro Gly Lys Leu Glu His Gly Gly Gly Leu Gly
545                 550                 555                 560

Leu Gly Ala Ala Leu Gly Ala Gly Val Ala Ala Leu Ala Phe Cys
            565                 570                 575

Ser Cys Leu Val Val Phe Arg Val Lys Ile Cys Arg Lys Glu Ala Arg
        580                 585                 590

Lys Arg Ala Ala Ala Glu Gln Asp Val Pro Ser Thr Leu Gly Pro Ile
            595                 600                 605

Ser Gln Gly His Gln His Glu Cys Ser Ala Gly Ser Ser Gln Asp His
            610                 615                 620

Pro Pro Pro Gly Ala Ala Thr Tyr Thr Pro Gly Lys Gly Glu Glu Gln
625                 630                 635                 640

Glu Leu His Tyr Ala Ser Leu Ser Phe Gln Gly Leu Arg Leu Trp Glu
            645                 650                 655

Pro Ala Asp Gln Glu Ala Pro Ser Thr Thr Glu Tyr Ser Glu Ile Lys
            660                 665                 670

Ile His Thr Gly Gln Pro Leu Arg Gly Pro Gly Phe Gly Leu Gln Leu
        675                 680                 685

Glu Arg Glu Met Ser Gly Met Val Pro Lys
    690                 695

<210> SEQ ID NO 12
<211> LENGTH: 602
<212> TYPE: PRT
<213> ORGANISM: Homo sapiens

<400> SEQUENCE: 12

Met Val Pro Gly Gln Ala Gln Pro Gln Ser Pro Glu Met Leu Leu Leu
1               5                   10                  15

Pro Leu Leu Leu Pro Val Leu Gly Ala Gly Ser Leu Asn Lys Asp Pro
            20                  25                  30

Ser Tyr Ser Leu Gln Val Gln Arg Gln Val Pro Val Pro Glu Gly Leu
        35                  40                  45

Cys Val Ile Val Ser Cys Asn Leu Ser Tyr Pro Arg Asp Gly Trp Asp
    50                  55                  60

Glu Ser Thr Ala Ala Tyr Gly Tyr Trp Phe Lys Gly Arg Thr Ser Pro
65                  70                  75                  80

Lys Thr Gly Ala Pro Val Ala Thr Asn Asn Gln Ser Arg Glu Val Glu
            85                  90                  95
```

```
Met Ser Thr Arg Asp Arg Phe Gln Leu Thr Gly Asp Pro Gly Lys Gly
            100                 105                 110

Ser Cys Ser Leu Val Ile Arg Asp Ala Gln Arg Glu Asp Glu Ala Trp
        115                 120                 125

Tyr Phe Arg Val Glu Arg Gly Ser Arg Val Arg His Ser Phe Leu
    130                 135                 140

Ser Asn Ala Phe Phe Leu Lys Val Thr Ala Leu Thr Lys Lys Pro Asp
145                 150                 155                 160

Val Tyr Ile Pro Glu Thr Leu Glu Pro Gly Gln Pro Val Thr Val Ile
                165                 170                 175

Cys Val Phe Asn Trp Ala Phe Lys Lys Cys Pro Ala Pro Ser Phe Ser
            180                 185                 190

Trp Thr Gly Ala Ala Leu Ser Pro Arg Arg Thr Arg Pro Ser Thr Ser
        195                 200                 205

His Phe Ser Val Leu Ser Phe Thr Pro Ser Pro Gln Asp His Asp Thr
    210                 215                 220

Asp Leu Thr Cys His Val Asp Phe Ser Arg Lys Gly Val Ser Ala Gln
225                 230                 235                 240

Arg Thr Val Arg Leu Arg Val Ala Tyr Ala Pro Lys Asp Leu Ile Ile
                245                 250                 255

Ser Ile Ser His Asp Asn Thr Ser Ala Leu Glu Leu Gln Gly Asn Val
            260                 265                 270

Ile Tyr Leu Glu Val Gln Lys Gly Gln Phe Leu Arg Leu Leu Cys Ala
        275                 280                 285

Ala Asp Ser Gln Pro Pro Ala Thr Leu Ser Trp Val Leu Gln Asp Arg
    290                 295                 300

Val Leu Ser Ser Ser His Pro Trp Gly Pro Arg Thr Leu Gly Leu Glu
305                 310                 315                 320

Leu Arg Gly Val Arg Ala Gly Asp Ser Gly Arg Tyr Thr Cys Arg Ala
                325                 330                 335

Glu Asn Arg Leu Gly Ser Gln Gln Ala Leu Asp Leu Ser Val Gln
            340                 345                 350

Tyr Pro Pro Glu Asn Leu Arg Val Met Val Ser Gln Ala Asn Arg Thr
        355                 360                 365

Val Leu Glu Asn Leu Gly Asn Gly Thr Ser Leu Pro Val Leu Glu Gly
    370                 375                 380

Gln Ser Leu Arg Leu Val Cys Val Thr His Ser Ser Pro Pro Ala Arg
385                 390                 395                 400

Leu Ser Trp Thr Arg Trp Gly Gln Thr Val Gly Pro Ser Gln Pro Ser
                405                 410                 415

Asp Pro Gly Val Leu Glu Leu Pro Pro Ile Gln Met Glu His Glu Gly
            420                 425                 430

Glu Phe Thr Cys His Ala Gln His Pro Leu Gly Ser Gln His Val Ser
        435                 440                 445

Leu Ser Leu Ser Val His Trp Lys Leu Glu His Gly Gly Gly Leu Gly
    450                 455                 460

Leu Gly Ala Ala Leu Gly Ala Gly Val Ala Ala Leu Leu Ala Phe Cys
465                 470                 475                 480

Ser Cys Leu Val Val Phe Arg Val Lys Ile Cys Arg Lys Glu Ala Arg
                485                 490                 495

Lys Arg Ala Ala Ala Glu Gln Asp Val Pro Ser Thr Leu Gly Pro Ile
            500                 505                 510
```

```
Ser Gln Gly His Gln His Glu Cys Ser Ala Gly Ser Ser Gln Asp His
        515                 520                 525

Pro Pro Pro Gly Ala Ala Thr Tyr Thr Pro Gly Lys Gly Glu Glu Gln
530                     535                 540

Glu Leu His Tyr Ala Ser Leu Ser Phe Gln Gly Leu Arg Leu Trp Glu
545                 550                 555                 560

Pro Ala Asp Gln Glu Ala Pro Ser Thr Thr Glu Tyr Ser Glu Ile Lys
            565                 570                 575

Ile His Thr Gly Gln Pro Leu Arg Gly Pro Gly Phe Gly Leu Gln Leu
                580                 585                 590

Glu Arg Glu Met Ser Gly Met Val Pro Lys
            595                 600

<210> SEQ ID NO 13
<211> LENGTH: 396
<212> TYPE: PRT
<213> ORGANISM: Homo sapiens

<400> SEQUENCE: 13

Met Leu Pro Leu Leu Leu Pro Leu Leu Trp Gly Gly Ser Leu Gln
1               5                   10                  15

Glu Lys Pro Val Tyr Glu Leu Gln Val Gln Lys Ser Val Thr Val Gln
                20                  25                  30

Glu Gly Leu Cys Val Leu Val Pro Cys Ser Phe Ser Tyr Pro Trp Arg
            35                  40                  45

Ser Trp Tyr Ser Ser Pro Pro Leu Tyr Val Tyr Trp Phe Arg Asp Gly
        50                  55                  60

Glu Ile Pro Tyr Tyr Ala Glu Val Val Ala Thr Asn Asn Pro Asp Arg
65                  70                  75                  80

Arg Val Lys Pro Glu Thr Gln Gly Arg Phe Arg Leu Leu Gly Asp Val
                85                  90                  95

Gln Lys Lys Asn Cys Ser Leu Ser Ile Gly Asp Ala Arg Met Glu Asp
            100                 105                 110

Thr Gly Ser Tyr Phe Phe Arg Val Glu Arg Gly Arg Asp Val Lys Tyr
        115                 120                 125

Ser Tyr Gln Gln Asn Lys Leu Asn Leu Glu Val Thr Ala Leu Ile Glu
    130                 135                 140

Lys Pro Asp Ile His Phe Leu Glu Pro Leu Glu Ser Gly Arg Pro Thr
145                 150                 155                 160

Arg Leu Ser Cys Ser Leu Pro Gly Ser Cys Glu Ala Gly Pro Pro Leu
                165                 170                 175

Thr Phe Ser Trp Thr Gly Asn Ala Leu Ser Pro Leu Asp Pro Glu Thr
            180                 185                 190

Thr Arg Ser Ser Glu Leu Thr Leu Thr Pro Arg Pro Glu Asp His Gly
        195                 200                 205

Thr Asn Leu Thr Cys Gln Val Lys Arg Gln Gly Ala Gln Val Thr Thr
    210                 215                 220

Glu Arg Thr Val Gln Leu Asn Val Ser Tyr Ala Pro Gln Asn Leu Ala
225                 230                 235                 240

Ile Ser Ile Phe Phe Arg Asn Gly Thr Gly Thr Ala Leu Arg Ile Leu
                245                 250                 255

Ser Asn Gly Met Ser Val Pro Ile Gln Glu Gly Gln Ser Leu Phe Leu
            260                 265                 270

Ala Cys Thr Val Asp Ser Asn Pro Pro Ala Ser Leu Ser Trp Phe Arg
        275                 280                 285
```

```
Glu Gly Lys Ala Leu Asn Pro Ser Gln Thr Ser Met Ser Gly Thr Leu
    290                 295                 300
Glu Leu Pro Asn Ile Gly Ala Arg Glu Gly Glu Phe Thr Cys Arg
305                 310                 315                 320
Val Gln His Pro Leu Gly Ser Gln His Leu Ser Phe Ile Leu Ser Val
                325                 330                 335
Gln Arg Ser Ser Ser Cys Ile Cys Val Thr Glu Lys Gln Gln Gly
                340                 345                 350
Ser Trp Pro Leu Val Leu Thr Leu Ile Arg Gly Ala Leu Met Gly Ala
                355                 360                 365
Gly Phe Leu Leu Thr Tyr Gly Leu Thr Trp Ile Tyr Tyr Thr Arg Cys
    370                 375                 380
Gly Gly Pro Gln Gln Ser Arg Ala Glu Arg Pro Gly
385                 390                 395

<210> SEQ ID NO 14
<211> LENGTH: 481
<212> TYPE: PRT
<213> ORGANISM: Homo sapiens

<400> SEQUENCE: 14

Met Leu Leu Leu Pro Leu Leu Pro Val Leu Gly Ala Gly Ser Leu
1               5                   10                  15
Asn Lys Asp Pro Ser Tyr Ser Leu Gln Val Arg Gln Val Pro Val
                20                  25                  30
Pro Glu Gly Leu Cys Val Ile Val Ser Cys Asn Leu Ser Tyr Pro Arg
                35                  40                  45
Asp Gly Trp Asp Glu Ser Thr Ala Ala Tyr Gly Tyr Trp Phe Lys Gly
    50                  55                  60
Arg Thr Ser Pro Lys Thr Gly Ala Pro Val Ala Thr Asn Asn Gln Ser
65                  70                  75                  80
Arg Glu Val Ala Met Ser Thr Arg Asp Arg Phe Gln Leu Thr Gly Asp
                85                  90                  95
Pro Gly Lys Gly Ser Cys Ser Leu Val Ile Arg Asp Ala Gln Arg Glu
                100                 105                 110
Asp Glu Ala Trp Tyr Phe Phe Arg Val Glu Arg Gly Ser Arg Val Arg
            115                 120                 125
His Ser Phe Leu Ser Asn Ala Phe Phe Leu Lys Val Thr Ala Leu Thr
    130                 135                 140
Gln Lys Pro Asp Val Tyr Ile Pro Glu Thr Leu Glu Pro Gly Gln Pro
145                 150                 155                 160
Val Thr Val Ile Cys Val Phe Asn Trp Ala Phe Lys Lys Cys Pro Ala
                165                 170                 175
Pro Ser Phe Ser Trp Thr Gly Ala Ala Leu Ser Pro Arg Arg Thr Arg
                180                 185                 190
Pro Ser Thr Ser His Phe Ser Val Leu Ser Phe Thr Pro Ser Pro Gln
                195                 200                 205
Asp His Asp Thr Asp Leu Thr Cys His Val Asp Phe Ser Arg Lys Gly
    210                 215                 220
Val Ser Ala Gln Arg Thr Val Arg Leu Arg Val Ala Ser Leu Glu Leu
225                 230                 235                 240
Gln Gly Asn Val Ile Tyr Leu Glu Val Gln Lys Gly Gln Phe Leu Arg
                245                 250                 255
Leu Leu Cys Ala Ala Asp Ser Gln Pro Pro Ala Thr Leu Ser Trp Val
```

```
                260              265              270
Leu Gln Asp Arg Val Leu Ser Ser Ser His Pro Trp Gly Pro Arg Thr
                275              280              285

Leu Gly Leu Glu Leu Pro Gly Val Lys Ala Gly Asp Ser Gly Arg Tyr
            290              295              300

Thr Cys Arg Ala Glu Asn Arg Leu Gly Ser Gln Arg Ala Leu Asp
305              310              315              320

Leu Ser Val Gln Tyr Pro Pro Glu Asn Leu Arg Val Met Val Ser Gln
                325              330              335

Ala Asn Arg Thr Val Leu Glu Asn Leu Arg Asn Gly Thr Ser Leu Arg
            340              345              350

Val Leu Glu Gly Gln Ser Leu Arg Leu Val Cys Val Thr His Ser Ser
                355              360              365

Pro Pro Ala Arg Leu Ser Trp Thr Trp Gly Glu Gln Thr Val Gly Pro
            370              375              380

Ser Gln Pro Ser Asp Pro Gly Val Leu Gln Leu Pro Arg Val Gln Met
385              390              395              400

Glu His Glu Gly Glu Phe Thr Cys His Ala Arg His Pro Leu Gly Ser
                405              410              415

Gln Arg Val Ser Leu Ser Phe Ser Val His Cys Lys Ser Gly Pro Met
            420              425              430

Thr Gly Val Val Leu Val Ala Val Gly Glu Val Ala Met Lys Ile Leu
            435              440              445

Leu Leu Cys Leu Cys Leu Ile Leu Leu Arg Val Arg Ser Cys Arg Arg
450              455              460

Lys Ala Ala Arg Ala Ala Leu Gly Met Glu Ala Ala Asp Ala Val Thr
465              470              475              480

Asp

<210> SEQ ID NO 15
<211> LENGTH: 14941
<212> TYPE: DNA
<213> ORGANISM: Homo sapiens

<400> SEQUENCE: 15
tctgctcaca caggaagccc tggaagctgc ttcctcagac atgccgctgc tgctactgct      60
gcccctgctg tgggcaggtg agtggctgtg gggagagggg ttgtcgggct gggccgagct     120
gaccctcgtt tccccacagg ggccctggct atggatccaa atttctggct gcaagtgcag     180
gagtcagtga cggtacagga gggtttgtgc gtcctcgtgc cctgcacttt cttccatccc     240
atccctact acgacaagaa ctccccagtt catggttact ggttccggga aggagccatt     300
atatccaggg actctccagt ggccacaaac aagctagatc aagaagtaca ggaggagact     360
cagggcagat tccgcctcct tggggatccc agtaggaaca actgctccct gagcatcgta     420
gacgccagga ggagggataa tggttcatac ttctttcgga tggagagagg aagtaccaaa     480
tacagttaca atctccccca gctctctgtg catgtgacag gtgaggcaca ggcttcagaa     540
gtggccgcaa gggaagttca tgggtactgc agggcagggc tgggatggga ccctggtact     600
gggaggggtt tagggtaaa gcctgtcgtg cttagcgggg gagcttgacc agaggttgat     660
cttctctcag gccctcacct ggaccctccc tctgattct gcatcccctc tttctcctca      720
ctagacttga cccacaggcc caaaatcctc atccctggca ctctagaacc cggccactcc     780
aaaaacctga cctgctctgt gtcctgggcc tgtgagcagg aacaccccc gatcttctcc      840
```

| | |
|---|---|
| tggttgtcag ctgccccac ctccctgggc cccaggacta ctcactcctc ggtgctcata | 900 |
| atcaccccac ggccccagga ccacggcacc aacctgacct gtcaggtgaa gttcgctgga | 960 |
| gctggtgtga ctacggagag aaccatccag ctcaacgtca cctgtaagtg ctgggccagg | 1020 |
| atgctggggt ccctgagggt gtaggggaga caggatgggc tggtgctggg gacatttagt | 1080 |
| gtcctggagg cctggctgag ttcgggagcc agaaggacat gagccctgtc ccttctgcat | 1140 |
| ttctgtggtt tctggcagga gtaaggggaa atgcctaccc ttatctcatc tctaccccca | 1200 |
| actgaaggaa atcctctctt cctctcctag atgttccaca gaacccaaca actggtatct | 1260 |
| ttccaggaga tggctcaggt aggaaggagc ctccccgcct ggggctgtta ctgacattga | 1320 |
| gtctgtgtca ggtttggtca gatctggact ttcagagtca aatgttcaga ggcaaggcct | 1380 |
| gcagttagac acgggtagac atcaggcacc ttggaaaagg atatttgggg atgactagca | 1440 |
| acttcccct tgcccatcca ataatgctc tttgtctccc tcctgtctct gaatgtcttg | 1500 |
| gggtatttta tttttaattg atatgtaata atagtacata tttatggatg gcatagtgat | 1560 |
| gtttccatac taataatgta tagtaatcag atcagggtaa tagcatatcc atcatcttga | 1620 |
| acatttatta tttcattgtt gttgggaaca ttcaatatcc cctttctagc tatttgaagc | 1680 |
| tatctattat tgttaagcat agtcatccta cagtggtata gaacaccaga acttattctt | 1740 |
| cctttccagg tgtaatctag tatcctttaa caaatctctc tccttatcat tgttccccta | 1800 |
| accttcccag cccttattat tctctgttct acttttact tctatgaaat caacttcttg | 1860 |
| tagcttccac ttatgagtga aacatgtgg tattcaactt tctgttccta gcttatttca | 1920 |
| tttaacataa tgtcctctag ttcaatctat gttatagtga ataacaagat ttcattattt | 1980 |
| tttatggctg aatgataatc cattgtgtat atacgccaca tttcctttat ttattcatct | 2040 |
| gttgttggac acttaggttt atttcatatc ttcctattgt ggataatgct gcaataaaca | 2100 |
| ttgaggtgca gacgtttctt caatatactg atttcctttc cttttctataa atgcccagta | 2160 |
| gtggggttgc tggatcatat ggtagttcta tttgtagttt tttgagaaac ttccatactc | 2220 |
| ttctccatag tggttatact agtttacatt ctggtcaaaa gtatataaga gttccctctt | 2280 |
| ctctacatcc tcaccatcat ttgttaattt tcatcttttt tttatcatag tcctcccaac | 2340 |
| tggggtgatg ttacctcatt gtggttttga tttgcatttc cctggtgatt ggtgacgttg | 2400 |
| agcatttttc atatacactt gttggccatc tgtatatctt ttcttgagaa atgtctactc | 2460 |
| agataatttg cccattttta aatgagattg ggtttctttg ccattgagat gtatgagttc | 2520 |
| ctcgtatgtt ctggatatga atcacttgtc agatgaatag ctgacaaata ttttctccta | 2580 |
| ttctgtaggt tgccttttca ctctgttggt tgtttccttt ctgcatagaa gcttttttagc | 2640 |
| ttgatatcat ctcatttatt tacttttgct tttgttgctt gtgctagtga ggtcttactc | 2700 |
| ataaaatatt tttccagacc aatgtcctaa agcatttccc ctatgttttt ttctagtatt | 2760 |
| ttttaaattt tgtgtcttat attcaggtct ttgatccatt ttgaattgat ttttgtatag | 2820 |
| gacgagaggt gtgagtctaa tgtcattctt ctgcatatgg caccagtttt cccagcatca | 2880 |
| tttattaaag aaactgctct ttcctcaatg agtgttcttc atgcatttgt caaaattcag | 2940 |
| ttggctgtag atcgtggatt aatttcggtg ttctctatta tgtattattg gtgtatgtat | 3000 |
| ctgctttat gccaatatca tgctgttttg gttactacag ctttgtagtt ttgaaatctt | 3060 |
| taaattttg aaattttgaa attttctagt tttgaaattt tgaaatcttg tagtgtgata | 3120 |
| cctccagctt tgttctttttt tgcttgggat tgctttgacc attcaggcta ttttagttc | 3180 |
| catatgaatt ttaagattgt ttcctctaat tctgtgaaga attacattga tattgata | 3240 |

```
gagccaggtt tgaatctgta gatttctttg ggtagtataa tcattttagc aatattaatt    3300
catctgatga gtaaggaatg tcttttccatt tgtttgtatc ctcttcagtt tatttcctca   3360
gtgttttgta gttttttctta ttaaggcttg tcacctcctt ggttaaattt attcctaggt   3420
atacttcatt ctcttatagc tattgtaaat gtgattgcct tcctgattta ttttcagcta   3480
attcattgtg tgtagaaatg ctactgattt tgtatattg attttgcatc ctgcaaattt    3540
actaaattca tttatcagtt ctgagagttt tattgttaga gtctttaggt ttttgttttg   3600
ttttgttttg ttttgttttg ttttgagat ggaatttcac catgttggcc aagctggtct    3660
tgatctcctg gcctcaagca atctgcccac tttggcctcc taaagtgctg gaattacagg   3720
catgagccac cacgcctggc caagtcttta ggttttgta tgttatttgc agagacaatt    3780
tgacttccgc ctttccagtt tggatggttt ttatttcttt ctcttgccta attgctctgg   3840
ctaggacttt cagtactatg taaaataaga gtcataacag tggacatcca gttcctagag   3900
gaaaagattt cagcttttct ccattcagta tgatgttagc catgggtttg tcatatatgg   3960 cctttttttgt gttgaggtac tttccttcta tacctaattt attgagagtt tctatcatga   4020
aacaatattg aattttaaca catgcttttt attctgcaac tatttaggtg atcatacggt   4080
ttatgtcctt cattctgttg acatatgtat aacatttatt gatttgcata tgttgaatca   4140
ttcttgcctt tctgggatta atcccacttt atcatggtat gttatctttt tgatgtattg   4200
ttggatttga tttgctacta ttttgttgaa tattttttgca tctatgttca tcagggatat   4260
tggcctctag ttttctttt ttattgtctc ctttctgatt ttggtgtcat ggttatgctg   4320
gccttgtaga atgagttagg aagagttgcc tccacttcaa ttttttggaa tagtttgaga   4380
agagttggca taattttttt ttctttaaag gttcagtaaa gttcagcact gaagccatcc   4440
agccctggaa ttttctttgt tgggggggcct tttattattc attcaatctc attacttgtt   4500
gtttgtctgc tgaagttttc tataccttct tgattcaatc tcggtagatt atatgtgtcc   4560
aggaacttat ccatttcttc tagactttca aatttgttgg catattgttc atagtagtgt   4620
ctaagatcct gtgtatttct gtggtaacca ttgtgacatc ttcttttta tttatgattt   4680 tattaatttt tatgtcttct gtctctttct tagtttagct aatgattgtc aatttttattt   4740 attttttccaa aaagcgaact tgttcattga tttttttta atttcattta tttctgctct   4800
gatctttatg atttctttca ttgtgctgat tttggatttg gttgttcttt gctttctagt   4860
ttcttgaaat gcacagttaa atggtttact tgaaatttgt ctaattgttt gatgtaggca   4920
tttatttctc tcaagttgtc tcttaaaact gttttttgctg tgtcccatag gttttggtat   4980
attttatttc tatttttatt tattttgaga aattttttaaa tatcattctt aatttcttcc   5040
ttcactattg gtcatttaga atcatttttgt ttcatttctg tgtatttgta tagtttgcat   5100
gtttcccttg gtattgattt ttagtttat tcaattgtag tcaaataaga tacttgatac    5160
attttggttt ttaaaaattt ttggcacttg ttttgtgttc taacatatgg tcgatccttg   5220
ggaatgttgc acatgctgat gaaaccatgt gtattctgca gctgtcggtt gaaatgttct   5280
gtaaatatct taggttcatt tggtatatgg tgcagtttaa atccaacgtt tatttgttaa   5340
tcttgtctag atgatttgtt caatgctgag agtggggcgt tgaagtcctc aactattatt   5400
gtattggagt ctatctctcc ctttatatct aataatatt gctttacata tctgggtgct    5460
ctggtgttgt gtgcatatgt atttacagtt gttatattat agtgctgaac tgaccccttt   5520
ataataatat aatgtccttc tttgtctctt tacagctttt gacttgtagt ccgttttgtc   5580
```

```
tgagataagt atagctattc ctgcttcctt tcatttccac ttgggtagaa tatctttttc    5640
catctcttcc tttcagtct atgtgtgtct tctaggtgag ataagtttct tgtaagcagt     5700
```
*Note: line 5700 second block shown as "atgtgtgtct" — reproducing as printed.*

```
tgagataagt atagctattc ctgcttcctt tcatttccac ttgggtagaa tatctttttc    5640
catctcttcc tttcagtct  atgtgtgtct tctaggtgag ataagtttct tgtaagcagt    5700
atatagctgt gttggtagaa gggctgaggc agggcttgct tgtctgacat aatgtaaaag    5760
agtcttggaa catgtcctgg gtccagggtc tcaaacccct cgtggcctat ggaacaccaa    5820
gctctgtgcc taagggtgga aggctgccct gccacactgc aatctaagcc cagggcataa    5880
aacccctcgt ggcttggaaa gaatccaggg ctctgggcat aaaacccctc atagcctctg    5940
gaatgtgtcc agacttgctg gccccttgct ccttgctctc ccaggatcat aaattgattg    6000
tatcttgagt gaaaagaact tgttctccat tatttcaagt agcagagcat atgctaaacc    6060
gtcacagcta tgcttgatgc accgctacct ttctaccccca aagtcctcac gttctcactt   6120
gtctatcccc acttctgcac gtcctcacca cctgcttctt tgtttgatta ccaataaata    6180
gtgtgggctc ccagagctcg ggccttcac  agcctccata ctagcgtcgg cccctggac    6240
tcactttatg tactattaac ttgtcttgtc tcattccttt gactccgctg gacttcgtgg    6300
cccccacggc ctagtgttgg atctgatcac cccaacaagc tgagtctaga ttttcttttc    6360
attcattcag gcagtccata tattttaaat gggacaattt aatccattta catacacatt    6420
attattaata ggttattttc atttcattga ttgttttctg attgttttat atattcctgg    6480
ttccttactt cccctcttat tgtttctttt tgtggttggc tgatgttttt tttttttttg    6540
tagtgataag atttgattcc tttctctttc ttctttgtgt atgggctgtc agtgagtttt    6600
aagttcacgt gtttttgcct tttcacttcc agatgtaaga ctcccttgag catttctttt    6660
cttttcttc  tcttatttat ttttattatt tttttttga  gaaagtgtct cactctgtcg    6720
cccaggcagg agtgcagtgg catgatcacg gctcactata gtctcgacct cctgggctta    6780
agcaatcttc ctgccttaac ctcccaagta gctgggacta caggcatgtg ccaccacgcc    6840
cagctaattt ttgtgtttct tgtagaggta gggtgttgcc atttgcctaa gctggtctca    6900
aattaaagag ctcaagtggt ccacctgcct gccttcacct cccaatgtgc tgggattata    6960
ggcatgagcc acactgtgcc tggcccttg  agcatttctt gtaaggccag tctaagagtg    7020
attagaattc cctttagtttt tgcttatcta tgaaatattt tatttctcct tcttttctga   7080
aagatagctt ttctgggtat agtattttg  actgttaagt tttttatctt tcagtacttt    7140
gagtatgtca tcccattcta tcctggccta tataatgtta ctgctgagaa actcactgtt    7200
agtctaataa ggataatcct atatgtgact agatacttt  accttgctgt ttttacaatt    7260
ctttacttga cttttgacaa tttggcataa tgagctttgg agaggacttg cttgggttga    7320
atattttgag agtactttga gcttcctgga cctggatgtc cttctagttc ccaaggcttg    7380
ggaagttttc acctattact ggattaaata tgttttctac accttttcca ttctcttctc    7440
ctcctggaaa taccataatg tgaatatttg cttgattgtg tcccatgagt cctgtaggtt    7500
tccttcgttc tattttattc tcttattttt acctgcctgt gttatttcag aagatctgtc    7560
ttcaagttca gaaattattt tttcttcttg acctagcctg ttgttgaagc tctcgattgc    7620
ggttttttat ttcatttatt gagttctcag ctgtaggagt tctgctttgt tcttttatat    7680
aatatctatc tctctgttaa atttctcttt caagtcatga attaaaacaa tgggacacag    7740
gtgcccaact acttggctga cctggggggca tatctgctgg aggtgccaac atggctgttt   7800
tgcagggctg agatgaagct gaatgactct tggctggcct aggtgtgttt ttgccaggag    7860
tagcactcag agctttatct agggtttggg atgtgagtgt aagactgctc agctggccta    7920
gggggtgtac cagccagtgg tagcccatgg ggctgtttct caggcctgga atgcaagcac    7980
```

```
attctgcctg gggtcatgtc taaaagggtt ggctcacaag gctgtttctc aggccctaat      8040
tgtgggagag tggcctttgg gcaggccaga gtcatgtcca cagaaggcgt ctgggcaccg      8100
taaggctgtt tctcagagcc tgtgtgtgag cacataacca ctaccccagc ctggggatgt      8160
atcaactctt tgttggctca gaggtctctc ccattcaggt gagcatgcac agtagtttgg      8220
ccaactcaat tgtgtgttcg ccctgagtgg gactataaga cctttcctcc agctggaagt      8280
acgggcagca ggggttggtt tctctgctgt tcagggccag agtcccagcc aatcctgggc      8340
ccaggctcca tgcagctcta attgtggtat tcagccacta ctgcaggttt agtggaatga      8400
agatgcacaa tgataaagag gtgcatgcca ctggccccca gaggagggtg cactccagag      8460
atggctgtgg tctcaagatg gttctgtgtt gtagcagctt gcccgcaggg gctggttagg      8520
gagttgggag tgcacaccaa atgctccatg cagctgtgtg aattcctggc agctcttcca      8580
actgtgctca gagcttgtga ggactgtaag attaacctgt agtaaggaat gtaggtatct      8640
gcagtggcac tggaggttgg ttggattcct ctgcttatca tttccctaca aggggaaatc      8700
cttcctgtct ctgggacaaa ccaatctggg ctggggagat ggagctgcaa agcccgggtg      8760
cctccatgct gccctcctgg gtttccaatt accacaggta actctccact cccttgctgc      8820
actacactac tctcccttcg acactccact caaatctttg ctgtggttta ttcattgcct      8880
tggtcctttc ttgtctggtg acacggggga ggatgagctc caggcacctc cggtgagcca      8940
ttttgctcca atgggggcat ttttttttaa taggttttat ttttcagagt agttttgtt      9000 tcacagcaaa attgagtgga atcttctagt cgctgatcat cttgggagca tttataaatg      9060
aaccttattt ttcatgaaga aattgagcag aagatactaa gacttcccgt atgccctcta      9120
cccttacaca tagtttcccc ggccatcagc atccccatc agagtggtac atttgttaca      9180
gtcaataaaa ctacattgac atatcattgt cacctgaagc ccatagttta cattaaagtt      9240
cactcttggt gttgtacatt ttacaggctt tttaaaaatg tataatgaca tgaatccacc      9300
atgagagtat catatagaat agtcacactt ccctaaaaat ctctttaggg cattttttc      9360 tactgtccat acctcaaccc ttagccctgg cctctgtcca aagaccagtg ctctctccac      9420
tgccctattc caattaataa tggcatctgg cacctcagtg gacagtgagc ccagtgagag      9480
caggaacagt tccctcagta gtggttatca aactgttaac aatgatgctc agagacacgc      9540
ccctgactct gagtgttggg acctagaagg cacagccagg caggtccagg agaactgtct      9600
gggtctaaga aggtctgaga accacctccc tgccccaccc tgcttccagg cccttttaa      9660 ggccaaaagg accaccttg accctaagtg atggggccag tgggaagaaa gaagagacaa      9720
ggcctatcag cattccagtg ctttctctct ctctcatcca agaggctcag agcttcacag      9780
tccttcaggg gctatgtctg aggttcattt cagaaagacc cagggtggag aggaacctga      9840
gtcctaggag agatgatgtt ttgtgcacca gagagagagg gtgggacaag aggtgtcagg      9900
tgcactgtgt acttcatctc atggtcgtgg tcaatattga tgtctatgat gggtgggaag      9960
atctaggagc taaaccccat tttggaggtg aagtcacccc tctctacatg ctggagagga      10020
ggatacacat acctgtttat ctagattaga attcacccca aatcttttt gtctgcaggg      10080 aaacaagaga ccagagcagg agtggttcat ggggccattg gaggagctgg tgttacagcc      10140
ctgctcgctc tttgtctctg cctcatcttc ttcatgtgag catttctct gggtcaggca      10200 tgggccagag gtgaagagga tggacctggt gtagaagggt cctggagggg ctgtgagggc      10260
tggagaaagg gcagggggtg tgatgatgta cagaatccag cctgtggcca ctgggatagg      10320
```

```
cgtgggtcta ttccagggcc ctgatctcag atgtccaagg agtgggaggt agagggagac    10380
cttgtgacta agtcttgttt gagggctcct ggattaatcc caccctttac ctgccaaagt    10440
ccctcattcc aggctcataa caatggcccc acagcctgag aaaaccaggc tcaaagaccc    10500
tggtgtctcc catcagagtg aagacccaca ggaggaaagc agccaggaca gcagtgggca    10560
ggaatgacac ccaccctacc acagggtcag cctccccggt gagtgatggg gcatcctggc    10620
atccagtctg tcctgcagac acctcctccc aatgtggccc accgtcatgc cccattcagc    10680
atttccagaa ctgagcttat tgtctttcct cctgtttaac agtgtaggtt ttaatatttt    10740
tcaggtacgt tgaggccaac agatcaggag atgatggcca ttgaaaagat agtttcttgg    10800
ccgggcacag tgtttcacac ctgcaatccc agcacctttg gaggccaagg cgggcggatc    10860
acgaggtcag gagattgaga ctatcctggc taacatggtg aaaccccgtc tctactaaaa    10920
atacaaaaaa ttagccagat gtggtggctg gcgcctgtag tcccagctac ttgggaggct    10980
gaggcaggag aatggtatga acccgggagg cagagcttgt agtgagccga catagcacca    11040
ctgcactcca gcctgggtga cagagagaga ctctgtccca aaaagaaaaa aaaaatagtt    11100
tcttattcac cgttcccgag agggcacacc acaccatgca aggccatatg gagaagcacc    11160
agggtcagtc aggaagcaga gggagcaagg agaaaatggg acaagagcct tcactgtggc    11220
tttcatggaa aagaatgggc aagacagggt aagcaagcta ggcaggttta ggattggcta    11280
cttagaacaa tttcagcaga ctctgggggta taggagttgt ctctagttgt ctggtacatg    11340
gccctgggtt tattaaggag gattgtggtc tggagtgtaa gagctcaata aaggatccag    11400
ctggtagtgt gggctttaga ttgactggtt tgcacatgaa aggtgcactt gtatgcaagt    11460
cctttattag ctctagaaat ctactatcct tgggaaaggc agtctctcaa gggtcagtaa    11520
tgccccagat gtcaaaacat cagaaacact tggttgacac ccccctaaac atacttctcc    11580
tgatgggttc tccatctcgc tgatggcact cttgtcccca ttacccaacc agagacatgg    11640
ccccctcctg tcccagtcct ccatctcttc ctgtgccagt atgctacgat gcatgtctga    11700
gcttcctctg aacacggctt aacacaacca ctcctgagcc gagagcccct cttactcctt    11760
attctgctgc agcctcacct cccatttctc ctctccagaa cattagcatc acctccctaa    11820
aaggtcattg tcccatcatt cccaagtttg aaatgcactg cttctctaca ctcctgaaag    11880
attggcattc caacaacttg gtctggcatt tggagcagga aaaccagagt cccccttcagt    11940 gctatgctcc cccaacatta gccactcaat cacctcaagc agggcaagct ttctcatctc    12000
agaatcattg ctgggctgtc ccctcctcct catatgccta atagctacct gcccaactcc    12060
agtgcatcct tcaagctctg attttttttt taatttattt aactctgact aaagtgaaca    12120
ccacagtaaa gttttgaac acagggtcaa ccagcaccca ttcattctga aatatctata    12180
taatcccatt tgccaattgc tctaggtcct tgtgccattc tgtattttta taaacacaca    12240
gtttacaaat ataaaatatt cctcctatcg ggggcttaac atttattggg gaaagggatg    12300
aaaataatga acaaataagc agtgcaaata tacatgaaat aggcatgaaa taagtgctat    12360
ggcaggaaat gaaatgggag aacggattgg acagtcctgg gggccaaaga atggcctttg    12420
ggcaaacacc tgcagaaaga aagtgagtac agtatgagca gtagagaatc atcaaggaag    12480
cagcaagtac catggctctg aggccggaac acatctgatg ttttagagaa acaaagtagg    12540
acagtgtgga taaggcagag ttacgtgttg ggggtggagt gtggactgaa caatggtagg    12600
taggaaatga ggttgaagag acataggagc tgcaaatatt gcaggatcct aagtccatca    12660
tagttattga tgcgtttaga gcagaagagt gacatgaact gacactcatt ttagtgggag    12720
```

```
tcactctggc tgctctgtga gaaactctag tatgtagtat agaagagaag ataccagaat   12780
agaagataca cagataatca agccaagaga tgactgactc agacttagtc ccaagtaaga   12840
ataatgaatc tgatgtggag aaattgggtt ccggatacat cttgaaggtg gagtcaacag   12900
tatttgcaag tggagtgatg gagtgcatgc aaggcatgag caaagatagc tcacgggctc   12960
tgctcgataa gtgtctcaga tgtcataggt gggtccacag atatcataga tgtcatggat   13020
gtccaagaag accccataga tgtcatagat gtctatagat gccaatgatg atgttcatgt   13080
ggttaactca gaattcaaac ttaaaaaatc aaattgccaa tgattaaaat tgccatcctt   13140
gaaggagaag tctattttca agtgtatatc aaacattatt ttggttaccg taagtttgag   13200
gtgcctctga gacatccatg tggagatgac aagtagcagg caagtgtctg gagctcagaa   13260
gagggctcca cgtgggagac acagaggttg ggagcttccc tatcaacatc caataatcga   13320
tgaatctaca agaagagaa ggggtccaca gacacagccc tggaaccctc cagcatttaa    13380
tgttagggag atgaggtgta aatggtgaga agctgagaa tgaataggag ccaatgacca    13440
ggaaattgca ggctgtagtg ttggtggcca agggaagatg gggcttcatg gaggagaggt   13500
tggtcatttg tttcaaatgc tggtaagtct ggtaagatgg aatctgagaa atggctatt    13560 gaatgtagct aagtggtatg acagcaaagc agatctgatt tttctgctgg aggaagatct   13620
cttgactaga gagagttcaa gagagaatgg gaggagaaga ggcagaaact gtgagttgaa   13680
ggactctttt gagaaacact gccccaaatc tagaaccaag aaatgggcct gcaccagcaa   13740
atggttgtac cctgtagact tgccatttct ccagcatctg ctcctgtgtc tcttatgata   13800
ccatgttccc tgtttgtgta gggctttgca ccacttgaac taactgcatt cccatagctt   13860
cccctaccac accatgagct ccacaaggaa aagcctgggt tttattagac ctccatcatt   13920
ctactctctc ctgttcatct gcacactgtc acaatttgca attaccagtc tgtttctgtc   13980
ttcatcccct gcagtactgg aaatcacagg gcccctgctc tgctctgctc cctcctgagg   14040
atccagtgcc cagcacatag gaggtcccag agacctggga ccgagttcag ggtcaacaga   14100
tgtgtgactt tggaaattac ctaagctctc tgagacctag tttcctggtc tgtaaaatgg   14160
attaaaataa tagatgccaa agatgatgtc agtgtagctg cccagaattt ttccacatta   14220
gtctctgtga gtattcaaga gaattgcgaa tcaatcaata cgtgctacat gtgttagata   14280
atgaataagt agagccttaa ttaattaaca tttgatgaaa gaatgaaaga gtgaataaat   14340
gttctgtcag agtcaaattt acttcattga ccctctttgc cttctcctgg tccccctcct   14400
cactgccctg ctctaaccc cttctttcct ctccataaga aacaccagaa gaagtccaag    14460
ttacatggcc ccactgaaac ctcaagctgt tcaggtgccg ccctactgt ggagatggat    14520 gaggagctgc attatgcttc cctcaacttt catgggatga atccttccaa ggacacctcc   14580
accgaatact cagaggtcag gacccagtga ggaacccaca agagcatcag gctcagctag   14640
aagatccaca tcctctacag gtcggggacc aaaggctgat tcttggagat ttaacacccc   14700
acaggcaatg ggtttataga cattatgtga gtttcctgct atattaacat catcttagac   14760
tttgcaagca gagagtcgtg gaatcaaatc tgtgctcttt catttgctaa gtgtatgatg   14820
tcacacaagc tccttaacct tccatgtctc cattttcttc tctgtgaagt aggtataaga   14880
agtcctatct catagggatg ctgtgagcat taaataaagg tacacatgga aaacaccagt   14940
c                                                                   14941

<210> SEQ ID NO 16
```

<211> LENGTH: 18972
<212> TYPE: DNA
<213> ORGANISM: Homo sapiens

<400> SEQUENCE: 16

```
gtgcgcgtcc acagctctca ctcaccctcc ggcttcctgt cggggctttc tcagccccac    60
cccacgtttg gacatttgga gcatttcctt ccctgacagc cggacctggg actgggctgg   120
ggccctggcg gatggagaca tgctgcccct gctgctgctg ccctgctgt ggggggtga    180
gtgagctgag ggaggaggga caggcacagg ggtgagaagg ggggctggag ctgcagctga   240
gcttctgtgt cccccaggg tccctgcagg agaagccagt gtacgagctg caagtgcaga   300
agtcggtgac ggtgcaggag ggcctgtgcg tccttgtgcc ctgctccttc tcttacccct   360
ggagatcctg gtattcctct cccccactct acgtctactg gttccgggac ggggagatcc   420
catactacgc tgaggttgtg gccacaaaca acccagacag aagagtgaag ccagagaccc   480
agggccgatt ccgcctcctt ggggatgtcc agaagaagaa ctgctccctg agcatcggag   540
atgccagaat ggaggacacg ggaagctatt tcttccgcgt ggagagagga agggatgtaa   600
aatatagcta ccaacagaat aagctgaact tggaggtgac aggtatggca gggaccccag   660
gagaggaccc tgggacgtgg agaccccgt atgagaacag ggacaggagt tgggcagggg   720
cggctggagg aggtgtagga cttggggcag gtcggggcct gaggcctggc cactctcggg   780
gtcacacctt acgtcctcaa gccctggggg cccaggtatc tccctgtctc ctcctcagcc   840
ctgatagaga aacccgacat ccactttctg gagcctctgg agtccggccg ccccacaagg   900
ctgagctgca gccttccagg atcctgtgaa gcgggaccac ctctcacatt ctcctggacg   960
gggaatgccc tcagccccct ggaccccgag accacccgct cctcggagct caccctcacc  1020
cccaggcccg aggaccatgg caccaacctc acctgtcaga tgaaacgcca aggagctcag  1080
gtgaccacgg agagaactgt ccagctcaat gtctcctgtg agtggtgctg gggacacagc  1140
tgagtcctca agggcagtgg gagtgagggg tgtgtgtgtg tgtgtgtgtg tgtgtgtgtg  1200
tgtaaggaag acagagagaa acaaaacaat aacttgagaa accttgtgtg tggatctaag  1260
ccttgggatc tgcggggagt gagacaggac agccttcccc gcttggtggg tttctgtggc  1320
tcctctttgg gtacctcctg ggcccatgcc catctcactc ctcactgctg aagccaagtt  1380
tatatctttt tatcccagat gctccacaga ccatcaccat cttcaggaac ggcataggta  1440
ggaaagacct cctctctgaa gctgggacct gcctctgggt ctgtctctga gcagaggtag  1500
agaatcagag cttgaatgca atcagatttg ggaagagcaa gaatgagaat tactgccttc  1560
tggcttccac cttctgtgag ccccatgtgc aggcacatat gcacacacgc acatacacac  1620
gcacacatgc acacacgcac acacacgcac acacacac atgcatatac accacacaca  1680
tacacatgca atacaccaca cacacacgca catacacaca cacatgcaca caggcacaca  1740
tgcacacaca ccacacacat atgcacacac acacatacac cacacaggca catgcacata  1800
cacacgcaca catgcacata caccacacac acatatgcag atacacccac acacgcacac  1860
atgtacgtac acccgcacac gcacacacac acgcacacag gtgcacactc atgcactctg  1920
ctcaaagcag tgaacagact ttagacccca cccatctccc atccctcctg tggtctggtt  1980
ctttccacag tcactaagga ccactccatg cccctctcat ctcagtcagc ccagctctgt  2040
ggttcttctc tcacccttcc actcctgcat cctcagtctt atttcctgtc acattagcgg  2100
actgtatttc ccaacgccac cggggggctct ctgtcctctc tccaccacag tccaggcatg  2160
taccagtgag atattgagcc tcctctggag acatgagact cagacacttt tggtcagttt  2220
```

```
cctgagtgtg caaaggccca gcctttgaac caggatgcaa tcaagccagc ataggccagg    2280
ggaggagagg gagatgtcat ctggatcctg ggaaggaggg aaggataggg actgtcagcc    2340
tccctggccc catctctctt tccccaccct tctctcccca aagccctaga gatcctgcaa    2400
aacacctcat accttccggt cctggagggc caggctctgc ggctgctctg tgatgctccc    2460 agcaacccce ctgcacacct gagctggttc cagggctccc ctgccctgaa cgccaccccc    2520
atctccaata ccgggatctt ggagcttcgt cgagtaaggt ctgcagaaga aggaggcttc    2580
acctgccgcg ctcagcaccc gctgggcttc ctgcaaattt ttctgaatct ctcagtttac    2640
tgtgagtgtg ggggcagctg gagcaggaac tgcatggtat taaagaagga agaggccccc    2700
tgctgagttc tgtcctccct ccccacagcc ctcccacagt tgctgggccc ctcctgctcc    2760
tgggaggctg agggtctgca ctgcagatgc tcctttcgag cccggccggc cccctccctg    2820
tgctggcggc ttgaggagaa gccgctggag gggaacagca gccagggctc attcaaggtc    2880
aactccagct cagctgggcc ctgggccaac agctccctga tcctcacgg ggggctcagc    2940 tccgacctca aagtcagctg caaggcctgg aacatctatg ggtcccagag cggctctgtc    3000
ctgctgctgc aaggtcaggg ggcgtattgc agagggcagg ggcctgaggg gaggggcatg    3060
gatcccagag tgatggatgg tgggagagag aggctggact ggtggtgggg agacagggtt    3120
cttcatctcc tgtctgagca gggccctgga gcaagttgcc cagcaggtgg gaggacaaga    3180
gtctgagtcc tgggagtgag ttattgcacg cccctcttt ctgcagggag atcgaacctc    3240
gggacaggag tggttcctgc agcccttggt ggtgctggtg tcatggccct gctctgtatc    3300
tgtctgtgcc tcatcttctt tttaatgtaa gtcttggtcc cagggaaggt acagggtggt    3360
gtttgtaggg agtaggagag actgaatctc agaaacacag agctaaggcc agaggtggtg    3420
atgtgtgctt gtggttccag atgctcagga gtctgaggca ggaggatcac ttgatcatgg    3480
aggttgaggc tgcagtgagc caggattgtg ccaatgcact ccatcctggg cctcagagtg    3540
agagaccctg tcttaaaaga aaaacaaaac aaaacaaaaa gcagaactga gtagatccag    3600
agaggtcttc tttctttttt tcttttctaa tagctttatt gagatacatg ttttgtacaa    3660
ttcatccact gaaagtgtac gagtcaatgg ctttaagtat attgacagag ttatgcatct    3720
gtcaccaaaa tcaattttag aacatttca tcagcctaaa gtgaaaaacg aagacataaa    3780
gaaaccttgc ccccttagc tatcactcct gcttctttcc cccagccta acctattcca    3840 tgtctctgtg gatttgtctg tcctgaagtt gcagttgtac tttgtgtgaa tggaatcacg    3900
cgatatgtgg tcctttgtgg ctggcttctt tcactcggcc taatgttttc aagattcatc    3960
tatgttgtag catgcatcga tacttcattc ctttttgttt tcaaataata ttccattata    4020
taaatggaac gcatttgatt tgtgggttca gctgttgacg ggtacttggg ttgcctctgc    4080
ttcttggcta tgatgcataa cactgctatg accattcctg ccatggtttt gtgtgtaaga    4140
gggggtctat atgatggaaa ttcagtccat ggccaccctg accaaatccc tggttatcca    4200
ggaggatgga gccctcactc cgaagtcagg aaggtctccg agtttagttc cggggcctgg    4260
atggcttcat tgtcattttc accatcttag catgggatgg gacaacccgc taacccgtgc    4320
ctgggtggtc ccagctgcac tgtgctggtt cttttcctta gagtgaaagc ccgcaggaag    4380
caagcagctg ggagaccaga gaaaatggat gatgaagacc ccattatggg taccatcacc    4440
tcggtgagtg gtttggggat cttctcatgt gcatgtccac tcggaaagtc caggctgagc    4500
tcttcagcat tccaccaaac ccactcctcc ctcatcacct gggagttctc ttctctcctg    4560
```

```
ttctccccct tcatatccca gagccaggaa atcattatgt cccattcaac cttctttgtt    4620
ttgtttgttt gtttgtttgt ttttgagatg gagtttcact cttgttaccc aggctggagt    4680
gcaatggtgc gatcttggct cactgcaaac tccacctccc aggttcaagc gattctcctg    4740
cctcagcctc ccaagtagct gggattacag gcgcacacca ccatgcccgg ctaattttg     4800 tatttttagt agagacggga ttttgccatg ttaggcaggc agttcttgaa ctcctgacct    4860
caggtgatcc gcccgcctcg gcctcccaaa gtgctgggat tacaggcgta agccaccgcg    4920
cccggccacc aaccttcttt ctaaaagtaa aactaacttg tcctttgctc atcttccctc    4980
cccacctcta ctgaccacag agcctgcctc acttcctccc tgcctccatc tctcattcca    5040
aacttcaggc tgccagaatc atcgcccaa aactattact tcccaggcag cctggagttt     5100
caatgttgtt gttgtttgtt cctgttgctt agagaatcag gcccatgttc cttgccccac    5160
accaggtggc cacttcagcc tgtttctgtc ctctgatcct gccccgtggc ctggccacgc    5220
tggccttctg tctccatacg gacctgctgt cctacaactt tgagcccttg caagtatagt    5280
ttcttccacc tttccttccc tgtttccacc agactacctc atctaatcct tccagctcta    5340
atctcagtat ctgctactct agtcatttcc cctcctgttg atatctgccc cttctcttct    5400
gtgtttacag ccctacatgc atccccgtcc ccatcacaca tcaccactgc ctttacctgt    5460
ctccacccac tcatcatatc tgtagaattc tttttatt ttatttttt ggagacggag       5520 tcctgctctg tcacccaggc tggagtgcac tggcgcaacc tcggctcact gcaacctctg    5580
cctcccaggc tcaagcaatt ctcctgcctc agcctcccaa gtagctggga ttacaggcat    5640
gcaccacctg gctaatttt gtatttttag tagagacggg gtttcaccat gttggccagg     5700
gtggtctcga actcctgacc tcaggtgatc tgcctgcctc agcctcccaa agtgctggga    5760
ttacaggtgt gagccaccgc gtgcggccaa tatctgtgga attcttgaag gacaggggct    5820
ggggcttctt tagcccctgc agttttctct cctgctgttt ctgtccagcg tgtctcctct    5880 cctctttat aaaattgatc tagtgttgcc ccgaacgaat tgtccaaaat gcttagttca    5940
tgaccaagct gtcatgactg gaacaagcat catttacttt tacttttca ctttggttca    6000 taatatgata aataactgca aacccaccat ccaacctaag acctaacaca ttggtgataa    6060
cttgtatcca cctgtgttgc tccctgatcc attcccagta accactgttg tgaatcttgt    6120
cttcctagtt ttgtcacata tatgtaggct tatgccacta tttagttta attgtttatg     6180 aatctacaga gggtatcatg ttccacgcac acttcttgga cttgctttgt agactcaaca    6240
ttgtattatg attcattcat gttgtataaa gttgcagttg tattcatttt tcctgcttat    6300
aatatatata ttttttgaga cagggtctga ctccattgcc caggttggag tgcagtggtg    6360
cgatctcggc tcattgcaac ctccacctcc cgggttcaag caactctcct gcctcagctt    6420
cctgagtagc tgggattaca ggcatgtacc accacgcaag gctcattttt gcatttttag    6480
tagcgatggg gtttcaccat gttggccagt ctggtcttga tccacccacc ttgacctccc    6540
aaagtgctgg gattataggt gtgacggctt ataatattat attttatgat tgtgtctatc    6600
acctaagctc atattgatgc acacttgagt tgtttccatt tgagccgttc tgaacattct    6660
tatccttgtc tcaccgtact aacacacacg agctttcctt tagcatcacc taaagattga    6720
gttgccgcat cgctgggcat gtgaatgggc atctttacaa ggtcatgaaa aatggctttc    6780
caaagcaatt atatccattt atactctcat ctatgcctag gaaatcttgt tgttctgtaa    6840
tctctccaac ttgcttttct cagttttgga ggctatttta ctatctcact atggtattga    6900
tttgcatttc ctcggttacc agtgaagatg aaaaatctct ctctgctttc atcttctata    6960
```

```
aaacacctgg tcacatctgg atcccatttt cctattgggt gtttgacttt ttcttaatga   7020
atttgttgga gggctttata catttttaca ctattttttct cattgtatgt gttgtaaata   7080
taaatatctt ctcccaatgc gtagcttgtc ttcacttctt aaagtgatct tcaatgaaca   7140
taagttccta gttgtaatat aatcatattc acaaatcctc tcttttctat tgagtacctt   7200
ttggatctca ttaaaaaaaa tttcacccat cctaagatta gaaagatatt caaatatagt   7260
ttctactaaa agttttatgc ttttattttt aattttgtgg gtacatatta gatgtatata   7320
tttatggggt acatgaactg tttcaataga ggcatgcagt gtgaaataaa cacttcatga   7380
agaattgggt acccagcccc tcaagcattg atccgttgag ttgcaaacaa tccagaagca   7440
acctaagtgt ccatcaatag atgaatggat aaagaaaatg ttgtgcatat acacaatgga   7500
gtactattca gccataaaaa agaatgagat ccagtcattt gcaacaacat ggatggaact   7560
ggagatcatt atgttaagtg aaataaggca ggcacagaaa gacaaacatt gcatgttctc   7620
acatatttgt gggatctaag aataaaaaaa aattgaactg atggacatag agagtatgct   7680
tttcttttga catttaagta ctcactctgt ctggggttga cttttgtgta tggtgtatag   7740
tgttgatcca tatatgtttc tccttcattt ctgaatagtc cttctccctt ctccattgag   7800
caacatgcca attctgccat gtattaaaat tctatatatt tgtcggtctc tttctgtggt   7860
ctctattcta ctccaatagt caattttact gtccctgagt catcactgtc tataaattca   7920
aaaataagtc ctgatataga gtacagcaaa acctcttcct taatctcctt caatagtatc   7980
ttgaccattc ttggtccttt tttttttttca ctttaatgtt agaatcaggt tgtcaaggcc   8040
gggcgcggtg gctcacgcct gtaatcccag cactttggga ggccgaggtg ggtggatcac   8100
gaggtcagga gatcgagacc atcctggctc acacggtgaa accccgtctt tactaaaaat   8160
acaaaaaaaa aaaaaattag ccaggcgtgg tggtgggcac ctgtagtccc agctactcgg   8220
gaggctgagg caggagaatg gcgtgaacct gggaggcaga gcttgcagtg agcggagatc   8280
gcgccagtgc actccagcct gggtgacaga acacgactcc gtctcaaaac aaaacaaaac   8340
aaaaaacaaa aaagcaaaac aaaacaaaac aaaaagaat caggttgtca aattccaaaa   8400
aatacattga atctatagct caatgtggaa aaaatttact tgtttagaaa ttcatgcctt   8460
cttatccatg acagtaggtc tttctctctc tattcctttta aatattttta agtgtttttaa   8520
agagataatg tagagtttct tcacacaggt cttacacatc ttttgttatt tttcttccta   8580
aataccagtt tttgttgcta ttgtaaatgc tatcttttta aaagtgcatt ttctgattcc   8640
ttatcagaat gcagaatgaa agtatttaaa aaatataaga gggttttttt ttgtaattaa   8700
aaaaaatcac aagttggtct tgcatgtgtc ctttagcatc ttcttgcttt ggtagctgga   8760
gaattcttag atcttattta taagcctgct gatctcttct ttttcagaaa tatagatacc   8820
atctgaaaaa ttagtgatat tcctattttt aactgtcatg gcttgctgaa tcaaagcagc   8880
tgggtttgat gcaagtgtaa tgctattttc ttaaagaatc aactcatcct tttgggcttc   8940
aggtactgag caagaaatgc ctgtcctcat gtatactctg cagatgtatt tctcttctaa   9000
cagatgtcag atttcaacaa atgacccact gtcctgaata atcacttttt ttgaggaagt   9060
gaggacacgc aaacctaacc tcatctggca acggaagtct gtgtaacacc tcagactgtg   9120
ggcagtttgt gactatggat ggtttgaaga atagccagtt accttcatt tccccaccat   9180
ttggcaacac agaacttctc cttttctctt cctatattga tggggttgaa tttctcagct   9240
gggttccttg agggggattca ctataactgt gcatctcttc atagtgacac ccatctcctc   9300
```

```
tgggatgtca gctctctgga tttagagaat tgtcataatt ctctcagtaa atgcagcaag   9360
taaaactcat tttaattga tttcatttcc ttccaacttg ccaagctccc ttattagttc    9420
aaataactag tatatagaaa ttgaagtatt ttaaataaat ttttttcaat taaaacaaaa   9480
tcacaaatta ggccaggttt ggtggctcat gcctgtaatc ccagaacttt gggaggctga   9540
ggcaggagga tctcttgagg ccaggagttc aaggccaggg ataacacag tgagccctcc    9600
atctctacaa aaagaaaaaa aatcacacat tgatcttggg tattatttag aatgttttgg   9660
gatttcaaat tagatgatta tatcatctgc aaaataataa cagtttattt cttccctttg   9720
tcctaagcac ttctttcctt tttcttgttt caatatgctg ggtgagatta tggtcaaagt   9780
tgagtagaca tagtgaccat gggcatcttt tgctactgct gattttgaag gaaatgcacc   9840
caatatcctg ccacttggtt ctgtgaactt tcatcaggtt aaggaagttc ctttctatca   9900
ctaaataagt ttttatccta aacttctgtt gtattttttg aatgcatcta ctgataggat   9960
tttttcctac ttaatctgtt accatgggga atgacaatta aagattttc tggtatgaaa   10020
ctactcctgc attcctggga gaaaaccata ttattcatag catttttta atactccagt    10080
aggttgtttg atcatctttt gctcagcact tttgcgtcta tatgcatggt caaatacact   10140
tgtcattttc cttttttcctc ctgtttcttc tgtttgggta tcaagataag attgagaaat   10200
tggggactag tctctctttt tctactgtct ggaagagtgt gtataaaact gaaatgactt   10260
gtttcctgaa tgattgatag atgtcactta tcaaactacc tgggcctggt ggcgtcacta   10320
tgtgcaattt tcctaattta atcatttat gtattcttca gcgagcttta ttctagggac     10380
gtgttccttt cacctaagtt atatatatat atatattttg acaaaaggat atgggtggca   10440
ttcttttgtc tttatattat ttgttttgt cgagattact tccccttta gaaatattcc     10500
tgacattggt tatttgtgac ttcttcttt ttttctagct aaatcttgtt aattgctttc    10560
cctattttat tatcagtttc aaggaaccaa cttttgggat tgtagaattt tctcactgta   10620
tctttgttt ctgttttatt gatttttact ctcatttct cagcaccttc cttctacttg     10680
ttttggttta ttctgatgat ctttgataaa ttttaagct ggatacttag cttcttagtg    10740
tctatatttt cattctctat aaaacgtagt tagggataaa tttctctcag aatttcattt   10800
tcatcccatt gcacaaattt tgatatgtat tatttgaata acattcagtt gtggatattg   10860
ttaaaacaac attgtgattt cttctttgaa tcttaaatta tttgggatta aaaattccaa   10920
aggtatgaag atttaaaaca tcttttcataa ttaaattcta agtagatgct ttttggtcag   10980
aatacatggt tttatgatat ctacttttaa aatttgttga gacttgatct gtggcctgta   11040
tacaatgaat ttttgtaaat gtttccctgt gtgcttaaga ataatgtatg ttttttagccg   11100
ggtgcggtgg ctcatacctg taatcccagc actttgggag gccgaggtgg gcagatcaca   11160
aggtcaggag ttcaagacca gcctggccaa tatggtgaaa ccccgtctct actaaaaata   11220
taaaaattac ctgggcatgc tggatggtgg caggcacctg tagtcccagc tactcaggag   11280
gctgaggcag gagaatcgta tgaacccagg aggtggaggt tgcagtgagc caagatcgtg   11340
ccactgcact ccagcctggg caacaatgta tattttttat ttcttaaatt aacagtccag   11400
tgtgttaatt gtaatgttca aatccaaatc ttcagatgtc aacagatctt cccaacatgt   11460
caatacttga gagaggtgtg ttgaaatctt acattatgat aatgtatttg tcaatttctt   11520
actgtaattc taacaattgt gtttcttata tttgatgtac ttttaaatta aaaccatata   11580
ttttagaaaa gcattatatc ttctcagtga actgaacatt ttatcaaaca tagtaattct   11640
ttctcttcat agtggtgctt tttttttttt tttttttttt ttggagacag agtctcactc   11700
```

```
tgtcacccag gcggcagtgc agtggcacga tctcggctca ctgcaacttc cacctcctgg   11760
gttcaagcaa ttctcctgct tcagcctcct gagtagctgg gattacaggt gcccgccacc   11820
atgcccaggt aattttttgta tttttagtgg agacagggtt ttatcatgtt gaccgggctg   11880
gtcttgaact cctgggctca agtgatctgc ccacctcgtc ctcccaaagt gctgggatta   11940
caggtgtgag ccactgtgcc cggctcataa tgatgctttt tgctttaaag tctgttcgac   12000
tggatgtttt tttttttttt tttttttttt taggcagggt ctcactcact catgcgggct   12060
ggaatgaagc ggcatgtgga tcttaatata gctactctag tttcttattg attagttaga   12120
tgcctgatac ttttccattt tctcccatcc tcccaacatt ttatgtattt atgctctacc   12180
agtgattttt gtaaacagta tataaccagg ttttaaaaaa tccaatttga catcccttgt   12240
tgagtttact ctgctggtat ttattatggt tactgacata tgtggatttc tttctactat   12300 tttaccttttt actttcactt agtcccactt tttcaatatt tcattttttct cctttcttac   12360 ttagaagctt aatatcttgc cgggcacagt gatgcatacc tgtaattcca gctacttggg   12420
agggtgaggt aggagcatcg cttgagccca ggactttgaa tctagtatga gcaacatagc   12480
aagactctcg cctcaaaaaa aaattaatat ctctgtctta catctaacaa aaagaatttt   12540
ggtgcgcttt tatatctctt ggcctctctt ccttcaactc tttacaatgt tgatattttc   12600
tacaaatgtg cagttttttgt tctgtgttat tatgaacata cttagcattt ttctattatt   12660 tgattttttta aaaatatac agctacacat tttgttgagg tattttgtca cctttctatt   12720
ccatacttat cacagatttt ctgttcttct ttctctttct ctcttttttat ttgaattctt   12780 cccccccagtg ggttttcagt ttgggttcct caaggcttct gaagacttat atgcctggaa   12840 atatattta tccccttaca ttttaattttt atttggcagg atatacattc taaaattaaa   12900 gtgatttttcc tttggtgctt taaactccac cccactgttt cttgcattta gtattgctgt   12960
taagacatct tacgtcattc ttaatctcac atatttgtag gtaatccact cattttccct   13020
ggaaactttt ataatttttct ctttggttct gatattctta agatccactg tcctgtgtct   13080
aggcatggga ttccctgcat ctttttttctt gcactcgtgg ggccctttca gctgaggtgt   13140
ttcatcttct ttaactctgg aaattttgtt tccactattt ttttcaaata ttttttccttt   13200 tctactttttt tttttttttt aaggtggagt cttgctctgt cgcccaggct ggagtgcagt   13260
ggcgcgatct cctctcactg caagctccgc ctcccgggtt cacgccattc tcctgcctca   13320
gccctccgag tagttgggac tacaggcgcc cgccaccatg cccggctaat tttttgtatt   13380
tttagtagag acggggtttc accgtcttag ccaggatggt cttgatctcc tgaccttgtg   13440
atccgccagc ctcggcctcc caaagtactg gcatgagcca ccacacccgg cctatttctt   13500
ttttatctta tttgaaaact attattatct aaatgttcaa gtgtttttttt ttttgttttt   13560 tttttttga cagtctcact ctgttgccca ggctggagtg cagtggcaca atctcggctc   13620
actgcaatct ctgcctcctg ggttcaagtg aatcttgtgc ctcagcctcc cgagtagctg   13680
ggattacagg tgcacatcat cacgcctggc taattttttgt atttttttag acaggatt   13740 ttgccatgtc ggccaagctg atcttgaact cctgacctca agtgatctgc ctgccttggc   13800
cttccaaagt gctaggatta caggcatgag ccaccacgcc tggccagttt tctatttcta   13860
tcttccatct atcttaacct ttttctcata tgttctagtc ttcatccttc cctacttcct   13920
tttaggggat acttctgacg gcccttctag ctcactaatt tgccctcaat tatagtcatt   13980
ctattctcca tcccatccat tgggctcttc ctatgatatt tttcagatat ttccacatgg   14040
```

```
cccttttttgc atcaagtaca caattacata attccttatt atgtttcaca ttcattttgc   14100
atgcacactt tgttattgac aaagtttctt atgcttgttt tcatgctgct aatattgcca   14160
catcttttta gtgcatgtaa tatgctcagt ttagcttctt gaccaaagcg tcctagtact   14220
tgtgcttcta gtggtctatc aggttctgtt ggtttgcttt tcttcaaagg tgcccagcct   14280
tctgagctgt gagctcacat tcccctgggg ttattggcta ctctggcagt gtttcttgaa   14340
tgagggaagg gcagatgctg gcctgtgtca ggcttactga gccaaagaaa tgacagggac   14400
gccgggcacg gtggctcacg cctataatcc cagcactttg ggaggccgag gtgggcagat   14460
cacctgaggt cgggagtttg aggccagccc aaccaacatg gagaaactcc gtctctacta   14520
aaaatacaaa attagccagg tgtggtggca catgcctgta atcccagcta ctcgggaggc   14580
tgaggcaggg gaatctcttg aacctgggag gtggaggttg cagtgagccg agatcatgcc   14640
attgcactcc agcctgggca acaacagtga agcatcgtct caaaaaaaga gaaatgactg   14700
ggacaagccc caggggtggat cccctcaaga acccaaacca cacccaacca gtcccacttc   14760
ctatcacccc agtaaggcag cttaagtcat ccctccatct tcagaccctc gtggagaagc   14820
aacattggtc aaggactctc gttgcattgt gatccaccag ccctgggagt ttggagtgga   14880
gaaaatggca aggagaatgt caaagaccag tgagcttcca cctccgttct ccttctcctc   14940
accccagtgg gcctctggtg cttacccaac acatgcctgt tggacactgg cacatcataa   15000
tcctgtccat actctgaatt ctgcagtgag gggcagacaa tgtttgtccc actgaagggg   15060
tagaggagag aaaggagcag aattcaagta tgtttgggct aacccatcct ctcaacaagc   15120
cagctgtccc cccgcccagt tctcccaccc cttttcttca aatgagcctt aactttcccc   15180
tagggatatc agtgtgattg attgatcata aattgatttg taaagttttg ttcacccagg   15240
agctccatct ttagttccat cattggtagg tcttggagaa cagagccggt gtatgaattc   15300
actcttttga caagaactat ggtagagaga gctttgtttt ctcctttatt ttaccttaa   15360 ccattctgca cactttcatg ccataggcag aatggtaaag cgaggcacag catggtccct   15420
ggagtttgac gtcctgcatt caggttctag attcacccac ttgcaagctg tgtgaccttg   15480
gataagctaa tgaacctctc tgttttttg ttttctccta tagaaattgg gttattaata   15540
tgctagtatc tgtctcggat tgttacaagg agtgcttagt aaagtggcaa gctcacaggg   15600
agctcactta taactgttac ccagtattac ttttccttct gtctaacaag gaactgcatg   15660
acggggaggt atttgggtgg tttcagtctg ctttatgtcc tcatttatac gaacggcatc   15720
tagcccaaag aaagcactca gcaaagagct attgagtgaa agggtgaaca tactgcattg   15780
tcctatttac taatctgagc tgtgcctttt ctttcagttg tcaatttcac ccttttatt   15840 tcatataccg cacacctatt gatagacata tgtctttatt tcttcctttg cctgcataat   15900
gctggtgtgc atagccactt tttcatttta tttcatcttt cttgtgccta atataagcag   15960
ctctctccag aaagtctatt ttttctgac acaatgaagc cattttttccc taactgcgga   16020 gtcctttaa aaaactgta tggccaggtg tggtggctca cacctgtaat cccaccactc   16080
tggaaggcta agctgggcca gtcgcttagc ccaggagttt gagaccaacc tgggtaacgt   16140
ggcgaaaccc tgtctttaca aaaattagct gggcatggtg gcttgtgcct gtggtctcag   16200
ctactcagga agctgaggtg ggaggattgc ttgagccagg acgggaggt tgcagtgaga   16260 cgaaatcaca ccactgccct ccagcctgga tgacagagtg aaactctgtc tcaaaaagaa   16320
aacttctgag ctactgtttg aagactcacg ttgcttcaa catatttttcc atagcgtgat   16380 gggtagggat atgggtgaag gtgggagagg aaagaaattg cttacttgta tctggttacc   16440
```

```
atctttgctg gggacaggat ctgctccatt ttgtttctct ttcatggaaa ctgggtccag   16500
gatcagaatt gccatctctt ttctggtttg cacataagac accttgtaac ctatgccgaa   16560
ggtatacatt tgcttcatca ataatccgct cctcctgcct aggtcagggt ctatgtctga   16620
tttctcacac tgtacgtgcc cagaacctga aacaggggag acagggctga gttcgaatcc   16680
tggcctcgcc atgtattaga tgaataaccc tgggcaagct acttaacctc tctccacctc   16740
agtttccctg tgtgtaaggt ggggataatt agaatatctt ttatactgtt gtgggttttt   16800
ttttggtgat gattcaatgt gattagtaag tcctcaatat ggtctgatca atcatagtat   16860
tacaaaattt tgaaagaatg agcgaatagt tgagttcaca ggaaatgtat atggacaggt   16920
ggggccggga tttgaaccca gccctgtctg ccctgtgccg gttcctgggc acgtacagtg   16980
tgagaaatca gacatagacc ctgacctagg cagcctatgg cctgtcctta ggaggagtgg   17040
attataaaag gatgaattga taaatgtcac atcagcccaa cttccctgtg ggaaccattt   17100
gttgtatttt tctcttattt ggtgttgagg tctctctttg gggagtggtc ataaaatcta   17160
gcccggcctt gaatgggaac cccagagatc tggccatcat gttcacagtg tgactttcac   17220
agaatactcc tttatcctgg cacaccacct gctgcctgag tgcccagcct gtgacccccct   17280 ctcacagcaa acttgtttat cctggcagat tcccttgcag cttttcctatg acctgtgtcc   17340 ggtttattcc caccaagaca gctattctct aggagagcct tgaccagaaa agaagtgagg   17400
ttcaggtctg ttgggcgggt gggacacaga ggagacagca caacaaaaca catgaaataa   17460
cagaagcagt ttattactca caggtccag agagaagata gcacagcaag cctggaaggg   17520
cgaatggaaa ggagggaact gaccaggacg caagtgctca tccagtgggt aggggcaag   17580 agagagagag agagagagaa gaacccatga gccaaagcct taattagagt ccagggcata   17640
atctaagcag gcttcccaca gggagttcta actgggggtt tagagctagc aggcaggagt   17700
tctgtggagc cacactgtga ctgagaggtg gttgctgcag tatatctgcg cagcctatga   17760
gggacacagg agtcaatacg taagtcaagt aggttgtagc tgtatgtccc ataggagct   17820 ggtcacaagg agatggttgt ataaggcaga catttggatt aaccaccttg gggaactggg   17880
aggaggtaga gaattggaaa ttgtgtccag gtgactaagc cctgcttctg gcatgagaaa   17940
gtccaactta cattcaaaat aaatcccaag gcaacatata aatataagaa ctcattattc   18000
tacacctgcc tctttattcc tactgtgaca cctttccttc cccttactc agggttccag   18060 gaagaagccc tggccagaca gccccggaga tcaagcatct cctcctgggg atgcccctcc   18120
cttggaagaa caaaaggagc tccattatgc ctcccttagt ttttctgaga tgaagtcgag   18180
ggagcctaag gaccaggagg ccccaagcac cacggagtac tcggagatca agacaagcaa   18240
gtgaggattt gcccagagtt cagtcctggc tggaggagcc acagcctgtc tgggggaaag   18300
gacaagtcag ggaccacttg ctgaagcacg aagagccctt gtggcaatgt taacattaac   18360
tgatgtttaa gtgctccaag cagatggaat tagagaggtg ggctcaaatc taggccctgg   18420
cactgtcatc aagcaattca ctgcatccct ctgtgcctca gtttcccatt ctgtaaatca   18480
gagatcatgc atgctacctc aaaggttgtt gtgaacatta agaaatcaa cacatggaaa   18540 tcaaccaaca tgggtcctgg aacagggcgt tgtgctcagt gctttctggt ctctcttcct   18600
tgaatagaaa ggtcctgctg gcaagttctc tcaaggctgg ggatgaccag gcacaaaaaa   18660
cagggcagca atatgttggt gtcactcccc ttcccaaaac tcttcgaaga ctccctagga   18720
aagaccagcc cctcagcctg gcacttggtt catgatgtgg gatcttatat ccttgccaga   18780
```

```
gtcatatctt tgcccacttt tacctgcaat ccttgcatca tattcctttg gctccagtcc   18840
ttcatttatg agaccatag gaatccttcc aacagccaaa gagttgagtc taactctttc    18900
ctgcccaaac ccattcacgg cccctggcc ttagacaata tatcacaagc atctcccctg    18960
acacataaag tc                                                       18972
```

<210> SEQ ID NO 17
<211> LENGTH: 11226
<212> TYPE: DNA
<213> ORGANISM: Homo sapiens

<400> SEQUENCE: 17

```
gcagttcctg agagaagaac cctgaggaac agacgttccc tcgcggccct ggcacctcca     60
accccagata tgctgctgct gctgctgctg cccctgctct gggggaggga gagggtggaa    120
ggacagaaga gtaaccggaa ggattactcg ctgacgatgc agagttccgt gaccgtgcaa    180
gagggcatgt gtgtccatgt gcgctgctcc ttctcctacc cagtggacag ccagactgac    240
tctgacccag ttcatggcta ctggttccgg gcagggaatg atataagctg gaaggctcca    300
gtggccacaa acaacccagc ttgggcagtg caggaggaaa ctcgggaccg attccacctc    360
cttggggacc cacagaccaa aaattgcacc ctgagcatca gagatgccag aatgagtgat    420
gcggggagat acttctttcg tatggagaaa ggaaatataa atgaattaa taaatatgac    480 cagctctctg tgaacgtgac aggtaaggca cgggctccaa gagaggccaa aggcaaatgt    540
gatgagggct ttagggcacg gctgagacgg acacatgtc ctgggagggg gccggggtg    600 atggactcag gagaggagct ggaccagagc ctgagcttcc ccaggaccgc accttggatg    660
cccctcctga tcctgcaggc ccctcccctc accagccctg acccacaggc ctgacatcct    720
catcctgcct ctgacgctgg cattgtggca tgtggggcct tatgactcct tgttttgggg    780
cctgtcctag gcatggccgg ggtttagcac catcccaggc ctctccccac cagatgccag    840
aagcacccac tccacccatg cagtgagaca ataacaatta tctccacaca ttgttaaacg    900
tcctgggggg ttaagtcctc cccagttgag agccttaggt ctacacaacc ccgtgactct    960
ctcaggccag gccagggagg aagcacttcc tggcgcaaac caagggcagc agaggcacct   1020
gagcctggac agggagactc agcacacggc ccctccatct ctcatgccct gaggtcctcg   1080
gagatccaca tttagatgct caaaagacag gagggacctc cacgatggtc cagaggccgg   1140
gagggcagga cctacgtgtc tggtgcaggc cctggtgctc cagggaagcc cggaggtagg   1200
aggtgggaca cggtctcttc tcctccctgg gtgggtctct agggtctctg agcttcaggg   1260
tttccttcac tctgtgcaga gggaaccagt tcctatagca tgtgggtttg tagtttctct   1320
ttcgtgctgg gttgaggtct ccagctcctc tccagcccct ctccagcccc ctgtgggtcc   1380
cacagccctg cccctcctct ccctcccact tctctgctca cacaaggagc ccaggaaccc   1440
tctgtctcag agatgctgct gcctctcttg tgggcaaatg aagagaggga cagtcggggc   1500
tgggctgagc ctcatttccc cacagcgtcc caggccccac tgtcaagata caggctggag   1560
gtgctggagt tggtgatggt gcaggagggc tagtgcgtct ctgtgccctg cagtgtcctt   1620
taaccctatt acaactgaac tgactctagc cctgtccatg gatgctggtt taagaaaggg   1680
atcaatatac aatggaataa tccagtggcc acaaacatcc caaatggaaa agtgcaggag   1740
acacggggcc gattccacct ccttggggac ctgaagacca caactgctc cctgagcatc    1800 agagatgcca ggaaggggga tttgaggaac tactacttcc aggtgagag aggacagata    1860 agatggaatt acaaaacgaa gcagctctct gtgaatgtga cagataaggc acaggctcca   1920
```

```
ggagacacca cagggaaagg tcatgggggt ggcagcgaaa gcctgggatg gggcccctgc   1980
cctgggagag ggctgagggt gaagcgagtt gggctcaggg cagaagctga accagagcct   2040
gagcttcccc cagggctgta ccatggatcc tctgtcctga tcctgagtcc ccctctcttc   2100
accagccttg acccacaggc ccaacatcct tatccccggt accctggagt ctggctgctt   2160
ccagaatctg acctgctctg tgccctgggc ctgtgagcag gggacgcccc ctatgatctc   2220
ctggatgggg acctctgtgt cccccctgca cccctccacc cccgctcct  cagtgctcac   2280 cctcatccca cagccccagc accacggcac cagcctcacc tgtcaggtga ccttgcctgg   2340
ggccggcgtg accacgaaca ggaccatcca actcaatgtg tcctgtgagt gctgagccag   2400
gacgccctgg tccctgatga gggggggacg tccctgaggg cagaggatgg ggtcagggct   2460
cgacactggg tgctgggtcc cagaatctgg gctggttgtg ggatcaggag gacgctggct   2520
ccgccttccc catttatgca gctcctgggg agacagggcc agtgtcccca gccctcacag   2580
tgatgcaggt ctccatgtct ttctgtccca gaccctcctc agaacttgac tgtgactgtc   2640
ttccaaggag aaggcacagg taggatggag cccctccct  ggggctgggg gagcagggcc   2700
ttcagctcag ggcagggcca ggtccctcct catcctggac tcaccctggt gatatgagac   2760
tcccttgtag ttgaacccag gcctcctccc catccttagc ctctgtggcc acctgagcac   2820
ctgtcctctt ccccccactc ccctcagact cttgcacaca cacccctc  agccctgcag   2880 ccaggacagg gggaaataca tatagcagga gcagcctttg ggcctcttat cttccatctc   2940
ctgaatatgc cacctaactc gtctttttat tttacccaat agttttgagc tacgttcttt   3000
tggatacatg ctataatcac gtgggcaaaa attttaaatt cacagtaaaa tgtgtcccca   3060
gaatcaacca gggtctgtcc aggctgtcct gagccttggt ttgtgcacct ggaagatctc   3120
agaggtggtt tgatgtcagc agtgagactg tttgcaccct cttctaggga tgtgtgtgat   3180
tccactgtct gaatagtctc tgattttgtg gcatctccta atggaagatc atggcactaa   3240
ttttatccta cggcacgaac actgcaatga ataatgttgt atctactccc acaaggaata   3300
tctaagtgta taggataaat tcctaaaagc cattttacc  agtgtcatat gttcttctg   3360 attttgaaag atatggtgaa gttgtcctca aataaaggtg gcaagtttta cattcccaac   3420
agtgagcggt gaacataagt atgtccctgc accagcctac atcactctct gttccattcc   3480
ccagtctcat tctgtatcct tcctccctgt ttcaatcact ttgtctcttt gaacctccaa   3540 cttttctct  acagcatcca cagctctggg gaacagctca tctctttcag tcctagaggg   3600
ccagtctctg cgcttggtct gtgctgttga cagcaatccc cctgccaggc tgagctggac   3660
ctggaggagt ctgaccctgt accctcaca  gccctcaaac cctctggtac tggagctgca   3720
agtgcacctg ggggatgaag gggaattcac ctgtcgagct cagaactctc tgggttccca   3780
gcacgtttcc ctgaacctct ccctgcaaca ggagtacaca ggtgggtaag ggaggggctg   3840
gaggaggaga acacacctgc cccaccctca tgggccaccc actgcccctg agcttcaagg   3900
gggagctcag ctctggtctg tgctcagctg tgaggcctgg aacttccctg caacccaggg   3960
cactgctgtc ctcttcctgc caggaaaggt gtgtaaggca ggaagagggg aggagtgggt   4020 cttgagggg  aggagctggg gcctggacag gtgtgtttgg ggagacacgt gccttgcttt   4080
ccagtgcctg gactagggtg acacaagcaa ggcactcact tctgggcaca cgactaaaaa   4140
acaaaaaata aaacaactca gcaagcaagt gaaataatat tggatgtgat tatctttatt   4200
aaaaactaaa aattattgca aaataatttg acagtgaata caaatcaaaa tttcaaatac   4260
```

```
aggcaggctg tgcttaccac tctcatgcct cagtgacctc aggagttgtc ccttcctcct      4320
ccctcccatt cttgcccttt gtttctggga aggggattag gggtacccaa gttgggggcc      4380
ttataggaag tgggaggaga agagacccag ttcttggagt tggatcacca aaacaattcc      4440
aatccatcct caggcaaaat gaggcctgta tcaggagtgt tgctggggc ggtcggggga      4500 gctggagcca cagccctggt cttcctctcc ttctgtgtca tcttcattgt gtgagcactg      4560
accctaggga gggagggaga gtcctggggg agggcggact gggagcagga tccctgaagc      4620
cagagctgga agggactgca tgggtcaaga gcttgggca agaatgagct cacgggtgcg      4680
tggcaagaat ttcaagagcg cccttgtctg tggggctcca catctgtggt gaaccttggg      4740
ccccaccacc caggaggcag gagcctctgt tttcaacact ggggtctctg ggactggacc      4800
accctcctcc cacctcagtt accctccag cgccccaaca ggaaatacag ggcaggggtt      4860
ggtctgccca ctgcaccccg atctgaccac actgaaaggc tctctggtct cttcactcag      4920
agtgaggtcc tgcaggaaga aatcggcaag gccagcagcg gacgtgggag acataggcat      4980
gaaggatgca aacaccatca ggggctcagc ctctcaggtg agtgatatgg gcgtctccac      5040
acccagcatc cagctgggac atctcccaca ggatggcctc caggattcct ctgcttatca      5100
tggccaaaat tatctcctca tctcctcctc cttcccacca tccagcttct cctgcaggat      5160
tccccatctt gctgactgca tgacagtccc tcctacctac tttctctcgg gccaggcatg      5220
gaggaggagt tatctcctct ctgtcctccc tttcttctct atagctccac attcaccaaa      5280
tcttgtccat ttttcctccc taagaatggc tagcattgct cccaccccca ccaatcctaa      5340
actctctcaa tgctgaggcc tgaggatctc tgtcttggac ttcctcacct ccctgcctct      5400
tgtgtcccct gccctgatgg gaggaatcat tcagaagcca tcactgatca gtttctttgc      5460
atctggacag ctgttcccac ccccaacact gtctagagca gaagccagaa aatactatct      5520
ggaaaggcca gataggaaat atttttggct ttctggccta cacagtctca ttgcagctcc      5580
tcaactctac tgatgtagca ggaaatcagc cgtagaccat gtgtaaatga ttagctggct      5640
gtgtgccagt aaaactttat ttataaaaac aagctgtggg tagaatttgt cccaagggct      5700
ctagtttgac aagcccctaac ctagagaaaa agcccaaact tcataactgc agccctgcac      5760
attctcgtct cttaaacatc tacctctcta gcagggctgg aattagtgtg agatgagtga      5820
ggtcctggcc tagcatgcaa aatttaagaa ggtgccaaaa atctcagtaa ttgtgatagt      5880
tttaaaaaaa actcttattt taggtttggg ggtacatgtg caggtttgtt acatacataa      5940
actctggtca gaggggtttg tggtacagat tattttgtca cccaggtcct aagcctagta      6000
ccccacagtt atttttttct gttcctctct ctcctcccac cctccacctt caagtgggcc      6060
ccagtgtctg ttgttctctt ctttgtgttc atgagttctc atcatttagc tctcactgat      6120
aagtgagaac atgcagtatt tggttttctg ttcctgtgtt cgtttgctaa ggataatggc      6180
ctccagctcc atccatgttc ccacaaaaga cataatctca ttctttttta tggctgcaca      6240
gtattccatg gtgtatttgt accatatttt ctttatccat tctgtcatgg atgggcattt      6300 aggttaatttt catatatttg ctattgtgaa tagtactaca atgaacattt gcttgtatgt      6360
gtctttatgg tagaatgatt tttattactc tgagtataaa accagtaatg tgattgctat      6420
gtcaaatgat agttctgctt ttagctcttc aggaaattac catactgctt tccacagtgg      6480
ttgaactaat ttacactcct gccgacagta taagtgttcc cttttctctg cagccttgcc      6540
agcctctgtg attttttttta ctttttaaaa gtagccattc tgactggtgt gagatgatat      6600
ttcattgtgg ttctgatttg cgtttctcta gtgatcagcg ataatgagct ttttctcata      6660
```

```
tgtctgttgg ccaaaaatgt ctgttcatgt cctttgctca ctttttaatg gggttgtttt      6720
tctcttgtaa atttgtttaa gttccttata gatgctggat attagacctt tgcctaatgc      6780
atagtttgca agtattttct cccattccgg ttgtttactc tgttgatggt ttattttgct      6840
gtgcaggagc tcttaagttt aattagatcc cattgtcaa ttttgctt tgttgtgatt        6900 gctttggcat ctttgtcagg aaatctttgc ctgtttatcc agaacgatat tgcctacatt     6960
gtcttccaga gttttatag ttttgagttt tacatttaag tttttaaccc atctcgagtt       7020
gatttttata tgtggtataa ggaagcagtc ccactcaatc ttctgcatgt ggctagacag     7080
ttatcccagc accatttatt gaatcaggag tcctttcccc attgctttt tttgtcagct     7140 ttgttgaaga tcaaattgtt gtaggtgtgt ggctttattt ctgggctctc tattccgttc    7200
cattggtcta tgtgtctgtt tttgtaccac taccatgctg ttttggttac tgtagacttg   7260
taatatagtt taaatttggg taacgtgatg cctccaggtt ttctttttgc ttaggattgc   7320
cttggctatt tgggcacttt tttggtttca tatgaatttt aaaattgttt tttctagttc   7380
tgtgaagaat ctcattggta gtttgataga aatagcattg aatgtataaa tttctttggg   7440
cagtatggcc atttttaatga ttttgattct ttttatccat gagcatagta tgttttccca  7500
tttgtgtcac ctttgattta tttgagcagt gttttgtaat tctcattgta gagttctttc  7560
acctccctgg ttagctgtat ttctaaaaat tttattcttt ttgtggcaat tgtgaatggg  7620
attgtgttcc taatgtgact cttggcttgg tagttcctga tgtatagaaa tactagtgat  7680
ttttctatat tgattttgta tcctgaaact ttgctgaagt tatttatcat ttaagaagct  7740
tttgggctgg gactacgagg ttttctagat atagaatcat gcatctgcaa agagggatag  7800
tttaaattcc tctcttccta tttggatgct ctttatttct ttctcttgcc tgattgctct   7860
ggccagaatt tccaatacta cgttaaacag gagtggtgag agagggcatc cttgtcttgt   7920
gctggctttc aaggggaatg ctttcagctt ttccatattc aatatgatgt tggctctgcg   7980
ttcaccatag atagctctta ttatttgag atatgttcct ttaataccta gtttactgag   8040 agttttaac acgaagcgat gctgaatttt atcaaaagcc tttctgcat ctattgagat    8100 aatcatgtgt ttttgtcttt agttctgttt gtgtggtgaa tcacatttat tgatttgtgt   8160
atgttgaacc aacatgaagc cgacttgatc atattggatt aaccttctga tgtgctgatg   8220
gattcagttt gcaagtattt tgttgaggat ttttgcatca atgttcatca aggatattgg   8280
cccgaagttt tcttctttg ttgtgtcttc gccagatttt ggtatcagga tgatactggc    8340
ctcatagaat gagttaggga agagtcagtc ttcctccgta tttgggaata gtttcagtag   8400
gaacagaagg aggctcagat ctgacattta ttgtgtgatt gaagagcctt ccaggcagag   8460
ggaggagcaa agcaaggccc aggcacagga agaggaaagg agaggagcca tgggacatct  8520
gtgtgattag acagagggag gcaggactga gagcaggaaa tgactttgga ggagttgagc  8580
ctatgtgaat tgtgtctgac tgcacaggct actgtgagca tttggagagt tttgagcaga   8640
aggacatgat cagacgagat tgggtccgtt cagggtggta tagctgtaga ccagaagaac   8700
atgatcaact ttcattttca tgggattcct ctggccactg tgtgcagaag agaccgtgtg   8760
tgtggcaggg gaaggagaga gcataggagg tagacaggag gctggtgaac atcccaggca   8820
gaaggtggtg ttggctggaa ccaagatagc agcagtggta gacatgactg tctcccagat   8880
gaattctgca gtgaacccta ctgggatttg ttaatgaatt ggaattagaa tgtgagccac   8940
agaaagggag caagaattac ttccagattt ttgccctgag cagtgggaag aatggaggtg   9000
```

```
ccaatcattg aggctgagaa gattgcagaa gaaatggatt tgggaaagaa aaggaggagt    9060
tcagattgaa taggttgagt tttgtgtgtc tttggacaag aacgcggggg tttgaattat    9120
accactggat caaagactat agtcaggaga aaggagtggg ctgggggtac agatttggga    9180
gtcattagcc tattgatggc atgaagccaa cacagtggat aagatcacaa ggcaaaggta    9240
aagaagaaaa gaacccgggg ctgctctgat atttaaggtc agggagacct gaagcaattg    9300
gcaaagaggt tgccaagaag gtgaggtgga cccagaaaag catgatgtcc tatagttgag    9360
tcaagaaggc cttctgtgta gggaaggtga gcagctgggt cctctgctgc tgaaaagtcc    9420
aggaaggaga agactgcaag gtggacattt agactcagcc acttaagtgg tagtcacagt    9480
gaccttgata gtagcagtgc ttagacttgg tatgtgtgtg aatattaatt tgagtaatca    9540
agagagaatc tggcaagcaa aatcactgac agttccatgg agcatcttct gcacagggga    9600
gcagcaggga agggctgcga tgaaggagga ccctcccagg cagcctctgt cactctctgc    9660
tgtgtgagtc tgtattagtt tcctgtggct gctgtgacaa attaccatgc atttcctggc    9720
ttccaacaac acacatggat taaagttctg aaggtcacaa cccaaaatg ggtgtcactg     9780 ggccaaaatc aaggcattgg caggcagggc tggttccttc tggaggctcc aggggaggat    9840
gcaatttctc acccttttctg gcttctagag gcacctgcat tccttggctc aagtcccttc    9900
ctctgtttgc aaggcaagta gcctggcatc ttccaatctc tctaagccct cctcctttca    9960
cttgtaagga ctcctgtcat tccactgggc ccacccaaat aatccaggat aacctcccca    10020
tgtcaatatc cttaacctag ctccatctgt aaagtccctt tagcaatgta acgtaacaga    10080
ttcacaggtt tcagggggatt aggtatgga cattttgggg agcagttata cttcttatca    10140
gaggatataa tttctttgac tgagttgtcc tccccatacc accgaactgt gagcttccta    10200
agagcaggtg ccccatccaa atcaaggccc tgtaattctc tctcacttag cctcttcctg    10260
cccatcttat aattcacaca tagatattcg tttgtttgac agtcattttt gccaaattcc    10320
ctcaattaaa aagtgagttt caggaggtca gggccaacac ctactgtgtc caccacagtc    10380
catccagcac ccggatcagg gcttcacaca cagagggccc cagcaggact ccaggctttg    10440
gggtcagaag gaagggactg gattgggtcc cggcataaca gggagtttgg gtacgctact    10500
ttcttcatgg agttgttgcg ggaagttaat aagattaata acaccaaac aagttgctca     10560 ataagtgtta aatattgcag gaaagtataa atgaaggaga tttctataaa atgaacgtgg    10620
gatagaggca ggaactcatg aagtttaatt ctatacagag gaatatatcc gaaccaacca    10680
accgatcaaa caacttgtga ctctcccctgc cttatcctat ttccactgct ctgctctgac   10740
tctcttctct ctctccattc agggtaacct gactgagtcc tgggcagatg ataacccccg    10800
acaccatggc ctggctgccc actcctcagg ggaggaaaga gagatccagt atgcaccct     10860 cagctttcat aaggggggagc ctcaggacct atcaggacaa gaagccacca acaatgagta    10920
ctcagagatc aagatccca agtaagaaaa tgcagaggct cgggcttgtt tgagggttca     10980
cgacccctcc agcaaaggag tctgaggctg attccagtag aattagcagc cctcaatgct    11040
gtgcaacaag acatcagaac ttattcctct tgtctaactg aaaatgcatg cctgatgacc    11100
aaactctccc tttccccatc caatcggtcc acactcccg ccctggcctc tggtacccac     11160
cattctcctc tgtacttctc taaggatgac tactttagat tccgaatata gtgagattgt    11220
aacgtg                                                                11226
```

<210> SEQ ID NO 18
<211> LENGTH: 5431

```
<212> TYPE: DNA
<213> ORGANISM: Homo sapiens

<400> SEQUENCE: 18
tagggcctcc tctaagtctt gagcccgcag ttcctgagag aagaaccctg aggaacagac    60
gttccctcgc ggccctggca cctctaaccc cagacatgct gctgctgctg ctgcccctgc   120
tctggggag  ggagagggcg aaggacaga  caagtaaact gctgacgatg cagagttccg   180
tgacggtgca ggaaggcctg tgtgtccatg tgccctgctc cttctcctac ccctcgcatg   240
gctggattta ccctggccca gtagttcatg gctactggtt ccgggaaggg gccaatacag   300
accaggatgc tccagtggcc acaaacaacc cagctcgggc agtgtgggag agactcggg    360
accgattcca cctccttggg gacccacata ccaagaattg caccctgagc atcagagatg   420
ccagaagaag tgatgcgggg agatacttct ttcgtatgga gaaggaagt  ataaaatgga   480
attataaaca tcaccggctc tctgtgaatg tgacaggtaa ggcacaggct ccaggaaagg   540
ccacagggaa aggtcatggg ggcggcaggg aaaggctggg atggagcccc tgccccagga   600
gagggcttag ggtgaagcga gttggctcag ggcaggagct ggaccagagc ctgagctccc   660
cccagggctg caccatggat cctctgacct gatcctgagt cccctctct  tcaccagcct   720
tgacccacag gcccaacatc ctcatcccag gcaccctgga gtccggctgc cccagaatc   780
tgacctgctc tgtgccctgg gcctgtgagc aggggacacc ccctatgatc tcctggatag   840
ggacctccgt gtcccccctg gacccctcca ccaccgctc  ctcggtgctc accctcatcc   900
cacagcccca ggaccatggc accagcctca cctgtcaggt gaccttccct ggggccagcg   960
tgaccacgaa caagaccgtc catctcaacg tgtcctgtga gtgctgggcc gggacgcctg  1020
ggtccctgat ggggtgagcg tcaagcctgg acactgggtg ctgggtcccg gaatctgggc  1080
tggtggtggg gtcaggagga cactggctct gccttccctg tttatgcggc tcctggggac  1140
agacagggcc agtgtcccca gccctcacag tgatgcgggt ctccatgtct ttctgtccca  1200
gacccgcctc agaacttgac catgactgtc ttccaaggag acggcacagg taggatggag  1260
ctccctccct ggggctggag gagcagggcc ttcaggtcag gatggggctg gcttattcct  1320
caacctggac tcactttggc aaacagggat gtccttgtgg gtgaactcag ggcccctctg  1380
tatccttagg ccccaaggcc acttgttccc atcctcccat cacctccctt ggactccccc  1440
acacaccccc ccctcagcct caaacaagaa gagggtggca ttcacacagc aggaccaggc  1500
tttgaggctc cttctcatgt atctcctgaa tacatctcca cccttatctg tttatttctg  1560
atagttctga tctaagtact tctggacagg tgataaatgt ccatgggcaa aaattcaaat  1620
tgcagagcaa aggctctcct ccgatgcctg ccccctccc  cagaaccaac cactgtccat  1680
ccaggctgcc ctgagtctcg gtttgtacac ctggaggatc tcagaggtgg tttgacgtcc  1740
gtagtgagac tgtccgcacc ctcctctagg gctgtgtgtg agtccactgc atggatggac  1800
tctgattttg tggcatctcc taatggaaga tcacggcact aatttcatcc tacggcagga  1860
tagaacaatc ttgtatctac ttccacagga atatctaagc ctgtgggtta agttcctaaa  1920
agcaaaatgt agctacatta tatgttcttt cttattttga aagataagcc caaactgttc  1980
tcgatgaagc ggggagaagt ttacattccc agcagtgagt ggtgaaagtg tgtgtttcca  2040
gaacttcagt ctatgtctgt gtgtcagttg ctgtcatcag tctctttctg tatccttcct  2100
ttttctccag atctatgtat ctctctgacc ctctgtctct ttttctacag tatccacagt  2160
cttgggaaat ggctcatctc tgtcactccc agagggccag tctctgcgcc tggtctgtgc  2220
```

```
agttgatgca gttgacagca atcccoctgc caggctgagc ctgagctgga gaggcctgac    2280
cctgtgcccc tcacagccct caaacccggg ggtgctggag ctgccttggg tgcacctgag    2340
ggatgcagct gaattcacct gcagagctca gaaccctctc ggctctcagc aggtctacct    2400
gaacgtctcc ctgcagagtg agtgcaccag tatgctgggg aggggctgga gaggagaaca    2460
cacctcctcc acccttagta actgctgagc gtggaccttc agagaggagc tccgctctgg    2520
tctgtgctca gctgtgaggt ctggaacttc cctgggaccc acagcaccac tgtcctcttc    2580
ctgccaggga agggttgtgg ggtggggaga gggcaggagt ggatctcaga ggggacagga    2640
tggggccgga caggtgtgtt tagggagaca agcgcctttc tttgcagggc tgaactggag    2700
tcacacaact gagatacttg ctttgagcat caaattaaaa aaagaaaaa gcccagcaag     2760 tcagcaatca aatgaaatca tattgcaatg caataatctt ttaaaaaaag taaaaattga    2820
atgcaaaaca aattcattaa tggataaaat attaaaattg tgaaaaaaaa ccccaaaagg    2880
aatggctggc acttgcacgc ctcactggcc tcaggaagag tctctccatg tcctgctctc    2940
tctcattcct gttctttgtg tctggaaagg ggaagtggaa atagaagtct aggaccctac    3000
aggaagtggg aggagaagag acccaattct ctatgatata tcacaaaaat aactcccatc    3060
tgtcaacagg caaagccaca tcaggagtga ctcaggggt ggtcggggga gctggagcca    3120
cagccctggt cttcctgtcc ttctgcgtca tcttcgttgt gtaagcatgg accctagaga    3180
gggagggagg gagagccctg ggggaggaca ggctggaagc tggatccctg aagccagagc    3240
tggagggacc tggatgggtc aagagcttgg ggcaagaagg aggtcacagg tgcatggtga    3300
gaattccatg tgggcctgtg tttgaggagc tttgagtctg tggcaaacct tggtacccac    3360
tgtccaggag aagagagcct ctgttctcaa ccttgggtc tctaagactg gaccactgct     3420 ttcccaccte agtcacccct gcagtccctt aataggaaac acatgggggt acctggtctg    3480
cccaccgcac cccaatctga ccacactgaa aggctctctg gtctcttcac tcagagtgag    3540
gtcctgcagg aagaaatcgg caaggccagc agcgggcgtg ggagatacgg catagagga    3600 tgcaaacgct gtcagggtt cagcctctca ggtgagtgat gtggactctc cacagccagc     3660
atgtagcctg gacacctccc acaggatgac ccccaggact aatcagctgg gcgtagccaa    3720
agttacctcc tctctgttct tcctttcttc tctgtagccc caaatcacaa tgtttggttg    3780
gtttcctccc ctaagaacag cttttattgt ctctgctccc tatcctgacc cttcattgct    3840
gaggcctgag gatctctgtc ttttgttccc tcacctgtct gcctgtctcc tctcctttcc    3900
tgcctggggg gactgtccag aagacatcat cgtccagttc ctctgcattt gaacagctgt    3960
tcccccaccc ctcaataccg tttagagcag aagccagcaa atactatctg tcagggacag    4020
atagaaacta ttttcggctt catgggccac acagtctcat tgcagctcct caaatctgct    4080
gttgtagcaa gaaagaagcc ataccctg tgtaaacaaa tgaatatggc tgtgtgccaa      4140
taaaactatt cacaaacata aagagtgggc tggatatgac tcagatactg tagtttgaca    4200
acccctgatc tagagtaaaa atcccaaact ctatagcctg cagcagtgca cattctgact    4260
ttttttgttt ttttttttt ttgttgttgt tgttttgag acagagtctt gctctgtcgc      4320
ccaggctgga gtgcagtggt gcgatctctg ctcactgcaa cttccacctt ccgggttcaa    4380
gccattctcc tgcctcagcc tccggagtag ctgggactac aggcgcctgc caccacgccc    4440
agctaatttt tttgtatttt tagtagagac ggggtttcac tgtgttagcc aggatggtct    4500
cagtctcctg accttgtgat ctgcccacct tggcttcccg aagtgctggg attacaggcg    4560
tgagccactg tgaccggcca cattctgacc ttttaagcac ctacctctcc actagggcaa    4620
```

```
gaacaagggt gaagtgagtg aggctgttgc ctcaagtgca ttttttcgtt tgtttgtttt    4680
tgttttttga gatggagtct cgctctgtca cccaggatgt agtgcagtgg cacaatcttg    4740
gcttactgca acctctgcct cctaggttca agcgattctc ctgcctcagc ctcctgagta    4800
gctgggatta aggtgcaca ccaccacacc tggctaattt tgtattttta gtagagacag     4860
ggtttcacca tgttggccag gctggtctca aactcctgac ctcaggtgat ccgcctacct    4920
cagcctcctg aagagctggg attacagatg tgagccaccg cgcccatcc tcactgtctg     4980 ctctgactca cttctctctc ccatgtctca ggggcccctg actgaacctt gggcagaaga    5040
cagtccccca gaccagcctc ccccagcttc tgcccgctcc tcagtggggg aaggagagct    5100
ccagtatgca tccctcagct tccagatggt gaagccttgg gactcgcggg gacaggaggc    5160
cactgacacc gagtactcgg agatcaagat ccacagatga gaaactgcag agactcaccc    5220
tgattgaggg atcacagccc ctccaggcaa gggagaagtc agaggctgat tcttgtagaa    5280
ttaacagccc tcaacgtgat gagctatgat aacactatga attatgtgca gagtgaaaag    5340
cacacaggct ttagagtcaa agtatctcaa acctgaatcc acactgtgcc ctccctttta    5400 ttttttaac taaagacag acaaattcct a                                    5431
```

<210> SEQ ID NO 19
<211> LENGTH: 12180
<212> TYPE: DNA
<213> ORGANISM: Homo sapiens

<400> SEQUENCE: 19

```
cgaggctcct cctctgtgga tggtcactgc ccctccacca ggcttcctgc tggaggagtt      60
tccttcccag ccaggccggc ccagaagcca gatggtcccg ggacaggccc agccccagag     120
cccagagatg ctgctgctgc ccctgctgct gcccgtgctg ggggcgggtg agtgggtcgg     180
tggctggggg tcccaggcag gggctggggc tgccgctgag cctctgcatc tccccagggt     240
ccctgaacaa ggatcccagt tacagtcttc aagtgcagag gcaggtgccg gtgccggagg     300
gcctgtgtgt catcgtgtct tgcaacctct cctaccccg ggatggctgg gacgagtcta     360
ctgctgctta tggctactgg ttcaaaggac ggaccagccc aaagacgggt gctcctgtgg     420
ccactaacaa ccagagtcga gaggtggaaa tgagcacccg ggaccgattc cagctcactg     480
gggatcccgg caaagggagc tgctccttgg tgatcagaga cgcgcagagg gaggatgagg     540
catggtactt ctttcgggtg gagagaggaa gccgtgtgag acatagtttc ctgagcaatg     600
cgttctttct aaaagtaaca ggtatggaat ggggtggaa cccctgcctg tcacactggg     660
gagggaccct ggggacaggc tatgggctga gcagagaggg ctctcaggga cccctgcagc     720
acaagaatct cccaccccgt ctctgtccca gccctgacta agaagcctga tgtctacatc     780
cccgagaccc tggagcccgg gcagccggtg acggtcatct gtgtgtttaa ctgggctttc     840
aagaaatgtc cagccccttc tttctcctgg acggggctg ccctctcccc tagaagaacc     900
agaccaagca cctcccactt ctcagtgctc agcttcacgc ccagccccca ggaccacgac     960
accgacctca cctgccatgt ggacttctcc agaaagggtg tgagcgcaca gaggaccgtc    1020
cgactccgtg tggcctgtga gtgtggcctg ggagggtggg gcgtgcagac agccccggtg    1080
ggtggggagg tggaggagcc cagcgggaca gtgagtggct cccagctcag gagcatccag    1140
ggagaggaag ctgtggggtc ccaggatgcc ggctcagccc tggaggggg atgggaatgg    1200 cgtctgatcc tctgtccaca tgtgtgagcc ctggagctgg ttgtcacttg tccatcctgg    1260
```

```
gatgttccca ctttcttttc cctgagggag ttttttccag gtgtgaggaa caaattgtcc    1320
ctccctgaag ccagctcaca atcttgttgc agatgccccc aaagacctta ttatcagcat    1380
ttcacatgac aacacgtcag gtactgaggg ccttcgggct ggggctgggc cagtcctctt    1440
tagggatgaa aaggcttcag gggggtgagg ggatgtggtc ctctttgcag ccccccctcc    1500
cacccattct ctctctccac ccccaccctc tctctttccc tgtcttcagc cctggaactc    1560
cagggaaacg tcatatatct ggaagttcag aaaggccagt tcctgcggct cctctgtgct    1620
gctgacagcc agcccctgc cacgctgagc tgggtcctgc aggacagagt cctctcctcg     1680 tcccaccct ggggcccag aaccctgggg ctggagctgc gtggggtaag ggccggggat      1740
tcagggcgct acacctgccg agcggagaac aggcttggct cccagcagca agccctggac    1800
ctctctgtgc agtgtgagtg tgcctagcag gggcctggag tccattggga gggcagaggg    1860
atacaggggc tgggctcagg gtcccagagc tgaggggggtc ttgaaccca ggcctcgggg    1920 actgaccttc ttacctgtgt agaccctcat gcagtttgtg tctgggactc agtgggtgat    1980
tctgccctgc ccttctatcc cacccacttc ccccacctca gtgtccagga tagttcccct    2040
tacccagagg gaagcccctg gtctgtctag agccggtccc ctgtctccat ttcagatcct    2100
ccagagaacc tgagagtgat ggtttcccaa gcaaacagga caggtaggaa aggagacaga    2160
ggagccaggg cctctcagtg ccaaactggg ggcccaggag tctggagggt ccccacacag    2220
gagggtccct gagccctgag ctgcacgtcg attctgcctc ttccttccct agtcctggaa    2280
aacctcggga acggcacatc cctcccggtc ctggagggcc aaagcctgcg cctggtctgt    2340
gtcacccaca gcagccccc agccaggctg agctggaccc ggtggggaca daccgtgggc    2400
ccctcccagc cctcagaccc cggggtcctg gagctgccac ccattcaaat ggagcacgaa    2460
ggagagttca cctgccacgc tcagcaccct ctgggctccc agcacgtctc tctcagcctc    2520
tccgtgcact gtgagtgggg gaaagggggac acctgggtcc caggaagggg cccctgctga   2580
gtcctgtcct ccctccccac agaccctcca cagctgctgg gccccctg ctcctgggag      2640 gctgagggtc tgcactgcag ctgctcctcc caggcagcc cggcccctc tctgcgctgg      2700 tggcttgggg aggagctgct ggagggaac agcagtcagg gctccttcga ggtcaccccc     2760
agctcagccg ggccctgggc caacagctcc ctgagcctcc atggagggct cagctccggc    2820
ctcaggctcc gctgtaaggc ctggaacgtc cacggggccc agagtggctc tgtcttccag    2880
ctgctaccag gtgaggggac tgtgggggc tgaggttcag ggagaaagga gacaggatcc     2940
tagaaagatg aaggttcaag gttgtgggga gagggtgtgg gcgtggtggg aagggatggg    3000
gacaaagtcc ctgctctgtg gctggtagtt gttgcgggaa actgaggaac ggagagagca    3060
atatggagaa caggaggatt gtttatttaa ggtaagttcc agcttagtgg atttacattt    3120
caaaagctga gcattaaata aagacaaaga agggggtttt tttgttttt ggttttttt     3180 ttgagatgga gtctcgctct gtcagcaagg ctggagtgca gtggctcgat ctcggctcac    3240
tgcaacctct gcctcccgga ttcaagcaat tctcctgcct cagccacctg agtagctggg    3300
attacaggca tgcgccacca cgcccagcta atttttttgt attttagtt tcactatgtt     3360 ggccaggctg gtctcgaact cctgaccttg tgattcacgc acctgaccct cccaaagtgc    3420
tgggattaca ggcgtgtgcc accgcgcccg gctaaagcag tgtgtttata agcggactta    3480
caaaagtaaa acaaaagcgg ttaattatat agtgcataac ttgtggcctt gtagctgtgt    3540
caaaagaaaa acaagaactg gttaaataca gacatttgtg aaacataatt gtgcttaaga    3600
agccagggaa aggagtaaca gtaaaagaat ttgtcttttt tttttttct ttaaccttgc     3660
```

```
tctggaaggg gtgtgtctgg agcccattcc tttggccttg cttttttaaa cagtgttatt   3720
ttatacctgt ccttgaagtg agcttgctag gcatagaaag acttgggttt tttttgtttt   3780 tttttttaacc cttgccttgc ctgttacttt tttgggagtg aatgaatgca tatttatttt   3840 taaattttg cctcagtttc cccctttga tgttttttat aaaagaagtt aatagaagg      3900 cattactatt acttaattct gcatgaagag acactttttt tctttagaca aaggttgata   3960
tttatgcaga gccgttagct gagtggtagt ttgcctagct gctattgcct ttatagttga   4020
ttgaatgctt ccaacaagga gagctaagag acaagggagt attcggcaac ttcctagtat   4080
ggccagaacc acttttatta aagtcttgaa ccctctgcaa aatgaaaacc agtccttaaa   4140
gagagaatct ggagaccacc ctttccaagt ttgaactgga acatgggcta attttttat    4200 ttttgcagtt attttttataa ttgccttttc attgtcagcg attttaggc agcagttagt   4260 tagattgaac ttttttacatt ttttttttttc tgggctagga gtagtccaaa gctaacctgt   4320
tctgatagat aacattcttc attttttgtgg gttgctgggc cagtaaatct aatgcatttg   4380
ctgttttatt agtgatgatt tcaagtactg cctgcaacct tatgatgcgg ttaagcatgt   4440
aaataggagt gtggtatccc catgacccat tttgtgccca ggtagctggc ctatactatt   4500
gaattatttt ttcaggggt taatttgtgt cttttcaatt tttttaattt ttattttttgt   4560 gtgtgtgttt gcattttttt taactttatt atagacagga taccttaaag tttctccctg   4620
ttgcagtggg aataggaaga aagacggtct aattgtttca agcacacagg cccctgtcca   4680
tttagctggc aactgttgat atgcccatgg cctacagatc caacaaagac taggaggtgc   4740
ttgccaagta tttggagctt tcggctgata gtaggtgtga tttaaagaag agaaacaggg   4800
aacggatttg gatgaggtca tttgcattca tctttgcccc gccacaaagt gtttcttagt   4860
gttttatcgt catattgctg tcctaagcag tttagttctt ttactgggtt tgtaaaaact   4920
tttccccagc gagcaacaca gtatttcctg ataatagaag ttttttaagag ccagacgctt   4980 gaacttgtgg gcgtcggttc gggagaagag tcagttaaat tattttgtgg cattaacttt   5040
tttgctttcc aaggccattg gtcttccgtg ttagtccctc cgcaaacata gtatgaggaa   5100
atgcctaggc tgccgacaat gttttaggc agccgagcaa acaggttttc tgctaaagga   5160
gtgggctctg gtaacaggat tacaggtgtg agccactgcg cccggccata agtacaagtt   5220
cttttttttt ttttttttga gacggagtct cgctctgttg ccctggctgg agtgcagtgg   5280
cgccatctct gctcactgca agctccaact cccaggttca cgccattctc ctgcctcagc   5340
ctcccgagta gctgggacta caggcgcccg ccaccaagcc cggctaattt ttttgtattt   5400
ttactagaga cagggtttca cagtgttagc caggatggtc tcaatctcct gaccctgtga   5460
tctgtccacc tcggcctccc aaagtgctgg gattacaggt gtgagccgcc atgcccggcc   5520
tgctaatttt tctttttatg agggctgctg ccaacagatt ggcctttttt tttaagccta   5580
tgttctgctt ccttttcct tcctgagtta tcctgctcct acagctggcc agtgggactg   5640
ggctacggcg tgggccccgc ccctgtgcac gcacgcactg ccatctatct ttactgtttc   5700
tttctgattt ttcttttttc cttttttcaca cttactttt tgggctaggt aggatctgca   5760
cagccgtagt ccaccoctgg gccgttatag gcccagaggc ttggtagatg cctgccgcaa   5820
gttgtaagaa ttatgccttt ctttttttttt tttttttggg ctttttttct ggggccagtc   5880
cccgccccgc tcttttcca gatagagcca ggctgaggag agggactaaa cccttggtgt   5940
gcctagctgc ttggtgcctc gcttgttgct ttcgctcttt cccgttttgt tctctggtca   6000
```

```
tggttcatgt acatcttggt ggtcactttt ataagctggg tggcattcat gcctgcagct   6060
gccgcttgac gtcaccctgg gcttgcccta caaatgctgt gtttaccatg cgctgatttt   6120
cagcagcctc agggtcaaat agggtgtaag gccggaatgc ttcacaaagt ttttttataaa  6180 actgacttgg gctctcgtca gctctctgaa gcacttttga aattttttcgt atattaattg   6240 ctttctttcc accagctttt atcccttgca gaagtgtctc ttggtacctt tgcaaatgct   6300
gaagctgagt tgcatcctct gggttccagt tgggatcttg gtatgagaac tgaccttgag   6360
tgtatgcctg agcattcact gcatctgctg gtgcatgggg ttttagccag gggagagctg   6420
cctatgttac tctcctgcgc ttttttagtgt taaataacgt taggaaaagc tgcctgcaat   6480
ctggccaggt tggactgtgt gtcagaaaga cggattgcgt cagatctata agagcttgag   6540
gcttctccat gtaggaggga gtatggtgtt tccagttcag tagatcagta gctcagtagt   6600
cagaaagggc tgatagatga aggtgcgttg ccccccacct ccgaacctgg ccttggttat   6660
tacaataagt gggtcctcac atctccctga caggcatttg catagctcga gcaggcattt   6720
gcatagctca agcacggcca gatctgagac agcctgcttg actattttga cttccttccc   6780 tggcctttttg aggctccagt ccttcccttc ggggtcagac tcagggcatg ctagctcctg   6840
aatttggttc ctggagggct gttggcctca gtaaagggggg gtaggctggg acatatggag   6900
gaggaatttc tgtttcctct ggcagctgtt gcaaaactgg cttctcttgc tctttctggg   6960 gttttttcttt taacttcgtg tcagtcggtg aagctgctct tacttttatt tttggctcgg   7020
gctacaagtg ttttgcaata agctgctaaa cagggcttga tccaggttag tcttgtctgt   7080
gctgtattta accatgaatc aatataagga aattgatcgg gatactcagg ctgtcctcag   7140
acccctatca ccatctttaa tacatgccca attgtttcct agtctacagt ttcttcggtc   7200
agccatccaa catcaaaaga aagtcattct aattcaaaga gagttctcaa cctttggggg   7260
gttagcttaa cttttataatc ccctgcaaaa ccttttcttaa agttttgtaa catgcacttc   7320
aatggagtaa gttttgatgg actttccttc tattccttcc tttacggccc agcacactca   7380
ctcttcctct agtttcggcc aactatacca tctcctatta cgggagtttt cagaagctac   7440 ttggcttttgg agagttcctt attcctgcta caactctgag ctgtagggca gctcctatta   7500
gccatacgca gatcaccact agtcttagtt ggccccacac tttgctcgga gcacccagtc   7560
cacactaaga gaattgtgac ttcccatttt gtggctgatc agcctaataa ggcttcttca   7620
tttacacact gttacacact tccccactcc cagttcctaa gttcctaatt agggtggtaa   7680
gccactctcg ccacctccag tttccttttc ctaatcgact tagcaaacca ttctcacatc   7740
ctgtgatggt tggggtgtga gtttcatcca aatcgacgag ccactctcgc tgcccccaac   7800
ccctctgggt cggactgtta ggcacccccgc aagaagtgat cagcctcccc ttccatccct   7860
atgggatggg tcctgccttg gtccccaaaa ggttactgtg gttcctgacg tacactgttt   7920
ctgaaatcat tctgtagctc ctttcaggtt tgttgtgct gctgggtagg ggcgccggct   7980 cagggggagag ctgatttctc ctccaggctg aagttcaccc agtggcacct ggggtcacag   8040
gtctcctgag gcccggggct ccagccccca gaggcaaagg aggcagtaaa cctaccgtct   8100
ctggtccctt cgtggtcgcc aaaaatgctg cgggaaactg aggactggtg agaccgatac   8160
ggagaacagg aggattgttt attttaggtg caaaccggct cagtggactc gcatctaaaa   8220
agctgagcat gaaacaaaga cagagcgagg ttttatgag cagacttaca aaagtaaaac   8280
agaggcagtt aattttagga taggtgacat aatttatagt atagcataac ttgtggcctt   8340
gcatagctgg tggccttgta gctgtatcaa aaggaaaaaa aaagaactgg ctaaatacag   8400
```

```
acatttgtaa aacatagtta tgcttaagaa gccagggaaa ggagtaacag taaaggaatt    8460 tgttttctt  tcttgttttc cttcaacctt gctctggaag ggggtgtgtc tggagcctat    8520
tcctttggcc ttggcttttt aaacagtatt atcttataac tgtccttgaa gtgagccttg    8580
ctaagcagag gaaaagttgt tctttttta  acctttcct  tgcctgttac ttttcttgga    8640
gtgaatgaat gcatatttat ttttaaattt ctgcctcagt tggggatgaa gaatccgaga    8700
gctctaggtc tgtgggagga aggggcagga gggtctcagg gccaggaggg caccacccca    8760
aaccctgctc ccatgcaggg aagctggagc atggggagg  acttggcctg ggggctgccc    8820
tgggagctgg cgtcgctgcc ctgctcgctt tctgttcctg ccttgtcgtc ttcaggtaag    8880
catcggaggg caggcaatgc agggtgtggg aagggtgagg gttctagaat cccagacagt    8940
cccagctgca ggaatctaga tggggcagtg ggtgtgagaa ctaggccttg gcaagagga    9000 tcagagcagg ggtctgctcc agagccctga tctgggccat ctatgagggt ccccagttct    9060
cactatggaa gtcaccccgt ggatatgtcc ccaccccact gggctctgca gccttccagc    9120
ctctgctaag ccatgtgggt agcagtttcc ccaggctctg gaccagcctg gaggctgaag    9180
ggcactgcct cctccctcag ggtgaagatc tgcaggaagg aagctcgcaa gagggcagca    9240
gctgagcagg acgtgccctc caccctggga cccatctccc aggtgagagc ccagcctctg    9300
tctgctgggg ccctgcctgt tccccttttcc ttgatggcca tgggtagtcc tcttggtgac    9360
ttgcagaatc attgtgcccc aaatagggtt ttgctcctgg gtccccatca atgcagtccc    9420
aagtcccatg atctgggagg caccctcccc actgctccct acatcccctc ccagaaccaa    9480
gggcccccca ggcctgtcca tactctgcct gtgctcagat ccagtggacc ctccacctcc    9540
cactcctcat ttcctcctgc atccccgact cctttgccct ccctcctatc tctcctcctc    9600
aacacaggat gccagagagt cctttcctca gatgactatt gtctactaca aagctaaggg    9660
tccccatcct cacttctgac accaaccaca gttgtggggt ccccacgacc actctgaggt    9720
tggataaccc cctaggactc gcaggactca ctgagagctg tgatcctcgt ggtgatggtt    9780
tatagtgacc gatacagatg aaaatcatgg acaggaagag gtgctcaggg caggtccagg    9840
agataccaaa cccacagctt ccggtggcct ttcccagggg agccatgggg acagcaccca    9900
attctcccag caaggaagtg tgacagatgc acggagcatc agggcaccgc tcacctggga    9960
agctccacca aacctgggtc cagggttcac tggggtggg  tcacgcaggc atgggggact   10020
tgccactgac ttcagttcct cagcccctgc agagccaaac tgatgctacg taggccccgc   10080
cgtaagtccc agtgctggcg taaactatgt ggcctggctt gtggtcccag gtcaacaggg   10140
atgctcctac cagcaggata ttccaaggcc ctacattaga ggttccttcc cagcacctgg   10200
gcacaaacgg ttgaagcttt ctctgggcaa ggggaatcct ttacttccag taaccttttct   10260 ttcttgagct cctagctcag tttcacaatt gtgtccgagt agatcttcca aggtctttga   10320
ggtcagtcca ggtccgagca aatccctgtc tttctcacac ctcctccttc ctgggcatcc   10380
acttataatt tgcaattaga tagtaacttc attgactata gctttaatgt gtctacttct   10440
tcttccatac tgcaagctgc ctgagatcag gggtggtgtc tccctagttc ccccgggaat   10500
atccaggggc tggcacaggg gagctgttcc ataaggcagc gggcactgga gtcagagaaa   10560
cctggacgtg aatcctggcc tgaccgctac ttagatgtgc gggtttgggg tatttactca   10620
gccttcattt ctccatctga tcatggagac aatagtgtct ccccagtgga ttgtggtgag   10680
gattttatga gtctggattg tggtgaggat tttatgagtc tggcagtgaa ttaccaagag   10740
```

```
ctagatgtta ttgttctcaa atatttgctg aatgagtgaa tgaatgaatg agtgaatgaa    10800
tgagggccca gctgaccttt gtggaatgag taggtgaaac aggaaatact caatttccag    10860
atcctcttgt gcatcctcct tgctctcgct tagcccccat gaccctaatt tgaccccctt    10920
tctcccctgc attcagggtc accagcatga atgctcggca ggcagctccc aagaccaccc    10980
gcccccaggt gcagccacct acaccccggg aaggggggaa gagcaggagc tccactatgc    11040
ctccctcagc ttccagggcc tgaggctctg ggagcctgcg gaccaggagg ccccagcac    11100 caccgagtac tcggagatca agatccacac aggacagccc ctgagggggcc caggctttgg    11160 gcttcaattg gagagggaga tgtcagggat ggttccaaag tgaagaggtc tccatggcaa    11220
caggacacca gcaagtgtgt gggagtcgca ctggtgtgac ggccagaact ggactcagat    11280
ttcagcccca tccccaatga agagcttgag tttgaagatt atactttttt tgagacaggg    11340
tctgactctg tcctccaggc cagagtccag tggtgcaatc tcagctcact gtagcctcaa    11400
cctgccaggt tgaagtgagc ctcccatttc agcctcccaa gtagctggga ctacaattgt    11460
gagccaccat gccaggctca ttgttatatt tttagtagag acagggtttt gccatgtttc    11520
cctggctggt ctcagactcc tgggctcaag caatctgccc gcctctgcct cccaaagtgc    11580
tgggattaca gacgtgagcc accacagctg gctgaagatt atactttcaa ttcagagcga    11640
gtttgaagat gacactttga ggcatcgtgt ctatggttca ttactacaga agcttctctg    11700
gatgtgtaaa gcacaggaaa ccaggcagag gaggcacagg gtgctctcca gaacgagaag    11760
ccagctcctg gagttgtttg ctgcaactgc cattccccgt tgatgaccat gctcttcctt    11820
cagaagaggg agagtgagag gaccaagtcc aagtggttcc catttgaaca tttaaaaaaa    11880 aaaaaaggc tgggcatggt ggctcacgcc tgtaatctca cactttggg aggctgaagt    11940 gggtggatca caagtcagga gttcaagacc agcctgggca agatggtgaa accccatctc    12000
tactaaaaat acaaaaatta gccgggcatg gtggcgggcg cctaaaatcc cagctactcg    12060
ggagactagg cagagaattg gttgaacccg ggaggtggag gttgcagtga gccgagatcg    12120
tcccactgca ctccagcctg ggcaacagag tgagactctg tttctaaata aataaatgaa    12180
```

<210> SEQ ID NO 20
<211> LENGTH: 4327
<212> TYPE: DNA
<213> ORGANISM: Homo sapiens

<400> SEQUENCE: 20

```
actcaccctc cggcttcctg tcggggcttt ctcagcccca ccccacgttt ggacatttgg      60
agcatttcct tccctgacag ccggacctgg gactgggctg gggccctggc ggatggagac     120
atgctgcccc tgctgctgct gcccctgctg tggggggggtg agtgagctga gggaggaggg     180
acaggcacag gggtgagaag ggggggctgga gctgcagctg agcttctgtg tcccccagg     240 gtccctgcag gagaagccag tgtacgagct gcaagtgcag aagtcggtga cggtgcagga     300
gggcctgtgc gtccttgtgc cctgctcctt ctcttacccc tggagatcct ggtattcctc     360
tcccccactc tacgtctact ggttccggga cggggagatc ccatactacg ctgaggttgt     420
ggccacaaac aacccagaca gaagagtgaa gccagagacc cagggccgat tccgcctcct     480
tggggatgtc cagaagaaga actgctccct gagcatcgga gatgccagaa tggaggacac     540
gggaagctat ttcttccgcg tggagagagg aagggatgta aaatatagct accaacagaa     600
taagctgaac ttggaggtga caggtatggc aggaacccta ggagaggacc ctgggacgtg     660
gagacccccg tatgagaaca gggacaggag ttgggcaggg gcggctggag gaggtgtagg     720
```

```
acttggggca ggtcggggcc tgaggcctgg ccactctcgg ggtcacacct tacgtcctca    780
agcccctggg gcccaggtat ctccctgtct cctcctcagc cctgatagag aaacccgaca    840
tccactttct ggagcctctg gagtccggcc gccccacaag gctgagctgc agccttccag    900
gatcctgtga agcgggacca cctctcacat tctcctggac ggggaatgcc ctcagccccc    960
tggaccccga gaccacccgc tcctcggagc tcaccctcac ccccaggccc gaggaccatg   1020
gcaccaacct cacctgtcag gtgaaacgcc aaggagctca ggtgaccacg gagagaactg   1080
tccagctcaa tgtctcctgt gagtggtgct ggggacacag ctgagtcccc aagggcagtg   1140
ggagtgaggg gggtgtgtgt gtgtgtgtgt gtgtgtgtgt agaagagaga gagagaaaga   1200
gaatgataac cagggaaaac tcgtgtgtgg gcaggaagga cagcggtccc cacctggtgg   1260
gtttctgtgg cccctccttg ggtccctccc gggaccacgc ccatccctct tgtcacctct   1320
gaagctggtg ctgtatcttt ctatcccaga tgctccacag aacctcgcca tcagcatctt   1380
cttcagaaat ggcacaggca caggtaggaa agaccctctt ccctctgggg ctgtgatggg   1440
agccttctat tagctcaggg ttcagcattg ggagaggaga ccctccctca cccctcagcc   1500
cctgggtctg ggtccttcct gctcccaacc ccccaatccc agtcactaag atcttgcacg   1560
aacagaccta gtatttcttt tggcttctcc cttttctctg ctctcttttt cagatttatt   1620
ttttcattgt gagaaaatac acatagcaca aaatttgtca tcttagccat tttaaagagt   1680
acagttcagc agtgttaaat gtgttcacat tgttgcaaaa ccaaactgca gagctccttt   1740
tatctggcaa aactgaaact ttgtacccac tgaacagcga cttccacttt cccccctcctg   1800
ccaccgagca gtcaccattc tacttttctg tctctgtgag tttgagtact caggacacgc   1860
tgttcccttt tcttgaattt ctgcctgctc cgatgtcctc tgatgcatgc cctgcttcat   1920
ctctaactga tcgtcctttt tgggagcctt cgactttccc acctcccaca gctctgtccc   1980
agaacccagt tcttccctc cacattcctg agtaatccga tctctccttg acctgtcct    2040
gatgcctccc acaactttat atccagccct ttctctgagg cacagatctg cacatttagc   2100
cacctccctc ggatgcttct cggctcctcc ttccctgttg atcccagggc tgttctggac   2160
atcgctgtag acagcaccct ttctcatcag ctgtttcatg agtccgcaag tcttaacacc   2220
tttacttcac caatcatcac ttccctcctc atcccttgg ttccaggccc agctcaagtc    2280
tcgtgctcaa ccctggccca ttgccccagc ctcctcccag cctccctgcc tcctatccca   2340
cttctctcca gtccgggacc tacttggctc cagcaggatc tttctagatc cagtgctaac   2400
tctgtttccc ttgcttatag ccccctcttg ctttccagga taaagcccaa ggccctcaat   2460
ctggcaccca atgctccaaa agatctgagc ctgcttctac ctccattatc gtgtcttggg   2520
agctctgggt cctccctgac aggttgcgga tctaggagcc tctttcctcg tctgcctgtc   2580
tcagttcttg gcacgtctgc acctgagctg cccatccact tctccttaat gtgagaactc   2640
ctcctcatct gtctttttctc agctcagcca ccttctttct ggtagcctga cctgatcacc   2700
aagtcctcat cctttcaccc atgactagcc cattctcagc actcaccaca cagtcttgtc   2760
tttcttcttg cagctcagtg ggaggaatga gggagaattg ggcctcccag ctccactcac   2820
ctggctgtgc ttctctttcc cagccctgcg gatcctgagc aatggcatgt cggtgcccat   2880
ccaggagggc cagtccctgt tcctcgcctg cacagttgac agcaaccccc ctgcctcact   2940
gagctggttc cggagggaa aagcccctcaa tccttcccag acctcaatgt ctgggaccct    3000
ggagctgcct aacataggag ctagagaggg aggggaattc acctgccggg ttcagcatcc   3060
```

```
gctgggctcc cagcacctgt ccttcatcct ttctgtgcag agtgagttgc aggacaggtg    3120
ctgagggtag acagcccggt gaggtattca ggttggtggg agggactgag gcctggtaac    3180
agcaccttac cttctccttt ctcccaggaa gctcctcttc ctgcatatgt gtaactgaga    3240
aacagcaggg ctcctggccc ctcgtcctca ccctgatcag gggggctctc atggggctg     3300 gcttcctcct cacctatggc ctcacctgga tctactatac caggtgagcc ggactgcctg    3360
tctccaggaa gctcctgagt tccaggtggg gctgagctgt cctgcccag  acagctcag     3420 ccccacctgg aattagaact gaagtggctg gtgctgatct gaggcccatg ttggctctgc    3480
aggtgtggag gcccccagca gagcagggct gagaggcctg gctgagcccc tcccgctcaa    3540
gacagaactg aggtgtggac acttagccct gtgggacaca tgcaggacat cactgtcagc    3600
ttctttctgg aagctcacat cccactgact accc ctcttt ccttcctgc  cccataccccc   3660 ttctacttat tcccctctgc ttgtgagtct tgccccacca cacctgcatc cccatctgca    3720
ccccatcccc tctccacctg cccttctctt ccctctccat ccaccatctc cagccctgtg    3780
aagggaatgt actttcggtc ttataccccc attacccatt acccaaaagt tacctttttt    3840
tttttttttt tttttttgaga cagagtctca ctctgttgca caggctggag ttcagtggca    3900
caatctccgt tcactgcaac ctccacctct ggggttcaag caattctcct gcctcagcct    3960
ccctagtagc tgggattaca ggtgcctgcc accacatcca gttaattttt ttttttttgta    4020 tgttagtaga gatggggttt taccatgttg gccaggtctc gaactcctga cctcaagcaa    4080
tccactgcat tggcctccca aagtgctggc attacaggta tgagccaccg tgcctggctg    4140
ccaaaagtta ccttcttaac acttgaattt ctggtctcct cagcttccct atccatatag    4200
gcacagagag gcagcatttg ttttccagtt aaaactctac ctcattgtga ttattatcca    4260
atacaattgt tacaaaataa gtaaaacttt tatgaaacaa tacaacataa ctgatttac     4320 tcttta                                                               4327
```

<210> SEQ ID NO 21
<211> LENGTH: 3932
<212> TYPE: DNA
<213> ORGANISM: Homo sapiens

<400> SEQUENCE: 21

```
actgcccctc caccaggctt cctgctggag gagtttcctt cccagccagg ccggcccaga     60
agccagatgg tcccgggaca ggcccagccc cagagcccag agatgctgct gctgcccctg    120
ctgctgcccg tgctggggc  gggtgagtgg gtcggtggct gggggtccca ggcaggggct    180
ggggctgccg ctgagcctct gcatctcccc agggtccctg aacaaggatc ccagttacag    240
tcttcaagtg cagaggcagg tgccggtgcc ggagggcctg tgtgtcatcg tgtcttgcaa    300
cctctcctac ccccgggatg ctgggacga  gtctactgct gcttatggct actggttcaa    360
aggatggacc agcccaaaga cgggtgctcc tgtggccact aacaaccaga gtcgagaggt    420
ggaaatgagc acccgggacc gattccagct cactggggat cccggcaaag ggagctgctc    480
cttggtgatc agagacgcgc agagggagga tgaggcatgg tacttctttc gggtggagag    540
aggaagccgt gtgagacata gtttcgtgaa caatttgttc taaaagtaac aggtatggaa    600
tggggtggga acccctgcct gtcacactgg ggagggaccc tggggacagg ctatgggctg    660
agcagagagg gctttcaggg accccctgcag cacaagaatt ccccaccccg gtctctgccc    720
cagccctgac tcagaagcct gatgtctaca tccccgagac cctggagccc gggcagccgg    780
tgacggtcat ctgtgtgttt aactgggctt tcaagaaatg tccagcccct tctttctcct    840
```

```
ggacggggc  tgccctctcc  cctagaagaa  ccagaccaag  cacctcccac  ttctcagtgc    900
tcagcttcac  gcccagcccc  caggaccacg  acaccgacct  cacctgccat  gtggacttct    960
ccagaaaggg  tgtgagcgca  cagaggaccg  tccgactccg  tgtggcctgt  gagtgtggcc   1020
tgggagggtg  gggcgtgcag  acagcccgg   tgggtggga   ggtggaggag  cccagcagga   1080
cagtgagtgg  ctcccagctc  aggagcatcc  agggagagga  agctgtgggg  tcccaggatg   1140
ccggctcagc  cctgggaggg  ggatgggaat  ggcgtctgat  cctctgtcca  catgtgtgag   1200
ccctggagct  ggttgtcact  tgtccatcct  gggatgttcc  cactttcttt  tccctgaggg   1260
agttttttcc  aggtgtgagg  aacaaattgt  ccctccctga  agccagctca  caatcttgtt   1320
gcagatgccc  ccaaagacct  tattatcagc  atttcacatg  acaacacgtc  aggtactgag   1380
ggccttcggg  ctgggctgg   gccagtcctc  tttagggatg  aaaaggcttc  agggggtga   1440 ggggatgtgg  tcctctttgc  agcccccct   cccacccatt  ctctctctcc  accccaccc   1500 tctctcttc   cctgtcttca  gccctggaac  tccaggaaaa  cgtcatatat  ctggaagttc   1560
agaaaggcca  gttcctgcgg  ctcctctgtg  ctgctgacag  ccagcccct   gccacgctga   1620 gctgggtcct  gcaggacaga  gtcctctcct  cgtcccaccc  ctgggccccc  agaaccctgg   1680
ggctggagct  gcgtggggta  agggccggg   attcagggcg  ctacacctgc  cgagcggaga   1740
acaggcttgg  ctcccagcag  cgagccctgg  acctctctgt  gcagtgtgag  tgtgcctagc   1800
aggggcctgg  agtccattgg  gagggcagag  ggatacaggg  gctgggctca  gtgtcccaga   1860 gctgagggg   tcttgaaccc  caggcctcgg  ggactgacct  tcttacctgt  gtagaccctc   1920
atgcagtttg  tgtctgggac  tcagtgggtg  attctgccct  gcccttctat  cccacccact   1980 tccccacct   cagtctccag  gacgcttccc  tttgcccaga  gggaagtccc  tggtccgtct   2040
agagccggtc  ccctgtctcc  atttcagatc  ctccagagaa  cctgagagtg  atggttttccc   2100 aagcaaacag  gacaggtagg  aaaggagaca  gaggagccag  ggcctctcag  tgccaaattg   2160
ggggcccagg  tgtctggagg  gtccccatgc  aggcgggtcc  ctgagccctg  agctgcacgt   2220
cgattctgcc  tcttccttcc  ctagtcctgg  aaaacctgag  gaacggcaca  tccctccggg   2280
tcctggaggg  ccaaagcctg  cgtctggtct  gtgtcacaca  cagcagcccc  ccagccaggc   2340
tgagctggac  ccggtgggga  cagaccgtgg  gcccctccca  gccctcagac  cctggggtcc   2400
tggagctgcc  tcgggttcaa  atggagcacg  aaggagagtt  cacctgccac  gctcggcacc   2460
cgctgggctc  ccagcgcgtc  tctctcagct  tctccgtgca  ctgtgagtgg  gaaaggggga   2520
cacctgggtc  ccaggaaggg  gcccctgctg  agtcctgtcc  tccctcccac  agagccccc    2580 cagctgctgg  gaccctcctg  ctcctgggag  gctgagggtc  tgcactgcag  ctgctcctcc   2640
caaggcagcc  cggccccgtc  tctgccctgg  tggattggtg  gggagctgcg  gagggaaaca   2700
gcagccagga  ctacttcaag  gtcacccca   gctcagccgg  gccctgggcc  aacagctccc   2760
tgatcctcca  aggggggct   tggctccaac  tcaggctca   cctttgaggc  ccagaacgtc   2820 catgggccc   agagctctct  gattcctggc  ggacagtcag  ggtatagggt  ggggaggcct   2880
gggctcacca  ggtcctgcat  ccagggatgt  aggaagggcc  tggagaacca  agttgcaata   2940
agagaggaag  gattcggaag  tgtggtttag  aaggtgaatg  ggccttatcc  cacttttcca   3000
ggcaaatcag  ggcccatgac  ggggtggtt   ctggtggctg  ttggggaggt  ggctatgaag   3060
atcctgcttc  tctgcctctg  cctcatcctc  tcaggtgag   ccctgcccca  gggaccaagg   3120
ggaggggcgg  agagggcaaa  ggatacaccg  ctgaatccca  gaatctcaat  cctgggggta   3180
```

```
cttggacagt taaagaggcc tgtggccagg cagaggctga gttgatcgtg atgattccac    3240
acgggccagt gttgtcagtc cccaactctg gaccaatgtc caggctgggg aggttcctgc    3300
ttgtatcagg gaggtcctgg gggctaggcc tgctctctct gcctcagtcc cctccaaccc    3360
cttagcaggg cacagggagg tgagtctgct gccctcttca cccccatcca gccacactca    3420
caggccctgg tctcttcacc cagagtgagg tcttgcagga ggaaggcagc aagggcagca    3480
ttgggcatgg aggctgcaga cgctgtcacg gactaatctc caggtgagtg tcgtgggcct    3540
cttaccctcc aacatcccgc tggacacctc ccctcgatg gccccaagga ctgctccact     3600
caacttggcc ataactgact catcacctcc ctttccaagc ccacttctct tgttgagagc    3660
cccatccctc tgatgacatg gtagccccat ctctaacgtc agaacccggg tgtgggtgtc    3720
caccttgacc tccctccctc ctccagatcc caaaaatcac tagcacttgt ccctcctcct    3780
aagtacaggt caccttggag cccttttctc catcctggcc ccggtcatgc ctgggcctca    3840
cctcttccct ggtcgctgaa cccacctcac ctcttgcctc catctctccc aacagactcc    3900
agactgcttc cagatgcctc ctcatccagt tc                                 3932

<210> SEQ ID NO 22
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 2, 3
<223> OTHER INFORMATION: Xaa = Any Amino Acid and up to 2 of them can be
      present or absent
<220> FEATURE:
<221> NAME/KEY: VARIANT
<222> LOCATION: 5, 6
<223> OTHER INFORMATION: Xaa = Any Amino Acid
<220> FEATURE:
<221> NAME/KEY: VARIANT
<222> LOCATION: 7
<223> OTHER INFORMATION: Xaa = Leu or Ile
<220> FEATURE:
<221> NAME/KEY: VARIANT
<222> LOCATION: 8, 9, 10, 11, 12, 13, 14, 15
<223> OTHER INFORMATION: Xaa = Any Amino Acid and up to 2 of them can be
      present or absent
<220> FEATURE:
<221> NAME/KEY: VARIANT
<222> LOCATION: 17, 18
<223> OTHER INFORMATION: Xaa = Any Amino Acid
<220> FEATURE:
<221> NAME/KEY: VARIANT
<222> LOCATION: 19
<223> OTHER INFORMATION: Xaa = Leu or Ile

<400> SEQUENCE: 22

Xaa Xaa Xaa Tyr Xaa Xaa Xaa Xaa Xaa Xaa Xaa Xaa Xaa Xaa Tyr
1               5                   10                  15

Xaa Xaa Xaa
```